US011542527B2

(12) United States Patent
He

(10) Patent No.: US 11,542,527 B2
(45) **Date of Patent: *Jan. 3, 2023**

(54) PARAINFLUENZA VIRUS 5 BASED VACCINES

(71) Applicant: UNIVERSITY OF GEORGIA RESEARCH FOUNDATION, INC., Athens, GA (US)

(72) Inventor: Biao He, Bogart, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 213 days.

This patent is subject to a terminal disclaimer.

(21) Appl. No.: 16/989,038

(22) Filed: Aug. 10, 2020

(65) Prior Publication Data

US 2020/0377908 A1 Dec. 3, 2020

Related U.S. Application Data

(62) Division of application No. 15/296,346, filed on Oct. 18, 2016, now Pat. No. 10,752,916, which is a division of application No. 14/374,061, filed as application No. PCT/US2013/022962 on Jan. 24, 2013, now Pat. No. 9,505,807.

(60) Provisional application No. 61/683,810, filed on Aug. 16, 2012, provisional application No. 61/590,070, filed on Jan. 24, 2012, provisional application No. 61/590,056, filed on Jan. 24, 2012.

(51) Int. Cl.

| | |
|---|---|
| *C12N 15/86* | (2006.01) |
| *C12N 7/00* | (2006.01) |
| *A61K 39/12* | (2006.01) |
| *A61P 31/06* | (2006.01) |
| *A61P 31/12* | (2006.01) |
| *A61K 39/155* | (2006.01) |
| *C07K 14/005* | (2006.01) |
| *A61K 39/04* | (2006.01) |
| *A61K 39/145* | (2006.01) |
| *A61K 39/205* | (2006.01) |
| *A61K 39/00* | (2006.01) |

(52) U.S. Cl.

CPC .............. *C12N 15/86* (2013.01); *A61K 39/04* (2013.01); *A61K 39/12* (2013.01); *A61K 39/145* (2013.01); *A61K 39/155* (2013.01); *A61K 39/205* (2013.01); *A61P 31/06* (2018.01); *A61P 31/12* (2018.01); *C07K 14/005* (2013.01); *C12N 7/00* (2013.01); *A61K 39/00* (2013.01); *A61K 2039/5256* (2013.01); *A61K 2039/53* (2013.01); *A61K 2039/552* (2013.01); *A61K 2039/585* (2013.01); *C12N 2760/16134* (2013.01); *C12N 2760/16171* (2013.01); *C12N 2760/18021* (2013.01); *C12N 2760/18034* (2013.01); *C12N 2760/18721* (2013.01); *C12N 2760/18732* (2013.01); *C12N 2760/18743* (2013.01); *C12N 2760/18771* (2013.01); *C12N 2760/20134* (2013.01); *C12N 2760/20171* (2013.01)

(58) Field of Classification Search

None

See application file for complete search history.

(56) References Cited

U.S. PATENT DOCUMENTS

| | | | | |
|---|---|---|---|---|
| 6,638,762 | B1 | 10/2003 | Chang et al. | |
| 10,227,569 | B2 | 3/2019 | Moore et al. | |
| 10,752,916 | B2 * | 8/2020 | He | A61P 31/12 |
| 2004/0043490 | A1 | 3/2004 | Shimada | |
| 2005/0048030 | A1 | 3/2005 | Pickels et al. | |
| 2006/0275774 | A1 | 12/2006 | Olivo et al. | |
| 2009/0208495 | A1 | 8/2009 | Beier et al. | |
| 2010/0119547 | A1 | 5/2010 | Haller et al. | |
| 2011/0008838 | A1 | 1/2011 | Smith et al. | |
| 2014/0370050 | A1 | 12/2014 | He | |
| 2015/0086588 | A1 | 3/2015 | He | |
| 2017/0067080 | A1 | 3/2017 | He | |
| 2019/0169579 | A1 | 6/2019 | Moore et al. | |

FOREIGN PATENT DOCUMENTS

| | | | |
|---|---|---|---|
| JP | 2002-507382 | A | 3/2002 |
| JP | 2002-153278 | A | 5/2002 |
| WO | WO 97/04124 | A1 | 2/1997 |
| WO | WO 1997/041245 | A1 | 11/1997 |
| WO | WO 1999/046278 | A1 | 9/1999 |
| WO | WO O01/03744 | A2 | 1/2001 |
| WO | WO 01/42445 | A2 | 6/2001 |
| WO | WO 03/029274 | A2 | 4/2003 |
| WO | WO 2013/112690 | A1 | 8/2013 |
| WO | WO 2013/112720 | A1 | 8/2013 |

OTHER PUBLICATIONS

ATCC No. VR-288, accessed online on Sep. 11, 2015, at atcc.org/Products/All/VR-288.aspx#generalinformation.

ATCC No. VR-399, accessed online on Sep. 14, 2015, at atcc.org/Products/All/VR-399.aspx.

(Continued)

*Primary Examiner* — Stacy B Chen

(74) *Attorney, Agent, or Firm* — Mueting Raasch Group

(57) ABSTRACT

The present invention provides safe, stable, efficacious, and cost-effective vaccines based on viral expression vectors that include a parainfluenza virus 5 (PIV5) genome including a heterologous nucleotide sequence expressing a heterologous polypeptide.

20 Claims, 59 Drawing Sheets

Specification includes a Sequence Listing.

(56) References Cited

OTHER PUBLICATIONS

ATCC No. VR-1573, accessed online on Sep. 11, 2015, at atcc.org/Products/All/VR-1573.aspx.
International Patent Application No. PCT/US2013/022962, filed Jan. 24, 2013; International Search Report and Written Opinion dated Apr. 10, 2013; 16 pages.
International Patent Application No. PCT/US2013/022962, filed Jan. 24, 2013; International Preliminary Report on Patentability dated Aug. 7, 2014, 12 pages.
International Patent Application No. PCT/US2013/022898, filed Jan. 24, 2013; International Search Report and Written Opinion dated Apr. 10, 2013; 16 pages.
International Patent Application No. PCT/US2013/022898, filed Jan. 24, 2013; International Preliminary Report on Patentability dated Aug. 7, 2014, 8 pages.
European Patent Application No. 13 74 1216.9, filed Aug. 22, 2014; Supplementary European Search Report dated Jul. 20, 2015; 4 pages.
"Influenza fact sheet" *Wkly Epidemiol Rec.*, Mar. 14, 2003; 78(11):77-80.
Abraham et al., "Sequential transcription of the genes of vesicular stomatitis virus" *Proc Natl Acad Sci USA*, 1976; 73:1504-8.
Abrams, "Competition and compensation: coupled to death in development and cancer" *Cell*, 2002; 110:403-6.
Adams et al., "The Bcl-2 protein family: arbiters of cell survival" *Science*, 1998; 281(5381):1322-6.
Adusumilli et al., "Real-time diagnostic imaging of tumors and metastases by use of a replication-competent herpes vector to facilitate minimally invasive oncological surgery" *The FASEB Journal*, 2006; 20(6): 726-8.
Andrejeva et al., "Degradation of STAT1 and STAT2 by the V proteins of simian virus 5 and human parainfluenza virus type 2, respectively: consequences for virus replication in the presence of alpha/beta and gamma interferons" *J Virol.* 2002; 76:2159-67.
Andrejeva et al., "The V proteins of paramyxoviruses bind the IFN-inducible RNA helicase, mda-5, and inhibit its activation of the IFN-{beta} promoter" *Proc Natl Acad Sci USA*, 2004; 101:17264-9.
Arimilli et al., "A simian virus 5 (SV5) PN mutant is less cytopathic than wild-type SV5 in human dendritic cells and is a more effective activator of dendritic cell maturation and function" *J Virol.* 2006; 80:3416-27.
Ashkenazi et al., "Death receptors: signaling and modulation" *Science*, 1998; 281(5381):1305-8.
Atoynatan et al., "Epidemiologic studies of latent virus infections in captive monkeys and baboons. II. Serologic evidence of myxovirus infections with special reference to SV5" *Am J Epidemiol*, 1969; 89(4):472-9.
Azetaka et al., "Kennel cough complex: confirmation and analysis of the outbreak in Japan" *Nippon Juigaku Zasshi*, 1988; 50(4):851-8.
Baez et al., "Gene composition of high-yielding influenza vaccine strains obtained by recombination" *J Infect Dis*, 1980; 141(3):362-5.
Ball et al., "Order of transcription of genes of vesicular stomatitis virus" *Proc Natl Acad Sci USA*, 1976; 73:442-6.
Baumgertner et al., "Persistent infection of Vero cells by paramyxoviruses. A morphological and immunoelectron microscopic investigation" *Intervirology*, 1987; 27(4):218-23.
Bernstein et al., "Clinical reactions and serologic responses after vaccination with whole-virus or split-virus influenza vaccines in children aged 6 to 36 months" *Pediatrics*, 1982; 69(4):404-8.
Bertram et al., "Establishment of a cloned line of Lewis Lung Carcinoma cells adapted to cell culture" *Cancer Lett*, 1980; 11(1):63-73.
Bever, "Woman's Cancer Killed by Measles Virus in Unprecedented Trial" The Washington Post, May 15, 2014; Obtained via washingtonpost.com on May 20, 2014.
Binn et al., "Viruses recovered from laboratory dogs with respiratory disease" *Proc Soc Exp Biol Med*, 1967; 126(1):140-5.

Bocangel et al., "Combinatorial synergy induced by adenoviral-mediated mda-7 and Herceptin in Her-2+ breast cancer cells" *Cancer Gene Ther*, 2006; 13:958-68.
Braciale et al., "On the role of the transmembrane anchor sequence of influenza hemagglutinin in target cell recognition by class I MHC-restricted, hemagglutinin-specific cytolytic T lymphocytes" *J Exp Med*, 1987; 166:678-92.
Brazil et al., "Ten years of protein kinase B signalling: a hard Akt to follow" *Trends Biochem Sci*, 2001; 26(11):657-64.
Browning, "Mayo Clinic Trial: Massive blast of measles vaccine wipes out cancer" The Star Tribune, May 14, 2014; Obtained via startribune.com on May 20, 2014.
Bukreyev et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse" J. Virol. 1997; 71(12):8973-82.
Bukreyev et al., "A Single Intranasal Inoculation with a Paramyxovirus-Vectored Vaccine Protects Guinea Pigs against a Lethal-Dose Ebola Virus Challenge" J. Virol. 2006; 80(5):2267-79.
Bukreyev et al., "Mucosal parainfluenza virus-vectored vaccine against Ebola virus replicates in the respiratory tract of vector-immune monkeys and is immunogenic" Virology, 2010; 399: 290-8.
Capraro et al., "Virus growth and antibody responses following respiratory tract infection of ferrets and mice with WT and P/V mutants of the paramyxovirus Simian Virus 5" *Virology*, Jul. 5, 2008; 376(2):416-28.
Centers for Disease Control and Prevention (CDC), "Possible congenital infection with La Crosse encephalitis virus—West Virginia, 2006-2007" *MMWR Morb Mortal Wkly Rep*, 2009; 58(1):4-7.
Chada et al., "MDA-7/IL-24 is a unique cytokine—tumor suppressor in the IL-10 family" *Int Immunopharmacol*, 2004; 4:649-67.
Chan et al., "AKT/PKB and other D3 phosphoinositide-regulated kinases: kinase activation by phosphoinositide-dependent phosphorylation" *Annu Rev Biochem*, 1999; 68:965-1014.
Chang et al., "Experimental infection of parainfluenza virus type 5 in mice, hamsters and monkeys" *J Immunol*, 1965; 95:591-601.
Chatziandreou et al., "Differences in interferon sensitivity and biological properties of two related isolates of simian virus 5: a model for virus persistence" *Virology*, 2002; 293:234-42.
Chatziandreou et al., "Relationships and host range of human, canine, simian and porcine isolates of simian virus 5 (parainfluenza virus 5)" *J Gen Virol*, 2004; 85(Pt 10):3007-16.
Chen et al., "Phosphorylated states of vesicular stomatitis virus P protein in vitro and in vivo" *Virology*, 1997; 228:200-12.
Chen et al., "Protection and antibody responses in different strains of mouse immunized with plasmid DNAs encoding influenza virus haemagglutinin, neuraminidase and nucleoprotein" *J Gen Virol*, 1999; 80(Pt 10):2559-64.
Chen et al., "Identification of two auto-cleavage products of nonstructural protein 1 (nsp1) in porcine reproductive and respiratory syndrome virus infected cells: nsp1 function as interferon antagonist" *Virology*, 2010; 398(1):87-97.
Chen et al., "Evaluating a Parainfluenza Virus 5-Based Vaccine in a Host with Pre-Existing Immunity against Parainfluenza Virus 5" *PLoS One*, 2012; 7(11):e50144, doi: 10.1371/journal.pone.0050144, Epub Nov. 20, 2012.
Chen et al., "A novel rabies vaccine based on a recombinant parainfluenza virus 5 expressing rabies virus glycoprotein," *J Virol*, Dec. 26, 2012; [Epub ahead of print], doi:10.1128/JVI.02886-12.
Chen et al., "Efficacy of parainfluenza virus 5 (PIV5)-based tuberculosis vaccines in mice" *Vaccine*, Dec. 16, 2015; 33(51):7217-24. Available online Nov. 6, 2015.
Chladek et al., "Canine parainfluenza-Bordetella bronchiseptica vaccine Immunogenicity" *Am J Vet Res*, 1981; 42(2):266-70.
Choppin, "Multiplication of a myxovirus (SV5) with minimal cytopathic effects and without interference" *Virology*, 1964; 23:224-33.
Clark et al., "Parainfluenza virus 5-based vaccine vectors expressing vaccinia virus (VACV) antigens provide long-term protection in mice from lethal intranasal VACV challenge" *Virology*, 2011; 419(2):97-106.

(56) References Cited

OTHER PUBLICATIONS

Cohn et al., "T cell responses to the paramyxovirus simian virus 5: studies in multiple sclerosis and normal populations" *Pathobiology*, 1996; 64:131-5.
Corbett et al., "Response of transplantable tumors of mice to anthracenedione derivatives alone and in combination with clinically useful agents" *Cancer Treatment Reports*, 1982; 66:1187-200.
Cornwell et al., "Isolation of parainfluenza virus SV5 from dogs with respiratory disease" *Vet Rec*, 1976; 98(15):301-2.
Cory et al., "The Bcl2 family: regulators of the cellular life-or-death switch" *Nat Rev Cancer*, 2002; 2(9):647-56.
Cox et al., "Rabies virus glycoprotein: II. Biological and serological characterization" *Infect Immun*, 1977; 16:754-9.
Crawford et al., "Baculovirus-derived hemagglutinin vaccines protect against lethal influenza infections byavianH5 andH7 subtypes" *Vaccine*, 1999; 17(18):2265-74.
Crawford et al., "Transmission of equine influenza virus to dogs" *Science*, 2005; 310(5747):482-5.
Daly et al., "Transmission of equine influenza virus to English foxhounds" *Emerg Infect Dis*, 2008; 14:461-4.
Dethlefsen et al., "Analysis of tumor growth curves" *J Natl Cancer Inst*, 1968; 40:389-405.
Didcock et al., "The V protein of simian virus 5 inhibits interferon signalling by targeting STAT1 for proteasome-mediated degradation" *J Virol*, 1999; 73:9928-33.
Dillon et al., "Exchange of P/V genes between two non-cytopathic simian virus 5 variants results in a recombinant virus that kills cells through death pathways that are sensitive to caspase inhibitors" *J Gen Virol*, 2006; 87(Pt 12):3643-8.
Driskell et al., "One-step assay for detecting influenza virus using dynamic light scattering and gold nanoparticles" *Analyst*, 2011; 136(15):3083-90.
Du et al. "Regulation of the Akt kinase by interacting proteins" *Oncogene*, 2005; 24:7401-9.
Duntsch et al., "Recombinant vesicular stomatitis virus vectors as oncolytic agents in the treatment of high-grade gliomas in an organotypic brain tissue slice-glioma coculture model" *J Neurosurg*, 2004; 100:1049-59.
Ellison et al., "Further evidence to support the melanocytic origin of MDA-MB-435" *Mol Pathol*, 2002; 55:294-9.
Emerson et al., "Both NS and L proteins are required for in vitro RNA synthesis by vesicular stomatitis virus" *J Virol*, 1975; 15:1348-56.
Emerson, "Reconstitution studies detect a single polymerase entry site on the vesicular stomatitis virus genome" *Cell*, 1982; 31:635-42.
Emery et al., "A canine parainfluenza viral vaccine: immunogenicity and safety" *Am J Vet Res*, 1976; 37(11):1323-7.
Enserink, "Avian influenza. 'Pandemic vaccine' appears to protect only at high doses" *Science*, 2005; 309(5737):996.
Epstein, et al. "Mechanisms of heterosubtypic immunity to lethal influenza A virus infection in fully immunocompetent, T cell-depleted, beta2-microglobulin-deficient, and J chain-deficient mice" *J Immunol*, 1997; 158(3):1222-30.
Epstein et al., "DNA vaccine expressing conserved influenza virus proteins protective against H5N1 challenge infection in mice" *Emerg Infect Dis*, 2002; 8:796-801.
Epstein, "Control of influenza virus infection by immunity to conserved viral features" *Expert Rev Anti Infect Ther*, 2003; 1(4):627-38.
Epstein et al., "Protection against multiple influenza A subtypes by vaccination with highly conserved nucleoprotein" *Vaccine*, 2005; 23(46-47):5404-10.
Evan et al., "A matter of life and cell death" *Science*, 1998; 281(5381):1317-22.
Evermann et al., "Isolation of a paramyxovirus from the cerebrospinal fluid of a dog with posterior paresis" *J Am Vet Med Assoc*, 1980; 177(11):1132-4.
Evermann et al., "Properties of an encephalitogenic canine parainfluenza virus" *Arch Virol*, 1981; 68:165-72.
Faber et al., "Immunogenicity and safety of recombinant rabies viruses used for oral vaccination of stray dogs and wildlife" *Zoonoses Public Health*, 2009; 56(6-7):262-9.
Fielding, "Measles as a potential oncolytic virus" *Rev Med Virol*, 2005; 15(2):135-42.
Fisher, "Apoptosis in cancer therapy: crossing the threshold" *Cell*, 1994; 78:539-42.
Flynn et al., "Virus-specific CD8+ T cells in primary and secondary influenza pneumonia" *Immunity*, 1998; 8(6):683-91.
Fouchier et al., "Characterization of a novel influenza A virus hemagglutinin subtype (H16) obtained from black-headed gulls" *J Virol*, 2005; 79:2814-22.
Fuentes et al., "Function of the respiratory syncytial virus small hydrophobic protein" *J Virol*, 2007; 81:8361-6.
Gabbard et al., "A humanized anti-M2 scFv shows protective in vitro activity against influenza" *Prot Eng Des Sel*, 2009; 22:189-98.
Gainey et al., "A Hyperfusogenic F Protein Enhances the Oncolytic Potency of a Paramyxovirus Simian Virus 5 P/V Mutant without Compromising Sensitivity to Type I Interferon" *J Virol*, 2008; 82(19):9369-80.
Ge et al., "Newcastle disease virus-vectored rabies vaccine is safe, highly immunogenic, and provides long-lasting protection in dogs and cats" *J Virol*, 2011; 85:8241-52.
Gerhard et al., "Identification of eight determinants in the hemagglutinin molecule of influenza virus A/PR/8/34 (H1N1) which are recognized by class II-restricted T cells from BALB/c mice" *J Virol*, 1991; 65:364-72.
Goff et al., "Construction of hybrid viruses containing SV40 and lambda phage DNA segments and their propagation in cultured monkey cells" *Cell*, 1976; 9(4 PT 2):695-705.
Gopalkrishnan et al., "Cytokine and tumor cell apoptosis inducing activity of mda-7/IL-24" *Int Immunopharmacol*, 2004; 4(5):635-47.
Goswami et al., "Does simian virus 5 infect humans?" *J Gen Virol*, 1984; 65(Pt 8):1295-303.
Goswami et al., "Antibodies against the paramyxovirus SV5 in the cerebrospinal fluids of some multiple sclerosis patients" *Nature*, 1987; 327(6119): 244-7.
Govorkova et al., "Lethality to ferrets of H5N1 influenza viruses isolated from humans and poultry in 2004" *J Virol*, 2005; 79(4):2191-8.
Graham et al. "Resistance to and recovery from lethal influenza virus infection in B lymphocyte-deficient mice" *J Exp Med*, 1997; 186(12):2063-8.
Gross et al., "BCL-2 family members and the mitochondria in apoptosis" *Genes Dev*, 1999; 13:1899-911.
Hallak et al., "Iduronic acid-containing glycosaminoglycans on target cells are required for efficient respiratory syncytial virus infection" *Virology*, 2000; 271(2):264-75.
Hanahan et al., "The hallmarks of cancer" *Cell*, 2000; 100(1):57-70.
Harms et al., "A small molecule antagonist of the alpha(v)beta3 integrin suppresses MDA-MB-435 skeletal metastasis" *Clin Exp Metastasis*, 2004; 21(2):119-28.
Harper et al., "Prevention and control of influenza. Recommendations of the Advisory Committee on Immunization Practices (ACIP)" *MMWR Recomm Rep*, 2005; 54(RR-8):1-40.
He et al., "Phage RNA polymerase vectors that allow efficient gene expression in both prokaryotic and eukaryotic cells" *Gene*, 1995; 164:75-9.
He et al., "Rapid mutagenesis and purification of phage RNA polymerases" *Protein Expr Purif*, 1997; 9(1):142-51.
He et al., "Recovery of infectious SV5 from cloned DNA and expression of a foreign gene" *Virology*, 1997; 237:249-60.
He et al., "The paramyxovirus SV5 small hydrophobic (SH) protein is not essential for virus growth in tissue culture cells" *Virology*, 1998; 250:30-40.
He et al., "Effect of inserting paramyxovirus simian virus 5 gene junctions at the HN/L gene junction: analysis of accumulation of mRNAs transcribed from rescued viable viruses" *J Virol*, 1999; 73:6228-34.
He et al., "The SH integral membrane protein of the paramyxovirus simian virus 5 is required to block apoptosis in mdbk cells" *J Virol*, 2001; 75:4068-79.

(56) References Cited

OTHER PUBLICATIONS

He et al., "Recovery of paramyxovirus simian virus 5 with a V protein lacking the conserved cysteine-rich domain: the multifunctional V protein blocks both interferon-beta induction and interferon signaling" *Virology*, 2002; 303:15-32.

Heise et al., "Intravenous administration of ONYX-015, a selectively replicating adenovirus, induces antitumoral efficacy" *Cancer Res*, 1999; 59: 2623-8.

Hiebert et al., "Cell surface expression and orientation in membranes of the 44 amino acid SH protein of simian virus 5" *J Virol*, 1988; 62:2347-57.

Hoffmann et al., "Role of specific hemagglutinin amino acids in the immunogenicity and protection of H5N1 influenza virus vaccines" *Proc Natl Acad Sci USA*, 2005; 102:12915-20.

Horimoto et al., "Reverse genetics provides direct evidence for a correlation of hemagglutinin cleavability and virulence of an avian influenza A virus" *J Virol*, 1994; 68(5):3120-8.

Hotte et al., "An Optimized Clinical Regimen for the Oncolytic Virus PV701" *Clin Cancer Res*, 2007; 13(3):977-85.

Hsiung et al., "Studies of Parainfluenza Viruses. 3. Antibody Responses of Different Animal Species After Immunization" *J Immunol*, 1965; 94:67-73.

Hsiung "Parainfluenza-5 virus. Infection of man and animal" *Prog Med Virol*, 1972; 14:241-74.

Hu et al., "Oncolytic Adenovirus Expressing Soluble TGFbeta Receptor Ii-Femediated Inhibition of Established Bone Metastases: A Safe and Effective Systemic Therapeutic Approach for Breast Cancer" *Mol Ther*, 2011; 19(9):1609-18.

Huang et al., "High-level expression of a foreign gene from the most 3'-proximallocus of a recombinant Newcastle disease virus" *J Gen Virol*, 2001; 82:1729-36.

Huang et al., "Parainfluenza virus 5 expressing the G protein of rabies virus protect mice after rabies virus infection" *J Virol*, 2015; 89(6):3427-9.

Hull et al., "New viral agents recovered from tissue cultures of monkey kidney cells. 1. Origin and properties of cytopathic agents $S.V._1$, $S.V._2$, $S.V._4$, $S.V._5$, $S.V._6$, $S.V._{11}$, $S.V._{12}$, and $S.V._{15}$" *Am J Hyg*, 1956; 63(2):204-15.

Ishikawa et al., "Expression of MDA-7/IL-24 and Its Clinical Significant in Resected Non-Small Cell Lung Cancer" *Clin Cancer Res*, 2005; 11:1198-1202.

Iverson et al., "Sequential synthesis of 5'-proximal vesicular stomatitis virus mRNA sequences" *J Virol*, 1982; 44: 356-5.

Jack et al., "The complete genome sequence of J virus reveals a unique genome structure in the family Paramyxoviridae" *J Virol*, 2005; 79:10690-700.

Jacques et al., "Pseudo-templated transcription in prokaryotic and eukaryotic organisms" *Genes Dev*, 1991; 5:707-13.

Jin et al, "Palmitylation of the influenza virus hemagglutinin (H3) is not essential for virus assembly or infectivity" *J Virol*, 1996; 70:1406-14.

Johnstone et al., "Apoptosis: a link between cancer genetics and chemotherapy" *Cell*, 2002; 108:153-64.

Ju et al., "Aktl governs breast cancer progression in vivo" *Proc Natl Acad Sci USA*, 2007; 104:7438-43.

Katz et al., "Molecular correlates of influenza A H5N1 virus pathogenesis in mice" *J Virol*, 2000; 74:10807-10.

Kau et al., "A chemical genetic screen identifies inhibitors of regulated nuclear export of a Forkhead transcription factor in PTEN-deficient tumor cells" *Cancer Cell*, 2003; 4:463-76.

Kieny et al., "Expression of rabies virus glycoprotein from a recombinant vaccinia virus" *Nature*, 1984; 312(5990):163-6.

Kim et al., "Studies on the antiviral mechanisms of protein kinase inhibitors K-252a and KT5926 against the replication of vesicular stomatitis virus" *Biol Pharm Bull*, 1998; 21(5):498-505.

Kirn et al., "ONYX-015: clinical data are encouraging" *Nat Med*, 1998; 4(12):1341-1342.

Knobel et al., "Re-evaluating the burden of rabies in Africa and Asia" *Bull World Health Organ*, 2005; 83:360-8.

Komada et al., "Immunological relationships between parainfluenza virus type 4 and other paramyxoviruses studied by use of monoclonal antibodies" *Arch Virol*, 1991; 116(1-4):277-83.

Kong et al., "Protective immunity to lethal challenge of the 1918 pandemic influenza virus by vaccination" *Proc Natl Acad Sci USA*, 2006; 103(43)15987-91.

Kontor et al., "Canine infectious tracheobronchitis: effects of an intranasal live canine parainfluenza-Bordetella bronchiseptica vaccine on viral shedding and clinical tracheobronchitis (kennel cough)" *Am J Vet Res*, 1981; 42(10):1694-8.

Kretzschmar et al., "High-Efficiency Incorporation of Functional Influenza Virus Glycoproteins into Recombinant Vesicular Stomatitis Viruses" *J Virol*, 1997; 71(8):5982-9.

Krishnamurthy et al., "Differentially regulated interferon response determines the outcome of Newcastle disease virus infection in normal and tumor cell lines" *J Virol*, 2006; 80:5145-55.

Krunkosky et al., "Effects of TNF-alpha on expression of ICAM-1 in human airway epithelial cells in vitro. Signaling pathways controlling surface and gene expression" *Am J Respir Cell Mol Biol*, 2000; 22(6):685-92.

Lamb et al., "The synthesis of Sendai virus polypeptides in infected cells. III. Phosphorylation of polypeptides" *Virology*, 1977; 81(2):382-97.

Lawson et al., "Primary pulmonary cytotoxic T lymphocytes induced by immunization with a vaccinia virus recombinant expressing influenza A virus nucleoprotein peptide do not protect mice against challenge" *J Virol*, 1994; 68(6):3505-11.

Lenard, "Host cell protein kinases in nonsegmented negative-strand virus (mononegavirales) infection" *Pharmacal Ther*, 1999; 83:39-48.

Li et al., "Recombinant influenza A virus vaccines for the pathogenic human A/Hong Kong/97 (H5N1) viruses" *J Infect Dis*, 1999; 179:1132-8.

Li et al., "Beilong virus, a novel paramyxovirus with the largest genome of non-segmented negative-stranded RNA viruses" *Virology*, 2006; 346(1):219-28.

Li et al., "A single immunization with a recombinant canine adenovirus expressing the rabies virus G protein confers protective immunity against rabies in mice" *Virology*, 2006; 356:147-54.

Li et al., "Avian-origin H3N2 canine influenza A viruses in Southern China" *Infect Genet Evol*, 2010; 10:1286-8.

Li et al., "Recombinant Parainfluenza Virus 5 Expressing Hemagglutinin of Influenza A Virus H5N1 Protected Mice against Lethal Highly Pathogenic Avian Influenza Virus H5N1 Challenge," *J Virol*, Jan. 2013; 87(1):354-62. doi: 10.1128/JVI.02321-12. Epub Oct. 17, 2012.

Li et al., "Single-Dose Vaccination of a Recombinant Parainfluenza Virus 5 Expressing NP from H5N1 Virus Provides Broad Immunity against Influenza A Viruses" *J Virol*, May 2013 87(10):5985-93.

Lin et al., "The RNA binding region of the paramyxovirus SV5 V and P proteins" *Virology*, 1997; 238:460-9.

Lin et al., "The V protein of the paramyxovirus SV5 interacts with damage-specific DNA binding protein" *Virology*, 1998; 249:189-200.

Lin et al., "The paramyxovirus simian virus 5 V protein slows progression of the cell cycle" *J Virol*, 2000; 74:9152-66.

Lin et al., "Induction of apoptosis by paramyxovirus simian virus 5 lacking a small hydrophobic gene" *J Virol*, 2003; 77:3371-83.

Lin et al., "The role of simian virus 5 V protein on viral RNA synthesis" *Virology*, 2005; 338:270-80.

Lin et al. "Inhibition of interleukin-6 expression by the V protein of parainfluenza virus 5" *Virology*, 2007; 368:262-72.

Lipatov et al., "Influenza: emergence and control" *J Virol*, 2004; 78:8951-9.

Lipatov et al., "Efficacy of H5 influenza vaccines produced by reverse genetics in a lethal mouse model" *J Infect Dis*, 2005; 191:1216-20.

Lipatov et al., "Cross-protectiveness and immunogenicity of influenza A/Duck/Singapore/3/97(H5) vaccines against infection with A/Vietnam/1203/04(H5N1) virus in ferrets" *J Infect Dis*, 2006; 194:1040-3.

Liston et al., "Measles virus V protein binds zinc" *Virology*, 1994; 198:399-404.

(56) References Cited

OTHER PUBLICATIONS

Liu et al., "Preparation of a standardized, efficacious agricultural H5N3 vaccine by reverse genetics" *Virology*, 2003; 314:580-90.
Lorence et al., "Newcastle disease virus as an antineoplastic agent: induction of tumor necrosis factor-alpha and augmentation of its cytotoxicity" *J Natl Cancer Inst*, 1988; 80(16):1305-12.
Lorence et al., "Overview of phase I studies of intravenous administration of PV701, an oncolytic virus" *Curr Opin Mol Ther*, 2003; 5(6):618-24.
Lu et al., "A mouse model for the evaluation of pathogenesis and immunity to influenza A (H5N1) viruses isolated from humans" *J Virol*, 1999; 73:5903-11.
Lu et al., "The Major Phosphorylation Sites of the Respiratory Syncytial Virus Phosphoprotein Are Dispensable for Virus Replication In Vitro" *J Virol*, 2002; 76:10776-84.
Maeda et al., "Live Bivalent Vaccine for Parainfluenza and Influenza Virus Infections" *J Virol*, 2005; 79(11):6674-9.
Martinez, "Global infectious disease surveillance" *Int J Infect Dis*, 2000; 4(4):222-8.
Mastro et al., "The skeleton as a unique environment for breast cancer cells" *Clin Exp Metastasis*, 2003; 20(3):275-84.
Mastro et al., "Breast cancer cells induce osteoblast apoptosis: a possible contributor to bone degradation" *J Cell Biochem*, 2004; 91(2):265-76.
Mayo, "Names of viruses and virus species—an editorial note" *Arch Virol*, 2002; 147(7):1463-4.
McCandlish et al., "A study of dogs with kennel cough" *Vet Rec*, 1978; 102(14):293-301.
Meslin et al., "Rationale and prospects for rabies elimination in developing countries" *Curr Top Microbiol Immunol*, 1994; 187:1-26.
Mooney, "PIV5 as a Novel Vaccine Vector for Pandemic Influenza" PhD Thesis, 2012; Retrieved online Oct. 1, 2015 from getd.libs.ega.edu/pdfs/mooney_alaina_j_201205_phd.pdf.
Mooney et al., "Recombinant Parainfluenza Virus 5 Vaccine Encoding the Influenza Virus Hemagglutinin Protects against H5N1 Highly Pathogenic Avian Influenza Virus Infection following Intranasal or Intramuscular Vaccination of BALB/c Mice" *J Virol*, 2013; 87(1):363-71.
Morales et al., "Absence of cancer-associated changes in human fibroblasts immortalized with telomerase" *Nat Genet*, 1999; 21(1):115-8.
Murphy et al., "Genome nucleotide lengths that are divisible by six are not essential but enhance replication of defective interfering RNAs of the paramyxovirus simian virus 5" *Virology*, 1997; 232:145-57.
Murray et al., "Rabies in vaccinated dogs and cats in the United States, 1997-2001" *J Am Vet Med Assoc*, 2009; 235(6):691-5.
Myers et al., "Oncolytic activities of approved mumps and measles vaccines for therapy of ovarian cancer" *Cancer Gene Ther*, 2005; 12(7):593-9.
Nakaya et al., "Recombinant Newcastle disease virus as a vaccine vector" *J Virol*, 2001; 75:11868-73.
Nayak et al., "Contributions of the avian influenza virus HA, NA, and M2 surface proteins to the induction of neutralizing antibodies and protective immunity" *J Virol*, 2010; 84(5):2408-20.
Neirynck et al., "A universal influenza A vaccine based on the extracellular domain of the M2 protein" *Nat Med*, 1999; 5(10):1157-63.
Nishikawa et al., "Adenoviral-mediated mda-7 expression suppresses DNA repair capacity and radiosensitizes non-small-cell lung cancer cells" *Oncogene*, 2004; 23(42):7125-31.
Nishikawa et al., "Adenovirus-mediated mda-7 (IL24) gene therapy suppresses angiogenesis and sensitizes NSCLC xenograft tumors to radiation" *Mol Ther*, 2004; 9:818-28.
Obuchi et al., "Development of recombinant vesicular stomatitis viruses that exploit defects in host defense to augment specific oncolytic activity " *J Virol*, 2003; 77:8843-56.
Okuda et al., "Protective immunity against influenza A virus induced by immunization with DNA plasmid containing influenza M gene" *Vaccine*, 2001; 19(27):3681-91.
Palese, "Genetic engineering of infectious negative-strand RNA viruses" *Trends Microbiol*, 1995; 3(4):123-5.
Parisien et al., "Selective STAT protein degradation induced by paramyxoviruses requires both STAT1 and STAT2 but is independent of alpha/beta interferon signal transduction" *J Virol*, 2002; 76:4190-8.
Parks et al., "Increased readthrough transcription across the simian virus 5 M-F gene junction leads to growth defects and a global inhibition of viral mRNA synthesis" *J Virol*, 2001; 75:2213-23.
Parks et al., "Controlled cell killing by a recombinant nonsegmented negative-strand RNA virus" *Virology*, 2002; 293(1):192-203.
Parks et al., "High avidity cytotoxic T lymphocytes to a foreign antigen are efficiently activated following immunization with a recombinant paramyxovirus, simian virus 5" *J Gen Virol*, 2002; 83(Pt 5):1167-72.
Paterson et al., "The paramyxovirus SV5 V protein binds two atoms of zinc and is a structural component of virions" *Virology*, 1995; 208:121-31.
Paterson et al., "Fusion protein of the paramyxovirus SV5: destabilizing and stabilizing mutants of fusion activation" *Virology*, 2000; 270:17-30.
Pecora et al., "Phase I trial of intravenous administration of PV701, an oncolytic virus, in patients with advanced solid cancers" *J Clin Oncol*, 2002; 20(9):2251-66.
Pekosz et al., "Reverse genetics of negative-strand RNA viruses: closing the circle" *Proc Natl Acad Sci USA*, 1999; 96:8804-6.
Phadke et al., "Kinetics of metastatic breast cancer cell trafficking in bone" *Clin Cancer Res*, 2006; 12:1431-40.
Phan et al., "A respiratory syncytial virus (RSV) vaccine based on parainfluenza virus 5 (PIV5)" *Vaccine*, May 23, 2014; 32(25):3050-7. Available online Apr. 8, 2014.
Phan et al., "Parainfluenza Virus 5 Expressing Wild-Type or Prefusion Respiratory Syncytial Virus (RSV) Fusion Protein Protects Mice and Cotton Rats from RSV Challenge" J Virol, Sep. 12, 2017; 91(19). pii: e00560-17. Print Oct. 1, 2017. 17 pages.
Poole et al., "The V proteins of simian virus 5 and other paramyxoviruses inhibit induction of interferon-beta" *Virology*, 2002; 303:33-46.
Precious et al., "Inducible expression of the P, V, and NP genes of the paramyxovirus simian virus 5 in cell lines and an examination of NP-P and NP-V interactions" *J Virol*, 1995; 69:8001-10.
Precious et al., "Simian virus 5 V protein acts as an adaptor, linking DDB1 to STAT2, to facilitate the ubiquitination of STAT1" *J Virol*, 2005; 79:13434-441.
Price et al., "Single-dose mucosal immunization with a candidate universal influenza vaccine provides rapid protection from virulent H5N1, H3N2 and H1N1 viruses" *PLoS One*, 2010; 5:e13162.
Racaniello et al., "Cloned poliovirus complementary DNA is infectious in mammalian cells" *Science*, 1981; 214(4523):916-9.
Ramesh et al., "Ectopic production of MDA-7/IL-24 inhibits invasion and migration of human lung cancer cells" *Mol Ther*, 2004; 9:510-18.
Randall et al., "Comparison between parainfluenza virus type 2 and simian virus 5: monoclonal antibodies reveal major antigenic differences" *J Gen Virol*, 1988; 69(Pt 8):2051-60.
Randall et al., "NP:P and NP:V interactions of the paramyxovirus simian virus 5 examined using a novel protein:protein capture assay" *Virology*, 1996; 224:121-9.
Redaelli et al. "Synthesis and biological activity of Akt/PI3K inhibitors" *Mini Rev Med Chem*, 2006; 6(10):1127-36.
Roberts et al., "Vaccination with a recombinant vesicular stomatitis virus expressing an influenza virus hemagglutinin provides complete protection from influenza virus challenge" *J Virol*, 1998; 72:4704-11.
Roberts et al., "Recovery of negative-strand RNA viruses from plasmid DNAs: a positive approach revitalizes a negative field" *Virology*, 1998; 247:1-6.
Roberts et al., "Attenuated Vesicular Stomatitis Viruses as Vaccine Vectors" *J Virol*, 1999; 73(5):3723-32.

(56) References Cited

OTHER PUBLICATIONS

Robinson et al., "Protection against a lethal influenza virus challenge by immunization with a haemagglutinin-expressing plasmid DNA" *Vaccine*, 1993; 11(9):957-60.
Robinson et al., "DNA immunization for influenza virus: studies using hemagglutinin—and nucleoprotein-expressing DNAs" *J Infect Dis*, 1997; 176 Suppl 1:S50-5.
Rosenberg et al., "Studies of canine respiratory viruses. I. Experimental infection of dogs with an SV5-like canine parainfluenza agent" *Am J Epidemiol*, 1971; 94(2):147-65.
Ross et al., "C3d enhancement of antibodies to hemagglutinin accelerates protection against influenza virus challenge" *Nat Immunol*, 2000; 1:127-31.
Ross et al., "Systematic variation in gene expression patterns in human cancer cell lines" *Nat Genet*, 2000; 24(3):227-35.
Rott et al., "Influenza viruses, cell enzymes, and pathogenicity" *Am J Respir Crit Care Med*, 1995; 152(4 Pt 2):S16-9.
Rubin et al., "Changes in mumps virus gene sequence associated with variability in neurovirulent phenotype" *J Virol*, 2003; 77:11616-24.
Rupprecht et al., "Ineffectiveness and comparative pathogenicity of attenuated rabies virus vaccines for the striped skunk (*Mephitis mephitis*)." *J Wildl Dis*, 1990; 26(1):99-102.
Rupprecht et al., "Human infection due to recombinant vaccinia-rabies glycoprotein virus" *N Engl J Med*, 2001; 345(8):582-6.
Rupprecht et al., "Current and future trends in the prevention, treatment and control of rabies" *Expert Rev Anti Infect Ther*, 2006; 4(6):1021-38.
Sarbassov et al., "Phosphorylation and regulation of Akt/PKB by the rictor-mTOR complex" *Science*, 2005; 307(5712):1098-101.
Sarmento et al., "Rabies virus-induced apoptosis involves caspase-dependent and caspase-independent pathways" *Virus Res*, 2006; 121(2):144-51.
Sauane et al., "Melanoma differentiation associated gene-7/interleukin-24 promotes tumor cell-specific apoptosis through both secretory and nonsecretory pathways" *Cancer Res*, 64:2988-93, (2004).
Schmitt et al., "Involvement of the cytoplasmic domain of the hemagglutinin-neuraminidase protein in assembly of the paramyxovirus simian virus 5" *J Virol*, 1999; 73:8703-12.
Schmitt et al., "Requirements for budding of paramyxovirus simian virus 5 virus-like particles" *J Virol*, 2002; 76:3952-64.
Sekaly, "The failed HIV Merck vaccine study: a step back or a launching point for future vaccine development?" *J Exp Med*, 2008; 205(1):7-12.
Sellappan et al., "Lineage infidelity of MDA-MB-435 cells: expression of melanocyte proteins in a breast cancer cell line" *Cancer Res*, 2004; 64:3479-85.
Sharma et al., "T cell-derived IL-10 promotes lung cancer growth by suppressing both T cell and APC function" *J Immunol*, 1999; 163:5020-8.
Sharma et al., "Targeting mitogen-activated protein kinase/extracellular signal-regulated kinase kinase in the mutant (V600E) B-Raf signaling cascade effectively inhibits melanoma lung metastases" *Cancer Res*, 2006; 66:8200-09.
Shizuya et al., "Cloning and Stable Maintenance of 300-kilobase-pair Fragments of Human DNA in *Escherichia coli* Using an F-factor-based Vector" Proc Natl Acad Sci USA, Sep. 1992; 89:8794-7.
Singh et al., "A recombinant measles virus expressing hepatitis B virus surface antigen induces humoral immune responses in genetically modified mice" *J Virol*, 1999; 73:4823-8.
Sinkovics et al., "Newcastle disease virus (NDV): brief history of its oncolytic strains" *J Clin Virol*, 2000; 16(1):1-15.
Soboleski et al., "Cold-adapted influenza and recombinant adenovirus vaccines induce cross-protective immunity against pH1N1 challenge in mice" *PLoS One*, 2011; 6(7):e21937.
Spadafora et al., "Constitutive phosphorylation of the vesicular stomatitis virus P protein modulates polymerase complex formation but is not essential for transcription or replication" *J Virol*, 1996; 70:4538-48.

Stambolic et al., "Functional distinctions of protein kinase B/Akt isoforms defined by their influence on cell migration" *Trends Cell Biol*, 2006; 16(9):461-6.
Stanziale et al. "Oncolytic herpes simplex virus-1 mutant expressing green fluorescent protein can detect and treat peritoneal cancer" *Hum Gene Ther*, 2004; 15(6): 609-18.
Steel, "New strategies for the development of H5N1 subtype influenza vaccines: progress and challenges" *BioDrugs*, 2011; 25:285-98.
Stephenson et al., "Confronting the avian influenza threat: vaccine development for a potential pandemic" *Lancet Infect Dis*, 2004; 4(8):499-509.
Steward et al., "The Newcastle disease virus V protein binds zinc" *Arch Virol*, 1995; 140(7):1321-8.
Stojdl et al., "Exploiting tumor-specific defects in the interferon pathway with a previously unknown oncolytic virus" *Nat Med*, 2000; 6(7):821-5.
Strasser et al., "Apoptosis signaling" *Annu Rev Biochem*, 2000; 69:217-45.
Subbarao et al., "Evaluation of a genetically modified reassortant H5N1 influenza A virus vaccine candidate generated by plasmid-based reverse genetics" *Virology*, 2003; 305:192-200.
Suguitan et al., "The multibasic cleavage site of the hemagglutinin of highly pathogenic A/Vietnam/1203/2004 (H5N1) avian influenza virus acts as a virulence factor in a host-specific manner in mammals " *J Virol*, 2012; 86:2706-14.
Sun et al., "AKT1/PKBalpha kinase is frequently elevated in human cancers and its constitutive activation is required for oncogenic transformation in N1H3T3 cells" *Am J Pathol*, 2001; 159: 431-7.
Sun et al., "Conserved cysteine-rich domain of paramyxovirus simian virus 5 V protein plays an important role in blocking apoptosis" *J Virol*, 2004; 78:5068-78.
Sun et al., "Akt Plays a Critical Role in Replication of Nonsegmented Negative-Stranded RNA Viruses" *J Virol*, 2008; 82:105-114.
Sun et al., "PLK1 down-regulates parainfluenza virus 5 gene expression" *PLoS Pathog*, 2009; 5(7):e1000525.
Sun et al., "Synthesis and biological evaluation of analogues of AKT (protein kinase B) inhibitor-IV" *J Med Chem*, 2011; 54(5):1126-39.
Sun et al., "Identification of a phosphorylation site within the P protein important for mRNA transcription and growth of parainfluenza virus 5" *J Virol*, 2011; 85:8376-85.
Sun et al., "Sumoylation of the P protein at K254 plays an important role in growth of parainfluenza virus 5" *J Virol*, 2011; 85:10261-8.
Takimoto et al., "Recombinant Sendai Virus Expressing the G Glycoprotein of Respiratory Syncytial Virus (RSV) Elicits Immune Protection against RSV" *J Virol*, 2004; 78(11):6043-7.
Taniguchi et al., "Qb DNA-containing hybrid plasmids giving rise to Qb phage formation in the bacterial host" *Nature*, 1978; 274(5668):223-8.
Teshigahara et al., "Oncolytic viral therapy for breast cancer with herpes simplex virus type 1 mutant HF 10" *J Surg Oncol*, 2004; 85:42-7.
Thomas et al., "Two mRNAs that differ by two nontemplated nucleotides encode the amino coterminal proteins P and V of the paramyxovirus SV5" *Cell*, 1988; 54(6):891-902.
Thorne et al., "Future directions for the field of oncolytic virotherapy: a perspective on the use of vaccinia virus" *Expert Opin Biol Ther*, 2004; 4(8):1307-21.
Timani et al., A Single Amino Acid Residue Change in the P Protein of Parainfluenza Virus 5 Elevates Viral Gene Expression *J Virol*, 2008; 82: 9123-33.
Tolson et al., "Immune response in skunks to a vaccinia virus recombinant expressing the rabies virus glycoprotein" *Can J Vet Res*, 1987; 51:363-6.
Tompkins et al., "De novo central nervous system processing of myelin antigen is required for the initiation of experimental autoimmune encephalomyelitis" *J Immunol*, 2002; 168:4173-83.
Tompkins et al., "Matrix protein 2 vaccination and protection against influenza viruses, including subtype H5N1" *Emerg Infect Dis*, 2007; 13:426-35

(56) References Cited

OTHER PUBLICATIONS

Tompkins et al., "Recombinant parainfluenza virus 5 (PIV5) expressing the influenza A virus hemagglutinin provides immunity in mice to influenza A virus challenge" *Virology*, 2007; 362(1):139-50.
Tordo et al., "Canine adenovirus based rabies vaccines" *Dev Biol (Basel)*, 2008; 131:467-76.
Treanor et al., "Safety and immunogenicity of a recombinant hemagglutinin vaccine for H5 influenza in humans" *Vaccine*, 2001; 19(13-14):1732-7.
Treanor et al., "Safety and immunogenicity of an inactivated subvirion influenza A (H5N1) vaccine" *N Engl J Med*, 2006; 354:1343-51.
Trent et al., "Tumorigenicity in human melanoma cell lines controlled by introduction of human chromosome 6" *Science*, 1990; 247(4942):568-71.
Tribe "An investigation of the incidence, epidemiology and control of Simian virus 5" *Br J Exp Pathol*, 1966; 47:472-9.
Tsurudome et al., "Extensive antigenic diversity among human parainfluenza type 2 virus isolates and immunological relationships among paramyxoviruses revealed by monoclonal antibodies" *Virology*, 1989; 171(1):38-48.
Tumpey et al., "Mucosal delivery of inactivated influenza vaccine induces B-cell-dependent heterosubtypic cross-protection against lethal influenza A H5N1 virus infection" *J Virol*, 2001; 75:5141-50.
Ulane et al., "Paramyxoviruses SV5 and HPIV2 assemble STAT protein ubiquitin ligase complexes from cellular components" *Virology*, 2002; 304:160-6.
Van Weeren et al., "Essential role for protein kinase B (PKB) in insulin-induced glycogen synthase kinase 3 inactivation. Characterization of dominant-negative mutant of PKB" *J Biol Chem*, 1998; 273:13150-6.
Vandvik et al., "Paramyxovirus SV5 and multiple sclerosis" *Nature*, 1989; 338(6218):769-71.
Vitiello et al., "Immunodominance analysis of CTL responses to influenza PR8 virus reveals two new dominant and subdominant Kb-restricted epitopes" *J Immunol*, 1996; 157(12):5555-62.
Wang et al., "Interleukin 24 (MDA-7/MOB-5) signals through two heterodimeric receptors, IL-22R1/IL-20R2 and IL-20R1/IL-20R2" *J Biol Chem*, 2002; 277:7341-7.
Wang et al., "A Single-Dose Recombinant Parainfluenza Virus 5-Vectored Vaccine Expressing Respiratory Syncytial Virus (RSV) F or G Protein Protected Cotton Rats and African Green Monkeys from RSV Challenge" J Virol, May 12, 2017; 91(11). pii:e00066-17. Print Jun. 1, 2017. 15 pages.
Wansley et al., "Naturally occurring substitutions in the P/V gene convert the noncytopathic paramyxovirus simian virus 5 into a virus that induces alpha/beta interferon synthesis and cell death" *J Virol*, 2002; 76:10109-21.
Wansley et al., "Apoptosis induction and interferon signaling but not IFN-beta promoter induction by an SV5 P/V mutant are rescued by coinfection with wild-type SV5" *Virology*, 2003; 316:41-54.
Wansley et al., "Growth sensitivity of a recombinant simian virus 5 P/V mutant to type I interferon differs between tumor cell lines and normal primary cells" *Virology*, 2005; 335:131-44.
Watabe et al., "Protection against influenza virus challenge by topical application of influenza DNA vaccine" *Vaccine*, 2001; 19(31):4434-44.
Welch, "Technical considerations for studying cancer metastasis in vivo" *Clin Exp Metastasis*, 1997; 15(3):272-306.
Welch et al., "Molecular biology of breast cancer metastasis. Genetic regulation of human breast carcinoma metastasis" *Breast Cancer Res*, 2000; 2:408-16.
Wen et al., "Rabies virus expressing dendritic cell-activating molecules enhances the innate and adaptive immune response to vaccination" *J Virol*, 2011; 85:1634-44.
Weyer et al., "Generation and evaluation of a recombinant modified vaccinia virus Ankara vaccine for rabies" *Vaccine*, 2007; 25(21):4213-22.

Weyer et al., "Poxvirus-vectored vaccines for rabies—a review" *Vaccine*, 2009; 27(51):7198-201.
Whelan et al., "Transcription and replication of nonsegmented negative-strand RNA viruses" *Curr Top Microbiol Immunol*, 2004; 283:61-119.
WHO, "Cumulative Number of Confirmed Human Cases of Avian Influenza A/(H5N1) Reported to WHO" May 31, 2007; Accessed online on Aug. 6, 2015 at apps.who.int/csr/disease/avian_influenza/country/cases_table_2007_05_31/en/index.html#, 1 page.
Wiktor et al., "Protection from rabies by a vaccinia virus recombinant containing the rabies virus glycoprotein gene" *Proc Natl Acad Sci USA*, 1984; 81:7194-8.
Wildner, "Comparison of replication-selective, oncolytic viruses for the treatment of human cancers" *Curr Opin Mol Ther*, 2003; 5(4):351-61.
Wilson et al., "Function of Small Hydrophobic Proteins of Paramyxovirus" J Virol, Feb. 2006; 80(4):1700-9.
Wollmann et al. "Variable deficiencies in the interferon response enhance susceptibility to vesicular stomatitis virus oncolytic actions in glioblastoma cells but not in normal human glial cells" *J Virol*, 2007; 81:1479-91.
Wu et al., "From brain passage to cell adaptation: the road of human rabies vaccine development" *Expert Rev Vaccines*, 2011; 10(11):1597-608.
Xu et al., "Rescue of wild-type mumps virus from a strain associated with recent outbreaks helps to define the role of the SH ORF in the pathogenesis of mumps virus" *Virology*, 2011; 417:126-36.
Yacoub et al., "MDA-7 regulates cell growth and radiosensitivity in vitro of primary (non-established) human glioma cells" *Cancer Biol Ther*, 2004; 3(8):739-51.
Yang et al., "Human endothelial cell life extension by telomerase expression" *J Biol Chem*, 1999; 274(37):26141-8.
Yin et al., "Structure of the parainfluenza virus 5 F protein in its metastable, prefusion conformation" *Nature*, 2006; 439(7072):38-44.
Yoeli-Lerner et al., "Akt/PKB signaling in cancer: a function in cell motility and invasion" *Cell Cycle*, 2006; 5(6):603-5.
Young et al., "Clearance of a persistent paramyxovirus infection is mediated by cellular immune responses but not by serum-neutralizing antibody" *J Virol*, 1990; 64(11):5403-11.
Young et al., "Paramyxoviridae use distinct virus-specific mechanisms to circumvent the interferon response" *Virology*, 2000; 269:383-90.
Young et al., "Simian Virus 5 Is a Poor Inducer of Chemokine Secretion from Human Lung Epithelial Cells: Identification of Viral Mutants That Activate Interleukin-8 Secretion by Distinct Mechanisms" *J of Virol*, Jun. 2003; 77(12):7124-30.
Young et al., "Variants of the paramyxovirus Simian virus 5 with accelerated or delayed viral gene expression activate proinflammatory cytokine synthesis" *Virology*, 2006; 350: 90-102.
Zakstelskaya et al., "Persistent SV5 virus infection in continuous cell cultures" *Acta Virol*, 1976; 20(6):506-11.
Zhan et al., "Respiratory syncytial virus (RSV) fusion protein expressed by recombinant Sendai virus elicits B-cell and T-cell responses in cotton rats and confers protection against RSV subtypes A and B" *Vaccine*, 2007; 25(52):8782-93.
Zhang et al., "Comparison of differing cytopathic effects in human airway epithelium of parainfluenza virus 5 (W3A), parainfluenza virus type 3, and respiratory syncytial virus" *Virology*, 2011; 421: 67-77.
Zhou et al., "A chimpanzee-origin adenovirus vector expressing the rabies virus glycoprotein as an oral vaccine against inhalation infection with rabies virus" *Mol Ther*, 2006; 14(5):662-72.
Zorn et al., "Induction of cytokines and cytotoxicity against tumor cells by Newcastle disease virus" *Cancer Biother*, 1994; 9(3):225-35.
Zwiebel, "Cancer gene and oncolytic virus therapy" *Semin Oncol*, 2001; 28:336-43.

\* cited by examiner

| Dog Swab | CFA | CLJ | CFB | CGW | CGU | CEM | CIJ | CGT |
|---|---|---|---|---|---|---|---|---|
| 3 dpi (PFU/mL) | 0 | 0 | 0 | 0 | 0 | 0 | 0 | 0 |
| 5 dpi (PFU/mL) | 0 | 0 | 0 | 0 | 0 | 0 | 0 | 0 |

| Dog Swab | 1 | 2 | 3 | 4 | 5 | 6 | 7 | 8 |
|---|---|---|---|---|---|---|---|---|
| 3 dpi (PFU/mL) | 0 | 0 | 0 | 0 | 0 | 0 | 0 | 0 |
| 5 dpi (PFU/mL) | 0 | 0 | 0 | 0 | 0 | 0 | 0 | 0 |

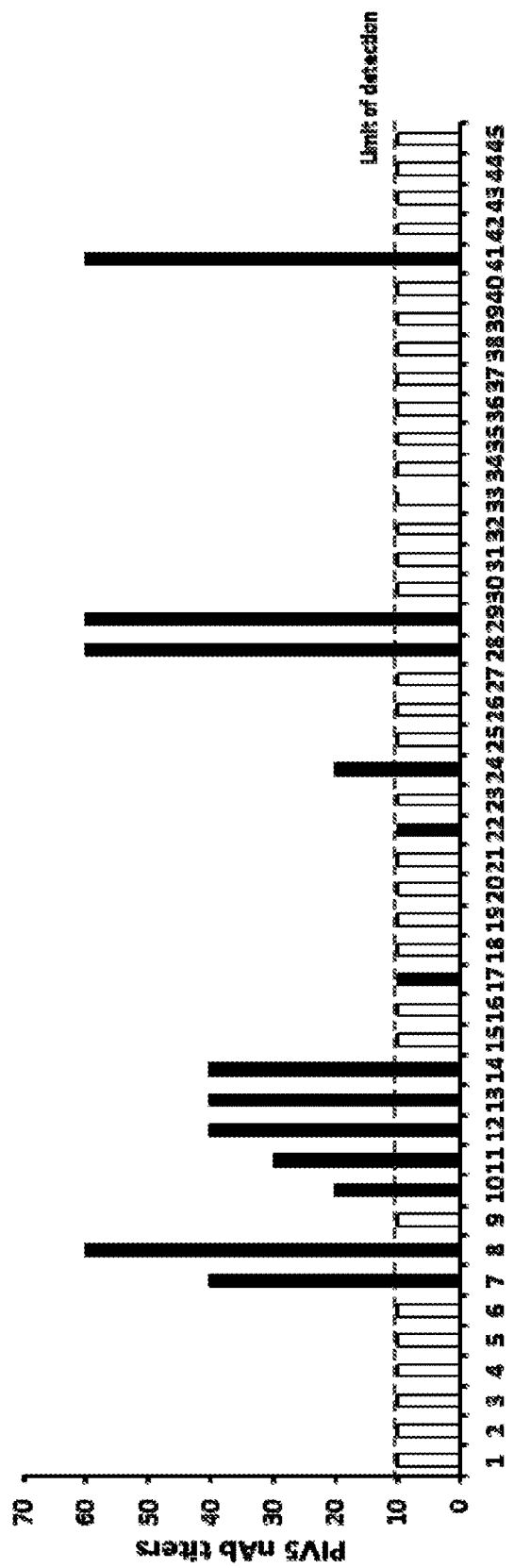

*Figure 18A*

Leader   NP   V/P   M   F   SH   HN        L        trailer

ZL48 (PIV5-H5-HN-L)

Wt HA₀:  NSPQRERRRKKRGLFG
H5:      NSPQ----------GLFG

ZL215 (PIV5-H5-Le-NP)
ZL209 (PIV5-H5-NP-VP)
ZL47 (PIV5-H5-VP-M)
ZL46 (PIV5-H5-SH-HN)

*Figure 18B*

| Virus | Highest Titers (pfu/ml) |
|---|---|
| PIV5 | $2 \times 10^8$ |
| ZL48 | $1 \times 10^8$ |
| ZL46 | $1 \times 10^8$ |
| ZL47 | $1 \times 10^8$ |
| ZL209 | $1 \times 10^5$ |

```
                          SEQUENCE LISTING

<160> NUMBER OF SEQ ID NOS: 10

<210> SEQ ID NO 1
<211> LENGTH: 16
<212> TYPE: PRT
<213> ORGANISM: artificial
<220> FEATURE:
<223> OTHER INFORMATION: synthetic wild-type H5N1 HA(0) peptide

<400> SEQUENCE: 1

Asn Ser Pro Gln Arg Glu Arg Arg Arg Lys Lys Arg Gly Leu Phe Gly
1               5                   10                  15

<210> SEQ ID NO 2
<211> LENGTH: 8
<212> TYPE: PRT
<213> ORGANISM: artificial
<220> FEATURE:
<223> OTHER INFORMATION: synthetic H5N1 H5 peptide

<400> SEQUENCE: 2

Asn Ser Pro Gln Gly Leu Phe Gly
1               5

<210> SEQ ID NO 3
<211> LENGTH: 26
<212> TYPE: DNA
<213> ORGANISM: artificial
<220> FEATURE:
<223> OTHER INFORMATION: synthetic oligonucleotide primer

<400> SEQUENCE: 3
ccagtgaggc tcagctaatt gacctc                                    26

<210> SEQ ID NO 4
<211> LENGTH: 25
<212> TYPE: DNA
<213> ORGANISM: artificial
<220> FEATURE:
<223> OTHER INFORMATION: synthetic oligonucleotide primer

<400> SEQUENCE: 4
ggtattcccc cgatcctgtt cgtag                                     25

<210> SEQ ID NO 5
<211> LENGTH: 51
<212> TYPE: DNA
<213> ORGANISM: artificial
<220> FEATURE:
<223> OTHER INFORMATION: synthetic oligonucleotide primer

<400> SEQUENCE: 5
aacaagcggc ggccgccgcc accatggttc tcaggctct cctgtttgta c          51

<210> SEQ ID NO 6
<211> LENGTH: 40
<212> TYPE: DNA
<213> ORGANISM: artificial
<220> FEATURE:
<223> OTHER INFORMATION: synthetic oligonucleotide primer

<400> SEQUENCE: 6
```

```
aacaagcgcg gccgctcaca gtctggtctc acccccactc                              40

<210> SEQ ID NO 7
<211> LENGTH: 29
<212> TYPE: DNA
<213> ORGANISM: artificial
<220> FEATURE:
<223> OTHER INFORMATION: synthetic oligonucleotide primer

<400> SEQUENCE: 7
cagattgtcc catttatccg tcaggtgac                                         29

<210> SEQ ID NO 8
<211> LENGTH: 29
<212> TYPE: DNA
<213> ORGANISM: artificial
<220> FEATURE:
<223> OTHER INFORMATION: synthetic oligonucleotide primer

<400> SEQUENCE: 8
aggtcgatct catttgggag gtttccaag                                         29

<210> SEQ ID NO 9
<211> LENGTH: 9
<212> TYPE: PRT
<213> ORGANISM: artificial
<220> FEATURE:
<223> OTHER INFORMATION: synthetic Flu-NP 147-155 peptide

<400> SEQUENCE: 9

Thr Tyr Gln Arg Thr Arg Ala Leu Val
1               5

<210> SEQ ID NO 10
<211> LENGTH: 9
<212> TYPE: PRT
<213> ORGANISM: artificial
<220> FEATURE:
<223> OTHER INFORMATION: synthetic Ebola GP P2 peptide

<400> SEQUENCE: 10

Glu Tyr Leu Phe Glu Val Asp Asn Leu
1               5
```

PARAINFLUENZA VIRUS 5 BASED VACCINES

This application is a divisional application of U.S. patent application Ser. No. 15/296,346, filed Oct. 18, 2016, which is a divisional application of U.S. patent application Ser. No. 14/374,061, filed Jul. 23, 2014, which is the § 371 U.S. National Stage of International Application No. PCT/US2013/022962, filed 24 Jan. 2013, which claims the benefit of U.S. Provisional Application Ser. No. 61/590,070, filed Jan. 24, 2012, U.S. Provisional Application Ser. No. 61/590,056, filed Jan. 24, 2012, and 61/683,810, filed Aug. 16, 2012, each of which is incorporated by reference herein in its entirety.

CONTINUING APPLICATION DATA

This application claims the benefit of U.S. Provisional Application Ser. Nos. 61/590,070, filed Jan. 24, 2012, U.S. Provisional Application Ser. No. 61/590,056, filed Jan. 24, 2012, and U.S. Provisional Application Ser. No. 61/683,810, filed Aug. 16, 2012, each of which is incorporated by reference herein in its entirety.

SEQUENCE LISTING

This application contains a Sequence Listing electronically submitted via EFS-Web to the United States Patent and Trademark Office as an ASCII text file entitled "235-01960102 SequenceListing_ST25.txt" having a size of 3 kilobytes and created on Nov. 7, 2016. The information contained in the Sequence Listing is incorporated by reference herein.

GOVERNMENT FUNDING

This invention was made with government support under Grant No. R01AI070847 and R56AI081816, awarded by the National Institutes of Health. The Government has certain rights in the invention.

BACKGROUND

Inactivated influenza vaccines have been available since the 1940's and are 60-80% effective against matched influenza virus strains, but are less effective against antigenic drift variants and are ineffective against different subtypes. Thus, annual vaccination is needed to prevent infections from new strains or subtypes. Current seasonal influenza vaccines consist of two influenza A viruses (H1N1 and H3N2) and one or two influenza B virus. Moreover, vaccination coverage and production continue to be problems worldwide. Current licensed influenza virus vaccines are produced in chicken eggs, requiring the availability of millions of eggs and significant time between identification of vaccine strains and availability of vaccines. Additionally, this vaccination strategy provides no protection against unexpected strains, outbreaks, or pandemics. New vaccination strategies are needed for the prevention and control of influenza virus infection.

SUMMARY OF THE INVENTION

The present invention includes a viral expression vector including a parainfluenza virus 5 (PIV5) genome including a heterologous nucleotide sequence expressing a heterologous polypeptide, wherein the heterologous nucleotide sequence is not inserted between the hemagglutinin-neuroaminidase (HN) gene and the large RNA polymerase protein (L) gene of the PIV5 genome.

In some embodiments, the heterologous nucleotide sequence is inserted closer to the leader than between the hemagglutinin-neuroaminidase (HN) gene and the large RNA polymerase protein (L) gene of the PIV5 genome.

In some embodiments, the heterologous nucleotide sequence is inserted between the small hydrophobic protein (SH) gene and the hemagglutinin-neuroaminidase (HN) gene of the PIV5 genome.

In some embodiments, the heterologous nucleotide sequence is inserted between the F gene and the SH gene of the PIV5 genome.

In some embodiments, the heterologous nucleotide sequence is inserted between the VP gene and the matrix protein (M) gene of the PIV5 genome.

In some embodiments, the heterologous nucleotide sequence is inserted between the M gene and the F gene of the PIV5 genome.

In some embodiments, the heterologous nucleotide sequence is inserted between the nucleocapsid protein (NP) gene and the V/P gene of the PIV5 genome.

In some embodiments, the heterologous nucleotide sequence is inserted between the leader sequence and the nucleocapsid protein (NP) gene of the PIV5 genome.

In some embodiments, a portion of the F or HN gene of PIV5 has been replaced with the heterologous nucleotide sequence.

In some embodiments, the heterologous nucleotide sequence replaces the SH gene nucleotide sequence.

In some embodiments, the heterologous nucleotide sequence is inserted within the SH gene nucleotide sequence, within the NP gene nucleotide sequence, within the V/P gene nucleotide sequence, within the M gene nucleotide sequence, within the F gene nucleotide sequence, within the HN gene nucleotide sequence, and/or within the L gene nucleotide sequence.

In some embodiments, the PIV5 genome further includes one or more mutations. In some embodiments, a mutation includes a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, a mutation inducing apoptosis, or a combination thereof. In some embodiments, a mutation includes PIV5VΔC, PIV5ΔSH, PIV5-P-S308G, or a combination thereof. In some embodiments, the PIV5 genome further includes one or more mutations.

In some embodiments, the heterologous polypeptide is derived from human immunodeficiency virus (HIV), parainfluenza virus 1, parainfluenza virus 2, parainfluenza virus 3, parainfluenza virus 4, human respiratory syncytial virus, bovine respiratory syncytial virus, human metapneumovirus, avian influenza, canine influenza, avian metapneumovirus, Nipah virus, Hendra virus, rabies virus, Ebola virus, porcine circovirus, porcine reproductive and respiratory syndrome virus, swine influenza virus, New Castle disease virus, mumps virus, measles virus, canine distemper virus, feline leukemia virus, human calicivirus, veterinary calicivirus, human norovirus, veterinary norovirus, rinderpest virus, *Mycobacterium tuberculosis*, and/or an emerging influenza virus in humans or animals. In some embodiments, the heterologous polypeptide is derived from a bacteria or a parasite.

The present invention includes a viral expression vector including a parainfluenza virus 5 (PIV5) genome including a heterologous nucleotide sequence expressing a heterologous polypeptide, wherein the heterologous nucleotide sequence is inserted between the hemagglutinin-neuroaminidase (HN) and large RNA polymerase protein (L) gene of the PIV5 genome and wherein the PIV5 genome further includes one or more mutations. In some embodiments, a mutation includes a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, a mutation inducing apoptosis, or a combination thereof. In some embodiments, the mutation includes PIV5VΔC, PIV5ΔSH, PIV5-P-S308G, or a combination thereof.

In some embodiments, the heterologous polypeptide is derived from human immunodeficiency virus (HIV), parainfluenza virus 1, parainfluenza virus 2, parainfluenza virus 3, parainfluenza virus 4, human respiratory syncytial virus, bovine respiratory syncytial virus, human metapneumovirus, avian influenza, canine influenza, avian metapneumovirus, Nipah virus, Hendra virus, rabies virus, Ebola virus, porcine circovirus, porcine reproductive and respiratory syndrome virus, swine influenza virus, New Castle disease virus, mumps virus, measles virus, canine distemper virus, feline leukemia virus, human calicivirus, veterinary calicivirus, human norovirus, veterinary norovirus, rinderpest virus, *Mycobacterium tuberculosis*, and/or an emerging influenza virus in humans or animals. In some embodiments, the heterologous polypeptide is derived from a bacteria or a parasite.

The present invention includes a viral expression vector including a parainfluenza virus 5 (PIV5) genome including a heterologous nucleotide sequence expressing a heterologous polypeptide, wherein the heterologous polypeptide includes an influenza nucleocapsid protein (NP). In some embodiments, the heterologous nucleotide sequence is inserted between the hemagglutinin-neuroaminidase (HN) gene and the large RNA polymerase protein (L) gene of the PIV5 genome. In some embodiments, the heterologous nucleotide sequence is inserted closer to the leader than between the hemagglutinin-neuroaminidase (HN) gene and the large RNA polymerase protein (L) gene of the PIV5 genome; is inserted upstream of the nucleocapsid protein (NP) gene of the PIV5 genome; is inserted immediately downstream of the leader sequence of the PIV5 genome; is inserted between the small hydrophobic protein (SH) gene and the hemagglutinin-neuroaminidase (HN) gene of the PIV5 genome; is inserted between the F gene and the SH gene of the PIV5 genome; is inserted between the VP gene and the matrix protein (M) gene of the PIV5 genome; is inserted between the M gene and the F gene of the PIV5 genome; is inserted between the nucleocapsid protein (NP) gene and the V/P gene of the PIV5 genome; is inserted between the leader sequence and the nucleocapsid protein (NP) gene of the PIV5 genome; wherein a portion of the F or HN gene of PIV5 genome has been replaced with the heterologous nucleotide sequence; replaces the SH gene nucleotide sequence; is inserted within the SH gene nucleotide sequence, within the NP gene nucleotide sequence, within the V/P gene nucleotide sequence, within the M gene nucleotide sequence, within the F gene nucleotide sequence, within the HN gene nucleotide sequence, and/or within the L gene nucleotide sequence. In some embodiments, the PIV5 genome further includes one or more mutations. In some embodiments, a mutation includes a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, a mutation inducing apoptosis, or a combination thereof. In some embodiments, a mutation includes PIV5VΔC, PIV5ΔSH, PIV5-P-S308G, or a combination thereof.

In some embodiments of a viral expression vector described herein, the heterologous polypeptide includes an influenza hemagglutinin (HA), an influenza neuraminidase (NA), an influenza nucleocapsid protein (NP), M1, M2, PA, PB1, PB2, PB1-F2, NS1 or NS2. In some embodiments, wherein the influenza includes influenza A, influenza B, or influenza C virus.

In some embodiments, wherein the heterologous polypeptide includes a hemagglutinin (HA) from influenza A virus strain subtype H1 to H18. In some embodiments, the heterologous polypeptide includes a hemagglutinin (HA) from influenza A virus strain H5N1, H3N2, or H1N1. In some embodiments, the heterologous polypeptide includes an influenza neuraminidase (NA) from influenza type A subtype N1 to N10. In some embodiments, the NP, M1, M2, PA, PB1, PB2, PB1-F2, NSI or NS2 is from influenza A virus strain H1 to H17 and the NA is from influenza A virus strain from N1 to N10.

The present invention includes a viral expression vector as described herein having two or more heterologous nucleotide sequence expressing a heterologous polypeptide.

The present invention includes a viral particle including a viral expression vector as described herein.

The present invention includes a composition of the viral expression vector or viral particle as described herein.

The present invention includes a method of expressing a heterologous polypeptide in a cell, the method including contacting or infecting the cell with a viral expression vector, viral particle, or composition as described herein.

The present invention includes a method of inducing an immune response in a subject to a heterologous polypeptide, the method including administering a viral expression vector, viral particle, or composition as described herein to the subject. In some embodiments, the immune response includes a humoral immune response and/or a cellular immune response.

The present invention includes a method of expressing a heterologous polypeptide in a subject, the method including administering a viral expression vector, viral particle, or composition as described herein to a subject.

The present invention includes a method of vaccinating a subject, the method including administering a viral expression vector, viral particle, or composition as described herein to a subject.

In some embodiments of the methods described herein, the viral expression vector, viral particle, or composition is administered intranasally, intramuscularly, topically, orally, or in ovo.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Throughout, all headings are for the convenience of the reader and should not be used to limit the meaning of the text that follows the heading, unless so specified.

BRIEF DESCRIPTION OF THE FIGURES

FIG. 2A is a schematic of ZL48, which has H5 inserted between HN and L (also known as PIV5-H5HL). FIG. 2B shows weight loss after H5N1 challenge. Mice (n=10/group) were inoculated with $10^6$ pfu of PIV5, ZL48, ZL46 and inactivated influenza A/VN/03/04 strain (HPAI H5N1). ZL46 has a H5 insertion between SH and HN gene. At 21 days post inoculation, the mice were infected with lethal dose of H5N1. Weights of mice were recorded and weight loss was presented. FIG. 2C shows survival rate. FIG. 2D shows virus titers in lungs after challenge. At four days after challenge with H5N1, the lungs of infected mice were collected and titers of H5N1 in the lungs were determined.

FIGS. 3A-3C show PIV5-N1 (H5N1) protected against lethal H5N1 challenge. FIG. 3A shows schematics of PIV5 expressing NA of H5N1 or H1N1. FIG. 3B shows weight loss after H5N1 challenge. Mice (n=10/group) were inoculated with $10^6$ pfu of PIV5, rPIV5-N1 (H5N1), rPIV5-N1 (H1N1) and recombinant influenza virus expressing HA and NA of H5N1 (rgA/VN-PR8). At 21 days post inoculation, the mice were infected with lethal dose of H5N1. Weights of mice were recorded and weight loss was presented. FIG. 3C shows survival rate.

FIGS. 4A-4C show PIV5-NP (H5N1) protected against lethal influenza virus challenge. FIG. 4A shows schematics of PIV5 expressing NP of H5N1. The PIV5-NP-P-S308G has a mutation at residue S308 of the P protein. PIV5ΔSH-NP has a deletion of the SH protein. FIG. 4B shows weight loss after lethal H1N1 challenge. Mice (n=10/group) were inoculated with $10^5$ pfu of PIV5, rPIV5-NP (H5N1), or influenza virus X31 strain. At 21 days post inoculation, the mice were infected with lethal dose of H1N1 (100 $TCID_{50}$). Weights of mice were recorded and weight loss was presented. FIG. 4C shows survival rate.

FIG. 5 presents schematics of PIV5-H5HL and PIV5-H5LN. H5 can be inserted between HN and L to give rise to PIV5-H5HL or between leader sequence and NP to give rise to PIV5-H5LN. A more detailed diagram of H5 insertion is shown. Sequences of gene start (GS), intergenic region (I) and gene end (GE), which are important for initiation and termination of viral mRNA synthesis, are indicated.

FIG. 6A shows schematics of PIV5 expressing HA of H5N1. Site of H5 insertion is indicated. FIG. 6B shows ELISA antibody titers of vaccinated mice. Mice were inoculated with 1000 pfu of viruses (this is 1/1,000 of the dose used in FIG. 2). At 21 days post inoculation, the mice were bleed and titers of anti-influenza virus were measured using ELISA. FIG. 6C shows neutralizing antibody titers of vaccinated mice. The samples in FIG. 6B were used in a neutralizing antibody titer assay.

FIG. 7A shows weight loss after lethal H1N1 challenge. Mice (n=10/group) were inoculated with $10^5$ pfu of PIV5, rPIV5-NP, PIV5-NP (S308G), PIV5ΔSH-NP or influenza virus X31 strain. PBS, a saline buffer was included as control. At 21 days post inoculation, the mice were infected with lethal dose of H1N1 (1000 $TCID_{50}$) (10 times of dose in FIG. 4). Weights of mice were recorded and weight loss was presented. FIG. 7B shows survival rate. PIV5-NP (Delta SH) is the same as PIV5ΔSH-NP.

FIG. 8A shows schematics of PIV5 mutants expressing H5. ZL48 is PIV5-H5, ZL128 is PIV5ΔSH-H5, ZL127 is PIV5VΔC-H5 and ZL154 is PIV5VΔCΔSH-H5. FIG. 8B shows immunity generated by mutant PIV5 expressing H5. Mice (n=10/group) were inoculated with 1000 pfu of PIV5, rPIV5-H5, PIV5ΔSH-H5 or PIV5VΔC-H5 (clone 1 and 3). At 21 days post inoculation, the mice bleed and anti-H5 IgG titers were measured with ELISA.

FIG. 10A shows schematics of PIV5 expressing Env or Gag of HIV. FIG. 10B shows expression of Env in PIV5-Env-infected cells. HeLa cells were infected with PIV5-Env. Cell lysates were used in Western Blot. FIG. 10C shows expression of Gag in PIV5-Gag-infected cells. HeLa cells were infected with PIV5-Gag. Cell lysates were used in Western blot.

FIG. 12A shows detection of virus with RT-PCR. FIG. 12B shows detection of virus with plaque assay. Swab samples were examined by plaque assay on BHK21 cells. Two replicates for each serially diluted swab sample ($1:10^0$ to $1:10^2$) were used in the assay.

FIGS. 15A and 15B show replication of PIV5 in dogs with prior PIV5 vaccination. The nasal swabs of dogs were collected at 3 and 5 dpi. Detections of virus were performed the same as in FIG. 12. FIG. 15A is results of RT-PCR and FIG. 15B is results of plaque assay.

FIGS. 17A and 17B show PIV5 antibodies in humans. 45 human serum samples were obtained from 18-50 year old healthy individuals. FIG. 17A is a comparison of anti-PIV5 and anti-MuV antibody levels. ELISA was performed on plates coated with purified PIV5 or purified MuV with sera serially diluted. PIV5 or Mumps virus specific ELISA $OD_{450}$ values were shown at 320-fold dilution for each human serum sample. FIG. 17B shows titers of neutralizing antibody against PIV5 in human sera. Data for the antibody titers were the average value of duplicate wells and presented for each human sample. The white column indicates that the PIV5 nAb titer is less than 10, the limit of detection. The black column indicates that the nAb titer is equal to or higher than 10.

FIGS. 18A and 18B present information of recombinant PIV5 expressing H5. FIG. 18A is schematics of recombinant PIV5 expressing H5N1 HA. The cleavage site that contains polybasic amino acid residues is deleted and the sequences are shown. FIG. 18B shows titers of recombinant PIV5 expressing H5N1 HA stocks. The plaque-purified viruses were grown in MDBK cells and titrated in BHK cells. NSPQRERRRKKRGLFG is SEQ ID NO:1 and NSPQGLFG is SEQ ID NO:2).

FIGS. 19A-19C show the generation and analysis of recombinant PIV5 expressing H5N1 HA between HN and L of the PIV5 genome. FIG. 19A is confirmation of H5N1 HA expression using immunoblotting. MDBK cells were infected with ZL48 and lysated at 24 hpi. The lysates were run on SDS-PAGE gel and immunoblotted with anti-H5N1 HA. FIG. 19B is confirmation of H5N1 HA expression using immunofluorescence (IF). MDBK cells were infected with ZL48 and stained with anti-H5N1 HA. Antibodies used for IF were shown on the left side of the panel. FIG. 19C shows the growth rate of rPIV5-H5. MDBK cells were infected with PIV5 or ZL48 at a MOI of 0.1. Media were collected at 24 hours interval. The titers of viruses in the media were determined using plaque assay.

FIGS. 20A-20D show immune responses in mice inoculated with rPIV5-H5. Mice were infected with PIV5 or ZL48 at a dose of $10^6$ pfu via intranasal route. FIG. 20A shows ELISA titers of anti-HA. Mice were infected with $10^6$ pfu of ZL48 or PIV5. At 21 dpi, mice were bled. Titers of ant-HA were determined using ELISA. FIG. 20B shows boost of anti-HA titers. The mice in FIG. 20A were boosted on 28 dpi and bled on 35 dpi. Titers anti-HA were measured using ELISA. FIG. 20C shows neutralization titers. Titers of nAbs in sera of mice vaccinated with PIV5 or ZL48 against H5N1 were determined as described in Materials and Methods. FIG. 20D shows cell-mediated responses. TFN-γ producing lymphocytes (pools of n=3 mice per group) in the mediastinal lymph nodes on day 12 post-vaccination as determined by ELISpot analysis. Data is presented as mean±SEM.

FIG. 22A shows weights of mice challenged with H5N1. Weights were monitored daily after challenge for 15 days. Weight is graphed as average of percentage of original weight (the day of challenge). FIG. 22B shows survival rate. FIG. 22C shows lung titers of mice challenged with H5N1. Mice (N=5) were sacrificed at 4 days after H5N1 challenge. The titers were determined using plaque assay in MDCK cells.

FIG. 23A is an analysis of H5N1 HA expression in cells infected with recombinant PIV5 expressing H5N1 HA. Cells were infected with ZL46, ZL47 and ZL48 as well as PIV5 at a MOI of 1. The expression levels of H5N1 HA in infected cells were determined using flow cytometry as described in Materials and Methods. FIG. 23B shows growth rate of the recombinant viruses in tissue culture cells. Cells were infected with viruses at a MOI of 0.1. The media from infected cells were collected at 24-hour interval and used for plaque assay to determine titers of viruses.

FIG. 25A is a log-rank survival analysis of mice challenged with 10 $LD_{50}$ of A/Vietnam/ 1203/04. Relative weights of mice vaccinated with $10^3$ pfu (FIG. 25B), $10^4$ pfu (FIG. 25C), or $10^5$ pfu (FIG. 25D) and challenged with 10 $LD_{50}$ of HPAI H5N1. Mice vaccinated with rgVN-PR8 received 2000 pfu of virus.

FIG. 26A-26C shows the generation of recombinant PIV5 expressing RV-G protein (rPIV5-RV-G). FIG. 26A schematics of rPIV5-RV-G. NP, nucleoprotein; P, phosphoprotein; V, V protein; M, matrix protein; SH, small hydrophobic protein; F, fusion protein; HN, Hemagglutinin-neuraminidase protein; L, RNA-dependent RNA polymerase. Leader and trailer sequences are important for PIV5 RNA replication. FIG. 26B shows detection of RV-G expression using IFA. RV-G expression was identified in rPIV5-RV-G infected MDBK cells by indirect immunofluorescence assay (IFA) using mouse anti-RV-G antibody, while the PIV5 infected cells were used as a negative control. FIG. 26C shows detection of RV-G expression using WB. RV-G expression was examined in rPIV5-RV-G infected MDBK cells by western blotting (WB) using mouse anti-RV-G antibody with the PIV5 infected cells as negative control.

FIGS. 27A and 27B is a comparison of growth kinetics of PIV5 and rPIV5-RV-G in cells. FIG. 27A is a multi-cycle growth assay. Multi-cycle growth curves of PIV5 and rPIV5-RV-G were performed in MDBK cells at an MOI of 0.01. The aliquots of supernatant from cell culture were harvested at 24 h intervals until 120 h postinfection. FIG. 27B is a single-cycle growth assay. Single-cycle growth curves of PIV5 and rPIV5-RV-G were performed in MDBK cells at an MOI of 5. The aliquots of supernatant from cell culture were harvested at 12 h intervals up to 60 h postinfection. The virus titers in the supernatant were determined by plaque assay in BHK21 cells. Values represent averages of the results from two independent experiments, and error bars show standard deviations.

FIG. 29A is a VNA test. Serum samples were collected before challenge and used for measuring VNA titers against rabies virus by the rapid fluorescent focus inhibition test (RFFIT). Briefly, VNA titers in sera were compared to a known standard, which contains known concentration of international unit (IU) per millimeter solution. VNA titers between $10^6$ PFU and $10^5$ PFU, $10^5$ PFU and $10^4$ PFU inoculations are statistically significant (P values are 0.0001 and 0.0004 respectively, which are calculated using student's t test); VNA titers between $10^4$ PFU and $10^3$ PFU are not statistically different (P value is 0.06). FIG. 29B shows survival rates. Infected animals were observed daily for 22 days for clinical signs of rabies, and survival rates were plotted.

FIG. 30A is a VNA test. Serum samples were collected before challenge and used for measuring VNA titer against rabies virus by RFFIT. VNA titers between IN $10^7$ and $10^6$ PFU, IM $10^7$ and $10^6$ PFU are statistically significant (P values are 0.018 and 0.008 respectively). VNA titers between IN $10^6$ and $10^5$ PFU, IM $10^7$ and $10^8$ PFU are not statistically different (P values arc 0.11 and 0.402 respectively). FIG. 30B shows survival rates. Infected animals were observed daily for 22 days for clinical signs of rabies.

FIG. 31A is a VNA test. Serum samples were collected before challenge and used for measuring VNA titer against rabies virus by RFFIT. VNA titers between IN ($10^6$ PFU) and IM ($10^8$ PFU) are not statistically different (P value is 0.66, calculated using student's t test). VNA titers between Oral and IN or IM arc statistically significant (P values arc 0.03 and 0.003 respectively). FIG. 31B shows survival rates. Infected animals were observed daily for 22 days for clinical signs of rabies.

FIG. 32 shows anti-influenza antibody titers of chickens inoculated with PIV5-H5 via in ovo route. 18-day old SPF embryos were in ovo vaccinated using with 100 μl of PIV5-H5 (titers are shown below each group). The chickens were bled at day 14 and 28 after hatch (ah). The hemagglination-inhibition (HI) titers were determined following the OIE recommendations. The y-axis is HI titers in log 2. The average titers from 12 chickens (10 chickens for the controls) and the appropriate standard deviations are shown in the columns. The HI titer of each co-mingled non-vaccinated contact chicken is above the appropriate column.

FIG. 33 shows schematics of recombinant PIV5 expressing HA of H5N1. PIV5-H5 (ZL48) has H5 insertion between HN and L genes of PIV5. PIV5ΔSH-H5 lacks the SH gene. PIV5VΔC-H5 lacks the conserved C-terminal of the V protein. Two different isolates of this virus have been obtained and will be tested. The SH deletion and the conserved C-terminal deletion have been combined to make PIV5VΔCΔSH-H5. Deletion of SH or VΔC causes attenuation in mice.

FIGS. 34A-34D show PIV5-H5 incorporates HA into the virion and expresses H5 during infection. FIG. 34A is a schematic showing the genome of ZL48 and ZL48, indicating the location of the H5HAgene insertion. In FIG. 34B MDBK cells were infected with PIV5, ZL48, or ZL46 (MOI=0.1) for 72 hours and supernatents collected and compared to purified supernatants separated on SDS-PAGE gel and imaged by Coomassie blue staining. In FIG. 34C MDBK cells were infected with PIV5, ZL48, or ZL46 (MOI=5) were lysed 24 hours later, separated on SDS-PAGE gel, transferred to PVDF, and blotted with a monoclonal antibody specific to the V/P proteins of PIV5 and hyperimmune serum from mice infected with rgA/VN-PR8 to detect HA. Sizes are in kDa. In FIG. 34D Vero cells were infected with PIV5 or ZL46 or were mock infected. At 24 h p.i., cells were fixed and stained with anti-H5 and anti-V/P monoclonal antibodies. Immunofluorescent micrographs were taken at ×20 magnification (bar, 200 μm).

FIGS. 35A-35E show immunization with live PIV5-H5 induces HA-specific immune responses. BALB/c mice (n=5 per group) were immunized with PIV5 IN, ZL46 IN or IM, inactivated ZL46 IM (iZL46), or inactivated A/VN/1203/04 (iA/VN/1203/04) IM. Mice were bled on days 7, 14 and 21 post-immunization. Serum was pooled for analysis. In FIG. 35A HA (H5) specific antibody titers were measured in serum samples using an IgG (H&L) specific ELISA. The dotted line represents the limit of detection. FIG. 35B shows rg A/VN-PR8-neutralizing antibody titers in post-immunization serum. Mice were immunized IN or IM with PIV5, ZL46, or a sub-lethal dose of rgA/VN-PR8 and nasal washes (FIG. 35C) and bronchial alveolar lavages (BAL) (FIG. 35D) were performed on days 14 or 21 post-infection. Samples were pooled for analysis by HA-specific IgG ELISA. FIG. 35E shows IFN-γ producing lymphocytes (pools of n=3 mice per group) in the mediastinal lymph nodes on day 12 post-vaccination as determined by ELISpot analysis. Data is presented as mean±SEM.

FIGS. 36A-36C show immunization with live PIV5-H5 protects against HPAI challenge. BALB/c mice were immunized IN or IM with PIV5, rPIV5-H5 (ZL46), inactivated rPIV5-H5 (iZL46) IM, a sublethal dose of rgA/VN-PR8 IN, or rgA/VN-PR8 IM. Twenty-eight days p.i., the mice were challenged IN with 10 LD50 A/VN/1203/04. In FIG. 36A weights of the mice were monitored and presented as the mean percentage ±SEM of their pre-challenge body weights (n=8). FIG. 36 shows percent of mice surviving post-challenge. FIG. 36C shows challenge virus titer in the lungs on day 3 post-challenge (n=5 per group) as measured by TCID50 on MDCK cells. Data are presented as mean log transformed $TCID_{50}$/ml lung homogenate ±SEM. The limit of detection was 100 $TCID_{50}$/ml.

FIGS. 37A-37C show boosting with PIV5-H5 enhances HA-specific antibody responses. BALB/c mice (n=5 per group) were immunized with PIV5 TN, ZL46 IN or TM, inactivated ZL46 IM (iZL46), or inactivated A/VN/1203/04 IM (iA/VN/1203/04). Mice were bled on days 7, 14, and 21 post-immunization. On day 28 post-immunization, mice were boosted as before and serum was collected on days 7 and 14 post-boost. Serum was pooled for analysis. In FIG. 37A HA (H5) specific antibody titers were measured in serum samples using an IgG specific ELISA. The dotted line represents the limit of detection. FIG. 37B shows rgA/VN-PR8-neutralizing antibody titers in post-immunization serum. Mice were challenged with rgA/VN-PR8 and virus titers in the lungs measured on day 3 post-challenge (n=5 per group) as measured by $TCID_{50}$ on MDCK cells. Data are presented as mean log transformed TCID50/ml lung homogenate ±SEM. The limit of detection was 100 $TCID_{50}$/ml. In FIG. 38C mice were challenged with rgA/VN-PR8, and virus titers in the lungs measured on day 3 postchallenge (n=5 per group) by $TCID_{50}$.)

FIG. 38 is a schematic of PIV5-NP viruses PIV5 genome contains seven genes in the order of 3'-NP-V/P-M-F-SH-HN-L-5' with leader and trailer regions located at the ends of the genome. The H5N1-NP gene was inserted into the PIV5 genome at the indicated gene junctions.

FIGS. 39A and 39B show growth of PIV5 and PIV5-NP-HN/L in vitro and in vivo. FIG. 39A shows multiple-step growth curves of PIV5 and PIV5-NP-HN/L in tissue culture cells. MDBK cells were infected with PIV5 or PIV5-NP-HN/L at an MOI of 0.1 and the media collected at 24 hr intervals. Virus titers were determined by plaque assay on BHK cells. In FIG. 39B mice were vaccinated with 105 pfu of PIV5 or PIV5-NP-HN/L intranasally. Mice were euthanized on day 3 post vaccination to determine lung virus titers.

FIG. 42C shows lung titers of mice challenged with H1N1. Mice (n=5) were sacrificed at 3 days post challenge. The titers were determined using $TCID_{50}$ assay using MDCK cells.

FIGS. 43A and 43B show protection of PIV5-NP-HN/L against H5N1 HPAI challenge. Mice were vaccinated with PBS, $10^7$ pfu of PIV5 or PIV5-NP-HN/L (n=10 per group). At day 21 post vaccination, mice were challenged with 10 LD50 H5N1 HPAI. Weight loss (FIG. 43A) and survival (FIG. 43B) were monitored for 16 days following influenza virus challenge.

FIGS. 44A-44C show an analysis of recombinant PIV5 expressing NP. FIG. 44A shows multiple-step growth curves of PIV5 and PIV5-NP viruses. MDBK cells were infected with PIV5 or PIV5-NP viruses at an MOI of 0.1 and the media collected at 24 hr intervals. Virus titers were determined by plaque assay using BHK cells. FIG. 44B shows H5N1-NP expression levels in PIV5-NP virus-infected cells. MDBK cells were infected with PIV5 or PIV5-NP viruses at an MOI of 5. The ratios of MFI of H5 NP to PIV5-VP were examined by flow cytometry. FIG. 44C shows growth of PIV5 and PIV5-NP viruses in vivo. Mice were vaccinated with 105 pfu of PIV5 or PIV5-NP viruses intranasally. Mice were euthanized on day 3 post vaccination to determine lung virus titers.

FIGS. 47A and 47B show schematics of recombinant PIV5 expressing H5N1 antigens. In FIG. 47A the default insertion site within the PIV5 genome is the junction between the HN and L gene. For insertion that is not between the HN and L gene, gene junction is added at the end of recombinant virus. For instance, the insertion of H5 between the SH and HN gene is rPIV5-H5-SH-HN. The inserted genes were flanked with gene start, gene end and junction sequences from PIV5 that are required for transcription. In FIG. 47B, the default insertion site within the PIV5 genome is the junction between the SH and HN gene. For testing of the effects of P-5308A mutation on vaccine, genes will be inserted at the junction between the HN and L gene to have the least impact on viral gene expression.

FIG. 48 shows schematics of recombinant PIV5 expressing rabies virus antigens to be generated. While the default insertion site for initial studies within the PIV5 genome is the junction between the HN and L gene, additional insertion sites will also be utilized.

FIGS. 49A-49H shows schematics of various OPIV5 antigen constructs. FIG. 49A shows schematics of PIV5 expressing RSV antigens F and G. FIG. 49B shows schematics of PIV5 expressing Nipah Virus antigens F and G. FIG. 49C shows schematics of PIV5 expressing *Mycobacteria tuberculosis* Antigens 85A, 85B and ESAT6. FIG. 49D shows schematics of PIV5 expressing PRRSV antigens. FIG. 49E shows schematics of PIV5 expressing Porcine circovirus (PCV2) antigens. FIG. 49F shows schematics of PIV5 expressing *T. cruzi* antigen Ts. FIG. 49G shows schematics of PIV5 expressing Norovirus antigens. FIG. 49H shows schematics of PIV5 expressing HIV antigens Env (gp160, gp140 or gp120 and Gag).

DETAILED DESCRIPTION OF ILLUSTRATIVE EMBODIMENTS

Parainfluenza virus 5 (PIV5), a negative-stranded RNA virus, is a member of the *Rubulavirus* genus of the family Paramyxoviridae which includes many important human and animal pathogens such as mumps virus, human parainfluenza virus type 2 and type 4, Newcastle disease virus, Sendai virus, HPIV3, measles virus, canine distemper virus, rinderpest virus and respiratory syncytial virus. PIV5 was previously known as Simian Virus-5 (SV5). Although PIV5 is a virus that infects many animals and humans, no known symptoms or diseases in humans have been associated with PIV5. Unlike most paramyxoviruses, PIV5 infect normal cells with little cytopathic effect. As a negative stranded RNA virus, the genome of PIV5 is very stable. As PIV5 does not have a DNA phase in its life cycle and it replicates solely in cytoplasm, PIV5 is unable to integrate into the host genome. Therefore using PIV5 as a vector avoids possible unintended consequences from genetic modifications of host cell DNAs. PIV5 can grow to high titers in cells, including Vero cells which have been approved for vaccine production by WHO and FDA. Thus, PIV5 presents many advantages as a vaccine vector.

The present invention provides PIV5 constructs and identifies mutations within the genome of PIV5 that improve the efficacy of PIV5 as a viral expression vector, including for uses as an improved vaccine vector. A vaccine vector of the present invention may be based on any of a variety of wild type, mutant, or recombinant (rPIV5) strains. Wild type strains include, but are not limited to, the PIV5 strains W3A, WR (ATCC® Number VR-288™), canine parainfluenza virus strain 78-238 (ATCC number VR-1573) (Evermann et al., 1980, *J Am Vet Med Assoc;* 177:1132-1134; and Evermann et al., 1981, *Arch Virol;* 68:165-172), canine parainfluenza virus strain D008 (ATCC number VR-399) (Binn et al., 1967, *Proc Soc Exp Biol Med;* 126:140-145), MIL, DEN, LN, MEL, cryptovirus, CPI+, CPI−, H221, 78524, T1 and SER. See, for example, Chatziandreou et al., 2004, J Gen Virol; 85(Pt 10):3007-16; Choppin, 1964, *Virology:* 23:224-233; and Baumgartner et al., 1987, *Intervirology;* 27:218-223. Additionally, PIV5 strains used in commercial kennel cough vaccines, such as, for example, BI, FD, Merck, and Merial vaccines, may be used.

Figure 1:
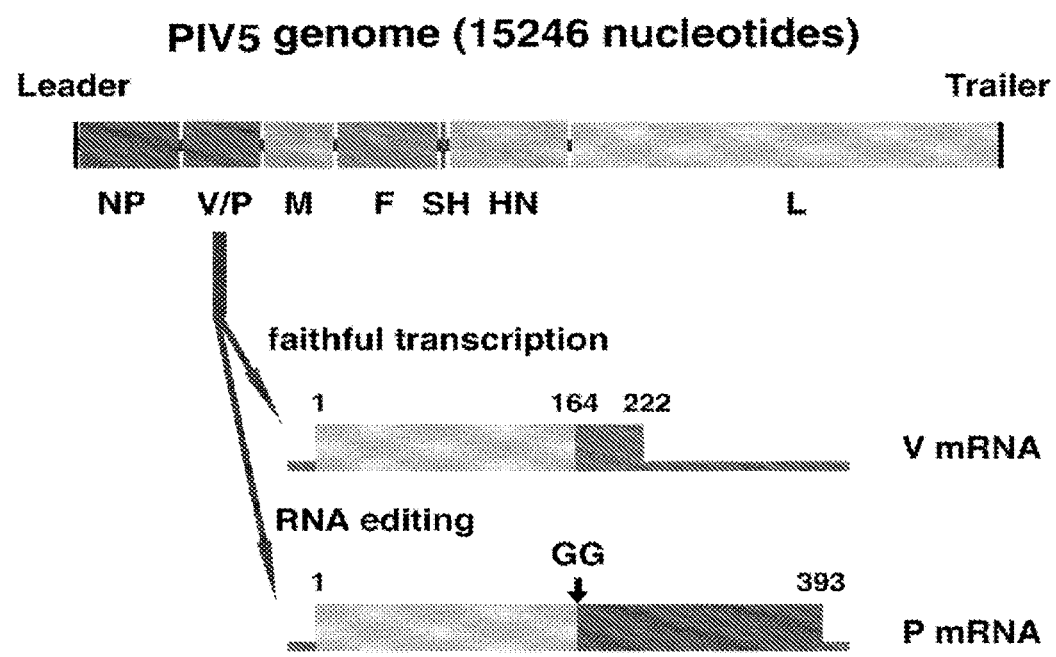
FIG. 1 shows the PIV5 genome structure. The PIV5 genome contains seven known transcriptional units and transcribes eight known viral mRNAs. The V and P mRNAs are both originated from the same V/P gene by an RNA editing process called pseudo-templated transcription. The V mRNA is faithfully transcribed from the V/P gene while the P mRNA arises from insertion of two non-templated G residues at a specific site due to RNA polymerase stuttering during the V mRNA transcription. Leader and trailer sequences are important for viral RNA synthesis and transcription initiations. For negative stranded RNA virus, transcription only initiates at the leader sequence and gene closest to the leader sequence is transcribed the most.
Figure 2A:
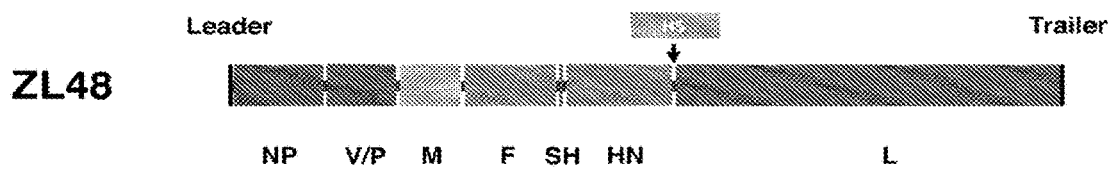
FIGS. 2A-2D show PIV5-H5 protected against lethal H5N1 challenge.
Figure 2B:
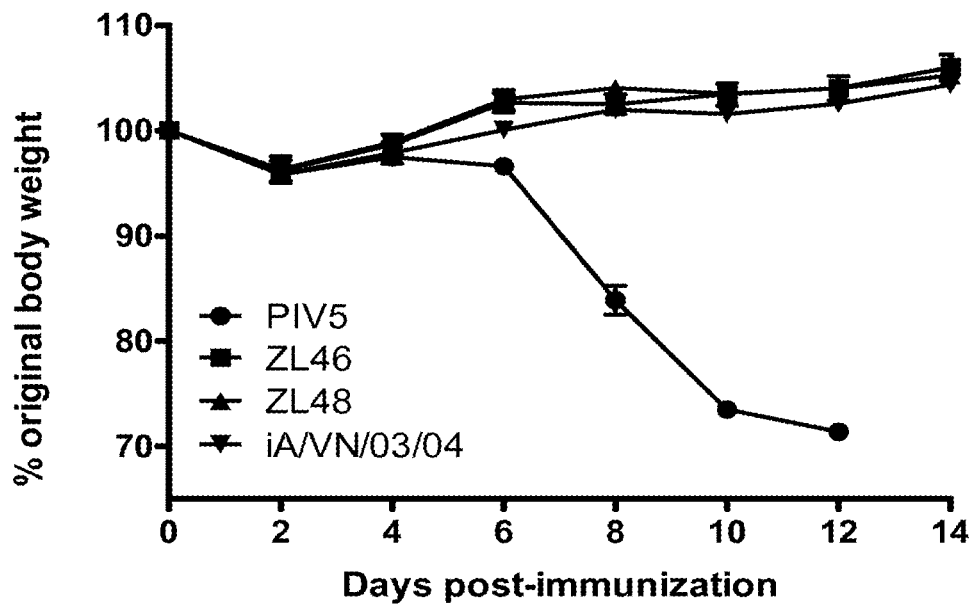
Figure 2C:
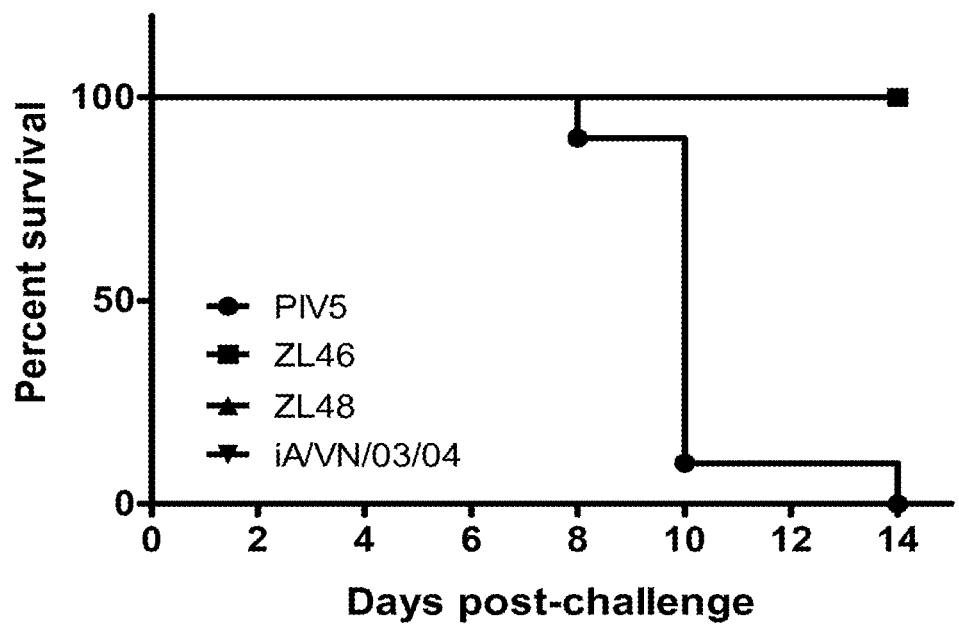
Figure 2D:
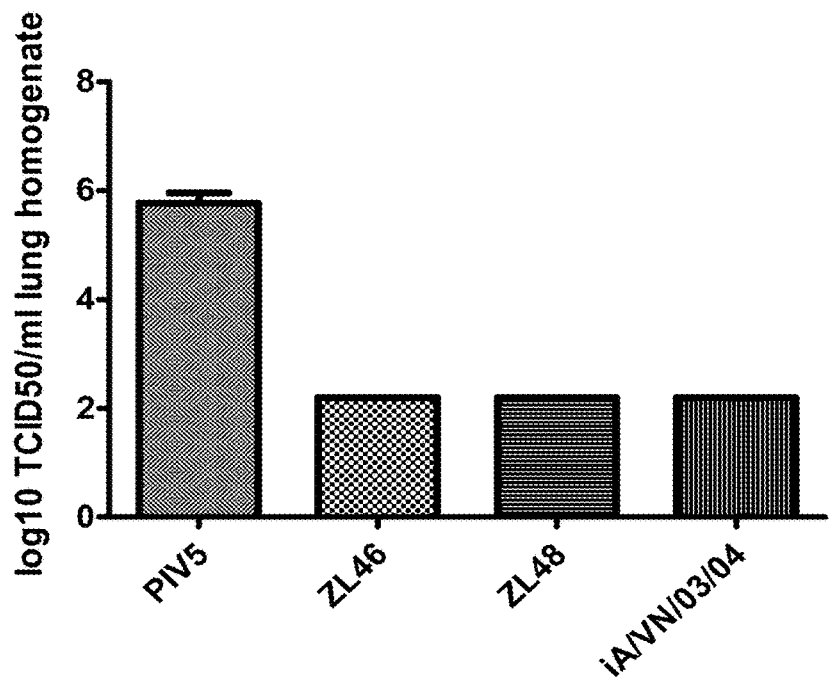

A PIV5 vaccine vector may be constructed using any of a variety of methods, including, but not limited to, the reverse genetics system described in more detail in He et al. (*Virology;* 237(2):249-60, 1997). FIG. 1 shows the PIV5 genome structure. PIV5 encodes eight viral proteins. Nucleocapsid protein (NP), phosphoprotein (P) and large RNA polymerase (L) protein are important for transcription and replication of the viral RNA genome. The V protein plays important roles in viral pathogenesis as well as viral RNA synthesis. The fusion (F) protein, a glycoprotein, mediates both cell-to-cell and virus-to-cell fusion in a pH-independent manner that is essential for virus entry into cells. The structures of the F protein have been determined and critical amino acid residues for efficient fusion have been identified. The hemagglutinin-neuraminidase (HN), another viral glycoprotein, is also involved in virus entry and release from the host cells. The matrix (M) protein plays an important role in virus assembly and budding. The hydrophobic (SH) protein is a 44-residue hydrophobic integral membrane protein and is oriented in membranes with its N terminus in the cytoplasm. For reviews of the molecular biology of paramyxoviruses see, for example, Whelan et al., 2004, *Curr Top Microbiol Immunol;* 283:61-119; and Lamb & Parks, (2006). Paramyxoviridae: the viruses and their replication. In Fields Virology, 5th edn, pp. 1449-1496. Edited by D. M. Knipe & P. M. Howley. Philadelphia, Pa.: Lippincott Williams & Wilkins. A PIV5 viral vaccine of the present invention may also have a mutation, alteration, or deletion in one or more of these eight proteins.

PIV5 can infect human (Hsiung et al., 1965, *J Immunol;* 94:67-73), but it has not been associated with any known illness. PIV5 infects mice and hamsters but does not cause any symptoms in the animals. PIV5 can be grown in cells and released to media at a titer up to $1 \times 10^8$ pfu/ml, indicating its potential as a safe gene delivery vector and a possible cost effective way for mass production of the virus. All evidence to date indicates that PIV5 is not a simian virus. There is no convincing evidence that PIV5 causes diseases in humans, despite completely unfounded speculation in the 1970's that PIV5 might be associated with a number of illnesses including multiple sclerosis (MS), subacute sclerosing panencepalitis (SSPE), Creutzfeldt-Jakob disease (CJD), pemphigus, athero-sclerosis, Paget's disease, hepatitis and the common cold. Subsequent studies have ruled out PIV5 as the etiological agent for any of these diseases. The virus was renamed parainfluenza virus 5 (PIV5) 2009.

PIV5, a negative non-segmented single-stranded RNA virus (NNSV), is a good viral vector candidate for vaccine development because it does not have a DNA phase in its life cycle, and thus the possible unintended consequences of genetic modifications of host cell DNA through recombination or insertion are avoided. In comparison to positive strand RNA viruses, the genome structure of PIV5 is stable. A recombinant PIV5 expressing green fluorescence protein (GFP) has been generated and the GFP gene was maintained for more than 10 generations. Thus, PIV5 is better suited as a vaccine vector than positive strand RNA viruses since the genomes of positive strand RNA viruses recombine and often delete the inserted foreign genes quickly. And, PIV5 infects a large range of cell types including primary human cells as well as established human cell lines. Given the possibility of PIV5 antigen cross-reactivity with antibodies against HPIV2 and mumps virus, it may be a concern to use PIV5 as a vaccine vector. However since in mice neutralizing antibodies against PIV5 do not prevent PIV5 infection (Young et al., 1990, *J Virol;* 64(11):5403-11), it is unlikely that cross-reactive antibody to PIV5 in humans will prevent PIV5 infection. Example 2 is the first demonstration that PIV5-based vector can be effective in dogs, including dogs with circulating anti-PIV5 antibody titers.

A heterologous nucleotide sequence may be inserted in any of a variety of locations in the PIV5 genome. For example, a heterologous nucleotide sequence may be inserted between the hemagglutinin-neuroaminidase (HN) and large RNA polymerase protein (L) gene of the PIV5 genome. In some embodiments, a heterologous nucleotide sequence is not inserted at a location between the hemagglutinin-neuroaminidase (HN) and large RNA polymerase protein (L) gene of the PIV5 genome.

In some embodiments, a heterologous nucleotide sequence is inserted at a location other than between the hemagglutinin-neuroaminidase (HN) and large RNA polymerase protein (L) gene of the PIV5 genome. For example, a heterologous nucleotide sequence may be inserted closer to the leader than between the hemagglutinin-neuroaminidase (HN) gene and the large RNA polymerase protein (L) gene of the PIV5 genome. For example, a heterologous nucleotide sequence may be inserted upstream of the nucleocapsid protein (NP) gene of the PIV5 genome. In some embodiments, a heterologous nucleotide sequence is not inserted upstream of the nucleocapsid protein (NP) gene of the PIV5 genome.

In some embodiments, a heterologous nucleotide sequence may be inserted between the nucleocapsid protein (NP) gene and the V/P gene of the PIV5 genome. For example, a heterologous nucleotide sequence may be inserted immediately downstream of the leader sequence of the PIV5 genome. For example, a heterologous nucleotide sequence may be inserted between the M gene and the F gene of the PIV5 genome. For example, a heterologous nucleotide sequence may be inserted between the F gene and the SH gene of the PIV5 genome. For example, a heterologous nucleotide sequence may be inserted between the VP gene and the matrix protein (M) gene of the PIV5 genome. For example, a heterologous nucleotide sequence may be inserted between the small hydrophobic protein (SH) gene and the hemagglutinin-neuroaminidase (HN) gene of the PIV5 genome. For example, a heterologous nucleotide sequence may be inserted between the leader sequence and the nucleocapsid protein (NP) gene of the PIV5 genome.

In some embodiments, a heterologous nucleotide sequence is not inserted between the hemagglutinin-neuroaminidase (HN) gene and the large RNA polymerase protein (L) gene of the PIV5 genome. In some embodiments, a heterologous nucleotide sequence may be inserted between the hemagglutinin-neuroaminidase (HN) and large RNA polymerase protein (L) gene of the PIV5 genome and wherein the PIV5 genome further includes one or more mutations.

In some embodiments, a heterologous nucleotide sequence encodes an influenza nucleocapsid protein (NP) and is inserted between the hemagglutinin-neuroaminidase (HN) gene and the large RNA polymerase protein (L) gene of the PIV5 genome.

The present invention includes PIV5 vaccine constructs with a heterologous nucleotide sequence inserted in a location as shown in any of the Figures and Example included herewith.

A heterologous nucleotide sequence may be inserted to replace all or part of a PIV5 gene within the PIV5 genome. For example, a heterologous nucleotide sequence may replace the F, HN, or SH gene of the PIV5 genome. In some embodiments, a heterologous nucleotide sequence encoding, for example, influenza HA or NA may replace a PIV5 gene. In some embodiments, the HA or NA influenza gene may replace a portion of the PIV5 F or HN gene.

A heterologous nucleotide sequence may be inserted within a PIV5 gene, resulting in the expression of a chimeric polypeptide. For example, the heterologous nucleotide sequence may be inserted within the SH gene nucleotide sequence, within the NP gene nucleotide sequence, within the V/P gene nucleotide sequence, within the M gene nucleotide sequence, within the F gene nucleotide sequence, within the HN gene nucleotide sequence, and/or within the L gene nucleotide sequence of a PIV5 genome.

PIV5 can infect cells productively with little cytopathic effect (CPE) in many cell types. In some cell types, PIV5 infection causes formation of syncytia, i.e., fusion of many cells together, leading to cell death. A mutation may include one or more mutations that promote syncytia formation (see, for example Paterson et al., 2000, *Virology;* 270:17-30).

PIV5 infection does not induce apoptosis (He et al., 2001, *J Virol;* 75:4068-4079. However, recombinant PIV5 lacking SH (rPIV5 ΔSH) induces apoptosis in L929 cells through a tumor necrosis factor (TNF)-γ mediated extrinsic apoptotic pathway (He et al., 2001, *J Virol;* 75:4068-4079; He et al., 1998, *Virology;* 250:30-40; and Lin et al., 2003, *J Virol;* 77:3371-3383).

The V protein of PIV5 plays a critical role in blocking apoptosis induced by virus. Recombinant PIV5 lacking the conserved cysteine-rich C-terminus (rPIV5V ΔC) of the V protein induces apoptosis in a variety of cells through an intrinsic apoptotic pathway, likely initiated through endoplasmic reticulum (ER)-stress (Sun et al., 2004, *J Virol;* 78:5068-5078). Mutant recombinant PIV5 with mutations in the N-terminus of the V/P gene products, such as rPIV5-CPI-, also induce apoptosis (Wansley and Parks, 2002, *J Virol;* 76:10109-10121). A mutation includes, but is not limited to, rPIV5 ΔSH, rPIV5-CPI-, rPIV5VΔC, and combinations thereof.

A mutation includes, but is not limited to, a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, and/or a mutation that enhances syncytial formation.

A mutation may include, but is not limited to, rPIV5-V/P-CPI-, rPIV5-CPI-, rPIV5-CPI+, rPIV5V ΔC, rPIV-Rev, rPIV5-RL, rPIV5-P-S157A, rPTV5-P-S308A, rPIV5-L-A1981D and rPIV5-F-S443P, rPIV5-MDA7, rPIV5 ΔSH-CPI-, rPIV5 ΔSH-Rev, and combinations thereof.

A PIV5 vaccine of the present invention includes a recombinant PIV5 construct including any one or more of the mutations described herein, including any one or more of the constructs described the in the Figures and Examples included herewith.

A PIV5 viral expression vector of the present invention includes a heterologous nucleotide sequence. Such a heterologous nucleotide sequence may encode, for example, a heterologous DNA, heterologous RNA, and/or heterologous polypeptide. In some aspects, a heterologous nucleotide sequence may encode a heterologous polypeptide, or fragment thereof. Such a polypeptide may be antigenic and have utility as a vaccine. Such an antigenic polypeptide may be from any of a wide variety of pathogens and diseases affecting humans and/or animals. In some aspects, a heterologous polypeptide may be derived from human immunodeficiency virus (HIV), parainfluenza virus 1, parainfluenza virus 2, parainfluenza virus 3, parainfluenza virus 4, human respiratory syncytial virus, bovine respiratory syncytial virus, human metapneumovirus, Mycobacterium tuberculosis, avian metapneumovirus, T. cruzi, Nipah virus, Hendra virus, rabies virus, Ebola virus, porcine circovirus, porcine reproductive and respiratory syndrome virus, swine influenza virus, New Castle disease virus, mumps virus, measles virus, canine distemper virus, swine influenza, human calicivirus, veterinary calicivirus, human norovirus, veterinary norovirus, rinderpest virus, influenza B virus, influenza C virus, or an emerging influenza virus in humans and in animals. In some aspects, a heterologous polypeptide may be derived from a bacteria or a parasite. In some aspects, a heterologous polypeptide may be a cancer antigen.

In some aspects, a heterologous polypeptide is from an influenza virus, including, but not limited to, influenza A, influenza B, or influenza C. Influenza is a negative-sense, segmented RNA virus in the family Orthomyxoviridae. It is classified into subtypes based on the major antigenic surface glycoproteins, hemagglutinin (HA) and neuraminidase (NA). Thus far there are 17 different HA subtypes and 9 different NA subtypes, all containing segments of avian origin. Influenza has the capacity to reassort, whereby gene segments are exchanged creating a new influenza virus to which the population is immunologically naive. A heterologous polypeptide may be a hemagglutinin (HA), neuraminidase (NA), nucicocapsid protein (NP), M1, M2, PA, PB1, PB2, NS1 or NS2 from an influenza virus. HA, NA, NP, M1, M2, PA, PB1, PB2, NS1, or NS2 may be for example, from influenza A virus strain H5N1, H3N2, or H1N1.

HA may be from, for example, influenza A subtype H1, influenza A subtype H2, influenza A subtype H3, influenza A subtype H4, influenza A subtype H5, influenza A subtype H6, influenza A subtype H7, influenza A subtype H8, influenza A subtype H9, influenza A subtype H10, influenza A subtype H11, influenza A subtype H12, influenza A subtype H13, influenza A subtype H14, influenza A subtype H15, or influenza A subtype H16. HA may be, for example, from influenza A virus strain H5N1, H3N2, or H1N1. In some aspects, the HA polypeptide may include a mutation to prevent cleavage.

NA may be from, for example, influenza A subtype N1, influenza A subtype N2, influenza A subtype N3, influenza A subtype N4, influenza A subtype N5, influenza A subtype N6, influenza A subtype N7, influenza A subtype N8, or influenza A subtype N9 of influenza A. NA may be, for example, from influenza A virus strain H5N1, H3N2, or H1N1.

A a heterologous polypeptide includes any of those described in the Figures and Example included herewith.

Rabies virus (RABV) infection leads to rabies in warm-blooded animals including humans characterized with acute encephalitis at early phase and fatality at later stage without post-exposure treatment (Rupprecht et al., 2006, *Expert Rev Anti Infect Ther;* 4:1021-1038). Untreated rabies virus (RABV) infection leads to death. Vaccine and post-exposure treatment have been effective in preventing RABV infection. However, due to cost, rabies vaccination and treatment have not been wildely used in developing countries. There are 55,000 human death caused by rabies annually. Stray dogs, wild carnivores and bats are the natural reservoirs of field RABV, and these rabid carriers are public health risk to human and domestic animals. Human rabies occurrence is largely attributed to the bite of stray dogs in the developing countries where vaccination of animals is limited, especially in rural areas. An efficacious and cost effective rabies vaccine is needed. In some aspects, a heterologous polypeptide is one or more a rabies polypeptides.

A PIV5 viral expression vector, as described herein, may demonstrate enhanced efficacy of the vaccine vector.

A PIV5 viral expression vector may include one or more mutations, including, but not limited to any of those described herein. In some aspects, a combination of two or more (two, three, four, five, six, seven, or more) mutations may be advantageous and may demonstrated enhanced activity.

Previously, to test the feasibility of using PIV5 as a live vaccine vector, the hemagglutinin (HA) gene from influenza A virus strain A/Udorn/72 (H3N2) was inserted into the PIV5 genome as an extra gene between the hemagglutinin-neuraminidase (HN) gene and the large (L) polymerase gene. Recombinant PIV5 containing the HA gene of Udorn (rPIV5-H3) was recovered and it replicated similarly to wild type PIV5, both in vitro and in vivo. The HA protein expressed by rPIV5-H3-infected cells was incorporated into the virions and addition of the HA gene did not increase virus virulence in mice. The efficacy of rPIV5-H3 as a live vaccine was examined and a single dose inoculation provides broad and considerable immunity against influenza A virus infection (Tompkins et al., 2007, Virology; 362(1):139-50). Thus, in some aspects, the present invention does not include the PIV5 viral construct of Tompkins et al., 2007, Virology; 362(1):139-50. For example, in some aspects, the present invention does not include a PIV5 viral vector construct that expresses the hemagglutinin (HA) gene from influenza A virus strain A/Udorn/72 (H3N2). For example, in some aspects, the present invention does not include a PIV5 viral vector construct that expresses the hemagglutinin (HA) gene from influenza A virus H3N2. For example, in some aspects, the present invention does not include a PIV5 viral vector construct that expresses the hemagglutinin (HA) gene from influenza A virus. For example, in some aspects, the present invention does not include rPIV5-HA. For example, in some aspects, the present invention does not include a PIV5 viral vector construct that expresses the hemagglutinin (HA) gene from influenza A virus strain A/Udorn/72 (H3N2) inserted into the PIV5 genome as an extra gene between the hemagglutinin-neuraminidase (HN) gene and the large (L) polymerase gene. For example, in some aspects, the present invention does not include a PIV5 viral vector construct that expresses the hemagglutinin (HA) gene from influenza A virus strain H3N2 inserted into the PIV5 genome as an extra gene between the hemagglutinin-neuraminidase (HN) gene and the large (L) polymerase gene. For example, in some aspects, the present invention does not include a PIV5 viral vector construct that expresses an influenza A hemagglutinin (HA) gene inserted into the PIV5 genome as an extra gene between the hemagglutinin-neuraminidase (HN) gene and the large (L) polymerase gene. For example, in some aspects, the present invention does not include a PIV5 viral vector construct that expresses a polypeptide inserted into the PIV5 genome as an extra gene between the hemagglutinin-neuraminidase (HN) gene and the large (L) polymerase gene. For example, in some aspects, the present invention does not include methods of making or using one or more of the PIV5 viral vector constructs described in this paragraph.

Further, in some aspects, the present invention does not include a PIV5 viral vector construct that expresses green fluorescent protein (GFP). In some aspects, the present invention does not include a PIV5 viral vector construct that expresses a detectable marker.

While it has been previously demonstrated that PIV5 expressing HA of influenza virus provides immunity, the present invention unexpectedly demonstrates that a PIV5 based viral vector results in the generation of protective levels of immunity with the expression of influenza NA and NP proteins. HA is very immunogenic and many vectors are capable of generating anti-HA immunity. However, from a showing that a given expression vector results in expression and immunity to HA, it cannot be assumed that the same vector will be useful to express and generate an immune response to other proteins, such as, for example, NA or NP of influenza virus. This is demonstrated by work with both the adenovirus virus (AdV) and New Castle Disease (NDV) vectors. Although both vectors can express HA for the generation of immunity, they do not generate immunity when used to express NA or NP. That PIV5 viral vectors, as described herein resulted in the generation of protective immunity is novel and unexpected.

In some aspects, a viral expression vector of the present invention is multivalent, expressing heterologous polypeptides from more than one source, for example, from two, three, four, five, six, seven, eight, nine, ten, or more sources.

Also included in the present invention are virions and infectious viral particles that includes a PIV5 genome including one or more heterologous nucleotide sequences expressing a heterologous polypeptide as described herein.

Also included in the present invention are compositions including one or more of the viral constructs or virions, as described herein. Such a composition may include a pharmaceutically acceptable carrier. As used, a pharmaceutically acceptable carrier refers to one or more compatible solid or liquid fillers, diluents or encapsulating substances which are suitable for administration to a human or other vertebrate animal. Such a carrier may be pyrogen free. The present invention also includes methods of making and using the viral vectors and compositions described herein.

The compositions of the present disclosure may be formulated in pharmaceutical preparations in a variety of forms adapted to the chosen route of administration. One of skill will understand that the composition will vary depending on mode of administration and dosage unit.

The agents of this invention can be administered in a variety of ways, including, but not limited to, intravenous, topical, oral, intranasal, subcutaneous, intraperitoneal, intramuscular, and intratumor deliver. In some aspects, the agents of the present invention may be formulated for controlled or sustained release.

As shown in the examples included herein, intramuscular or intranasal immunization with PIV5-H5 induces HA-specific immune responses. One advantage of intranasal immunization is the potential to induce a mucosal immune response. Unlike influenza virus, which generally replicates in airway or gut epithelial cells, PIV5 has the potential for broader cellular tropism. This feature makes it an appealing candidate for use as a live intramuscular vaccine. Intramuscular immunization with PIV5-H5 induces robust HA-specific and neutralizing serum antibody responses, comparable to intranasal immunization. Moreover, it provides an opportunity for combining this vaccine with other injectable vaccines, as well as an injectable vaccine formulation, which may be appealing for agricultural applications.

Also included in the present invention are methods of making and using PIV5 viral expression vectors, including, but not limited to any of those described herein.

For example, the present invention includes methods of expressing a heterologous polypeptide in a cell by contacting or infection the cell with a viral expression vector, viral particle, or composition as described herein.

For example, the present invention includes methods of inducing an immune response in a subject to a heterologous polypeptide by administering a viral expression vector, viral particle, or composition as described herein to the subject. The immune response may include a humoral immune response and/or a cellular immune response. The immune response may enhance an innate and/or adaptive immune response.

For example, the present invention includes methods expressing a heterologous polypeptide in a subject by administering a viral expression vector, viral particle, or composition as described herein to the subject.

For example, the present invention includes methods of vaccinating a subject by administering a viral expression vector, viral particle, or composition as described herein to the subject.

With the methods of the present invention, any of a variety of modes of administration may be used. For example, administration may be intravenous, topical, oral, intranasal, subcutaneous, intraperitoneal, intramuscular, intratumor, in ovo, maternally, and the like. In some aspects, administration is to a mucosal surface. A vaccine may be administered by mass administration techniques such as by placing the vaccine in drinking water or by spraying the animals' environment. When administered by injection, the immunogenic composition or vaccine may be administered parenterally. Parenteral administration includes, for example, administration by intravenous, subcutaneous, intramuscular, or intraperitoneal injection.

An agent of the present disclosure may be administered at once, or may be divided into a number of multiple doses to be administered at intervals of time. For example, agents of the invention may be administered repeatedly, e.g., at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that any concentration ranges set forth herein are exemplary only and are not intended to limit the scope or practice of the claimed compositions and methods.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

In some aspects, any of the PIV5-based constructs and methods described in PCT application PCT/US2013/022898, "PIV5 as an Oncolytic Agent," inventor Biao He, filed Jan. 24, 2013 (which is hereby incorporated by reference herein in its entirety) may be used in the present invention.

As used herein, the term "subject" represents an organism, including, for example, a mammal. A mammal includes, but is not limited to, a human, a non-human primate, and other non-human vertebrates. A subject may be an "individual," "patient," or "host." Non-human vertebrates include livestock animals (such as, but not limited to, a cow, a horse, a goat, and a pig), a domestic pet or companion animal, such as, but not limited to, a dog or a cat, and laboratory animals. Non-human subjects also include non-human primates as well as rodents, such as, but not limited to, a rat or a mouse. Non-human subjects also include, without limitation, poultry, horses, cows, pigs, goats, dogs, cats, guinea pigs, hamsters, mink, and rabbits.

In some embodiment, a PIV5 vaccine of the present invention may be administered to poultry, and although vaccines according to the present invention may be used effectively in chickens, other poultry, such as, for example, turkeys, guinea fowl, ducks, and partridges may be successfully inoculated. Chickens include, but are not limited to, hens, roosters, broilers, roasters, breeder, the offspring of breeder hens, and layers. The vaccine of the present invention may be administered to poultry before or after hatching. Poultry may receive a vaccine at a variety of ages. For example, broilers may be vaccinated in ovo, at one-day-old, in ovo, or at 2-3 weeks of age. Laying stock or reproduction stock may be vaccinated, for example, at about 6-12 weeks of age and boosted at about 16-20 weeks of age. Such laying stock or reproduction stock may be vaccinated at about 6, at about 7, at about 8, at about 9, at about 10, at about 11, or at about 12 weeks of age. Such laying stock or reproduction stock may be boosted at about 16, at about 17, at about 18, at about 19, or at about 20 weeks of age. With such a PIV5 vaccine, the vaccine may express one or more immunogens derived from a pathogen infectious to poultry. Such immunogens may be derived from, for example, Marek's disease virus (MDV), infectious bronchitis virus (IBV), Newcastle disease virus (NDV), egg drop syndrome (EDS) virus, turkey rhinotracheitis virus (TRTV), poxvirus, or reovirus.

As used herein "in vitro" is in cell culture and "in vivo" is within the body of a subject. As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

For any method disclosed herein that includes discrete steps, the steps may be conducted in any feasible order. And, as appropriate, any combination of two or more steps may be conducted simultaneously.

The description exemplifies illustrative embodiments. In several places throughout the application, guidance is provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

EXAMPLES

Example 1

Parainfluenza Virus (PIV5) as a Vaccine Vector

To test whether PIV5 expressing HA of influenza virus can protect challenge by the H5N1, a lethal highly pathogenic avian influenza H5N1 (HPAI) and the most virulent strain of influenza virus, a recombinant PIV5 expressing HA of H5N1 (PIV5-H5) was generated and tested the efficacy of the virus in animals. As shown in FIGS. 2A-2D, a single dose inoculation of PIV5-H5 protected lethal H5N1 challenge, demonstrating that PIV5 is an excellent vector for vaccine development.

Figure 3A:
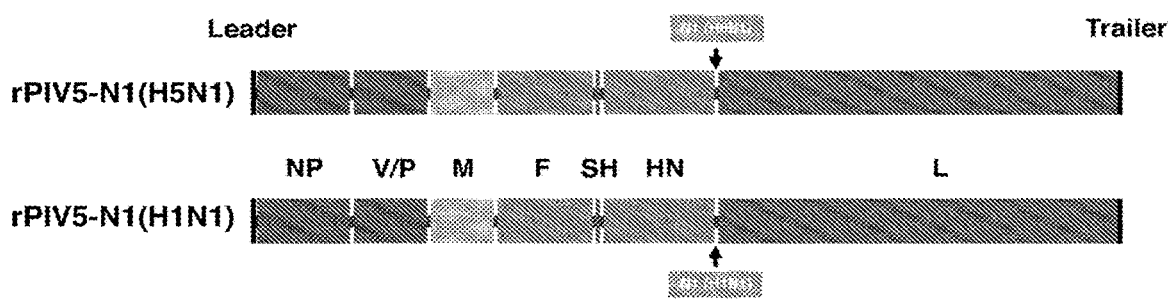
Figures 3B, 3C:
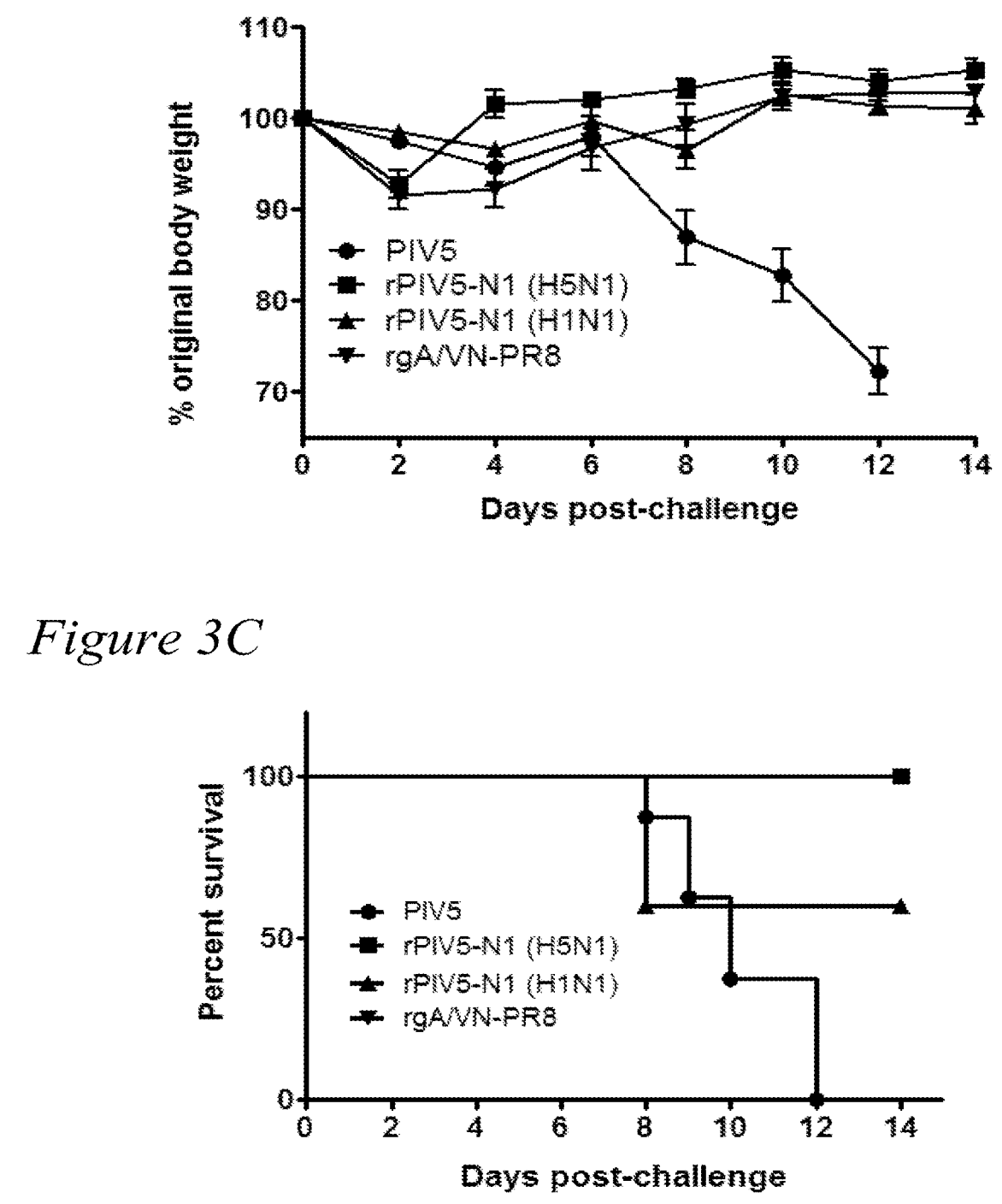

NA of influenza virus is a potentially valuable target for vaccine development. However, efforts to express NA as an antigen have not been successful. In the case of New Castle Diseases (NDV) expressing NA, the recombinant virus did not provide any protection (Nayak et al., 2010, J Virol; 84(5):2408-20). To test whether PIV5 is a better vaccine vector, a recombinant PIV5 expressing NA of H5N1, rPIV5-N1(H5N1) and a recombinant PIV5 expressing NA of pandemic H1N1, rPIV5-N1(H1N1) were generated. As shown in FIGS. 3A-3C, recombinant PIV5 expressing NA provides sterilizing immunity against lethal HPAI H5N1 challenge. Interestingly, even rPIV5-N1 (H1N1) provided partial immunity against H5N1 challenge. This is the first time a viral vector-based vaccine expressing NA provided immunity against H5N1 challenge. This PIV5-based vector is best to date in providing immunity against influenza virus challenge than any other viral vectors.

Figures 4A, 4B:
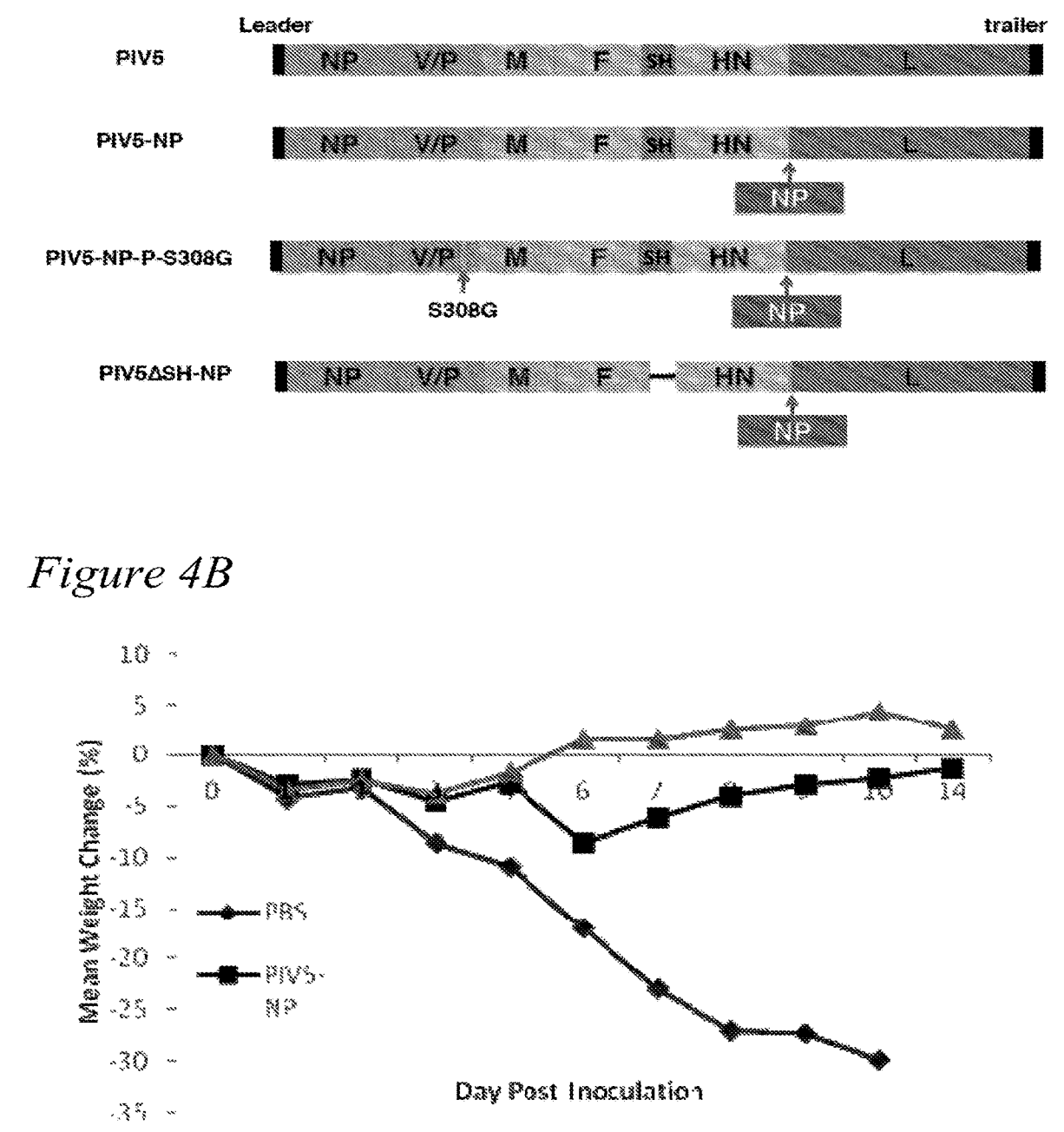
Figures 4C, 5:
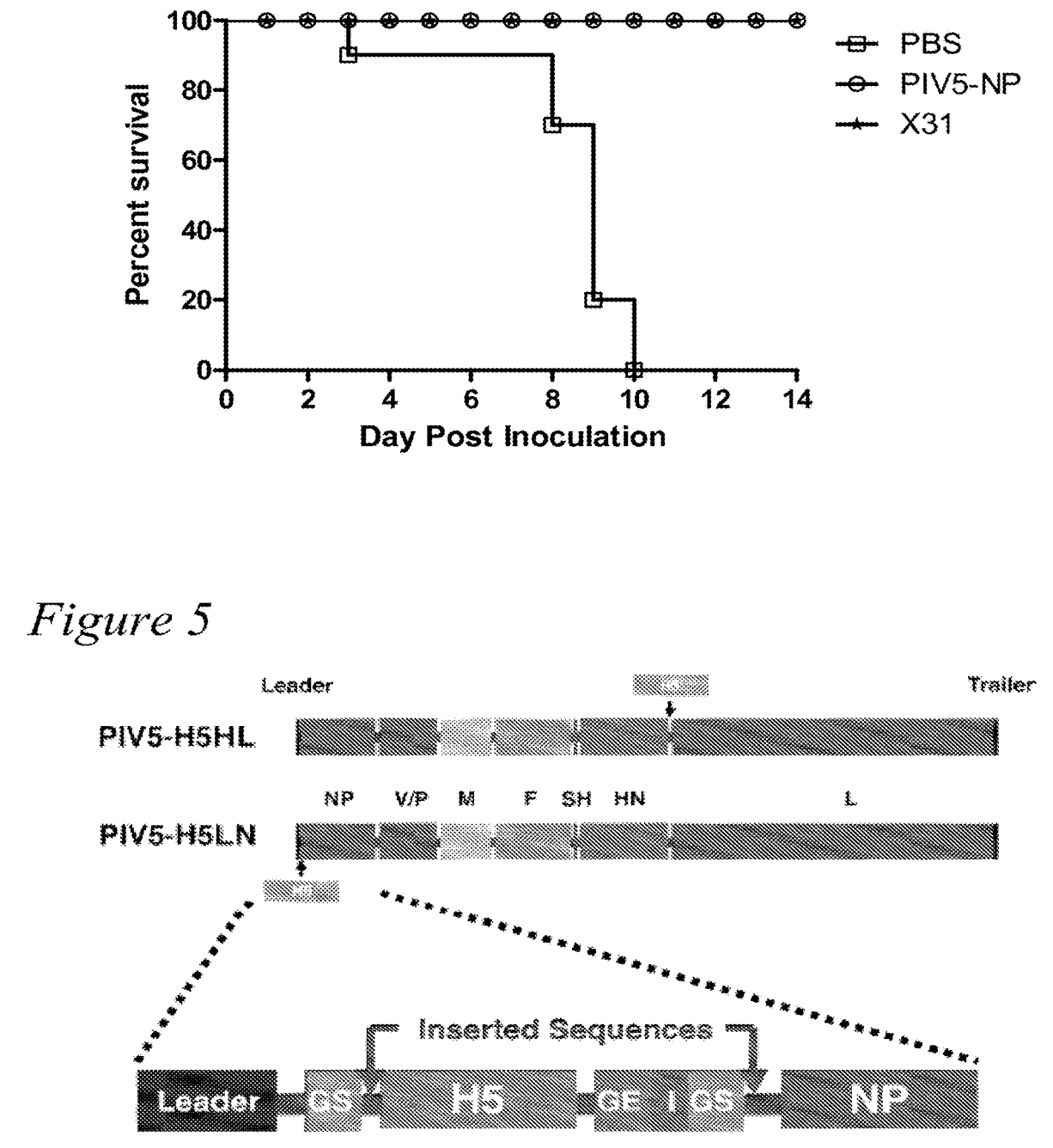

Towards a universal influenza virus. The NP protein of influenza virus is very well conserved among all strains of influenza virus, and it is thought to be an excellent target for developing a broadly protective influenza virus vaccine. However, efforts to develop a NP-based vaccine have not been successful. Vaccinia virus (VV) expressing NP do not protect against influenza virus challenge (Lawson et al., 1994, J Virol; 68(6):3505-11). To examine whether PIV5 can be a good vector for expressing NP, a recombinant PIV5 expressing the NP gene of H5N1 (PIV5-NP) was generated. Incredibly, PIV5-NP provided protection against challenge from H1N1 as well as H5N1, demonstrating that the PIV5-based NP vaccine can protect a heterotypical influenza virus challenge (FIGS. 4A-4C). It is known that NP-based cellular immune response (T-cells based immune responses) is protective while humoral immune response (antibody-based immune response) is sufficient for HA-mediated immunity (Graham and Braciale, 1997, J Exp Med; 186(12):2063-8; Crawford et al., 1999, Vaccine; 17(18):2265-74; and Kong et al., 2006, Proc Natl Acad Sci USA; 103(43):15987-91). That PIV5 based vaccine provided protection likely through cellular immune response is novel and unexpected. Furthermore, because the protection afforded by expressing NP through PIV5, it is possible to generate a universal influenza virus vaccine based PIV5 and NP.

Figure 6A:
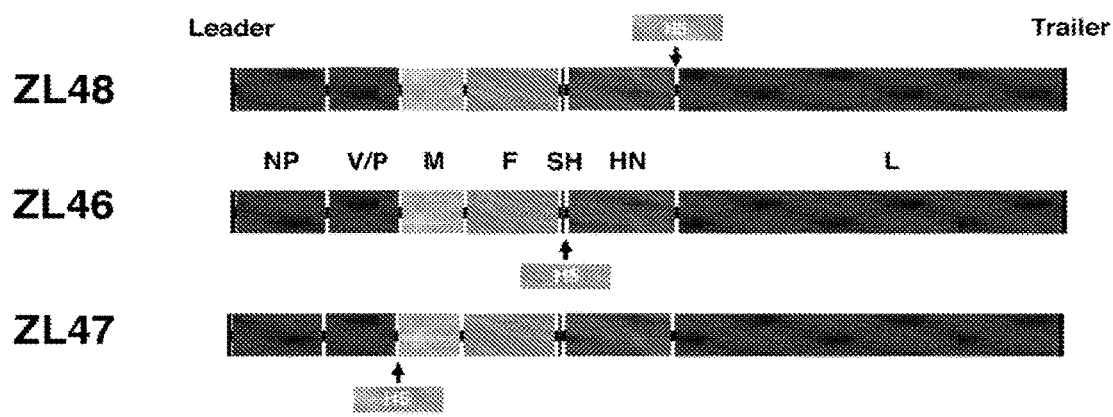
FIG. 6A-6C show expression levels of HA of H5N1 PIV5H5 impacted immunity.
Figure 6B:
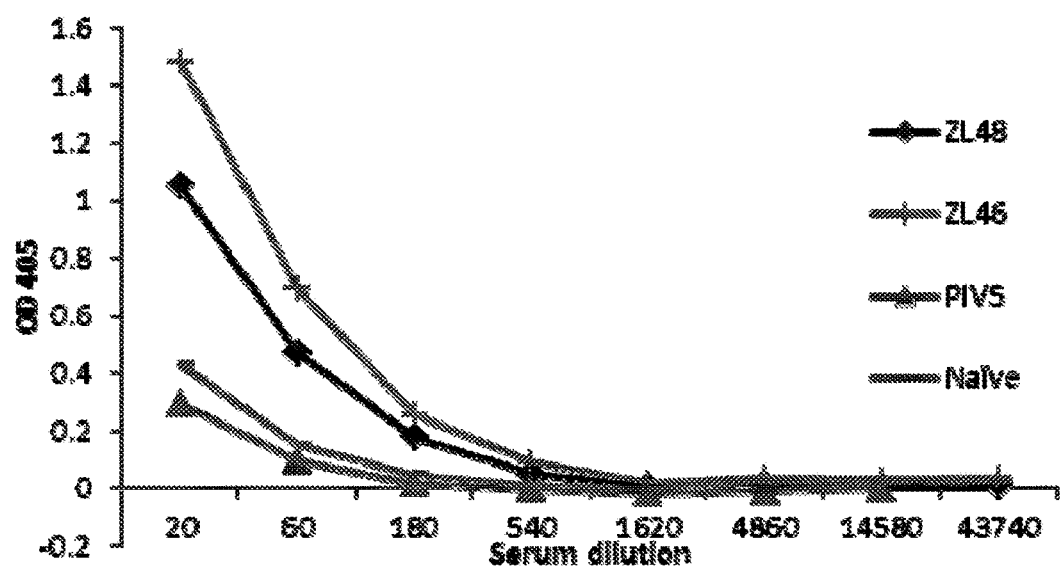
Figure 6C:
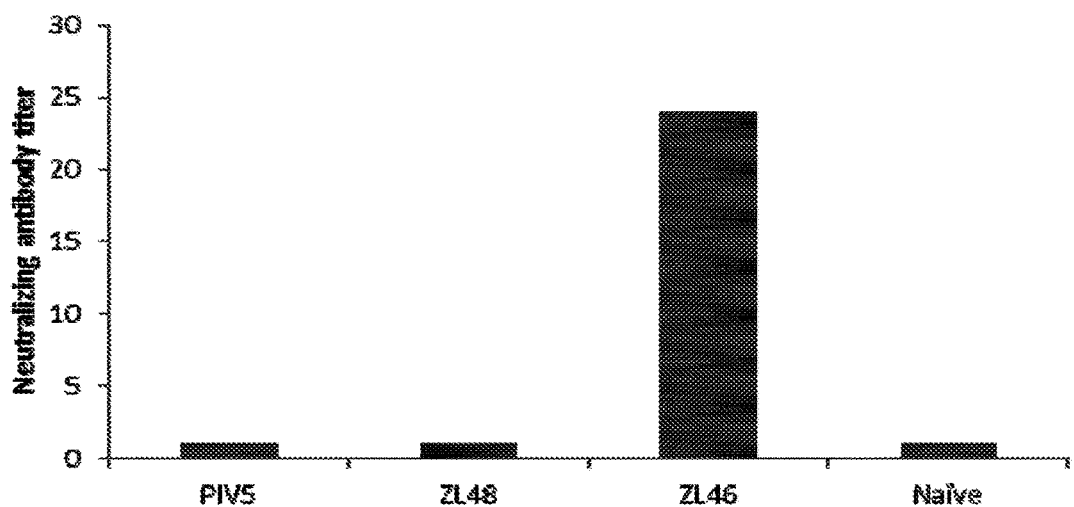

Insertion of forgein genes closer to the leader sequence to increase efficacy of vaccine. Negative strand RNA viruses, such as PIV5, initiate transcription from the 3' end leader sequence, and transcription levels of the viral genes arc affected by their distances to the leader sequence. For example, the NP gene of PIV5 that is the closest to the leader sequence is the most abundantly transcribed, whereas the L gene that is the located most distance from the leader sequence is least transcribed (FIG. 5). Foreign genes have been inserted between the HN gene and the L gene, the most distal gene junction from the leader sequence, the de facto promoter sequence because this is the junction with least potential to disrupt the viral replication (He et al., 1997, Virology; 237:249-260; Tompkins et al., 2007, Virology; 362(1):139-50; and Sun et al., 2011, J Med Chem; 54(5): 1126-39. The vaccine candidate will be enhanced by increasing the expression level of the antigens. To increase the expression level of antigen such as the HA gene of H5N1 virus (H5), the H5 gene was inserted immediately downstream of the leader sequence and upstream of the NP gene (PIV5-H5LN) (FIG. 5). Unfortunately, unlike other paramyxoviruses such as RSV, the insertion of foreign gene between the leader sequence and the NP gene did not result in a viable virus. A PIV5-H5HL (also known as ZL48) has been generated. This recombinant virus protected lethal highly pathogenic avian influenza H5N1 (HPAI) challenge (see FIG. 2). Other gene junctions have been tried and it was determined that the junction between V/P and M, and the junction between SH and HN are suitable for insertion of foreign genes. The expression levels of foreign gene are higher when the H5 gene is closer to the leader sequence. Most importantly, the recombinant PIV5 with H5 closer to the leader sequence was better in generating immunity against the desirable antigen (FIGS. 6A-6C).

Figure 7A:
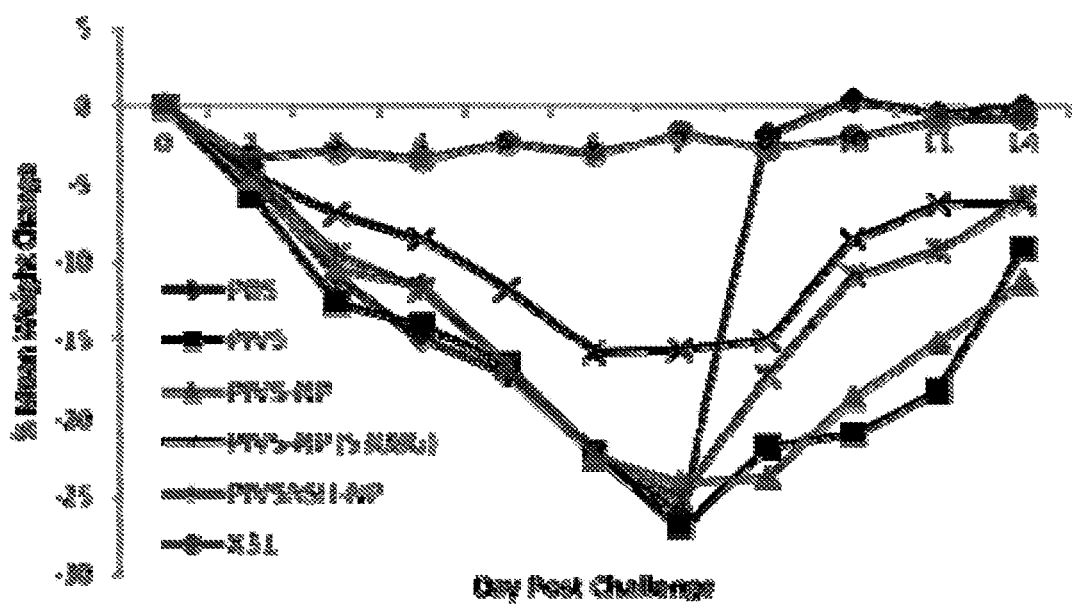
FIGS. 7A and 7B show mutant PIV5 expressing NP had better protection.
Figure 7B:
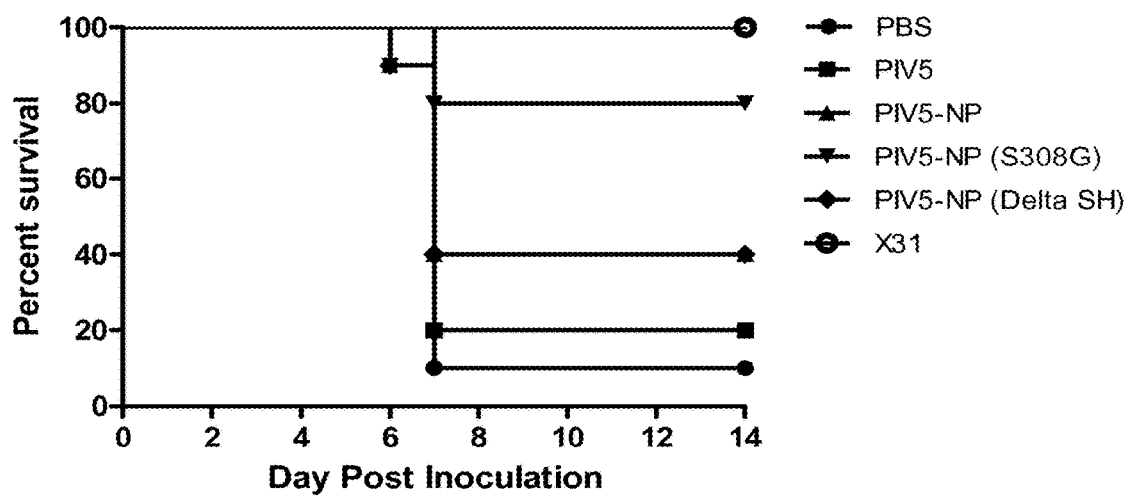
Figure 8A:
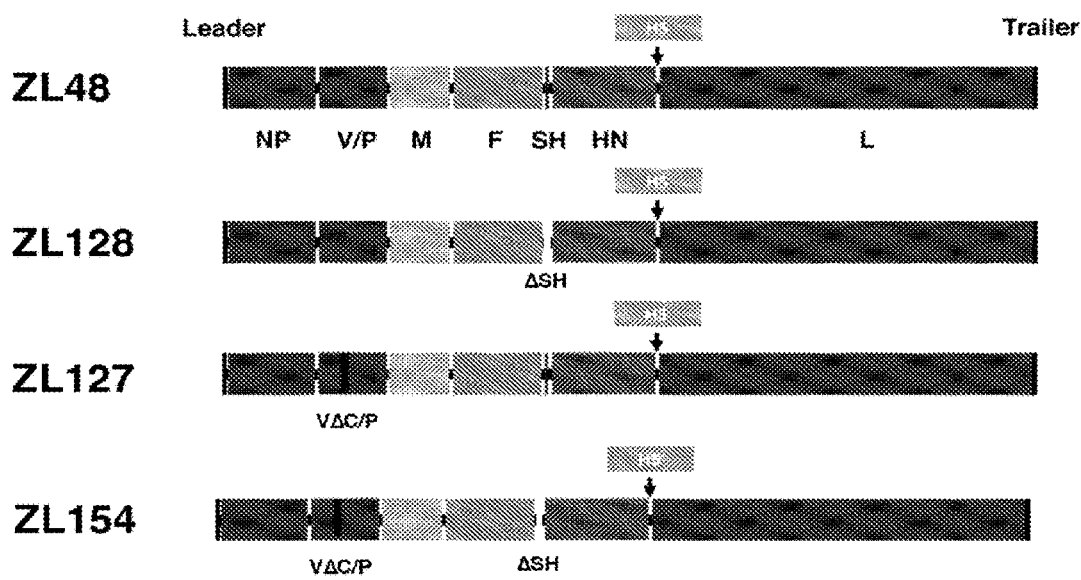
FIGS. 8A and 8B show mutant PIV5 expressing H5 had impact on antibody titers.
Figure 8B:
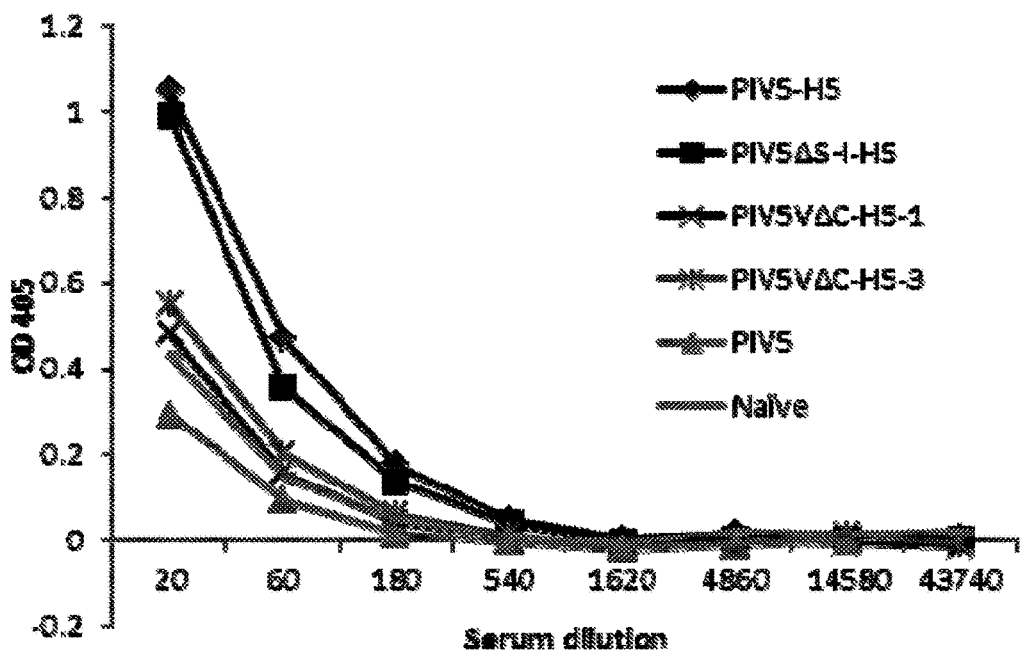

Mutant PIV5 viruses as vaccine vectors. Apoptosis plays an important role in antigen presentation. Apoptotic cells are a source of antigens for professional APC such as dendritic cells. It is thought that the apoptotic pathway activated by virus infection may also play a role in antigen presentation, and that different apoptotic pathways may affect antigen presentation differently. Wild type PIV5 infection does not induce cell death. However, it has been shown that mutant PIV5 viruses lacking small hydrophobic (SH) gene (PIV5ΔSH) or the conserved region of the V protein (PIV5VΔC) induce apoptosis in infected cells via different apoptotic pathways (Sun et al., 2004, J Virol; 78(10):5068-78; and Lin et al., 2003, J Virol; 77(6):3371-83). It has also been reported that the mutations in the V/P gene of PIV5 induce apoptosis as well as cytokine expressions (Sun et al., 2009, PLoS Pathog; 5(7):e1000525). It is likely that mutant PIV5 viruses that induce apoptosis as well as cytokines will be better vectors to present foreign antigens such as H5N1 proteins than wild type PIV5. Mutant recombinant PIV5 expressing foreign antigens such as H5N1's H5 and NP have been generated and some of the mutations resulted in better protection while some of the mutations resulted in less protection for some antigens. Among rPIV5-NP, rPIV5ΔSH-NP and rPIV5-P-S308G-NP (which contains a point mutation at residue S308 to G of the P protein), rPIV5-P-S308G-NP had the best protection (FIGS. 7A and 7B). Although rPIV5ΔSH-NP had the same survival rate as rPIV5-NP after lethal influenza virus challenge, rPIV5ΔSH-NP lost a little more weight and they appeared to be sicker than rPIV5-NP-immunized mice. Thus deleting the SH gene from PIV5 did not appear to enhance immunity for NP, and may even be a little detrimental. Interestingly, with rPIV5-H5, rPIV5ΔSH-H5 and rPIV5VΔC-H5-1 and rPIV5VΔC-H5-3, deletion of SH had no impact on the immunogenicity, which mutations in the V/P gene appeared to have negatively affected immunogenicity (FIGS. 8A and 8B). Because cellular immunity is required for NP-mediated immunity, and humoral immunity is often effective in HA-mediated immunity, it is likely that deletion of SH negatively affect cellular immunity and the V/P gene mutations may impact humoral immunity.

Figure 9:
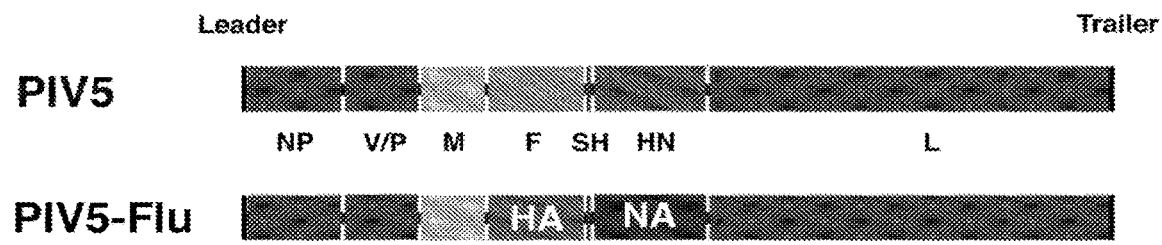
FIG. 9 shows a schematic for the production of an improved PIV5 vector, a chimeric PIV5 expressing viral proteins from the intended vaccine target replacing PIV5 proteins.

Chimeric PIV5 as a vaccine. To reduce interference from PIV5-generated immunity in a PIV5-based vaccine, it is desirable to reduce host immunity targeting PIV5. PIV5 proteins will be replaced with proteins from intended vaccine targets. For instance, F and HN of PIV5 will be replaced with HA and NA of influenza virus (FIG. 9). This will generate a viable chimeric PIV5 expressing antigens of vaccine target to minimize the effects of PIV5 proteins-generated immunity.

Figure 10A:
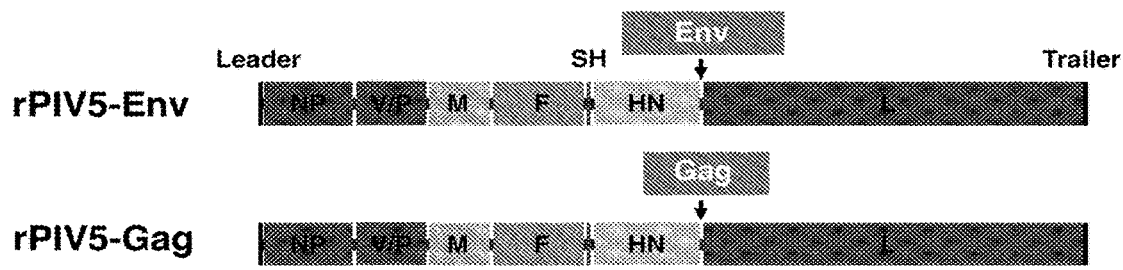
FIG. 10A-10C shows PIV5-based HIV vaccine candidates.
Figure 10B:
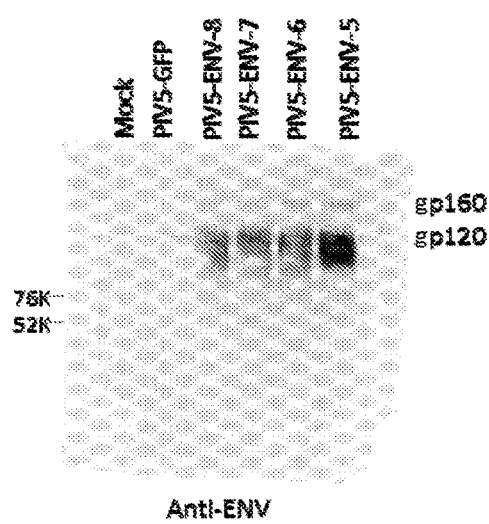
Figure 10C:
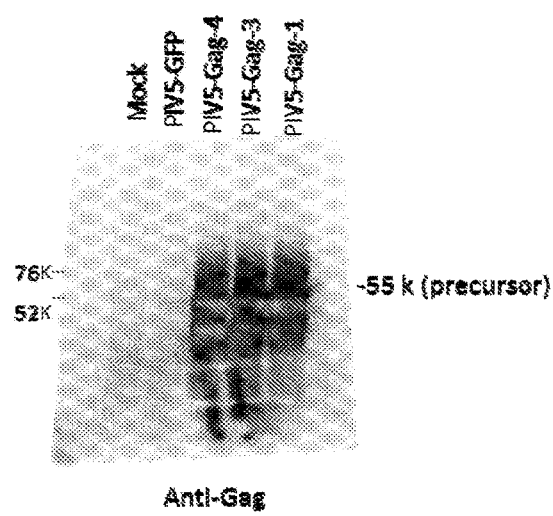

Additional vaccine candidates under development. As shown in this example, PIV5 is an excellent vaccine vector for many pathogens (viral as well as bacterial). Additional vaccine candidates are being developed, including but not limited to human vaccines, such as, for example, PIV5-HIV, PIV5-PIV2 (Parainfluenza Virus 2), PIV5-RSV (Respiratory Syncytial Virus), PIV5-Nipah Virus (for humans and swine), and PIV5-Ebola Virus, and animal vaccines, such as, for example, PIV5-Rabies Virus (for animals), PIV5-PCV (Porcine Circovirus), PIV5-PRRSV (Porcine reproductive and respiratory syndrome virus), and PIV5-Swine-influenza virus. For example, PIV5-based HIV vaccine candidates have been generated and tested in tissue culture cells, as shown in FIGS. 10A-10C.

Example 2

Evaluating a Parainfluenza Virus 5-based Vaccine in Host with Pre-Existing Immunity Against Parainfluenza Virus 5

A critical question concerning the use of PIV5 as a vector is whether prior exposure to PIV5 would prevent the use of PIV5-based vaccines. In this example, the immunogenicity of a recombinant PIV5 expressing hemagglutinin (HA) of influenza A virus subtype 3 (rPIV5-H3) was examined in dogs that were immunized against PIV5. It was found that vaccination of the dogs containing neutralizing antibodies against PIV5 with rPIV5-H3 generated immunity against influenza A virus, indicting that PIV5-based vaccine is immunogenic in dogs with prior exposure. Furthermore, exposure of PIV5 in human populations was examines. Neutralizing antibody (nAb) against PIV5 has been detected in 13 out of 45 human serum samples (about 29 percent). The nAb titers in humans were lower than that in vaccinated dogs, suggesting that nAb in humans is unlikely to prevent PIV5 from being an efficacious vector in humans.

It is believed that PIV5 may contribute to kennel cough in dogs (Binn et al., 1967, *Proc Soc Exp Biol Med*; 126:140-145; Rosenberg et al., 1971, *Am J Epiclemiol*; 94:147-165; Cornwell et al., 1976, *Vet Rec*; 98:301-302; McCandlish et al., 1978, *Vet Rec*; 102:293-301; and Azetaka and Konishi, 1988, *Nippon Juigaku Zasshi*; 50:851-858). Even though infection of dogs with PIV5 did not lead to kennel cough (Chladek et al., 1981, *Am J Vet Res*; 42:266-270; and Kontor et al., 1981, *Am J Vet Res*; 42:1694-1698), kennel cough vaccines containing live attenuated PIV5 have been used on dogs over 30 years. Dogs are vaccinated intranasally and dogs often sneeze during the vaccination, exposing veterinary workers and owners as well. The wide use of kennel cough vaccines that contain live PIV5 suggests that PIV5 may be a safe vaccine in humans. A single dose inoculation of recombinant PIV5 expressing hemagglutinin (HA) of subtype 3 (H3) protected against influenza virus challenge in mice (Tompkins et al., 2007, *Virology*; 362:139-150 and a single dose vaccination as low as 1,000 plaque forming units (PFUs) of a recombinant PIV5 expressing HA of H5N1 protected lethal challenge by highly pathogenic avian influenza virus H5N1 in mice (see Example 3 and Li et al., 2012, *J Virol*; 87(1):354-62).

One critical question concerning the use of PIV5 as a vector is whether prior exposure to PIV5 would prevent the use of PIV5-based vaccine. This example examined efficacy of a recombinant PIV5 expressing HA (PIV5-HA) of influenza virus in dogs that were immunized against PIV5. Furthermore, this example examined exposure of PIV5 in humans.

Materials and Methods

Virus and cells. MDBK, BHK21 and Vero cells were grown in Dulbecco's modified Eagle medium (DMEM) (Invitrogen) containing 10% fetal bovine serum (FBS) and 100 IU/ml penicillin-100 μg/ml streptomycin. The rPIV5-H3 virus was constructed as previously described (Tompkins et al., 2007, *Virology*; 362:139-150), which contains influenza A virus (A/Udorn/72, H3N2 subtype) hemagglutinin (HA) gene. The PIV5 viruses were grown in MDBK cells for 4 to 5 days using DMEM containing 2% FBS and the virus titers were examined by plaque assay on BHK21 cells as previously reported (He et al., 1997, *Virology*; 237:249-260). Briefly, the BHK21 cells in 6-well plates were infected with serially diluted virus ($1:10^1$ to $1:10^7$). After 2 hours (h), the inoculating mixture was removed and replaced with 4 ml DMEM containing 2% FBS, 100 IU/ml penicillin, 100 μg/ml streptomycin, and 1% low-melting-point agarose. The plaques were counted at 4 to 6 days post infection (dpi). Two replicates for each time point were set for titer calculation. The mumps virus, Jeryl Lynn (JL) vaccine strain, was grown in Vero cells and was harvested at 4 to 7 dpi. Virus titer was measured in Vero cells by plaque assay as described previously (Xu et al., 2011, *Virology*; 417:126-136). The influenza A/Udorn/72 virus was grown in eggs (Paterson and Lamb, 1993, The molecular biology of influenza viruses and paramyxoviruses. In: Davidson A, Elliott RM, editors. Molecular Virology: A Practical Approach. Oxford: IRL Oxford University Press. pp. 35-73).

To purify the PIV5 and mumps virus for ELISA assay, viruses in the cleared supernatant were pelleted in a Thermo Scientific ultracentrifuge Type F40L-8×100 rotor at 37,000 rpm for 1 h. The pellets were then resuspended in TNE buffer (10 mM Tris [pH 7.4], 100 mM NaCl, 1 mM EDTA) and loaded onto 10% to 80% sucrose gradient and centrifuged in a TH-641 rotor for 1 h at 37,000 rpm. The virus bands were collected and pelleted in a F40L-8×100 rotor for 1 h at 37,000 rpm. The purified viruses were resuspended in phosphate buffered saline (PBS) buffer (pH 7.4).

Ethic statement about animal use. This study was carried out in strict accordance with the recommendations in the Guide for the Care and Use of Laboratory Animals of the National Institutes of Health. The protocol was approved by the Committee on the Ethics of Animal Experiments of the University of Georgia (Permit Number: A2011 12-012-Y1-A3). All efforts were made to minimize suffering. Dogs used in this study were housed and cared for in accordance with The Guide for the Care and Use of Laboratory Animals (eighth edition).

Infection of dogs with PIV5 or rPIV5-H3. Purpose-bred dogs utilized in this study were purchased from Covance Research Products (482 Frenchs Store Road, Cumberland, Va.). In the first experiment, a total of eight PIV5 vaccine naive beagles at age of 3 months were divided into two groups, four dogs each infected intranasally (IN) with PIV5 or rPIV5-H3. The dogs were sedated but not anesthetized with Acepromazine (PromAce, Fort Dodge, Iowa) at a dose of 0.05-0.1 mg/kg intramuscularly for vaccination, and for blood collection and nasal swabs as needed. Blood samples were collected on day 0 (prebleed) and on day 21 after infection. Sera were separated from the blood samples and stored at −20° C. Nasal swabs were obtained at 3 and 5 days post infection (dpi). In the second experiment, eight PIV5 vaccinated beagles at age of 5 months were separated into a PBS control group (n=2) and rPIV5-H3 group (n=6) immunized via the intranasal route. The dogs were bled on 0 and 21 days following immunization. Nasal swabs were obtained at 3 and 5 dpi. Each IN immunization involved administration of 1 mL of PBS or rPIV5-H3 containing $8 \times 10^7$ plaque forming unit (PFU).

Detecting virus using RT-PCR. To obtain nasal swab from dogs, a polyester-tipped flexible aluminum-shafted applicator (Puritan, Me., USA) was inserted into the naris until resistance was felt at the nasopharynx, then rotated 180 degrees and withdrawn. The swab applicator was removed and absorbent swab was placed into a vial containing 0.5 mL of DMEM with 2% FBS. Vials were stored at −70° C. The specimens were vortexed, and a 140 μL volume was used for total RNA extraction using the QIAamp viral RNA extraction mini kit (Qiagen, Calif.) according to the manufacturer's instructions. RT-PCR was performed as described before (Sun et al., 2011, *J Virol;* 85:8376-8385). Briefly, 11 μL of purified RNA template in 30 μL total volume was amplified in a 20 μL reaction volume using Superscript III reverse transcriptase (Invitrogen) to generate virus cDNA. Random primers were used in RT, while gene specific primers PN-F1 and M-R1 annealing to the PIV5 P/V and M gene of the genomic RNA were used in PCR. PN-F1 primers was 5'-CCAGTGAGGCTCAGCTAATTGACCTC (SEQ ID NO:3) and M-R1 primer was 5'-GGTATTCCCCC-GATCCTGTTCGTAG) (SEQ ID NO:4). 5 μL of the cDNAs in 20 μL total volume from RT were used for PCR in a 50 μL reaction volume. Relative levels of viral genome were compared to viral genome levels of PIV5 virus with known titer.

ELISA. PIV5 or mumps virus-specific antibody titers were determined by Enzyme-linked immunosorbent assays (ELISAs). Ninety-six-well ELISA plates (Thermo Scientific), coated overnight with 100 μl/well of 100 ng purified whole PIV5 virus proteins in PBS (pH 7.4), were blocked first with 0.5% BSA and 0.5% nonfat dry milk in washing solution (KPL) for 1 h and then washed three times with KPL wash solution. Serial dilutions of sera from dogs or humans were prepared in blocking buffer, and incubated for 1 h at room temperature. The plates were washed three times and incubated for 1 h with a 1:2,000 dilution of an secondary antibody, horseradish peroxidase (HRP)-conjugated goat anti-dog IgG (Santa Cruz, Calif.) or goat anti-human IgG (KPL, Gaithersburg, Md.). The plates were washed three times and developed with SureBlue TMB 1-Component Microwell Peroxidase Substrate (KPL). The development was stopped by the addition of equal volume of 1N HCl, and optical density (OD) was read at 450 nm using a BioTek plate reader. ELISA endpoint titers were defined as the highest serum dilutions at which the mean OD values of duplicate wells were >2-fold above the mean OD value plus 2 standard deviations (SD) for sera.

Determining neutralizing antibody (nAb) titers against PIV5. PIV5 neutralizing antibody titers were measured in serum samples by virus neutralizing assay. Sera were serially diluted in 50 μl DMEM containing 2% FBS. 200 $TCID_{50}$ of PIV5 virus was added to diluted sera and incubated for 2 h at 37° C. Serum and virus were added to 96-well microtiter plates containing 90-100% confluent MDBK cells and incubated at 37° C. for 3 days. Individual wells were examined by indirect immunofluorescence assay (IFA). Cells were fixed with 3.7% formaldehyde in PBS (pH 7.4) for 10 min, and then permeabilized with 0.1% Triton X-100 plus 1% FBS in PBS for 30 min at room temperature. Fixed cells were incubated for 1 h with primary antibody (mouse anti-PIV5 NP antibody at dilution of 1:400) at 37° C. FITC-conjugated goat anti-mouse (1:400 dilution; KPL, Inc.) was used as the secondary antibody. The neutralizing antibody titer was the highest serum dilution completely neutralizing 200 $TCID_{50}$ of PIV5 virus.

HAI assay. The hemagglutination inhibition (HAI) assay was performed according to the WHO Manual on Animal Influenza Diagnosis and Surveillance (WHO (2002) Manual on Animal Diagnosis and Surveillance). Briefly, chicken red blood cells (cRBCs) were washed and resuspended to a final concentration of 0.5% in PBS. The influenza A virus (A/Udorn/72, H3N2 subtype) was adjusted to 4 hemagglutination units (HAU) per 25 μl in PBS. In 96-well round-bottom plates, 25 μl of individual RDE-treated serum samples were serially diluted in a two-fold manner. After preparing serial dilution of sera, 25 μl (4 HAU) of the diluted virus was added. The plate was gently mixed and incubated at room temperature for 1 h. Then 50 ul of 0.5% cRBCs were added to each well, gently mixed, and incubated at room temperature for 30-45 minutes. The hemagglutination was scored by tilting the plate at a 45 degree angle. The HAI titer is the reciprocal of the last dilution antiserum that completely inhibits hemagglutination.

Human serum samples. Human blood samples were collected from 45 random volunteers. Participants were healthy, non-pregnant, 18-50 years old and weighed more than 110 pounds. Volunteers signed informed consent forms. The volunteers were anonymous. No personal data were collected. The human subjects protocol was approved by The University of Georgia (UGA) Institutional Review Board. 10 mL venous blood was drawn by venipuncture into a 10 mL tube without anticoagulant. After clotting, blood samples were centrifuged at 400 g for 5 min. Cell-free supernatants were filtered through 0.22 μm pore size filter units and were used as serum. Serum samples were stored at −80° C.

Statistical analysis. In this study, the correlation analysis of antibodies for PIV5 and JL was performed using the Pearson correlation method. $OD_{450}$ readings at 1:320 was chosen because the readings were in the linear range of sera dilution. The analysis was done with the use of cor.test function in the statistical package R (Team RDC (2003) The R project for statistical computing University of Wisconsin, Madison, Wis.). The statistical significant difference was considered when p-value was less than 0.05. The result indicates that there is no significant correlation between PIV5 and JL with Pearson's r equals 0.06 (p-value=0.6941).

Results

Infection of "naive" dogs with PIV5 and rPIV5-H3. While additional examples included herewith indicate that rPIV5-

Figure 11A:
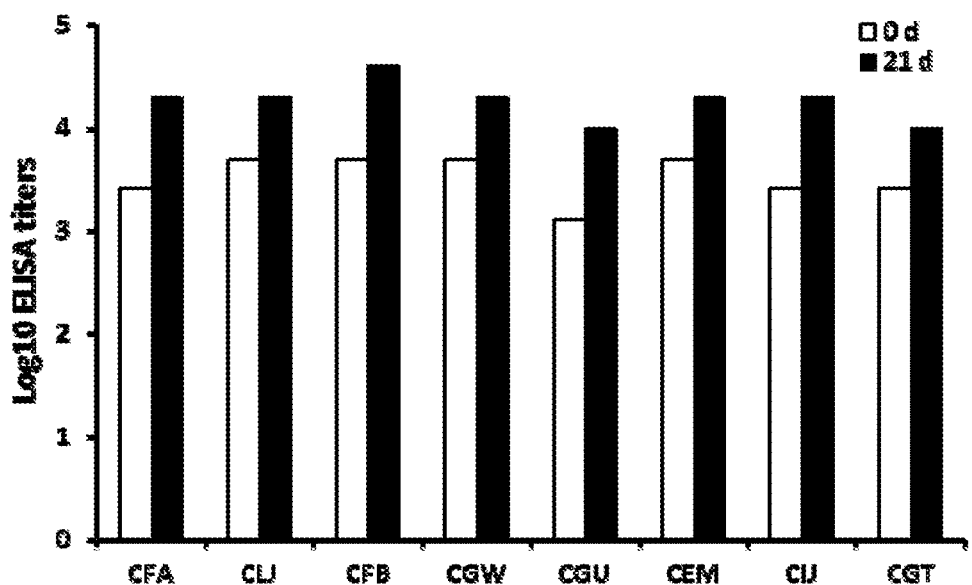
FIGS. 11A and 11B show titers of anti-PIV5 antibodies in dogs without PIV5 exposure. Eight PIV5 naive dogs were immunized with one dose of $8 \times 10^7$ PFU of PIV5 or rPIV5-H3 viruses by intranasal route. The dogs were divided into two groups: PIV5-infected dogs and rPIV5-H3-infected dogs. Blood samples were collected at 0 and 21 days post infection for ELISA (FIG. 11A) and virus neutralization antibody (nAb) assay (FIG. 11B). The grey columns indicate that the PIV5 nAb titer is less than 10, the limit of detection in this assay. The black columns indicate that the nAb titer is equal to or higher than 10.
Figure 11B:
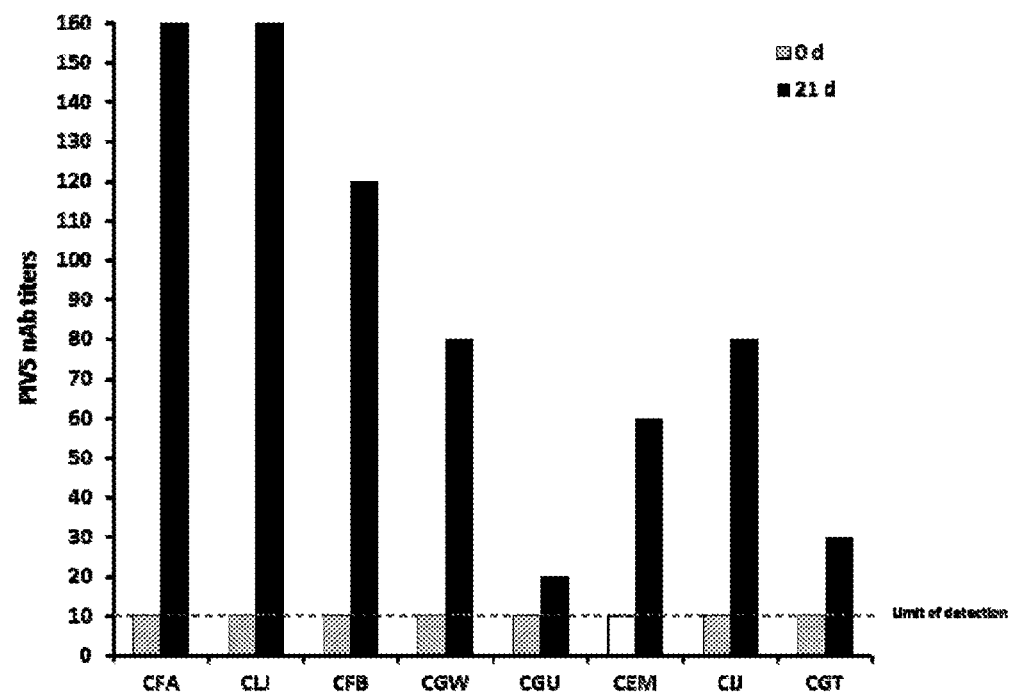
Figures 12A, 12B:
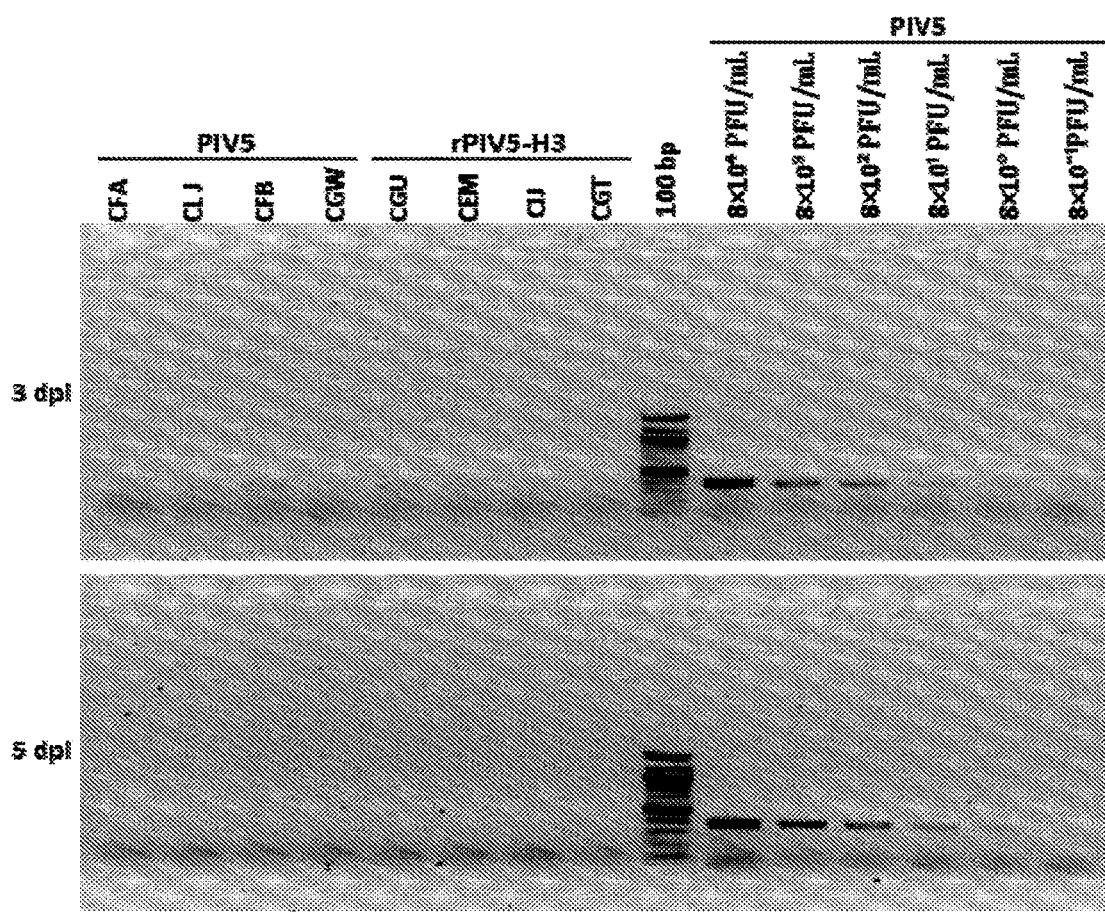
FIGS. 12A and 12B show replication of PIV5 in dogs without PIV5 exposure. The nasal swabs of dogs were collected at 3 and 5 days post infection, and placed into a vial containing 0.5 mL of DMEM with 2% FBS.
Figure 13:
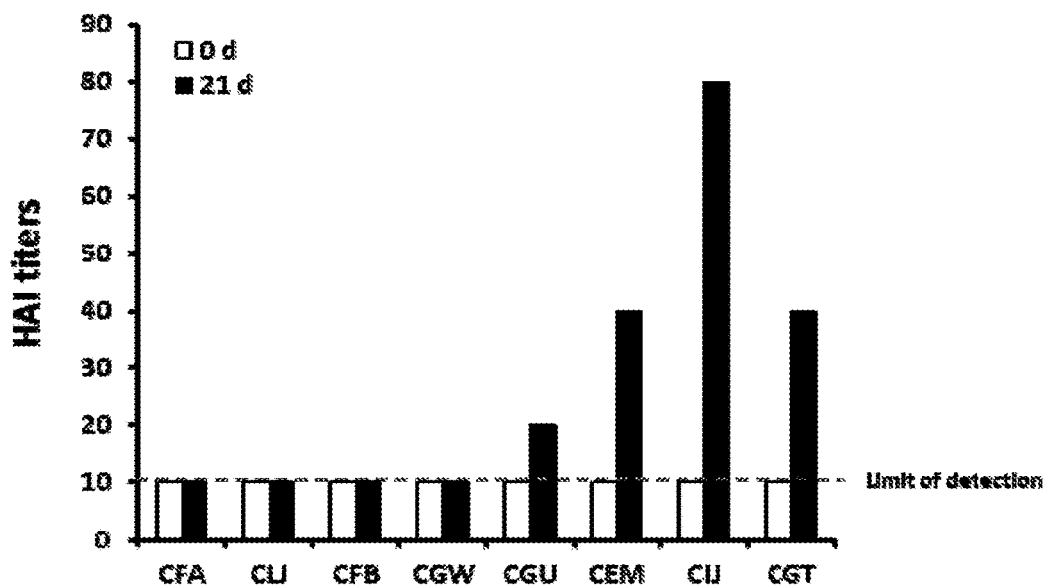
FIG. 13 shows immune responses in the PIV5 naive dogs inoculated with rPIV5-H3. The dog blood samples were collected at 0 and 21 days post infection. 4 HAU of the influenza A virus (A/Udorn/72, H3N2 subtype) were mixed with serially diluted dog sera in 96-well round-bottom plates. The hemagglutination inhibition (HAI) titer was scored as the reciprocal of the highest dilution antiserum that completely inhibits hemagglutination. The graph shows the mean value of duplicate wells for each dog. The limit of detection of the HAI titer (10) is indicated.

H3 is effective in generating immunity in mice against influenza virus, it is not clear whether the same virus can be effective in generating immunity in dogs. Thus, dogs were inoculated with rPIV5-H3 via intranasal route, and determined replication of virus in dogs and measured immune responses to the virus. Dogs are routinely vaccinated with vaccines containing live PIV5 at a young age (as early as 3-week old). Through an arrangement with the animal vendor, 8 dogs at 12-week of age without vaccination of live PIV5 were obtained. The titers of PIV5 antibodies in these dogs were determined using ELISA and neutralization assay. All dogs were positive to PIV5 in ELISA (FIG. 11A). However, neutralization antibody (nAb) titers were undetectable (FIG. 11B). The dogs (n=4) were infected with PIV5 or rPIV5-H3 via intranasal (IN) route. At 3 and 5 days post infection, nasal swabs were taken from infected dogs, and assayed for existence of viruses. While no virus was detected when the swabs were analyzed using plaque assay (FIG. 12), RT-PCR products were detected in 7 of 8 dogs at 3 days post infection (dpi) and very weak RT-PCR signals were detected in 5 of 8 dogs at 5 dpi, suggesting that limited replication of PIV5 in naris of infected dogs at 3 days post-infection and the infection was being cleared at 5 days post-infection. The dogs were bled at 21 days post infection. Increases in anti-PIV5 titers were detected in all dogs, suggesting that the dogs were infected. Measurement of anti-HA titers using HAI assay indicated that all rPIV5-H3 inoculated dogs seroconverted and had HAI titers at average 42.5 (range from 20 to 80) at 3-week post-infection (FIG. 13). No HAI was detected in dogs-inoculated with PIV5.

Figure 14A:
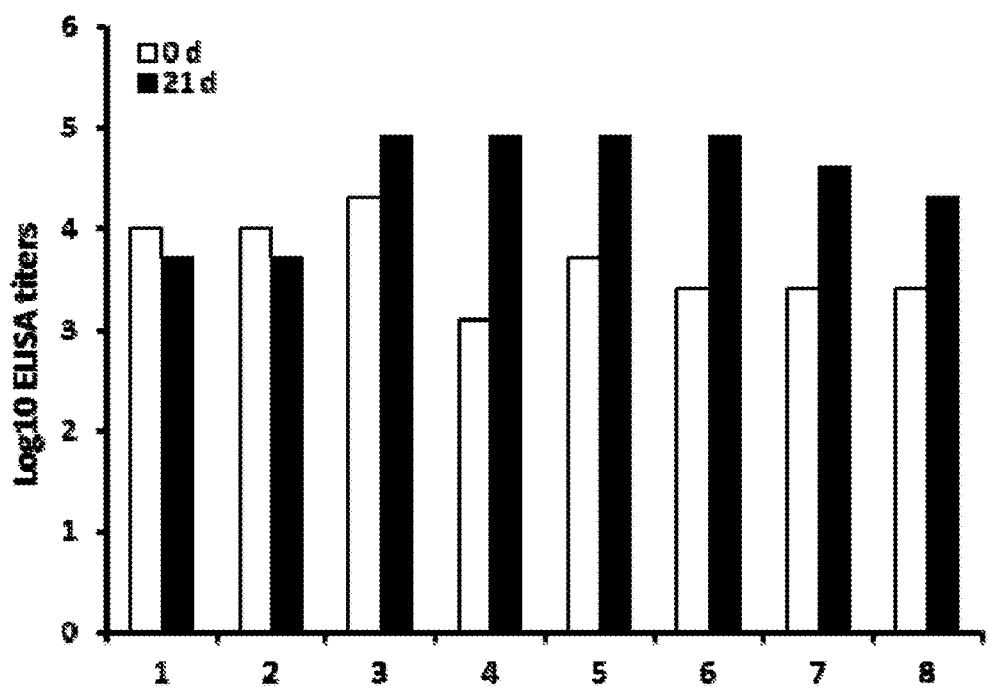
FIGS. 14A and 14B show titers of anti-PIV5 antibodies in the PIV5-vaccinated dogs. Eight dogs which had been vaccinated with live PIV5 were immunized with one dose of $8 \times 10^7$ PFU of rPIV5-H3 viruses in 1 mL or PBS via intranasal route. The dogs were divided into two groups: two dogs received PBS; the remaining six dogs received rPIV5-H3. Blood samples were collected at 0 and 21 days post infection for ELISA (FIG. 14A) and viral neutralization antibody assay (FIG. 14B). Data were presented as average value of duplicate wells. In the neutralization antibody assay, the white column indicates the PIV5 nAb titer is equal to or higher than 10.
Figure 16:
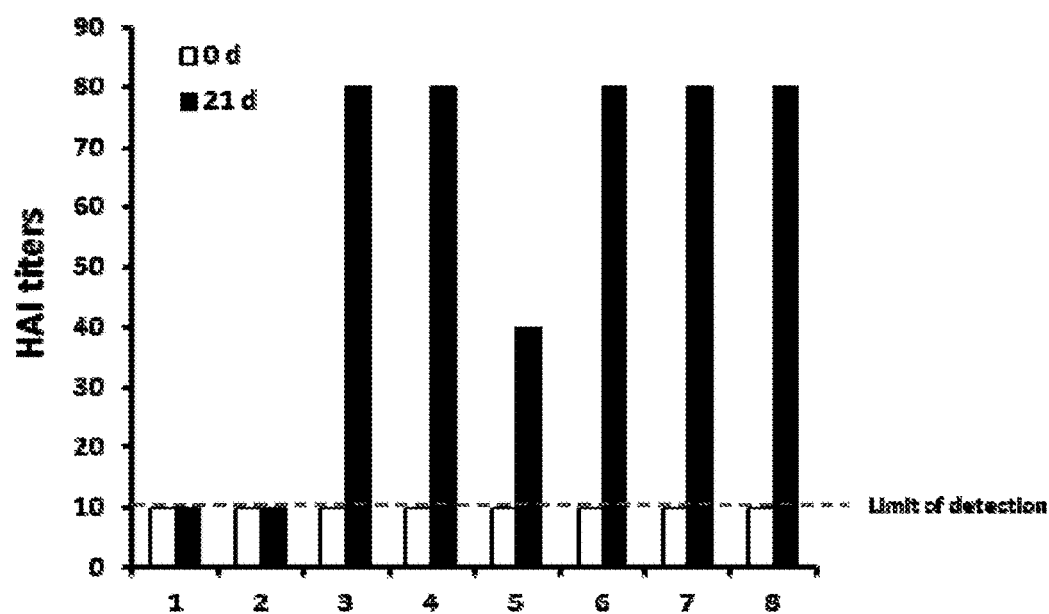
FIG. 16 shows immune responses in the PIV5-vaccinated dogs inoculated with rPIV5-H3. The dog blood samples were collected at 0 and 21 dpi. Anti-PIV5 and anti-HAI titers were determined using the same approach as in FIG. 13.

Infection of dogs with exposure to PIV5 with PIV5-HA. To examine whether dogs with prior exposure with PIV5 can still be vaccinated with recombinant PIV5-based vaccines, dogs were obtained that were vaccinated against PIV5 multiple times and had anti-PIV5 neutralizing antibodies (FIG. 14). The dogs were infected with rPIV5-H3 via IN route. No virus was detected using plaque assay at 3 and 5 dpi in naris of infected dogs. One out of eight dogs tested positive using RT-PCR at 3 dpi (FIG. 15). Dogs were then bled at 3 weeks post-infection. The dogs vaccinated with rPIV5-H3 had HAI titers ranging between 40 to 80 (average 77, 1 at 40 and 5 at 80) (FIG. 16), indicating that rPIV5-H3 vaccination generated immunity against influenza virus (a 4-fold increase of HAI titer or a HAI titer of 40 is considered protective against influenza virus infection). The nAb titers against PIV5 also increased in rPIV5-H3-infected dogs, confirming the infection of the dogs with rPIV5-H3.

Figure 17A:
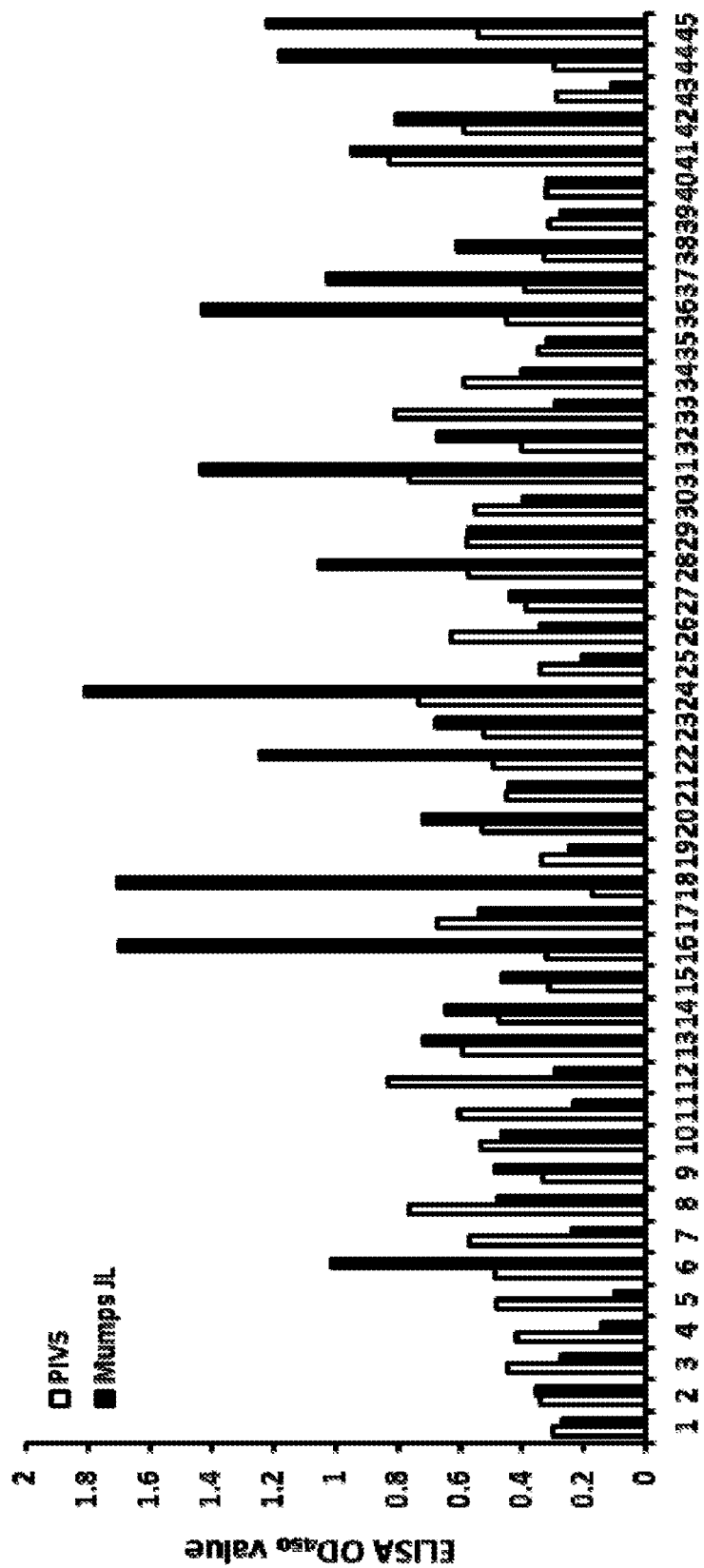

Exposure to PIV5 in humans. As reported before, anti-PIV5 antibodies have been detected in humans (Goswami et al., 1984, J Gen Virol; 65:1295-1303; and Goswami et al., 1987, Nature; 327:244-247). To determine whether the anti-PIV5 in humans is due to cross-reactivity from antibody against closely related paramyxoviruses, antibody titers of PIV5 and mumps virus were examined in human sera. Mumps virus (MuV) is most closely related to PIV5 as they have same genome structure. Since mumps virus exposure in humans is close to 100 percent due to vaccination and natural infection in the US, the detection of anti-mumps virus antibodies was expected in all our samples that were collected from 18 to 50-year old in the US. All 45 samples were positive for mumps virus as expected (FIG. 17A). Interestingly, all sera were positive for PIV5 antigen as well on ELISA (FIG. 17A). If reactivity to PIV5 antigen in human sera came from cross-reactivity from anti-mumps virus, titers of anti-PIV5 should correlate to the titers of anti-mumps virus. However, statistical analysis indicated there is no correlation between the titers of anti-MuV in serum and the titers of anti-PIV5 in serum, suggesting that the reactivity of human sera to PIV5 is not due to cross reactivity from mumps virus. Furthermore, titers of nAb against PIV5 were examined in human sera and anti-PIV5 nAb was detected in 13 out of 45 samples (about 29 percent) (FIG. 17B).

Discussion

Since the discovery of PIV5, many diseases in humans were associated with PIV5, which all were ultimately proved false. In retrospect, several possible explanations exist for why PIV5 may have been linked to these diseases. One is based on the conditions used for virus isolation in the human studies, i.e. the labs used monkey cell lines which can be persistently infected with PIV5, and these cells often show no detectable cytopathic effects (Hsiung, 1972, Prog Med Virol; 14:241-274; and Chatziandreou et al., 2004, J Gen Virol; 85:3007-3016). Another possibility is antigen cross-reactivity of PIV5 to ubiquitous paramyxoviruses such as mumps virus, which are closely related to PIV5 and have almost 100 percent exposure in human population (Randall and Young, 1988, J Gen Virol; 69(Pt 8) 2051-2060; Tsurudome et al., 1989, Virology; 171:38-48; and Komada et al., 1991, Arch Virol; 116:277-283). This example examined exposure of PIV5 in human populations and found anti-PIV5 antibodies in human sera. Interestingly, a correlation between titers of anti-mumps virus and anti-PIV5 was not detected, suggesting that PIV5-positive humans, at least some of them, might have been exposed to PIV5. About 29% of the human serum samples had neutralizing antibodies against PIV5. Some of which did not have robust antibody against mumps virus (FIG. 17), suggesting that at least some humans have been exposed to PIV5 separately from mumps virus. It is likely that close contact between dogs and humans may be a contributing factor in exposure of humans to PIV5 from dogs. Dogs are vaccinated intranasally and often sneeze during the vaccination, exposing veterinary workers and owners as well. In addition, PIV5 was detected in naive dogs at 3 dpi using RT-PCR, suggesting that it is possible that vaccinated dogs may shed virus after vaccination, resulting in humans being exposed to the virus. This is consistent with the wide spread use of kennel cough vaccines that contain live PIV5 and that approximately 40% of the US population are dog owners.

It is encouraging that PIV5 antibody is detected in a large percentage of the US population without causing clinical disease, which suggests that PIV5 is safe in human populations. However, because a large percentage of the US population may have been exposed to PIV5, it raises the question whether PIV5 will be an effective vector for vaccine development in humans. The very same problem of prior exposure of vector has created a major obstacle for using adenovirus-based vector for vaccine development. This example found that recombinant PIV5 expressing HA was immunogenic in dogs with pre-existing immunity against PIV5, indicating that PIV5-based vaccine vector can overcome pre-existing immunity. The results were consistent with a previous report that in mice neutralizing antibodies against PIV5 do not prevent PIV5 infection (Young et al., 1990, J Virol; 64:5403-5411). The dog's ability to clear a PIV5 infection remains undetermined. In mice, it is thought that cell-mediated immune responses play a critical role in clearing PIV5 infection (Young et al., 1990, J Virol; 64:5403-5411). Since PIV5 has self-limiting replication in dogs, it is likely that cell-mediated immunity plays a critical role in clearing infection as well. Because it takes time for cell-mediated immunity to respond and be effective, this time period provides a window of opportunity for PIV5- based live vaccine to replicate and generate a robust immune response. This is consistent with the observations that PIV5 infects all kinds of cells, including primary cells (Arimilli et al., 2006, *J Virol;* 80:3416-3427; Tompkins et al., 2007, *Virology;* 362:139-150; and Zhang et al., 2011, *Virology;* 421:67-77).

Figure 14B:
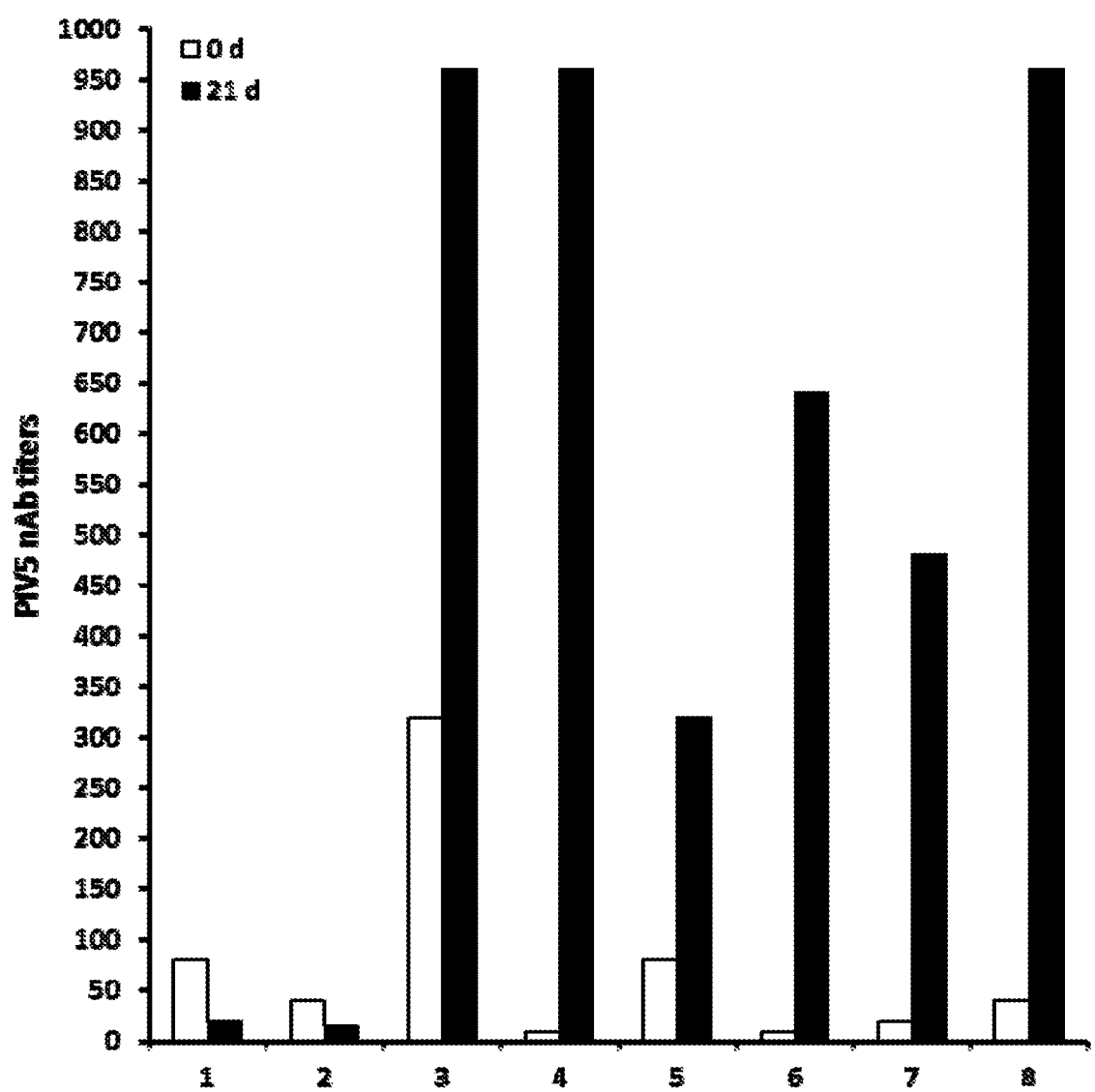

The nAb titers against PIV5 in vaccinated dogs were higher than the "naïve" dogs and were as high as 300 (FIG. 14B). All dogs with nAb against PIV5 seroconverted after a single dose IN inoculation of rPIV5-H3, and the titers of anti-H3 antibody had no correlation to the nAb titters against PIV5, further confirming that nAbs of PIV5 had no predictive value in determining immune responses to a PIV5-based vaccine in dogs. The highest titer of nAb against PIV5 in humans is 60, lower than the titers of nAb against PIV5 in dogs. Thus, neutralizing antibody against PIV5 in humans will likely not prevent PIV5-based vaccine candidates from generating protective immunity.

Outbreaks of canine influenza A virus subtype H3 have occurred in canine populations (Crawford et al., 2005, *Science;* 310:482-485; Daly et al., 2008, *Emerg Infect Dis;* 14:461-464; and Li et al., 2010, *Infect Genet Evol;* 10:1286-1288). The fact that rPIV5-H3 seroconverted dogs and generated immunity that is considered protective suggests that a recombinant PIV5 expressing H3 may be an effective vaccine against canine influenza virus. Furthermore, these results suggest that PIV5 can be a novel vector for expressing other antigens for vaccine development for dogs, other animals and humans.

Furthermore, pigs have been infected with PIV5. While PIV5 was detected in nasal swaps at 5 days post-infection (dpi), PIV5 was not detected in internal organs or tissues at 35 dpi, suggesting that PIV5 did not establish persistent infection in pigs This example has published as Chen et al., "Evaluating a Parainfluenza Virus 5-Based Vaccine in a Host with Pre-Existing Immunity against Parainfluenza Virus 5," *PLoS One;* 2012; 7(11):e50144, doi: 10.1371/journal.pone.0050144, Epub 2012 Nov. 20, which is incorporated by reference herein in its entirety.

Example 3

Recombinant Parainfluenza Virus 5 Expressing HA of Influenza A Virus H5N1 Protected Mice Against Lethal High Pathogenic Avian Influenza H5N1 Challenge A safe and effective vaccine is the best way to prevent large-scale high pathogenic avian influenza virus (HPAI) H5N1 outbreaks in the human population. Currently FDA-approved H5N1 vaccine has serious limitations. A more efficacious H5N1 vaccine is urgently needed. As shown herein, a single dose of a live recombinant PIV5 expressing a HA gene of H5N1 (rPIV5-H5) from the H5N1 subtype provided sterilizing immunity against lethal dose of HPAI H5N1 infection in mice. Furthermore, with examination of the effect of insertion of H5N1 HA at different locations within the PIV5 genome on efficacy of PIV5-based vaccine, it was shown that insertion of H5N1 HA between the leader sequence, the de facto promoter of PIV5, and the first viral gene, NP, did not lead to a viable virus. Insertion of H5N1 HA between NP and the next gene V/P led to a virus that was defective in growth. The insertion of H5N1 HA at the junction between the SH gene and the HN gene gave the best immunity against HPAI H5N1 challenge: a dose as low as 1000 plaque forming unit (PFU) was sufficient to protect against lethal HPAI H5N1 challenge in mice. Thus, recombinant PIV5 expressing H5N1 HA has great potential as HPAI H5N1 vaccine. This example tested the effectiveness of recombinant PIV5 viruses with HA transgenes inserted in sequentially at sites proximal to the leader sequence. Moreover, PIV5 was used to express the HA of H5N1 highly pathogenic avian influenza (HPAI) virus and tested their effectiveness as vaccine candidates in an established mouse model of lethal HPAI challenge.

Materials and Methods

Cells. Monolayer cultures of BSR T7 cells were maintained in DMEM containing 10% fetal bovine serum (FBS), 10% tryptose phosphate broth (TPB) and 400 µg/ml G418. Monolayer cultures of Vero cells, MDBK cells, MDCK cells and BHK cells were maintained in DMEM containing 10% FBS, 100 IU/ml penicillin, and 100 µg/ml streptomycin. All cells were incubated at 37° C., 5% $CO_2$. Virus-infected cells were grown in DMEM containing 2% FBS. Plaque assays of PIV5 were performed using BHK cells and plaque assays of influenza virus were performed using MDCK cells.

Influenza viruses. Influenza A viruses used include VNH5N1-PR8/CDC-RG (H5N1; rgVN-PR8 provided by Dr. Ruben Donis, CDC, Atlanta, Ga.) and A/Vietnam/1203/04 (H5N1; provided by Richard Webby, St. Jude Children's Research Hospital, Memphis, Tenn.). A/VN-PR8 was propagated in the allantoic cavity of embryonated hen eggs at 37° C. for 48-72 hours. β-propiolactone (BPL)-inactivated A/Vietnam/1203/04 was provided by Richard Webby from St. Jude Children's Research Hospital (Memphis, Tenn.). A/Vietnam/1203/04 was propogated in the allantoic cavity of embryonated hen eggs at 37° C. for 24 hours. All viruses were aliquoted and stored at −80° C. All experiments using live, highly pathogenic avian influenza viruses were reviewed and approved by the institutional biosafety program at the University of Georgia and were conducted in biosafety level 3, enhanced containment following guidelines for use of Select Agents approved by the CDC.

Mice. Female 6 to 8 week old BALB/c mice (Charles River Labs, Frederick, Md.) were used for all studies. Mouse immunizations and studies with BSL2 viruses were performed in enhanced BSL2 facilities in HEPA filtered isolators. Mouse HPAI infections were performed in enhanced BSL3 facilities in HEPA filtered isolators following guidelines approved by the institutional biosafety program at the University of Georgia and for use of Select Agents approved by the CDC. All animal studies were conducted under protocols reviewed and approved by the Institutional Animal Care and Use Committee of the University of Georgia.

Construction of recombinant plasmids. To generate ZL48 (rPIV5-H5-HN/L) plasmid, the coding sequence of GFP in the plasmid BH311 containing full length genome of PIV5 and an extra EGFP gene insertion between HN and L gene was replaced with a HA gene of H5N1. To generate ZL46 (rPIV5-H5-SH/HN), ZL209 (rPIV5-H5-NP/VP), ZL215 (rPIV5-H5-Le/NP) plasmids, the plasmid BH276 containing full length genome of PIV5 was used as the vector. To generate ZL47 (rPIV5-H5-VP/M) plasmid, the plasmid pSV5-M-NS containing full length genome of PIV5 was used as the vector. The plasmid containing H5N1 HA gene without cleavage site was used as DNA template for PCR amplification using appropriate oligonucleotide primer pairs.

Rescue and sequence recombinant PIV5. The rescue of infectious recombinant PIV5 was performed as described before (He et al., 1997, *Virology;* 237:249-260). Briefly, the plasmids, pZL48 encoding full length genome of PIV5 with HA gene insertion between HN and L gene, pZL46 encoding full length genome of PIV5 with HA gene insertion between SH and HN gene, pZL47 encoding full length genome of PIV5 with HA gene insertion between V/P and M gene, pZL209 encoding full length genome of PIV5 with HA gene insertion between NP and V/P gene, or pZL215 encoding full length genome of PIV5 with HA gene insertion between Leader and NP gene, and three helper plasmids pPIV5-NP, pPIV5-P, and pPIV5-L encoding NP, P, and L proteins, were co-transfected into BSR T7 cells at 95% confluency in 6-cm plates with Plus and Lipofectamine (Invitrogen). The amounts of plasmids used were as follows: 5 μg pZL48/ZL46/ZL47/ZL209/ZL215, 1 μg pPIV5-N, 0.3 μg pPIV5-P, and 1.5 μg pPIV5-L. After 3 h incubation, the transfection media were replaced with DMEM containing 10% FBS and 10% TPB. After 72 h incubation at 37° C., the media were harvested, and cell debris was pelleted by low speed centrifugation (3,000 rpm, 10 min). Plaque assays were used to obtain a single clone of recombinant viruses. The full length genome of plaque-purified single clone of ZL48, ZL46, ZL47, and ZL209 viruses were sequenced as previously described (Sun et al., 2009, *PLoS Pathog;* 5:e1000525; and Sun et al., 2011, *J Virol;* 85:8376-8385). Total RNAs from the media of ZL48, ZL46 ZL47 and ZL209 viruses-infected Vero cells were purified using the viral RNA extraction kit (Qiagen Inc, Valencia, Calif.). cDNAs were prepared using random hexamers and aliquots of the cDNA were then amplified in PCR reactions using appropriate oligonucleotide primer pairs.

Growth of recombinant PIV5 in vitro and in vivo. MDBK cells in 6-well plates were infected with PIV5, ZL48, ZL46 or ZL47 at an MOI of 0.1. The cells were then washed with PBS and maintained in DMEM-2% FBS. Media was collected at 0, 24, 48, 72, 96 and 120 hpi. The titers of viruses were determined by plaque assay on BHK cells.

To compare the growth of viruses in mice, wild type BALB/c mice of 6 weeks old were infected with $10^6$ pfu of PIV5, ZL48, ZL46 or ZL47 in 100 1 volume intranasally. Mice were euthanized on 4 days post infection and the lungs were collected to determine virus titers.

Detection of protein expression. Immunoblotting was performed on MDBK cells in 6-well plates that were infected with PIV5 and ZL48 at an MOI of 5. At 24 hpi, the cells were lysed with whole-cell extract buffer (WCEB) (50 mM Tris-HCl [pH 8], 280 mM NaCl, 0.5% NP-40, 0.2 mM EDTA, 2 mM EGTA, and 10% glycerol). The lysates were run on SDS-PAGE gel and immunoblotted with anti-H5N1 HA and anti-PIV5 antibody.

Immunofluorescence of H5N1 HA expression was carried out in MDBK cells in 24-well plates that were infected with PIV5 and ZL48 at an MOI of 0.1. At 2 dpi, the cells were washed with PBS and then were fixed in 0.5% formaldehyde. The cells were permeabilized in 0.1% PBS-Saponin solution, incubated for 30 min with polyclonal anti-PIV5-VP or anti-H5N1 HA at 1:200 dilution, then FITC-labeled goat anti-mouse antibody was added to the cells. The cells were incubated for 30 min and were examined and photographed using a Nikon FXA fluorescence microscope.

Expression levels of H5N1 HA in virus-infected cells was compared using MDBK cells in 6-well plates that were mock infected or PIV5, ZL48, ZL46 or ZL47 at an MOI of 1. The cells were collected at 24 hpi and fixed with 0.5% formaldehyde for one hour. The fixed cells were pelleted by centrifugation and then resuspended in 500 μl of solution containing fetal bovine serum (FBS)-DMEM (50:50). The cells were permeabilized in 70% ethanol overnight. The cells were washed once with PBS and then incubated with mouse anti-H5N1 HA antibody in PBS/1% BSA (1:200) for 1 h at 4° C. The cells were stained with antimouse antibody labeled with phycoerythrin (1:200) for 1 h at 4° C. in the dark and then washed once with PBS/1% BSA. The fluorescence intensity was measured using a flow cytometer.

ELISA. HA (H5N1 HA)-specific serum antibody titers were measured using an IgG ELISA. Immulon 2 HB 96-well microtiter plates (ThermoLabSystems) were coated with 2 μg/m1 recombinant H5N1 HA protein and incubated at 4° C. overnight. Plates were then washed with KPL wash solution (KPL, Inc) and the wells blocked with 200 μl KPL Wash Solution with 5% non-fat dry milk and 0.5% BSA (blocking buffer) for 1 hr at room temperature. Serial dilutions of serum samples were made (in blocking buffer) and transferred to the coated plate and incubated for 1 hr. To detect bound serum antibodies, 100 μl of a 1:1000 dilution alkaline phosphatase-labeled goat anti-mouse IgG (KPL, Inc) in blocking buffer was added per well and incubated for 1 hr at room temperature. Plates were developed by adding 100 μl pNPP phosphatase substrate (KPL, Inc) per and the reaction allowed to develop at room temperature. Optical density (OD) was measured at 405 nm on a Bio-Tek Powerwave XS plate reader. The IgG titer was determined to be the lowest serum dilution with an OD greater than the mean of naive serum plus 2 standard deviations above the mean OD.

Infection of mice with PIV5. For vaccination with PIV5 and rPIV5-H5, $10^6$ PFU PIV5, rPIV5-ZL46, or rPIV5-ZL48 in 50 μl PBS was administered intranasally to mice anesthetized with 2,2,2-tribromoethanol in tert-amyl alcohol (Avertin; Aldrich Chemical Co). For sub-lethal rgVN-PR8 infection, 2000 PFU virus in 50 μl PBS was administered as described for PIV5 vaccination. For BPL inactivated A/VN/1203/04 vaccination, the 256 hemagglutination units (HAU)/ml in 50 μl PBS was then injected into each of the caudal thigh muscles. Blood was collected on day 21 post-immunization. If boosted, this process was repeated on day 28 post-prime. Mice were monitored daily and, for some experiments, body weights recorded every other day.

Measurement of neutralizing antibody titer. Influenza neutralizing antibody titers were measured in serum by a micro-neutralization assay with an ELISA endpoint. Heat inactivated serum was serially diluted in DMEM with 1% BSA, antibiotic/antimycotic, and 1 μg/ml TPCK trypsin. Diluted serum was then incubated 1000 TCID50 rg A/VN-PR8 or rg A/Anhui-PR8 for two hours at 37° C. MDCK cells were then added and incubated at 37° C. for 18-24 hours. At the end of the incubation, wells were fixed with ice cold methanol and acetone (80:20 respectively) and an ELISA was performed as described above. The neutralization titer was determined to be the lowest serum dilution capable of neutralizing 1000 TCID50 rgA/VN-PR8 or rgA/Anhui-PR8, as determined by an OD readout two times above the background OD.

Cellular responses. ELISpot to detect T-cell responses in lymphocytes to inactivated AIVN/1203/04 were performed as described (Tompkins et al., 2007, *Emerg Infect Dis;* 13:426-435). Cells were re-stimulated with inactivated A/VN/1203/04 (the equivalent of 10 HAU per well), Ebola GP P2 EYLFEVDNL as an irrelevant peptide (1 μg/ml), and PMA/ionomycin (25 ng/ml; 1.25 ng/ml respectively) in 50 μl Complete Tumour Medium (CTM). Spots were counted using AID ViruSpot Reader (Cell Technology, Inc).

Infection of mice with influenza A virus. BALB/c mice were first vaccinated with wild type PIV5, rPIV5-ZL46, rPIV5-ZL48 IN, or inactivated A/VN/1203/04 IM as described above. 21 days post-vaccination, the mice were bled for serum analysis via the tail vein. On day 24 post-vaccination, mice were anesthetized and inoculated intranasally with 10 LD$_{50}$ A/Vietnam/1203/04 diluted in 50 μl PBS. Mice were then monitored daily for morbidity and mortality with body weights measured every other day. On day 3 post-challenge, groups of mice were euthanized and their lungs collected into 1.0 ml PBS and homogenized. Homogenate was then cleared by centrifugation. A TCID$_{50}$ assay was then used to determine virus titers in cleared homogenate as described (Soboleski et al., 2011, *PLoS One;* 6:e21937).

Results

Figure 19A:
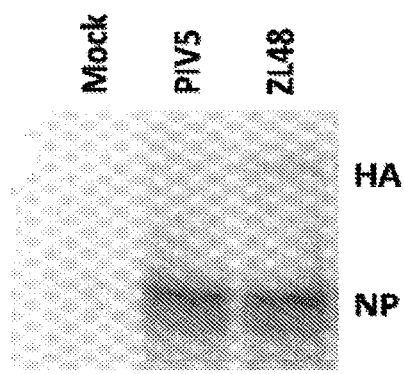
Figure 19B:
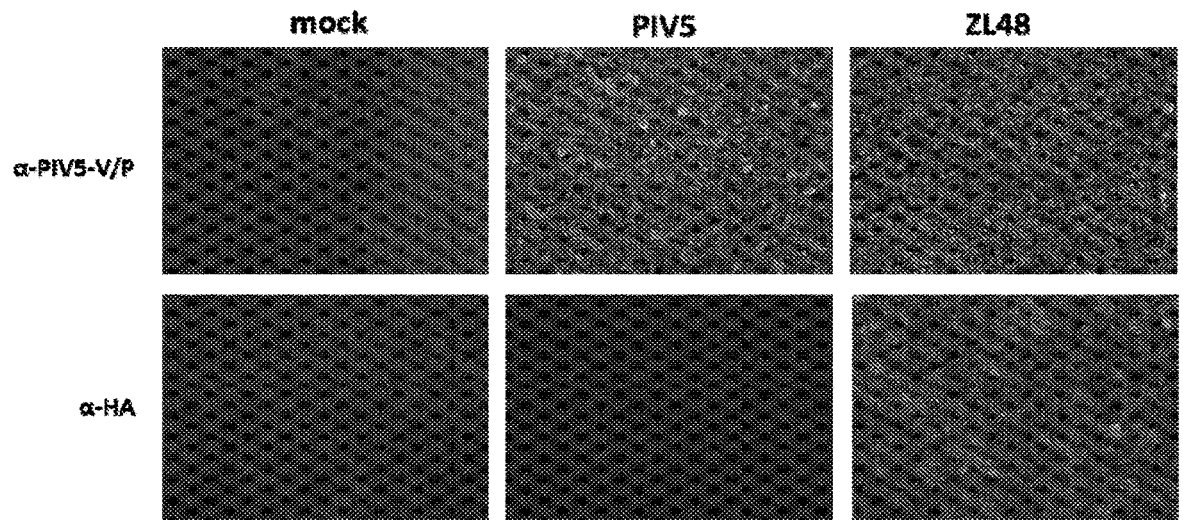
Figures 19C, 20A:
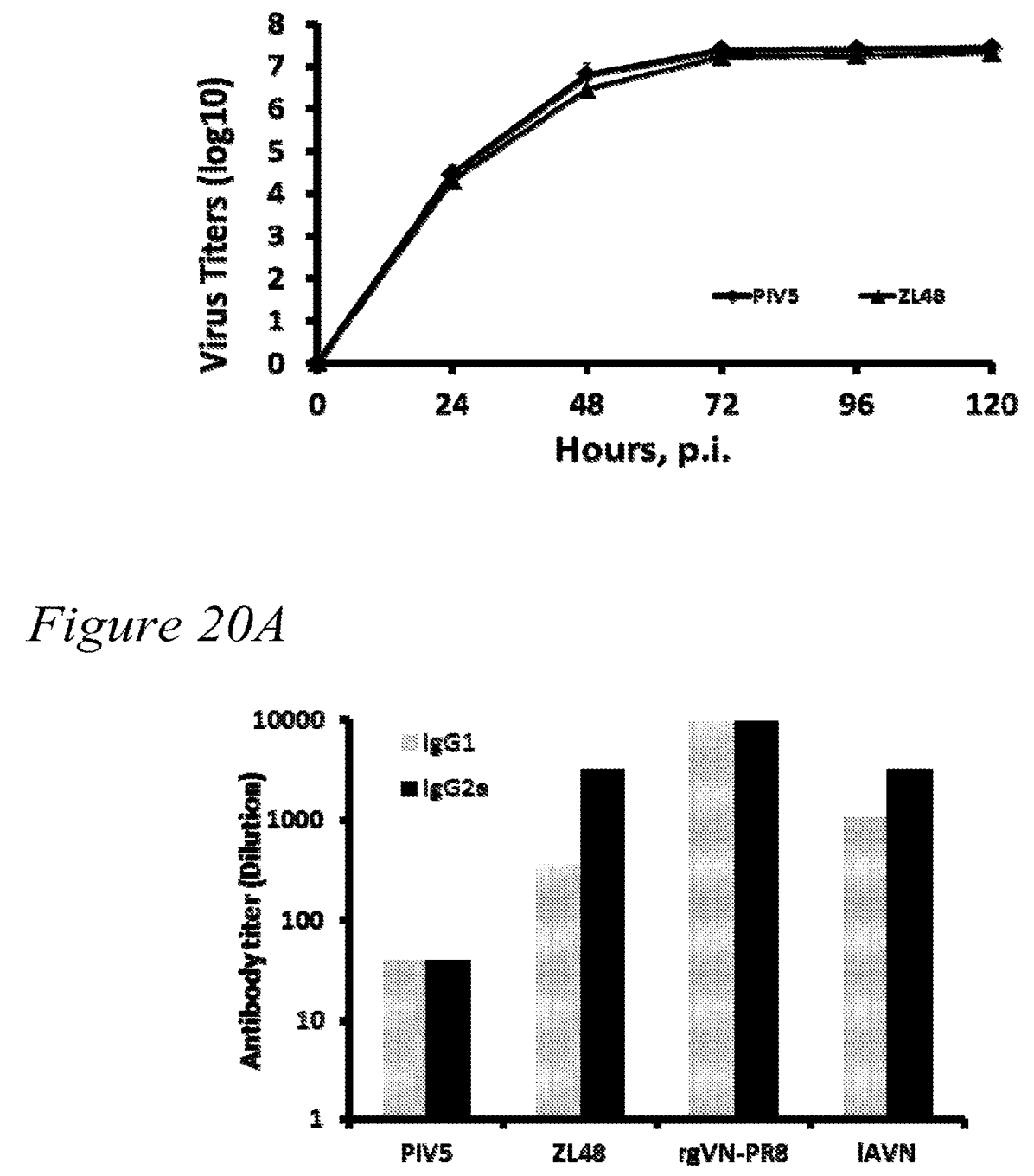

Generating and analyzing recombinant PIV5 expressing HA of H5N1 (rPIV5-H5) in vitro. To test whether recombinant PIV5 expressing HA of H5N1 can protect mice against lethal challenge HPAI H5N1, the HA gene of a HPAI H5N1 without the polybasic cleavage site (Horimoto and Kawaoka, 1994, *J Virol;* 68:2130-3128; and Suguitan et al., 2012, *J Virol;* 86:2706-2714) was inserted into a plasmid containing the full-length cDNA genome of PIV5 at the junction between the HN and L gene of PIV5 (ZL48) (FIG. 18A). Infectious virus ZL48 (rPIV5-H5) was recovered by transfecting the plasmid into BSR T7 cells along with plasmids encoding NP, P and L as described before (Sun et al., 2011, *J Virol;* 85:8376-8385). Recovered virus was plaque-purified and grown in Vero cells. The full-length genome of plaque-purified virus was sequenced using direct RT-PCR sequencing. A large stock of the virus was grown in MDBK cells. Titer of the virus was $10^8$ pfu/ml (FIG. 18B). Expression of H5N1 HA from ZL48-infected cells was confirmed using immunoblotting (FIG. 19A) and immunofluorescence (FIG. 19B). ZL48 grew similarly to wild type PIV5, as shown in a low MOI growth curve (FIG. 19C).

Figure 20B:
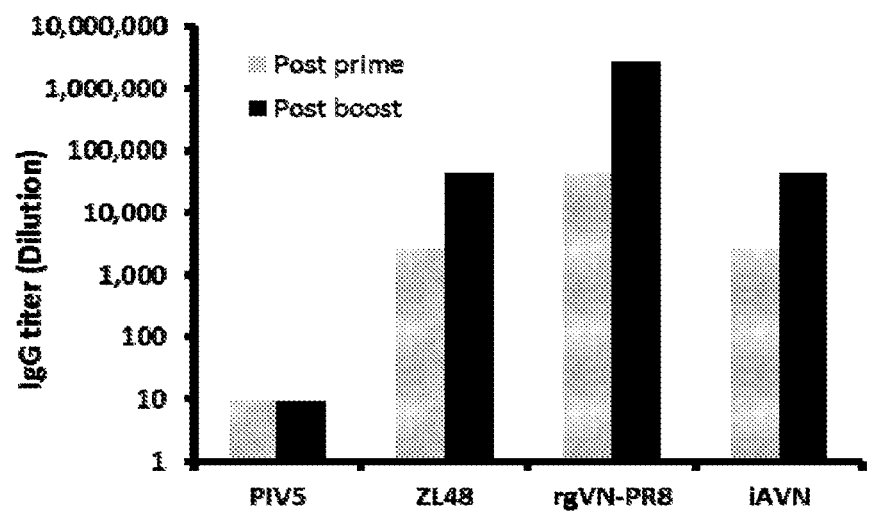
Figure 20C:
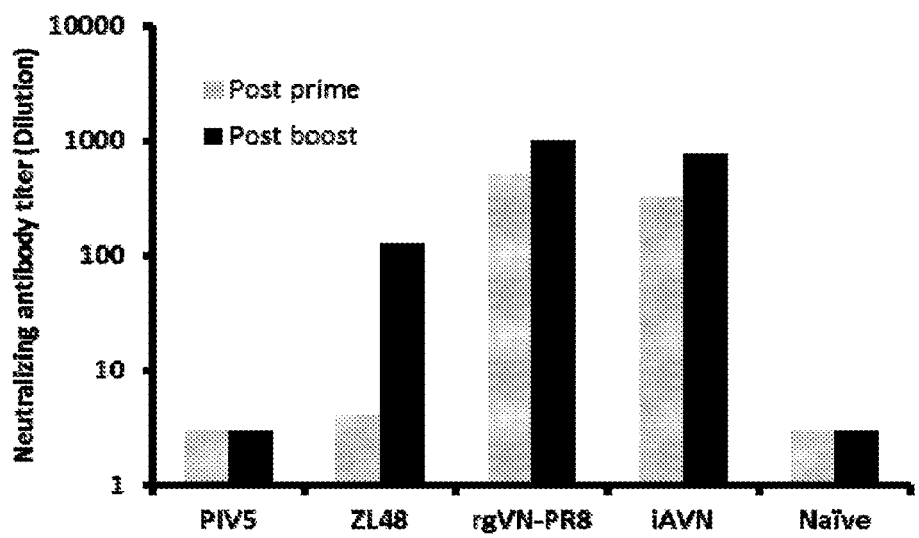
Figure 20D:
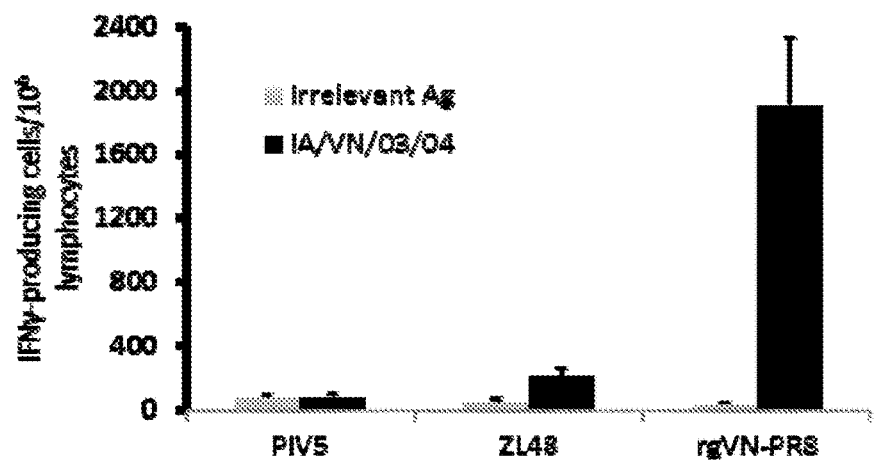

Immunogenicity of rPIV5-H5 in mice. To determine whether ZL48 could generate HA-specific immunity in vivo, mice were infected intranasally with a single dose of $10^6$ pfu of ZL48 or wild type PIV5 and immune responses compared to mice infected with an H5N1 reverse genetics vaccine construct (rgVN-PR8) or immunized with inactivated H5N1 virus (iA VN). Mice were bled at 21 days post inoculation/immunization. Serum levels of anti-HA IgG were determined using ELISA (FIGS. 20A and 20B). The infection of ZL48 generated comparable and balanced levels of IgG1 and IgG2a to inactivated H5N1 virion and recombinant H5N1 that contains internal genes from PR8 and HA and NA from H5N1. The neutralizing antibody (nAb) titers of the sera from ZL48-infected mice were low (FIG. 20C). However, a boost at 21 dpi enhanced the levels of serum nAb to a level that is considered protective. Cellular responses were examined using Elispot assay. ZL48-infected mice generated cellular responses (FIG. 20D). While the Th1 (IFNγ producing T cell) response was limited as compared to mice infected with the reverse genetics H5N1 virus, these mice had responses to the entire influenza virus, including immunodominant antigens contained in internal and non-structural proteins cells (Vitiello et al., 1996, *J Immunol;* 157: 5555-5562), as compared to ZL48, which had only the influenza HA, and the lymphocytes were restimulated with whole virus.

Figure 21A:
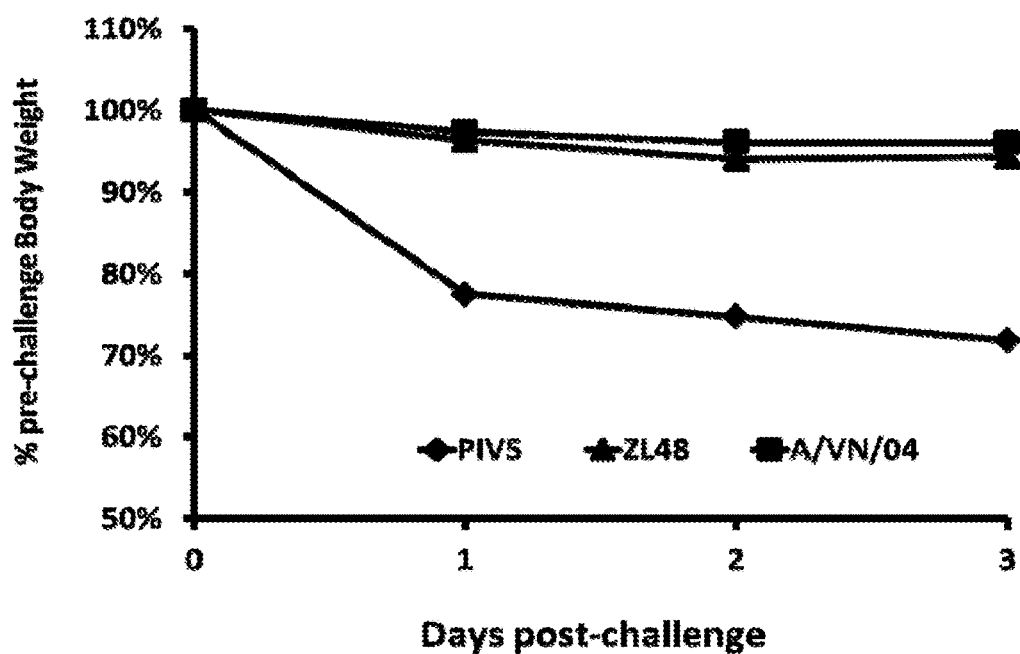
FIGS. 21A and 21B show efficacy of rPIV5-H5 against rgVN-PR8 (H5N1) challenge in mice. The mice were inoculated with PBS, PIV5 or ZL48 (n=10 per group) at a dose of $10^6$ pfu per mouse. At 21 dpi, the mice were challenged with rgVN-PR8 (H5N1) at a dose of 1,000 TCID50. The lungs were collected at 4 days post challenge. Titers of rgPR8H5N1 in the lungs of mice were determined using plaque assay.
Figure 21B:
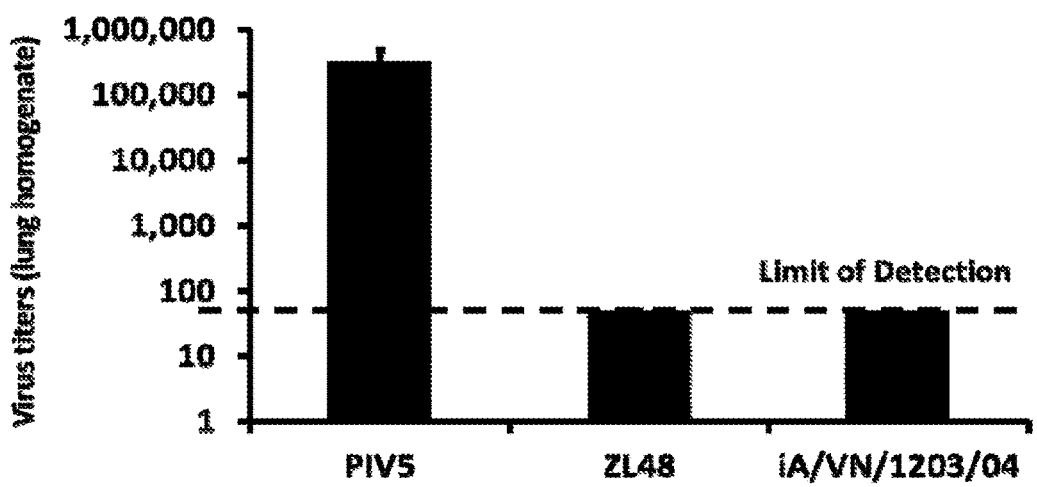

Efficacy of rPIV5-H5 against recombinant H5N1 influenza virus challenge in mice. Because of the cost and the relative low nAb titer, efficacy of ZL48 against the homotypical virus challenge was first examined in mice using a recombinant influenza virus, rgVN-PR8 (H5N1) that contains all internal genes from PR8 and HA and NA from HPAI H5N1 (with the polybasic cleavage site within HA removed). This virus is less virulent in mice than wildtype HPAI H5N1 in mice and can be used in BSL2 biocontainment. Mice were immunized with a single dose of $10^6$ pfu of ZL48 or wild type PIV5 via intranasal route. A separate group of mice received the inactivated H5N1 virus (iA VN) as a positive control. The mice were challenged with 1,000 TCID$_{50}$ rgA-PR8 (H5N1) at 21 days post immunization. Because rgVN-PR8 (H5N1) does not cause mortality in mice, efficacy of ZL48 immunization was examined using titers of the challenge virus in the lungs of the mice. No rgVN-PR8 (H5N1) virus was detected in the lungs of ZL48-immunized mice at 4 days post challenge (FIGS. 21A and 21B), suggesting that ZL48 was effective in preventing H5N1 infection.

Figure 22A:
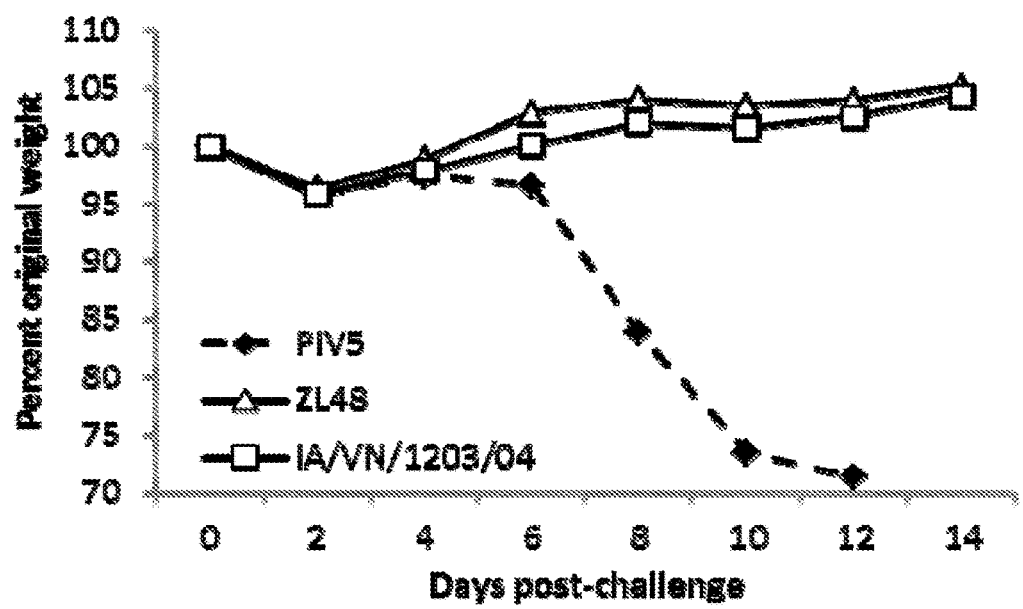
FIGS. 22A-22C show efficacy of rPIV5-H5 against HPAI H5N1 challenge in mice. The mice were inoculated with PBS, PIV5 or ZL48 (n=15 per group) at a dose of $10^6$ pfu per mouse. At 21 dpi, the mice were challenged with HPAI H5N1 at a dose of 10 LD50.
Figure 22B:
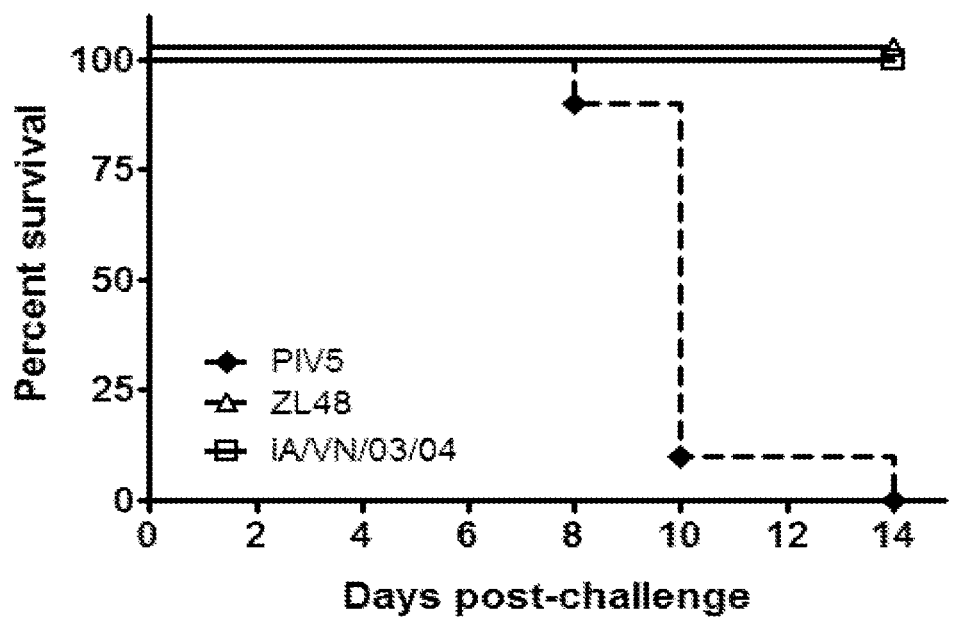
Figure 22C:
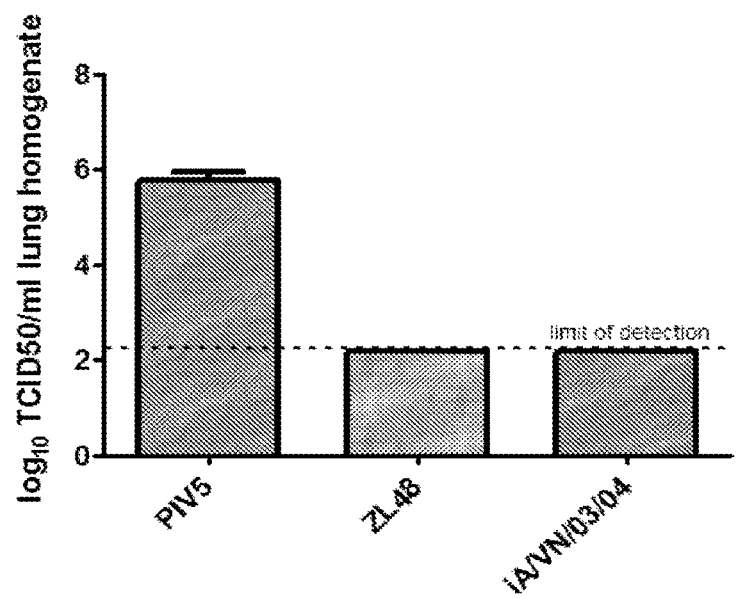

Efficacy of rPIV5-H5 against HPAI H5N1 challenge in mice. The efficacy of ZL48 against HPAI H5N1 was examined in mice with the A/Vietnam/1203/2004 strain (Govorkova et al., 2005, *J Virol;* 79:2191-2198). Mice were immunized with a single dose of $10^6$ pfu of ZL48 via intranasal route. The mice were challenged with H5N1 at 21 days post immunization. PIV5-immunzed mice lost substantial weight and 90 percent of them were dead by day 10 after challenge, and all died at day 14 after challenge (FIG. 225B). In contrast, all mice immunized with ZL48 survived challenge and no weight loss (FIG. 22A) was observed during the time of experiment. Furthermore, no challenge virus was detected in the lungs of ZL48-immunized mice (FIG. 22C), indicating that ZL48 is effective in preventing H5N1 infection in mice.

Figure 23A:
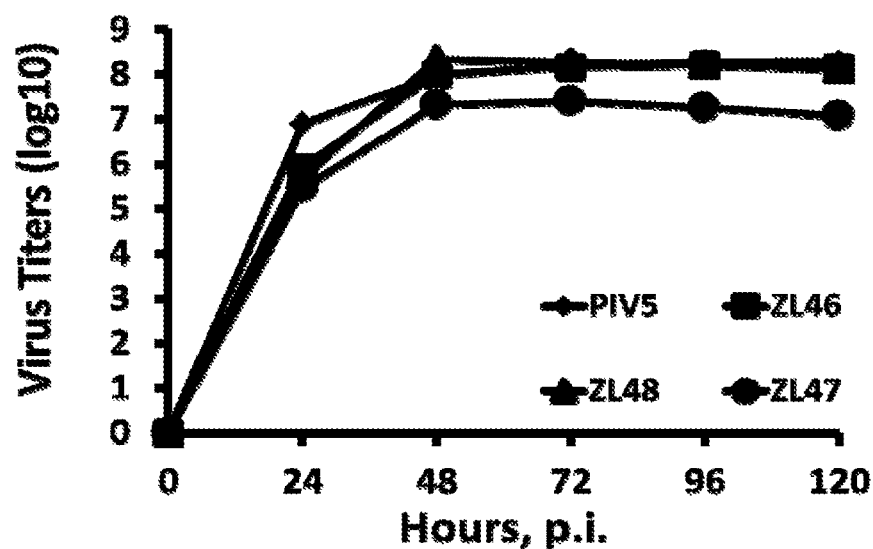
FIGS. 23A and 23B are an analysis of recombinant PIV5 expressing H5N1 HA.
Figure 23B:
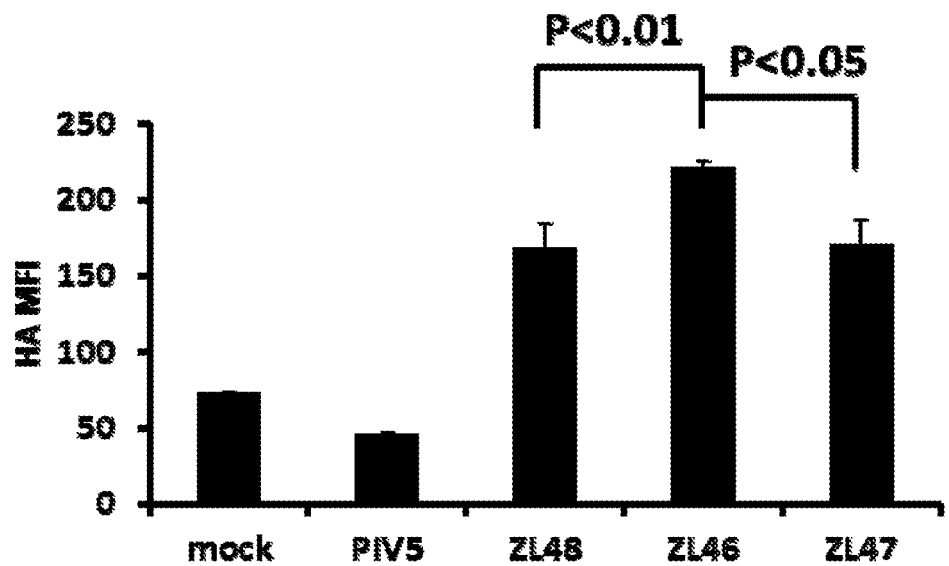
Figure 24:
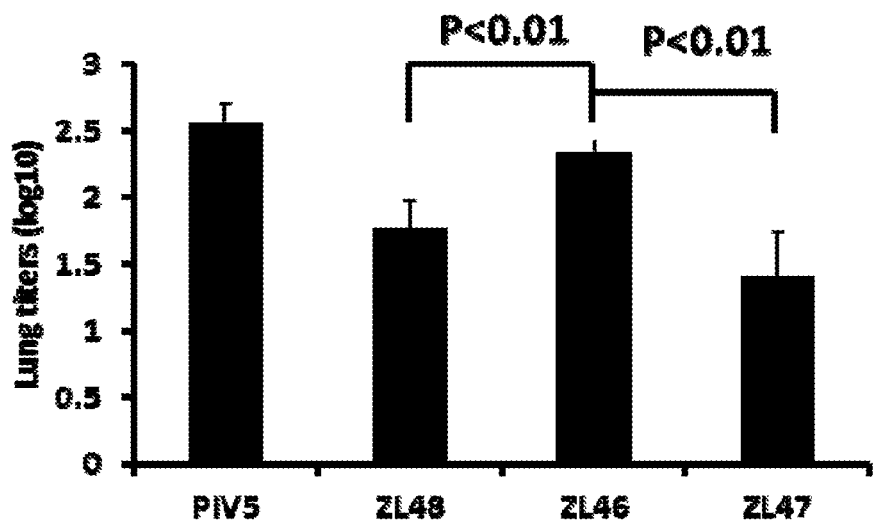
FIG. 24 shows growth of the recombinant viruses in vivo. Mice (n=5) were infected with viruses at a dose of $10^6$ pfu via intranasal route. At 4 dpi, the lungs were collected and used for plaque assay to determine titers of viruses.

Generating recombinant PIV5 expressing HA of H5N1 (rPIV5-H5) at different locations within PIV5 genome and analyzing them in vitro and in vivo. The distance to the leader sequence, the only de facto promoter for PIV5, inversely affects gene expression levels. The gene junction between the HN and L genes where H5N1 HA in ZL48 were inserted is the most distant to the leader sequence in PIV5 (FIG. 18A). Moving H5N1 HA from the HN-L gene junction closer to the leader sequence will increase level of the gene expression level of H5N1 HA protein. Reasoning that increasing expression level of H5N1 HA would increase efficacy of vaccine, the H5N1 HA gene was inserted between the Leader sequence and the NP gene. Unfortunately, while a plasmid with an insertion between the Leader sequence and the NP gene was generated, the plasmid was not able to generate a viable infectious virus (FIG. 18), suggesting that the insertion is detrimental to virus life cycle. The H5N1 HA gene was then inserted at the next gene junction, the NP and V/P gene junction (ZL209). While recombinant viruses were recovered from plasmid ZL209, the viruses did not grow well in tissue culture cells. In addition, the viruses contained mutations at the other sites (see, for example, FIG. 18B). The H5N1 HA gene was inserted at the next gene junction that is the V/P and the M gene junction (ZL47, FIG. 18) as well as at the junction of SH and HN (ZL46, FIG. 18). ZL46 and ZL48 grew similarly to wild type PIV5, while ZL47 had a slight reduction in titer (FIG. 23A). Expression level of H5N1 HA was highest in ZL46-infected cells, while in ZL47-infected cells the level of H5N1 HA was similar to that in ZL48-infected cells (FIG. 23B). The abilities of these viruses to replicate in mice were compared by determining titers of virus the lungs of infected mice. The titers of PIV5 and ZL46 were similar at 4 days post infection (FIG. 24). The titers of in the lungs of ZL48- and ZL47-infected mice were lower than that of PIV5 or ZL46-infected mice. On average, ZL47 was the lowest (FIG. 24) (however, the difference between ZL47 and ZL48 is not statistically significant).

Determining efficacy of recombinant PIV5H5 expressing H5N1 HA against HPAI H5N1 challenge in mice. As all recombinant PIV5 vaccines expressing H5N1 HA provided complete protection against H5N1 challenge in mice after a single high inoculation dose ($10^6$ pfu), a dose-response study was performed to determine if the location of the H5N1 HA gene within the PIV5 genome modified the efficacy of the vaccine. Mice were infected with ZL46, 47 and 48 at a dose of $10^3$, $10^4$ or $10^5$ pfu via intranasal route. Mice were bled at 21 dpi and scra were analyzed.

Figure 25A:
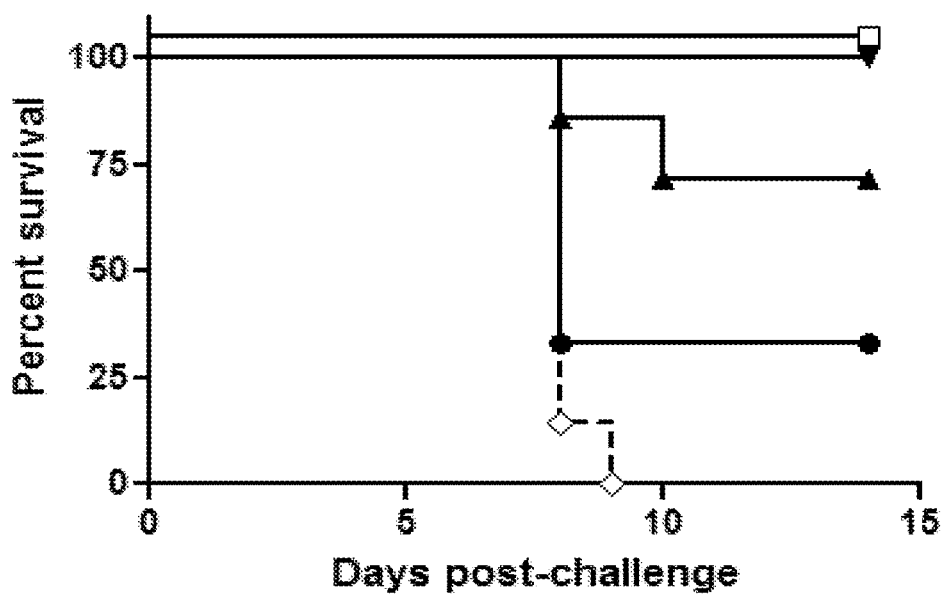
FIGS. 25A-25D show efficacy of recombinant PIV5 expressing H5N1 HA against HPAI H5N1 challenge. Mice were infected with PIV5 or ZL48 at a dose of $10^3$, $10^4$, or $10^5$ pfu via intranasal route. At 24 dpi, the mice were challenged with 10 $LD_{50}$ of H5N1. The weights of the mice were monitored daily.
Figure 25B:
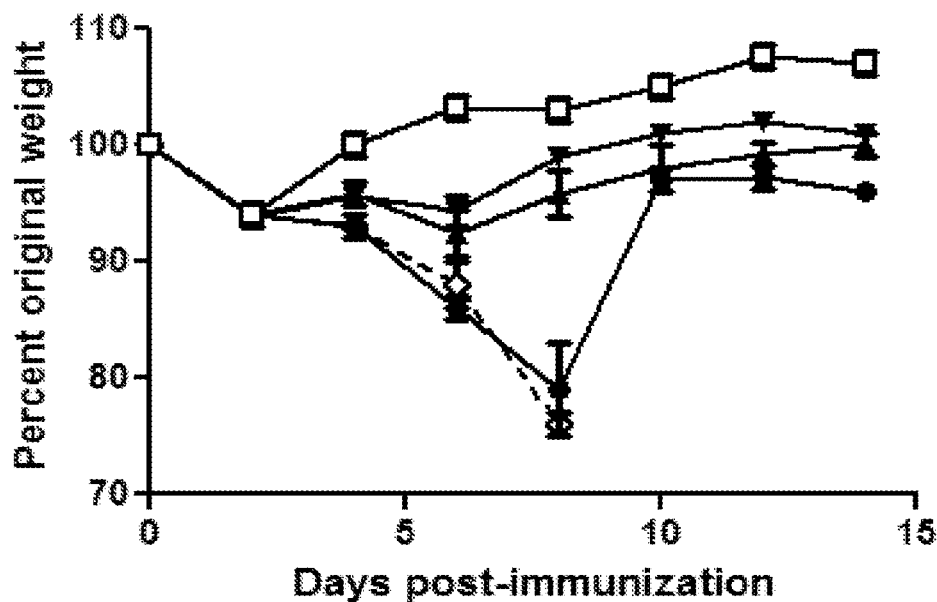
Figure 25C:
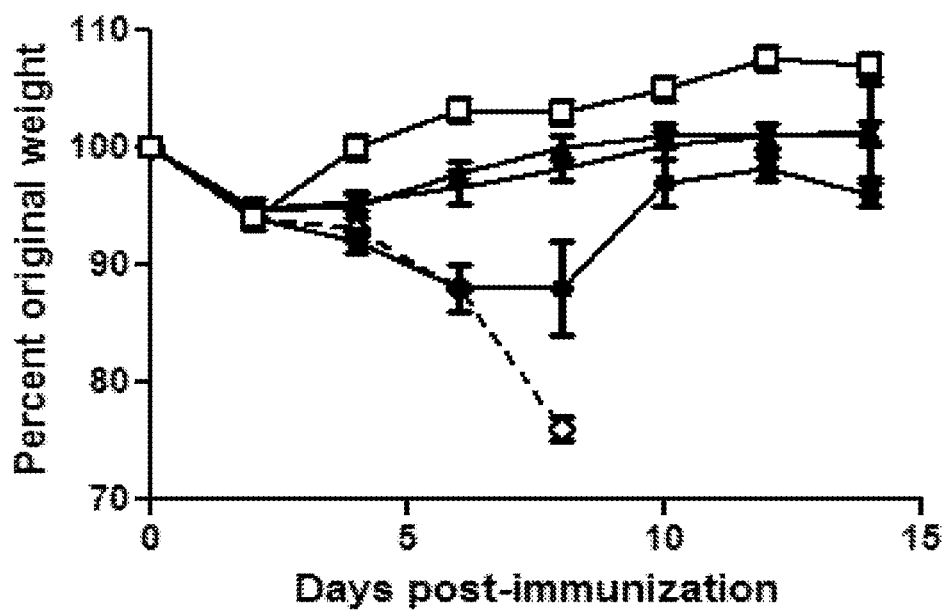
Figure 25D:
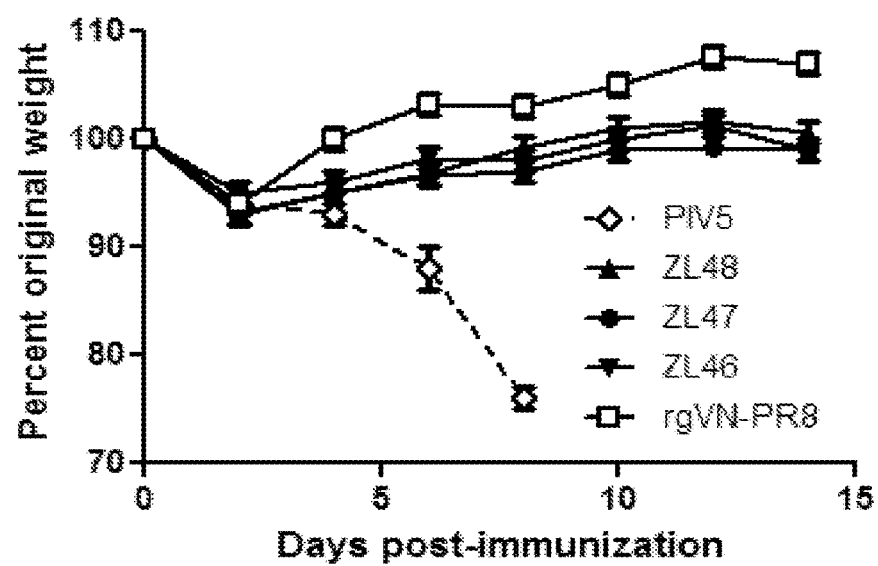

All mice inoculated with $10^4$ pfu and above of ZL46, ZL47 or ZL48 survived lethal H5N1 challenge. However low dose immunization revealed distinct outcomes. One thousand ($10^3$) pfu of ZL46 protected 100% mice against a lethal challenge with HPAI H5N1, while ZL48 protected 70% of immunized animals, and ZL47 only protected 30% of mice (FIG. 258A), suggesting insertion of the H5N1 HA gene between SH and HN enabled most potent priming of protective immune responses. Examining weight loss, a similar trend was observed. At a $10^3$ inoculum, mice immunized with ZL47 had the greatest weight loss, while ZL46 had the least weight loss (FIG. 25B). At the $10^4$ inoculum, the ZL48 and ZL46 were similarly protected from weight loss, while ZL47-immunized mice still lost 10-15% of their starting weight (FIG. 25C). At the $10^5$ and higher immunization doses, all of the mice were similarly protected from weight loss due to HPAI infection (FIG. 25D).

Discussion

In this example, recombinant PIV5 expressing HA of H5N1 was tested against challenge with the most virulent influenza virus in mice, HPAI H5N1. This recombinant vaccine was efficacious in protecting mice against HPAI H5N1 challenge, even at very low doses, indicating that PIV5 is a viable vector for development of H5N1 vaccine. Currently, the only FDA-approved vaccine against H5N1 has serious limitations, particularly as it has to be given twice and requires substantially higher concentrations of the vaccine to achieve a moderate level of efficacy compared to conventional influenza vaccines. Conventional vaccines utilizing the HA and NA of H5N1 viruses have been poorly immunogenic and have safety and production issues (reviewed in Stephenson et al., 2004, *Lancet Infect Dis;* 4:499-509). A PIV5-based H5N1 vaccine has the advantages over the current FDA-approved H5N1 vaccine because a PIV5-based H5N1 vaccine such as ZL46 can generate protective immunity with a single and low dose ($10^3$ PFU per mouse), while the vaccine can be grown to $10^8$ PFU/ml in tissue culture cells, free of special pathogen-free eggs and the production of the vaccine does not pose a health risk to workers. Furthermore, because of the cost-effective nature of PIV5-based H5N1 vaccine, it is possible to use it on animal carriers of H5N1 such as chickens.

Paramyxoviruses such as PIV5 only initiate transcription at the leader sequence. Thus, the distance to the leader sequence is in reversely proportion of levels of viral gene. The gene junction between the HN and L genes is the most distant to the leader sequence in PIV5. It has been often used to insert foreign genes to avoid any potential adverse effects of inserting foreign genes (He et al., 1997, *Virology;* 237: 249-260; and Tompkins et al., 2007, *Virology;* 362:139-150) (FIG. 18). Moving H5N1 HA from the HN-L gene junction closer to the leader sequence should increase level of the gene expression. It is interesting that insertion of a foreign gene between the leader sequence and the NP gene did not lead to a viable virus, suggesting that the insertion is detrimental to virus life cycle and the region between leader and NP gene is critical for PIV5 replication. While insertion of H5N1 HA between NP and V/P generated a viable virus, the virus was defective in its growth and mutations rose in the other regions of the recovered viruses, suggesting that the region is important for virus replication, as well. It has been reported before that the ratio of NP expression to V/P gene expression is critical for optimal virus replication in mini-genome system (Lin et al., 2005, *Virology;* 338:270-280). It is likely that insertion of H5N1 HA between NP and V/P disrupted ratio of NP to V/P, resulting in the defects in virus replication. This result is similar to the insertion of GFP between N and P in VSV. While ZL46, ZL47 and ZL48 all provided complete protection against H5N1 challenge in mice after a single inoculation dose as low as $10^4$ pfu per mouse, it is surprising that insertion of H5N1 HA between V/P and M did not provide better protection than ZL48 (insertion between HN and L) or ZL46 (insertion between SH and HN). It is possible that the insertion between V/P and M had negatively affected replication of recombinant virus in vitro (FIG. 23) and in vivo (FIG. 24), resulting in a less efficacious vaccine candidate. In a following example, it shown that live recombinant PIV5 is needed for efficacious vaccination. These results indicate that fitness of virus in vivo and the insertion site within the PIV5 genome has a major impact on efficacy of vaccine candidate.

Neutralizing antibody against influenza virus is the hallmark of protective immunity. However, at lower dose of inoculation with recombinant PIV5 expressing H5N1 HA of H5N1, low levels of nAb were barely detected, yet the mice were completely protected. The results suggest that cellular-mediated immune responses from a live vaccine can contribute to the protection against highly pathogenic influenza virus challenge. This is supported by studies utilizing the NP protein of influenza as a vaccine antigen (Epstein et al., 2005, *Vaccine;* 23:5404-5410). It is interesting that boost of ZL48 enhanced immunity in mice, suggesting that prime inoculation did not prevent re-immunization or infection of PIV5-based vaccine. This is consistent with the report that in mice neutralizing antibodies against PIV5 do not prevent PIV5 infection (Young et al., 1990, *J Virol;* 64:5403-5411). While people have been exposed to PIV5, PIV5 is not associated with human diseases, suggesting that PIV5 may be safe to use in humans.

This example has published as Li et al., "Recombinant Parainfluenza Virus 5 Expressing Hemagglutinin of Influenza A Virus H5N1 Protected Mice against Lethal Highly Pathogenic Avian Influenza Virus H5N1 Challenge," *J Virol,* 2013 January; 87(1):354-62. doi: 10.1128/JVI.02321-12. Epub 2012 Oct. 17, which is herein incorporated by reference in its entirety.

Example 4

Rabies Vaccine Based on a Recombinant Parainfluenza Virus 5 Expressing Rabies Virus Glycoprotein An efficacious and cost effective rabies vaccine is needed. In this example a PIV5-vectored rabies vaccine was tested in mice. A recombinaint PIV5 encoding RABV glycoprotein (G) (rPIV5-RV-G) was administered to mice via intranasal (IN), intramuscular (IM) and oral inoculation. The vaccinated mice were challenged with 50 lethal intracerebral rabies challenge dose ($LD_{50}$) of CVS-24. A single dose of $10^6$ PFU of rPIV5-RV-G was sufficient for 100% protection when administered via IN route. The mice vaccinated with a single dose of $10^8$ PFU of rPIV5-RV-G via IM route provided very robust protection (90%-100%). Intriguingly, the mice vaccinated orally with a single dose of $10^8$ PFU of rPIV5-RV-G showed 50% survival rate, which is comparable to the 60% survival rate of an attenuated rabies vaccine strain rLBNSE-inoculated mice. This is first report of an orally effective rabies vaccine candidate in animals based on PIV5 as a vector and indicates that the rPIV5-RV-G is an excellent candidate for a new generation of recombinant rabies vaccine and PIV5 is a potential vector for oral vaccines.

As one of the zoonotic diseases, rabies virus (RABV) infection leads to rabies in warm-blooded animals including humans characterized with acute encephalitis at early phase and fatality at later stage without post-exposure treatment (Rupprecht et al., 2006, *Expert Rev Anti Infect Ther;* 4:1021-1038). Untreated rabies virus (RABV) infection leads to death. Vaccine and post-exposure treatment have been effective in preventing RABV infection. However, due to cost, rabies vaccination and treatment have not been widely used in developing countries. Approximately 55,000 human deaths caused by rabies are reported annually with most of these cases occurring in developing countries (see, for example, Martinez, 2000, *Int J Infect Dis;* 4:222-228). Stray dogs, wild carnivores and bats are the natural reservoirs of field RABV, and these rabid carriers are public health risk to human and domestic animals. Human rabies occurrence is largely attributed to the bite of stray dogs in the developing countries where vaccination of animals is limited, especially in rural areas.

Vaccination is the most effective method of pre-exposure treatment against RABV infection and has been used in both human and reservoir animals. For the post-exposure treatment, multiple inoculations of inactivated cell culture vaccines and injection of immunoglobulin are utilized together to prevent the development of rabies. However, the rabies vaccine immunization and immunoglobulin treatment are relatively expensive for families in rural or remote areas of developing countries (Knobel et al., 2005, *Bull World Health Organ;* 83:360-368). Vaccinating stray dogs is a potential cost-effective strategy to prevent rabies infection as well. Therefore, an efficacious and cost-effective vaccine is needed. To vaccinate stray dogs, needle free vaccination such as oral immunization will be ideal.

Currently, killed rabies vaccines are prepared from chicken embryo cells, BHK, or Vero cells, and are available for human use and for pet animals via intramuscular (IM) injection (Wu et al., 2011, *Expert Rev Vaccines;* 10:1597-1608). Pre-exposure rabies vaccines are routinely administered by three successive injections of inactivated vaccines. For rabies prevention in domestic and wildlife animals, live attenuated rabies vaccines (SAD- and ERA-based modified live rabies vaccines) and recombinant rabies vaccines based on vaccinia virus expressing RABV G (V-RG) have been developed (Kieny et al., 1984, *Nature;* 312:4; Meslin et al., 1994, *Curr Top Microbial Immunol;* 187:26; and Wiktor et al., 1984, *Proc Natl Acad Sci USA;* 81:7194-7198). Despite the fact that these vaccines generated good protective immune response in many species, poor protective immunities were observed in dogs and skunks (Murray et al., 2009, *J Am Vet Med Assoc;* 235:691-695; Rupprecht et al., 2001, *N Engl J Med;* 345:5; and Tolson et al., 1987, *Can J Vet Res;* 51:363-366). The use of live attenuated RABVs also raised the safety concerns about reversion to pathogenic phenotype due to RNA genome mutation, residual virulence caused by vaccine overdose or change of target species. Vaccinia virus as a vaccine was reported to cause adverse local and systemic reactions in humans, and vaccina virus-vectored rabies vaccine (V-RG) was reported to have caused reactions in humans as well (CDC, 2009, *MMWR* 58:4; and Rupprecht et al., 1990, *J Wildl Dis;* 26:99-102). Although a modified vaccinia virus Ankara (MVA) expressing RV G has thereafter been developed as a safer substitute for the widely used V-RG vaccine, oral immunization of the recombinant MVA failed to induce anamnestic immune responses in dogs and raccoons with prior exposure (Weyer et al., 2009, *Vaccine;* 27:7198-7201). Therefore, there is a need to develop an efficacious and safe rabies vaccine for animals as well as for humans. For vaccinating wild animals, rabies vaccine that can be orally administered is needed.

RABV, a member of the genus Lyssavirus of the Rhabdoviridae family, is an enveloped RNA virus possessing a single-stranded negative-sense genome with a bullet-shaped structure. The RNA genome encodes five structural genes with order as follows: nucleoprotein (N), phosphoprotein (P), matrix protein (M), glycoprotein (G), and the viral RNA polymerase (L) (9). The N, P, L proteins combined with virus RNA genome to form the ribonuleoportein (RNP). The RABV G is the major antigen for virus neutralizing antibodies (Cox et al., 1977, *Infect Immun;* 16:754-759).

Parainfluenza virus type 5 (PIV5) is a non-segmented negative strand RNA virus with a genome of about 15 kilobases in size and belongs to the family of paramyxovirus family. The PIV5 infects a broad spectrum of cell lines without significant cytopathic effect (CPE), which supports the growth of PIV5 in continuous cell lines to obtain high titers, providing an economical means for mass production. There is association of PIV5 with human disease, no risk of integration of virus genome into host DNA, and stability of negative strand RNA virus genome over positive sense RNA viruses suggest that PIV5 is a good vaccine vector and protein expression tool. Because kennel cough vaccines containing live PIV5 have been used in dogs for many years without raising safety concerns for animals or humans, PIV5 expressing RABV G will be an effective vaccine for dogs and it can be readily incorporated into existing dog vaccination programs. This example demonstrates PIV5 expressing RABV G as a novel rabies vaccine.

Materials and Methods

Cells. BHK21, BSR-T7 cells and BSR cells, a cloned cell line derived from BHK21 cells (Sarmento et al., 2006, *Virus Res;* 121:144-151), were maintained in Dulbccco's modified Eagle medium (DMEM) with 10% tryptose phosphate broth, 10% fetal bovine serum (FBS) and 1% penicillin-streptomycin. MDBK cells were grown in DMEM with 10% FBS. Mouse neuroblastoma (NA) cells were maintained in RPMI 1640 medium supplemented with 10% FBS. G418 was added to the medium of BSR-T7 cells to make a final concentration of 400 µg/ml. For virus infection, monolayers were washed with phosphate-buffered saline (PBS) and then inoculated with virus in DMEM plus 1% bovine serum albumin. The monolayers were then washed with PBS and incubated with DMEM containing 2% FBS at 37° C. with 5% $CO_2$.

Viruses. Wild-type PIV5 was described previously (He et al., 1997, *Virology;* 237:249-260). To concentrate PIV5, the supernatant containing virus was loaded onto 20% sucrose and pelleted in a Thermo scientific ultracentrifuge Type F40L-8×100 rotor at 37,000 rpm for 1 h. The pellets were then resuspended in DMEM medium with 1% BSA and stored at −70° C. The suckling-mouse-brain-adapted CVS-24 rabies virus strain (where CVS is challenge virus standard) was propagated in suckling mice. Rabies vaccine strain LBNSE was derived from L16 strain which was reported previously (Wen et al., 2011, *J Virol;* 85:1634-1644), and grown in BSR cells. Challenge virus standard 11 (CVS-11) was propagated in NA cells. Fluorescein isothiocyanate (FITC)-conjugated antibody against the RV-N protein was purchased from Fujirebio Diagnostics, Inc. (Malvern, Pa.).

Construction of virus infectious clone. The PIV5 infectious clone plasmid pBH311 contains the green fluorescent protein (GFP) gene as an extra gene between the HN and L genes in PIV5 genome and the GFP is expressed (He et al., 1997, *Virology;* 237:249-260).

Full-length RABV G gene (1,575 nucleotides) was amplified by PCR from a plasmid containing the G gene from RABV ERA strain. The primer sequences are as follows: RV-G1, 5' AACAAGCGGCGGCCGCCGCCAC-CATGGTTCCTCAGGCTCTCCTGTTTGTAC (SEQ ID NO:5); and RV-G2, 5'AACAAGCGCGGCCGCT-CACAGTCTGGTCTCACCCC CACTC (SEQ ID NO:6). The PCR fragment was inserted into PIV5 infectious clone vector to generate a plasmid containing RABV G between HN and L as an extra gene, pPIV5-RV-G. The length of rPIV5-RV-G genome was maintained as multiple of six.

Rescue of rPIV5-RV-G virus. To rescue rPIV5-RV-G virus, plasmid pPIV5-RV-G (3 μg), along with plasmids pCAGGS-PIV5-L (1.5 μg), pCAGGS-PIV5-NP (1 μg), and pCAGGS-PIV5-P (200 ng), were transfected into BSRT-7 cells. At 4 days posttransfection, supernatant containing rPIV5-RV-G was collected and plaque purified in BHK21 cells. Plaques (developing 4 to 7 days postinfection [dpi]) were selected and further amplified in MDBK cells. RNA was extracted from the supernatant using a QIAmp viral RNA minikit, and reverse transcription (RT) was performed with random primers. The reverse transcription product was further amplified by PCR using specific primers binding HN 3' end or L 5' end. The primer sequences are as follows: 311-10699-F1, 5' CAGATTGTCCCATT-TATCCGTCAGGTGAC (SEQ ID NO:7); and 311-11764-R1, 5' AGGTCGATCTCATTTGGGAGGTTTCCAAG (SEQ ID NO:8). The PCR products were sequenced.

Growth curve and plaque assay. MDBK cells in 6-well plates were infected with PIV5 or rPIV5-RV-G at an MOI of 0.01. The supernatants were collected at 0, 1, 2, 3, 4, and 5 days postinfection. For high-MOI infection, MDBK cells in 6-well plates were infected with PIV5 or rPIV5-RV-G at an MOI of 5, and the supernatants were collected at 0, 12, 24, 36, 48, and 60 h postinfection. BHK21 cells in 6-well plates were infected with the virus stocks in serial dilution (1:10 to $1:10^6$). After 2 h, the inoculating mixture was removed and replaced with 5 ml DMEM containing 2% FBS, 100 IU/ml penicillin, 100 μg/ml streptomycin, and 1% low-melting-point agarose. The plaques were counted at 5 to 6 days postinfection. Two replicates for each time point were used.

Indirect immunofluorescence assay. To detect expression of the RABV G, rPIV5-RV-G infected MDBK cells were examined by indirect immunofluorescence assay (IFA) (Chen et al., 2010, *Virology;* 398:87-97). Briefly, cells were fixed with 3.7% formaldehyde in PBS (pH 7.4) for 10 min, and then permeabilized with 0.1% Triton X-100 plus 1% FBS in PBS for 30 min at room temperature. Fixed cells were incubated for 1 h with primary antibody (mouse anti-RABV-G antibody at dilution of 1:200; Novus biologicals, Inc) at 37° C. FITC-conjugated goat anti-mouse (1:200 dilution; KPL, Inc.) was used as the secondary antibody.

Western blotting. rPIV5-RV-G infected MDBK cells were lysed with whole-cell extraction buffer (WCEB) (50 mM Tris-HCl [pH 8], 280 mM NaCl, 0.5% NP-40, 0.2 mM EDTA, 2 mM EGTA, and 10% glycerol) (Timani et al., 2008, *J Virol;* 82:9123-9133). The lysates were cleared by centrifugation at 4000 rpm for 15 minutes and the supernatants were mixed with the same volume of 2× SDfS loading buffer (100 mM Tris-HCl [pH 6.8], 20% glycerol, 4% SDS, 200 mM dithiothreitol [DTT], and 0.1% bromophenol blue), heated at 95° C. for 5 min, and resolved by 10% SDS-PAGE. The proteins were transferred onto a polyvinylidene difluoride (PVDF) membrane using an iBlot dry blotting system (Invitrogen). The membrane was incubated with mouse anti-RABV-G antibody (1:2000 dilution) or mouse anti-PIV5-V/P antibody (1:2000 dilution, used for PIV5 virus infection control) (Sun et al., 2011, *J Virol;* 85:10261-10268), followed by incubation with goat anti-mouse secondary antibody labeled with horseradish peroxidase (HRP) at dilution of 1:2000. After washing, the PVDF membrane was incubated with ECL Advance Substrate (GE Healthcare) and scanned using a Kodak Image Station 440.

Purification of virus. To determine whether RABV G is incorporated into recombinant PIV5 particles, viruses in the cleared supernatant were loaded onto 20% sucrose and pelleted in a Thermo scientific ultracentrifuge Type F40L-8×100 rotor at 37,000 rpm for 1 h. The pellets were then resuspended in TNE buffer (10 mM Tris [pH 7.4], 100 mM NaCl, 1 mM EDTA) and loaded onto 10% to 80% sucrose gradient and centrifuged in a TH-641 rotor for 1 h at 37,000 rpm. The virus bands were collected and pelleted in a F40L-8×100 rotor for 1 h at 37,000 rpm. The purified viruses were resuspended in phosphate buffered saline (PBS) buffer (pH 7.4). The proteins from purified virus particles were subjected to SDS-PAGE and western blotting analysis.

Animal studies. Six- to eight-week-old female BALB/c mice were used in the animal studies. All animal experiments were performed following protocols approved by the Institutional Animal Care and Use Committee, University of Georgia. The mouse immunization is performed by intranasal (IN), intramuscular (IM), or oral routes. For intranasal immunization, six-week-old BALB/c mice were first anesthetized by injecting intraperitoneally with Avertin (180-250 ul/kg) and then inoculated intranasally by dropping 100 μl rPIV5-RV-G or PTV5 at different doses. PBS-treated mice served as controls. Three weeks later, the mice were boosted by the same dose of the first innoculation in the two doses response experiments. The mice were also immunized via orally administering rPIV5-RV-G particles, or intramuscularly injected with 100 μl rPIV5-RV-G at different doses in the thigh muscle of the hind leg. As a rabies vaccine control, a group of mice were immunized by the IM route with $1 \times 10^7$ FFU of rabies vaccine strain LBNSE. The mice were bled from tail prior to challenge for serological assessment.

The mouse challenge was carried out at 3 weeks postimmunization for one dose experiment or at 1 week post boost for two doses experiment. Mice were infected with 50 intracerebral (I.C.) 50% lethal doses ($LD_{50}$) of CVS-24 strain by the I.C. route. Infected animals were observed daily for 22 days for symptoms of rabies virus infection.

Rabies neutralization antibody measurement. Blood was collected from each mouse in different groups for the measurement of virus neutralizing antibodies (VNA) using the rapid fluorescent focus inhibition test (RFFIT), which is the standardized test for World Health Organization (WHO). Briefly, 50 μl of serial five-fold dilutions of serum were prepared in Lab-Tek Chamber slides (Nalge Nunc International, Rochester, N.Y.). Fifty $FFD_{50}$ (50% Fluorescing Foci dose) of CVS-11 was added to each chamber and incubated for 90 min at 37° C. NA cells ($10^5$ cells) were added into each chamber and the slides were incubated at 37° C. for 20 h. Then the cells were fixed with ice-cold 80% acetone and stained with FITC-conjugated anti-RV N antibody for 1 h at 37° C. Twenty fields in each chamber were observed under a fluorescent microscope, and the 50% endpoint titers were calculated according to the Reed-Meunch formula. The values were compared with that of the reference serum (obtained from the National Institute for Biological Standards and Control, Herts, UK), which contains a known concentration (international units, IU/ml) of VNA.

Results

Figure 26A:
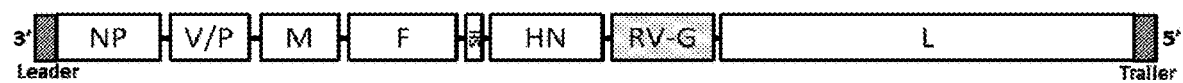

Generation and analysis of recombinant PIV5 expressing RABV G. A recombinant rabies vaccine using PIV5 vector was constructed as follows. The glycoprotein gene of rabies EAR strain (RV-G) was inserted between the HN and L genes of PIV5 (FIG. 26A). The RV-G gene in the PIV5 genome was flanked with gene start (GS), intergenic sequences (I) and gene end (GE) sequences from the junction region of the NP and V/P genes, which gave rise to a high level of transcription (He et al., 1997, Virology; 237: 249-260). The virus was recovered and the genome was confirmed by reverse transcription (RT)-PCR analysis and sequencing.

Figure 26B:
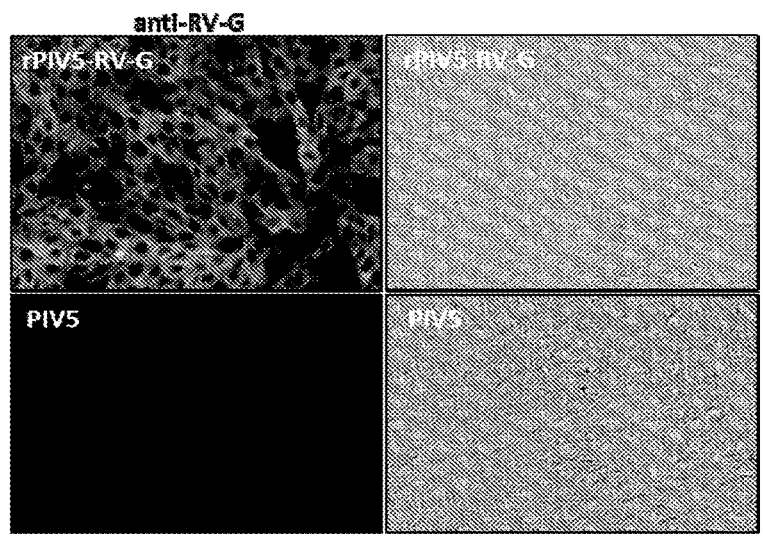
Figures 26C, 27A:
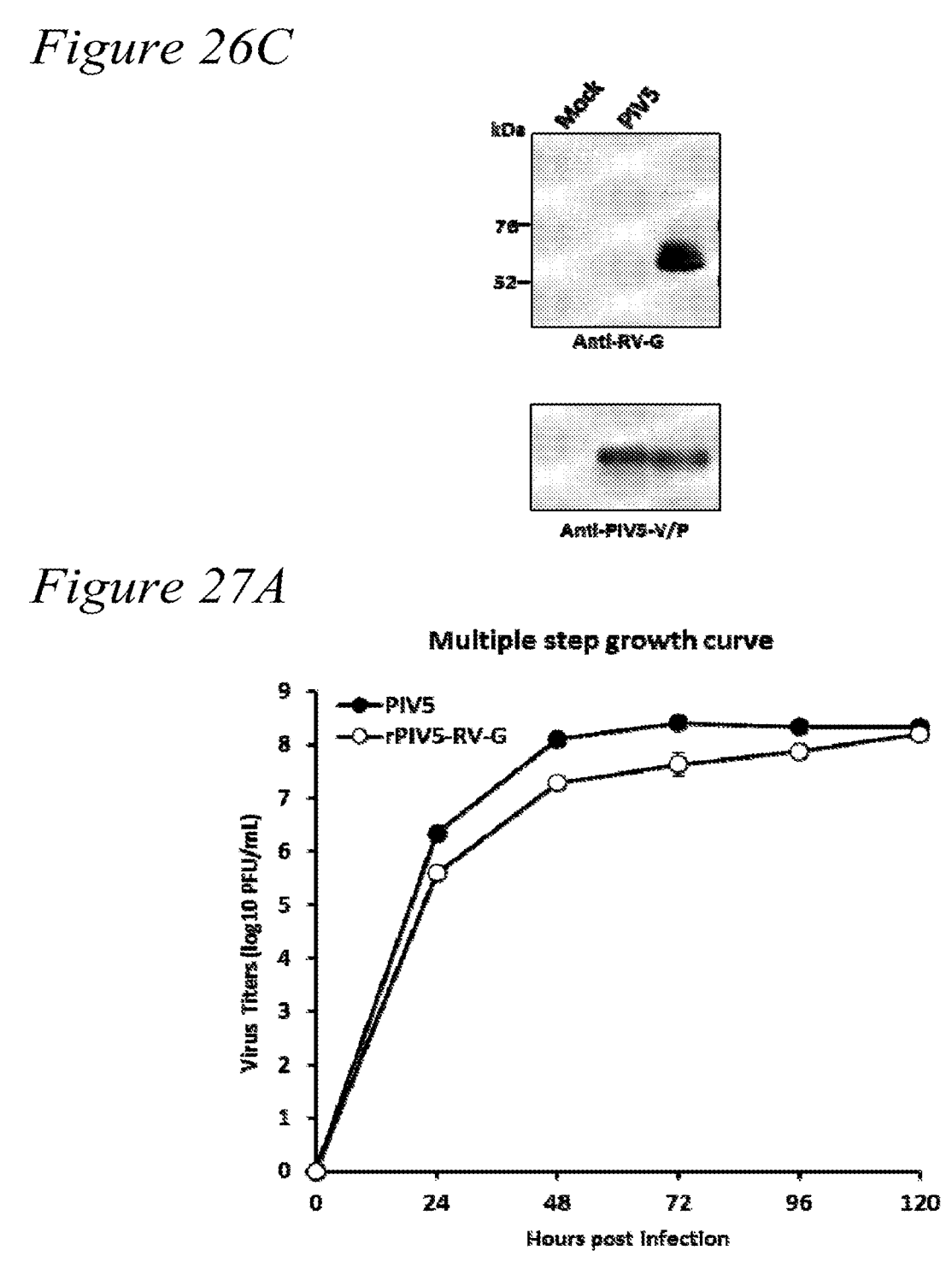

Expression of the RV-G protein in rPIV5-RV-G-infected cells was detected by indirect immunostaining assay (IFA). Cells infected with rPIV5-RV-G were stained by mouse monoclonal antibody against RABV G, while PIV5 infected cells were not stained (FIG. 26B). RABV G expression in rPIV5-RV-G infected cells was further confirmed by Western blot analysis with mouse monoclonal antibody against RV-G (FIG. 26C). The size of recombinant RABV G (~65 kDa) is expected to that of the native RABV (Zhou et al., 2006, Mol Ther; 14:662-672).

Figure 27B:
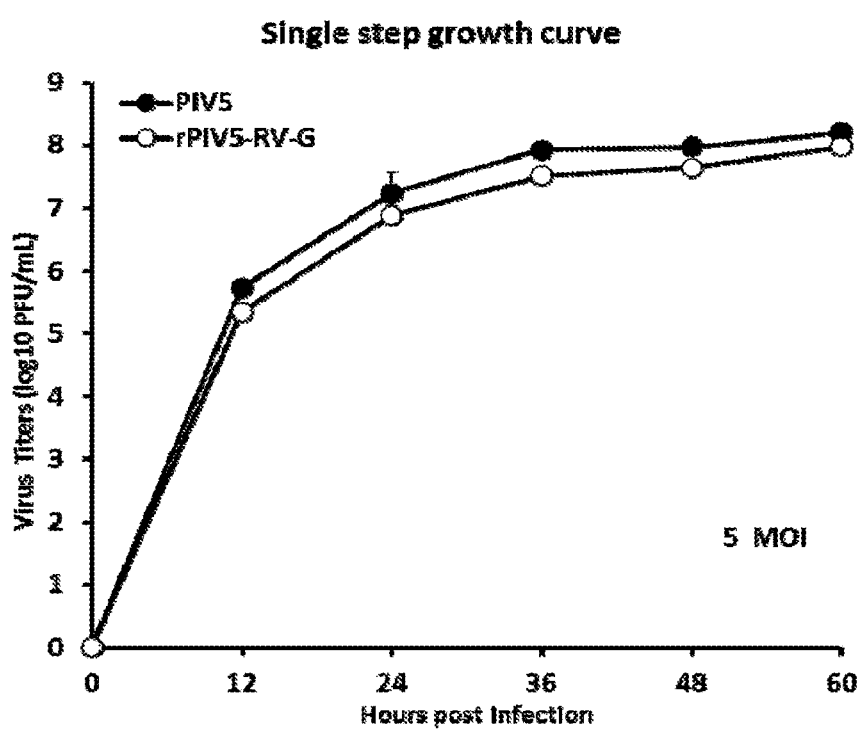

To determine the effect of insertion of the RABV G gene on virus replication, multiple-step and single-step growth curves of PIV5 and rPIV5-RV-G viruses were determined. In multiple-step growth curve assay, MDBK cells were infected with 0.01 plaque-forming units (PFU) per cell of (multiplicity of infection, MOI of 0.01) rPIV5 or rPTV5-RV-G and supernatants were collected at 24 h intervals for up to 120 h. In single-step growth curve assay, MDBK cells were infected with 5 MOIs of rPIV5 or rPIV5-RV-G and supernatants were collected at 12 h intervals for up to 60 h. Viruses were quantified by plaque assay in BHK21 cells. As shown in FIGS. 27A and 27B, both viruses had similar initial growth kinetics, though the growth rate for rPIV5-RV-G was a little lower than that of wild type PIV5 between 24 h to 96 h in multiple-step growth and between 12 h to 48 h in single-step growth. Both viruses reached the similar maximum titers at about 120 h post-infection (p.i.) in multiple-step growth and 60 h p.i. in single-step growth. The result indicated the introduction of RABV G gene into PIV5 genome as an extra expression unit did not significantly affect the growth of PIV5 virus in vitro.

Figure 28:
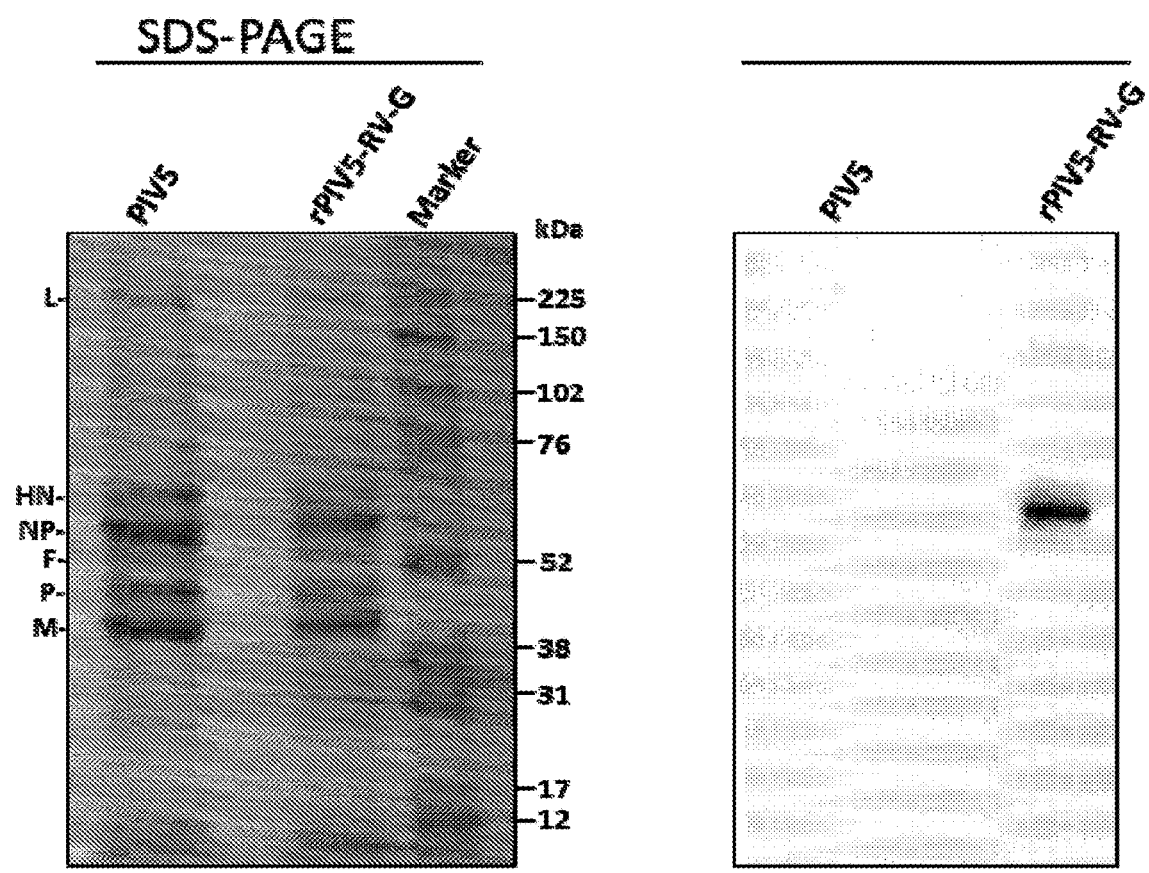
FIG. 28 shows incorporation of RV-G in rPIV5-RV-G virion. The virus particles were purified through 10%-to-80% (wt/vol) sucrose gradients. Viral proteins were analyzed by using 10% SDS-PAGE and were subjected to western blot analysis with mouse antibody against RV-G. The position of the RV-G protein is indicated.

Identification of the RABV G incorporation into rPIV5-RV-G virus particle. Since RABV G is an envelope protein, its incorporation into PIV5 particles was examined. The PIV5 and rPIV5-RV-G were grown in MDBK cells and purified, and polypeptides were analyzed by SDS-PAGE and western blotting. SDS-PAGE separated the purified virions of PIV5 and rPIV5-RV-G into the major PIV5 structural proteins, including L, HN, NP, F, P and M (FIG. 28). Western blot analysis of purified viruses with RABV G specific antibody detected the presence of the RABV G band in the rPIV5-RV-G virions, whereas no RABV G band was found in the PIV5 virions (FIG. 28). The result indicated that the RABV G is incorporated into the recombinant PIV5 particles.

Figure 29A:
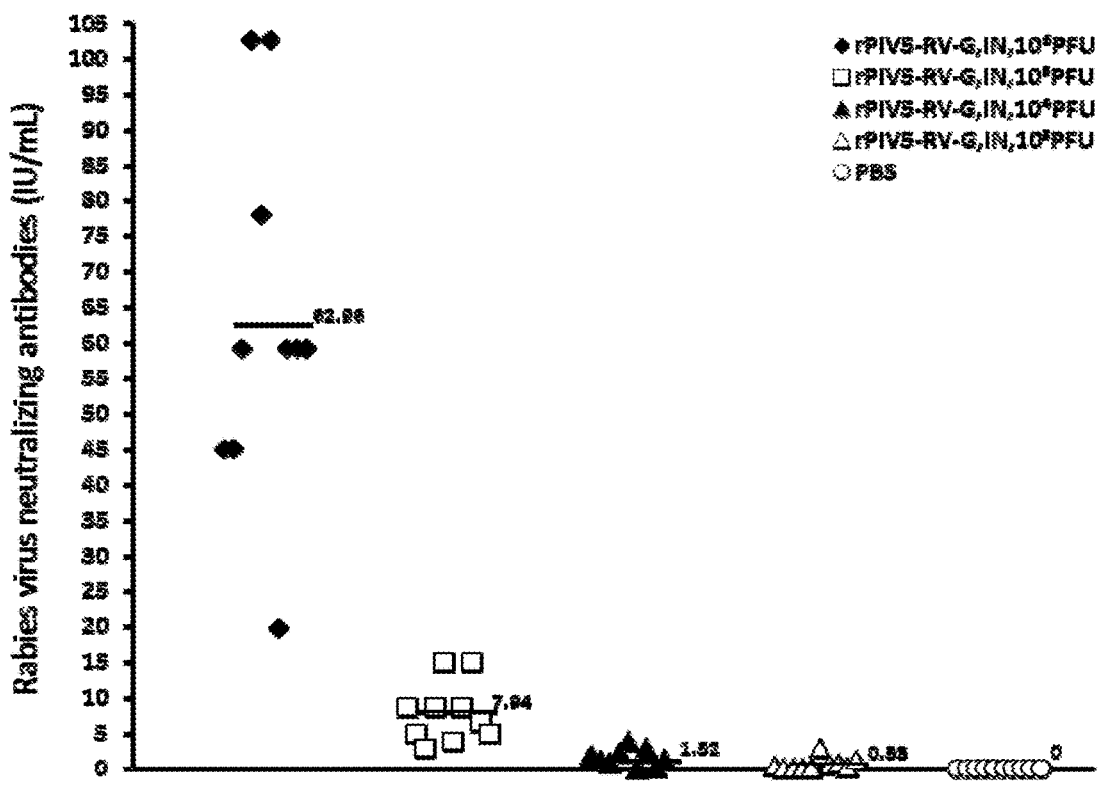
FIGS. 29A and 29B show efficacy of prime-boost immunization of rPIV5-RV-G against rabies challenge in mice. Groups of mice (n=10, each group) were immunized intranasally with 10-fold diluted rPIV5-RV-G virus ($10^3$ PFU to $10^6$ PFU). Control mice were inoculated with $10^6$ PFU of PIV5 or with PBS. At three weeks after prime vaccination, animals were boosted with the same amount of vaccines. One week after the boost, all mice were challenged with 50 $LD_{50}$ of CVS-24 strain by the I.C. route.
Figure 29B:
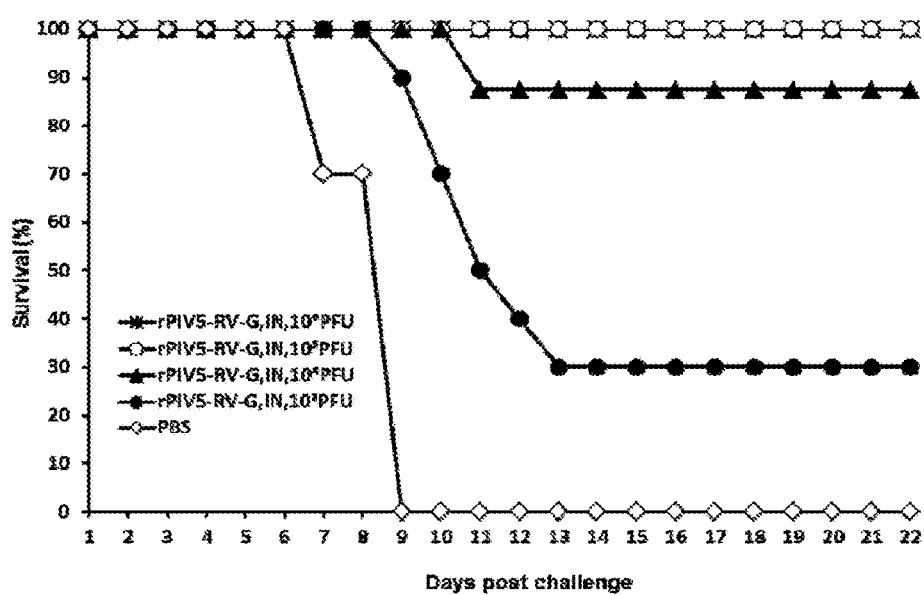

Efficacies of rPIV5-RV-G in mice via intranasal inoculation. Determine rPIV5-RV-G can elicit enough protective immunity against a robust rabies challenge in mouse model, a two-dose immunization regimen was performed. Because current vaccines containing live PIV5 are administered to dogs via IN route, efficacy of rPIV5-RV-G was first tested using IN vaccination. Four groups of mice were IN vaccinated with $10^3$, $10^4$, $10^5$ or $10^6$ PFU of rPIV5-RV-G. A control group received PBS by IN route. Three weeks after prime vaccination, all mice were boosted with the same amount of initial inoculum. One week later, sera were collected and used for for rabies VNA assays. Thereafter the mice were challenged with 50 $LD_{50}$ of rabies CVS-24 strain by I.C. route. Titers of RABV neutralizing antibody (nAb) were determined following WHO guideline. As shown in FIGS. 29A and 29B, both of the survival rate and RABV nAb level displayed dose-dependent responses. The average VNA titers and survival rates (VNA/Survivor) for the groups vaccinated with $10^3$, $10^4$, $10^5$ or $10^6$ PFU of rPIV5-RV-G were 0.53 IU/30%, 1.52 International Unit (IU)/77.8%, 7.94 IU/100%, 62.96 IU/100%, as contrast to 0 IU/0 in PBS treated group. 0.5 IU is considered to be the minimal level of protective antibody. The ratio of individual mouse with no less than 0.5 IU in each group correlated strongly with survivor rate, such as in the group of $10^3$ PFU of rPIV5-RV-G, three of ten mice (30%) with more than minimal protective antibody level, survival rate is 30%. All mice in the PBS group died within 9 days after challenge with the RABV. The result showed that the rPIV5-RV-G was able to elicit protective immune responses against rabies challenge in mice with a two-dose immunization schedule. The minimal effective two-dose of rPIV5-RV-G for 100% protection is the $10^5$ PFU of rPIV5-RV-G.

Figure 30A:
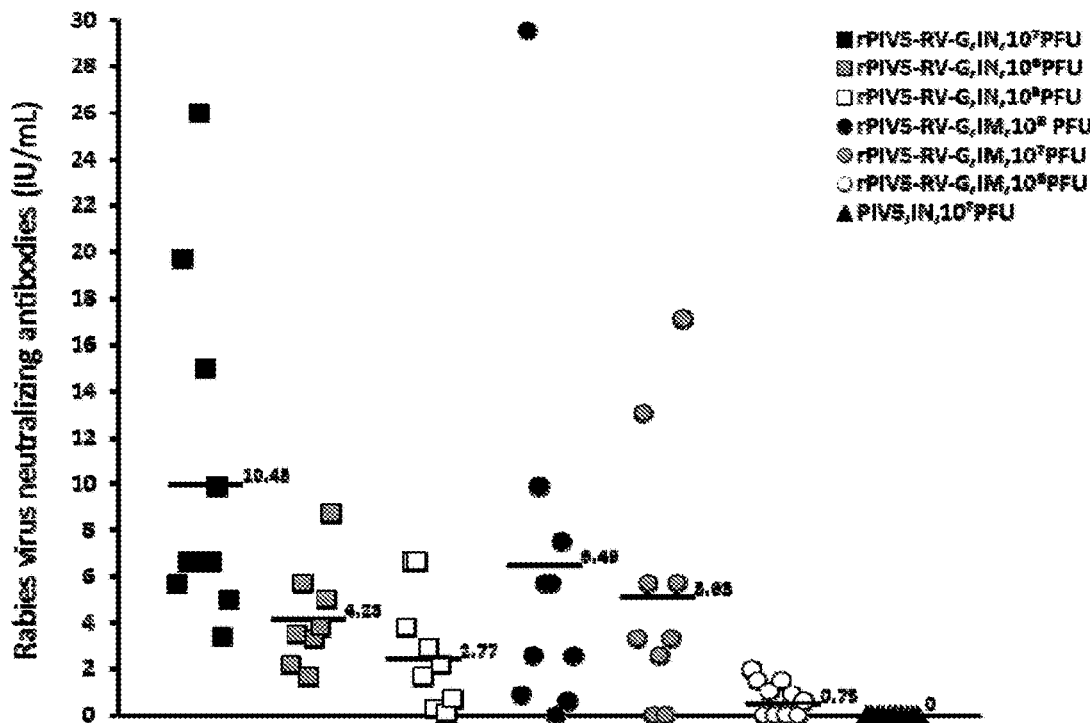
FIGS. 30A and 30B show efficacy of one dose immunization of rPIV5-RV-G against rabies challenge in mice. Groups of mice (n=10, each group) were immunized intranasally with 10-fold diluted rPIV5-RV-G virus ($10^5$ PFU to $10^7$ PFU), or vaccinated intramuscularly with rPIV5-RV-G virus ($10^6$ PFU to $10^8$ PFU). Control mice were inoculated with $10^6$ PFU of PIV5. Three weeks later, all mice per group were challenged with 50 $LD_{50}$ of CVS-24 strain by the I.C. route.
Figure 30B:
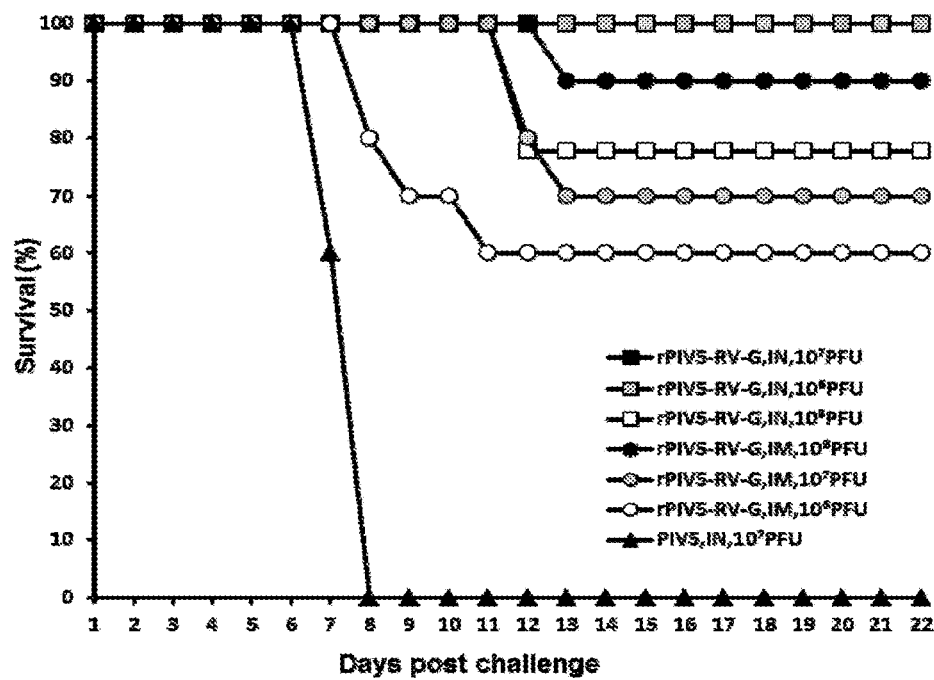

While the result of two-dose regimen test demonstrated the immunogenic potential of rPIV5-RV-G against rabies challenge, whether rPIV5-RV-G can be effective with one dose vaccination in mice was further examined. Three groups of mice were IN vaccinated with $10^5$, $10^6$ or $10^7$ PFU of rPIV5-RV-G. A control group received $10^7$ PFU of PIV5 by IN route. Three weeks after immunization, the mice were challenged with 50 $LD_{50}$ of rabies CVS-24 strain by I.C. route. As shown in FIGS. 30A and 30B, the groups of mice IN immunized with $10^5$, $10^6$ or $10^7$ PFU of rPIV5-RV-G displayed dose-dependent increase in average VNA titers with survival rates at 77.8%, 100%, and 100%. Thus, a single dose of $10^6$ PFU of rPIV5-RV-G with IN vaccination was the minimal dose for 100% protection against rabies virus challenge.

Efficacies of rPIV5-RV-G in mice via intramuscular inoculation. In some circumstances, IM vaccination may be preferred. Thus, efficacy of IM immunization was examined. At the same time as the IN inoculation, three groups of mice were injected with $10^6$, $10^7$ or $10^8$ PFU of rPIV5-RV-G via IM route. Three weeks post immunization, the mice were challenged with 50 $LD_{50}$ of rabies CVS-24 strain by I.C. route. As shown in FIGS. 30A and 30B, the groups vaccinated with $10^6$, $10^7$ or $10^8$ PFU via IM displayed dose-dependent increase in average VNA titers and showed survival rates of 60%, 70% and 90% respectively.

Figure 31A:
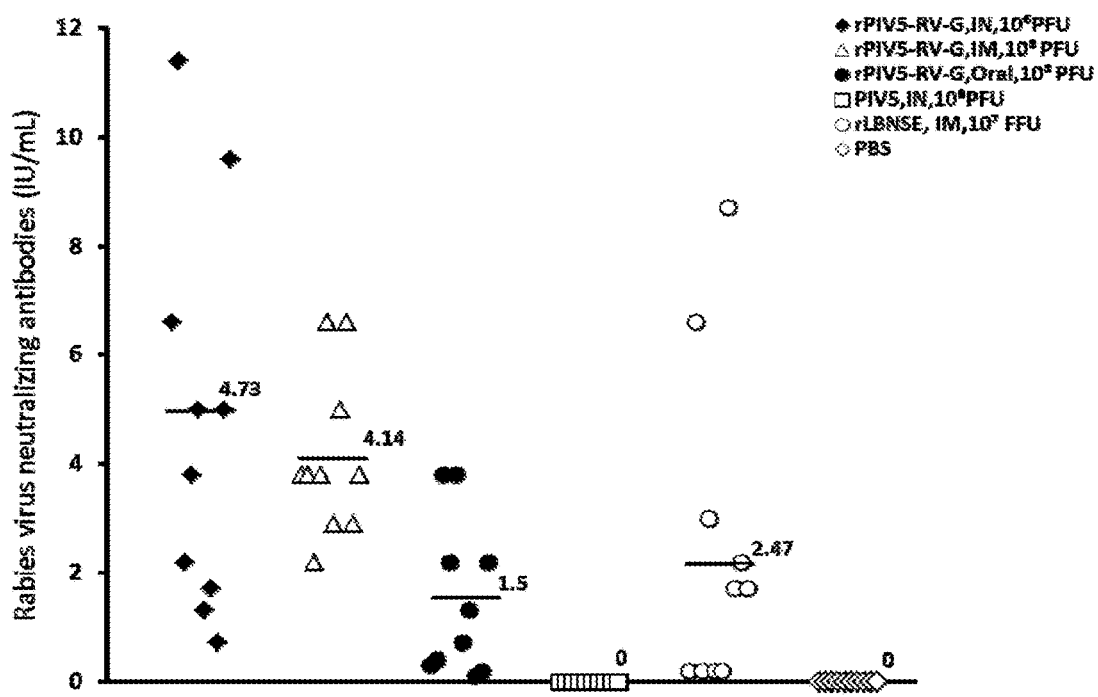
FIGS. 31A and 31B show efficacy of oral immunization of rPIV5-RV-G against rabies challenge in mice. Groups of mice (n=10, each group) were immunized intranasally with one dose of $10^6$ PFU of rPIV5-RV-G, or vaccinated with $10^8$ PFU of rPIV5-RV-G virus in IM or oral routes. As a positive control, a group of mice were immunized by the IM route with $1\times10^7$ FFU of rabies vaccine strain LBNSE. Control mice were inoculated with $10^6$ PFU of PIV5 or with PBS. Three weeks later, all mice per group were challenged with 50 $LD_{50}$ of CVS-24 strain by the I.C. route.
Figure 31B:
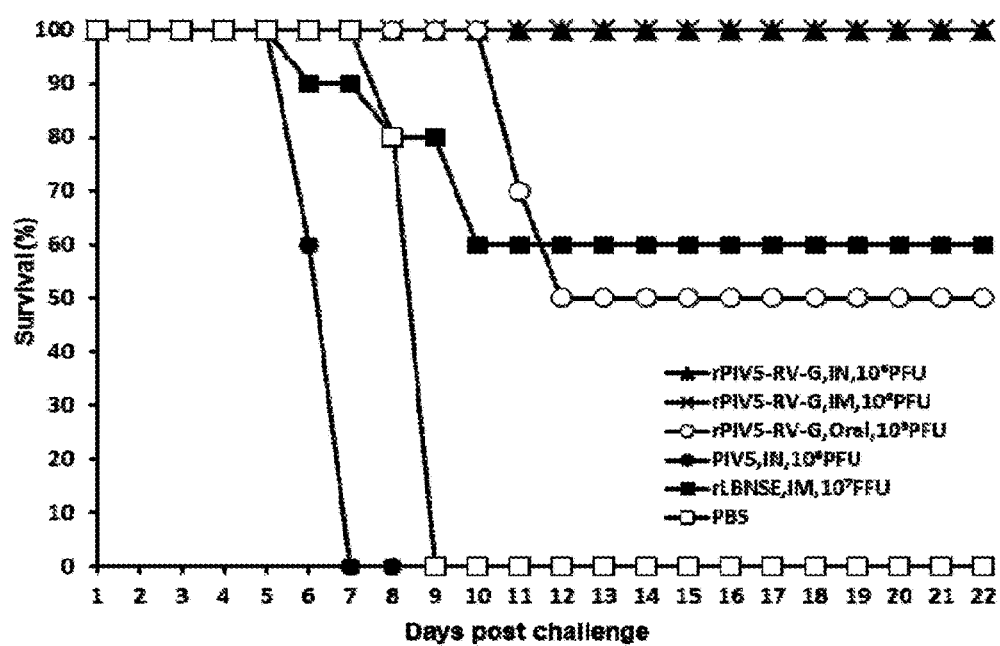

Efficacies of rPIV5-RV-G in mice via oral inoculation. Effective vaccination via oral route will be critical for successful vaccination of wild animals. To determine efficacy of the vaccine candidate via oral immunization, three groups of mice were vaccinated with $10^6$ PFU of rPIV5-RV-G via IN route, $10^8$ PFU of rPIV5-RV-G via IM route, or $10^8$ PFU of rPIV5-RV-G via oral route. Two negative control groups received inoculation with $10^6$ PFU of PIV5 or PBS via IN route. In addition, a control group of mice were vaccinated with $10^7$ FFU of rLBNSE strain, an attenuated rabies vaccine via IM route. Sera were collected for RV VNA assays three weeks after vaccination and the mice were challenged with 50 LD$_{50}$ of rabies CVS-24 strain by I.C. route. As shown in FIG. 31B, all mice receiving 10$^6$ PFU of rPIV5-RV-G via IN route and 10$^8$ PFU of rPIV5-RV-G via IM route survived the challenge. The mice vaccinated via oral route with 10$^8$ PFU of rPIV5-RV-G had 50% survival rate, while 60% of the rLBNSE strain vaccinated mice survived. All mice in either PIV5 or PBS groups were dead within 9 days after challenge. The highest average level of VNA was detected in the group with 10$^6$ PFU of rPIV5-RV-G via IN route (FIG. 31A). Overall, the average level of VNA correlated positively with survival rate as expected.

Discussion

During the past decade, a number of recombinant rabies vaccine candidates based on live attenuated RABV or recombinant viruses expressing RABV G (such as V-RG) have been developed as potential alternatives to current rabies vaccines (Ge et al., 2011, *J Virol;* 85:8241-8252; Li et al., 2006, *Virology;* 356:147-154; Tordo et al., 2008, *Dev Biol (Basel);* 131:467-476; Weyer et al., 2007, *Vaccine;* 25:4213-4222; Weyer et al., 2009, *Vaccine;* 27:7198-7201; and Zhou et al., 2006, *Mol Ther;* 14:662-672). While some of the vaccine candidates generated protective immunity when administrated via IM, data on efficacy of oral immunization with these candidates are lacking. Of those reported, the oral immunization with canine adenovirus carrying rabies G gene did not confer protection against rabies infection in mice (Li et al., 2006, *Virology;* 356:147-154). As a safer alternative for V-RG, the recombinant MVA vaccine expressing a rabies virus glycoprotein gene was generated and tested in mice and the result showed that protection was only observed in mice vaccinated with dose as high as 10$^9$ PFU by peripheral route (Weyer et al., 2009, *Vaccine;* 27:7198-7201).

This example demonstrates the insertion of the G gene of RABV between HN and L gene of PIV5 provides an effective vaccine effective via oral immunization as well as IN and IM immunization. This is the first demonstration of oral immunization efficacy in mice for rabies virus vaccine using paramyxovirus as a vaccine vector, indicating that PIV5 can be used as a vector for developing vaccines that oral delivery is essential.

Three immunization routes were tested in mice. Of those, IN inoculation gave the best immune responses and protection, demonstrating that rPIV5-RV-G can elicit protective immune response against rabies. IN immunization such as kennel cough vaccination has been used in many pet dogs in the US for many years. The fact that PIV5-RV-G was effective via IN immunization suggests that it is possible to incorporate it into existing canine vaccination program. IM route of immunization was more effective at higher doses. It is likely that the higher the dose of PIV5-RV-G, the more G protein was injected in IM immunization since G was detected in purified PIV5-RV-G virion. However, as shown in the previous examples, highly efficacious immunization with PIV5-based vaccine via IM route does require virus to be live since inactivated PIV5-based vaccine only provides partial immunity administrated via IM (see Example 7 and Mooney et al., 2013, *J Virol;* 87(1):363-71). While a single dose inoculation provided immunity against lethal rabies virus challenge in mice, a boost further enhanced efficacy of rPIV5-RV-G: prime-boost with 10$^5$ PFU of rPIV5-RV-G provided 100% protection vs. 77% protection afforded by a single dose of 10$^5$ PFU via IN route of inoculation. Average VNA titers increased from 2.76 IU in one dose of 10$^5$ PFU to 7.94 IU in two-doses vaccination. Most remarkably, VNAs were increased from 4.73 IU to 62.96 IU in mice with one dose to with two doses of 10$^6$ PFU of rPIV5-RV-G via IN inoculation. The anamnestic immune response was elicited in mice vaccinated with rPIV5-RV-G, suggesting that prior exposure to PIV5 did not prevent a robust immune response to PIV5-vectored antigen. One of the concerns for using rPIV5-RV-G vaccine is whether preexisting anti-PIV5 immunity will negatively influence the efficacy of PIV5-vectored vaccine.

The robust immune responses from boost with live vaccine suggests that pre-existing immunity to viral vector did not affect efficacy of PIV5-based vaccine. Further, as shown in Example 2, dogs with neutralizing antibodies against PIV5 generated protective immune response against influenza virus after immunization with PIV5 expressing HA of influenza A virus, demonstrating that PIV5-based vaccine is effective in dogs with prior exposure (see Example 2 and Chen et al., 2012, *PloS One;* 7(11):e50144). The use of rabies vaccines, especially live atentuated ones, in new born dogs is limited due to maternal anti-rabies antibody, which can last as long as 6 months. The PIV5-based rabies vaccine provides an alternative to effectively vaccinate new born dogs.

While IN immunization provided the best protection for rPIV5-RV-G, to vaccinate stray dog or wild animals, oral immunization will be the best approach. Oral vaccine has advantages over traditional vaccines such as its ease to use, compatibility with mass immunization campaigns, and ability to reach for hard to reach species (Faber et al., 2009, *Zoonoses Public Health;* 56:262-269). Half of the mice in our study were protected with one dose vaccination. This is comparable to current live rabies vaccine. The protection mechanism of oral vaccination is poorly understood. The VNA titer of sera from peripherial blood from mice vaccinated orally indicated a systemic immune response. The range of VNA titers from the oral inoculation was between 0.1 IU and 3.8 IU with average titer at 1.5 IU. PIV5 was likely able to delivery antigen by oral route to mucosal cells which resulted in specific immune responses including a systemic response to PIV5-vectored antigen. It is possible to further increase protection efficacy of oral inoculaton by using prime-boost regimen. In addition, modification of PIV5 vector may increase efficacy of PIV5-vectored rabies vaccine. As shown in the previous example, the insertion site of foregin gene within PIV5 affects immunogenicity of the PIV5-based vaccine (see also Li et al., 2013, *J Virol;* 87(1):354-62). For instance, insertion of HA of H5N1 between SH and HN within PIV5 results in a vaccine candidate that generates better immunity against H5N1 challenge than a vaccine with the insertion of HA of H5N1 between HN and L within PIV5 in mice. The efficacy of PIV5-based vaccine can be further improved for oral immunization by inserting the G gene in different places within the PIV5 genome. In addition, expression of additional rabies virus antigens may enhance the potency of PIV5-based vaccine. It has been reported before that the rabies RNP can be protective. For example, expression of one of rabies N, P or L proteins together with G protein using PIV5 may enhance immune protection efficacy.

As shown in this example, a PIV5-based rabies vaccine generated a robust immune response that protected a lethal challenge from rabies virus infection and demonstrates the potential of PIV5 as a vaccine for rabies for control rabies infection in dogs as well as its potential as a vector for other infectious diseases in dogs and other animals as well as in humans.

This example has also published as Chen et al., "A novel rabies vaccine based on a recombinant parainfluenza virus 5 expressing rabies virus glycoprotein," *J Virol;* 2012 Dec. 26

Example 5

Immunogenicity of PIV5-based Vaccine for In Ovo Vaccination

This example demonstrates the efficacy of PIV5-based vaccine as a potential vaccine for in ovo inoculation. As shown in Table 1, the in ovo injection of PIV5 expressing HA of H5N1 (PIV5-H5, also known as ZL46; in which H5 was inserted between SH and HN gene within the PIV5 genome) did not affect hatch rate.

TABLE 1

Hatch rates of 18-day old embryos inoculated with PIV5-H5. 54 18-day old SPF embryos were infected with various dose of PIV5-H5 as listed or PBS (group c).

| Grp. No. | pfu/Emb. | Eggs/ Grp. | Unhatched today | dead | LIVE | % hatch | % live |
|---|---|---|---|---|---|---|---|
| c. | 0 | 54 | 12 | 0 | 42 | 77.78 | 77.78 |
| 4 | $1 \times 10^1$ | 54 | 11 | 0 | 43 | 79.63 | 79.63 |
| 3 | $1.8 \times 10^2$ | 54 | 11 | 0 | 43 | 79.63 | 79.63 |
| 2 | $3 \times 10^4$ | 54 | 16 | 0 | 36 | 66.67 | 66.67 |
| 1 | $3 \times 10^5$ | 54 | 10 | 0 | 44 | 81.48 | 81.48 |

Figures 32, 33:
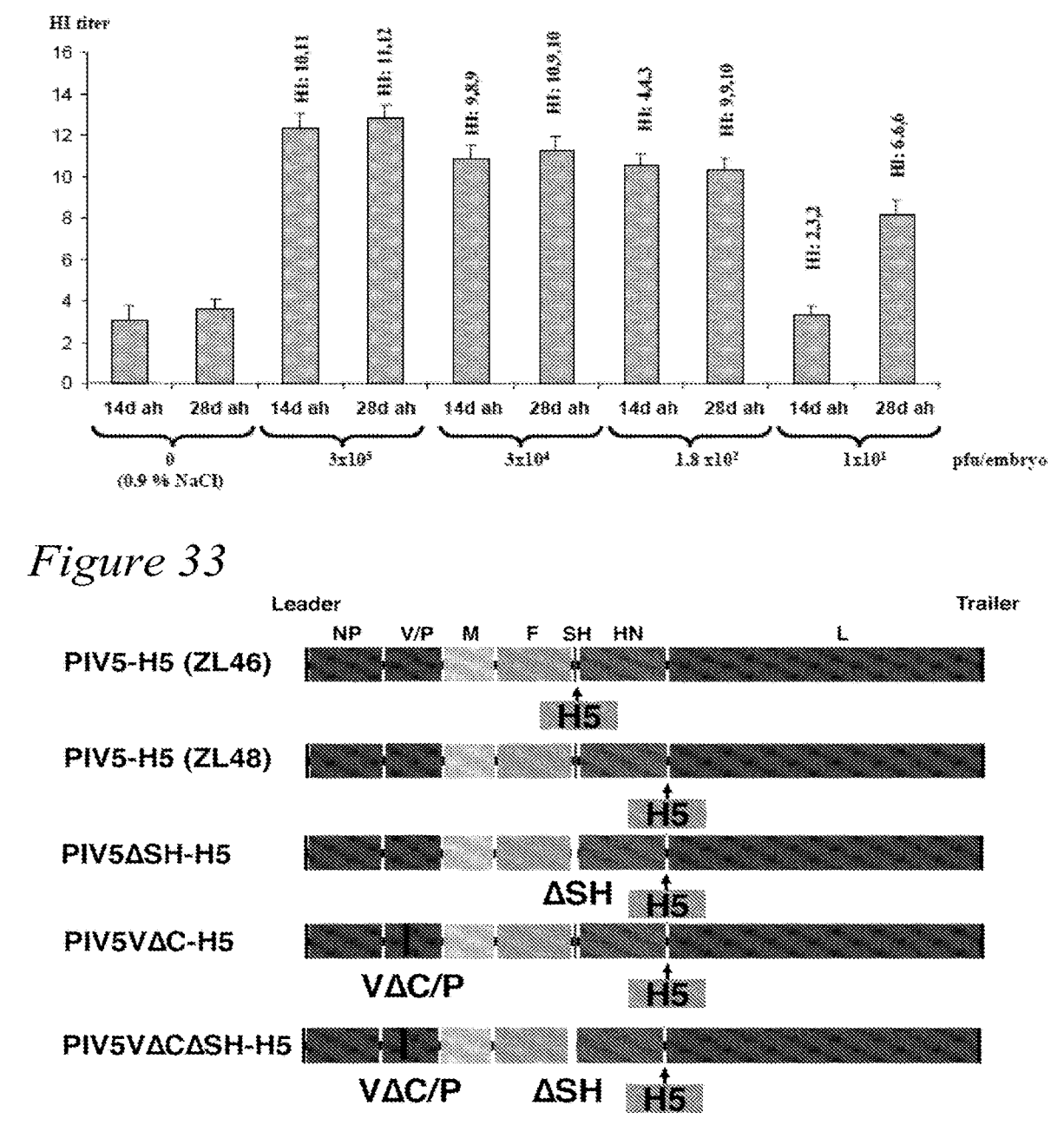

Then, anti-influenza virus antibody titers were examined in chickens at 14 and 28 days after hatch. A dose as low as 10 plaque forming unit (PFU) was able to generate robust anti-influenza virus immunity (FIG. 32). Briefly, anti-influenza antibody titers of chickens inoculated with PIV5-H5 via in ovo route were determined. 18-day old SPF embryos were in ovo vaccinated using with 100 μl of PIV5-H5 (titers are shown below each group in FIG. 32). The vaccination was performed using the Inovoject automat (Pfizer Animal Health, former Embrex). After hatch the chickens were kept in positive pressured Horsfall-Bauer units. To investigate whether the vaccinated chickens shed virus three naive hatch mates of the control group were added to each virus-inoculated group. The chickens were bled at day 14 and 28 after hatch (ah). The hemagglination-inhibition (HI) titers were determined following the OIE recommendations.

Anti-influenza antibodies were also detected in naive and co-mingled chickens, suggesting shedding of PIV5-H5 (ZL46). While the shedding of live vaccine is potentially beneficial for generating herd immunity, it may pose challenge for regulatory concern. Thus, other PIV5-based H5 vaccines will be tested in ovo, to identify a PIV5-based vaccine that generates robust immunity without shedding.

Several PIV5 constructs have been generated that are attenuated and express H5 and will be tested as described above. This includes, but is not limited to, constructs as described in the examples included herewith and shown in FIG. 33. FIG. 33 shows schematics of recombinant PIV5 expressing HA of H5N1. PIV5 is a paramyxovirus with a negative sense RNA genome. It encodes eight known viral proteins. The leader and trailer sequences are important for virus RNA replication and transcription. Results for PIV5-H5 (ZL46) are shown in Table 1 and FIG. 32. PIV5-H5 (ZL48) has H5 insertion between HN and L genes of PIV5. PIV5ΔSH-H5 lacks the SH gene. PIV5VΔC-H5 lacks the conserved C-terminal of the V protein. The SH deletion and the conserved C-terminal deletion have been combined to make PIV5VΔCΔSH-H5. Deletion of SH or VΔC causes attenuation in mice.

As before, 18-day old embryos will be inoculated in ovo with viruses at different dose (10,000, 1,000, 100 and 10 PFU/egg). 54 eggs per dilution will be used. PBS inoculation will be used as control. Hatch rates of virus-inoculated and PBS-inoculated eggs will be compared. After hatch, 10 chickens will be taken from each group and mixed with 5 chickens from the negative control (PBS-inoculated). To analyze where the virus is shed, from the respiratory or digestive tract, cloacal and oropharyngial swabs will be taken and presence of virus will be determined by virus isolation using cells and/or by qRT-PCR. Swabs from every chicken at 2 days (d), 5 d, 7 d, 14 d post hatch will be taken and checked for virus. 14 days and 28 days after hatch chickens will be bled and anti-HA titers will be determined using HI test.

Example 6

Vaccines for Animal Health

PIV5-Canine Influenza Vaccine Development. To develop PIV5-H3 vectored vaccines for canine influenza, the following will be done:
Determine DNA sequence for H3 gene of canine influenza;
Select expression control elements;
Synthesize and clone HA gene in the desired insertion site of RG plasmid system;
Confirm sequence of HA gene and expression control elements;
Transfect and rescue recombinant virus in appropriate cell lines;
Confirm expression of HA protein from recombinant virus;
Prepare and store recombinant virus stocks;
Plaque purify recombinant viruses;
Confirm in vitro stability of H3 protein expression and DNA sequence, including promoter and terminator sequences at 5, 10 and 15 passages of plaque purified virus;
Prepare sufficient virus stock at P10-12 to conduct at least two animal studies; and
Conduct POC animal studies in dogs.
PIV5-Canine Distemper Vaccine Development. To develop PIV5-F+H vectored vaccine for canine distemper virus (CDV), the following will be done:
Determine DNA sequence for F and H genes of CDV;
Select expression control elements;
Clone F and H genes in the desired insertion site of RG plasmid system;
Confirm Sequence of F and H gene and expression control elements;
Transfect and rescue recombinant virus in appropriate cell line;
Confirm expression of F and H protein from recombinant virus;
Prepare and store recombinant virus stocks;
Plaque purify recombinant viruses;
Confirm in vitro stability of F and H protein expression and DNA sequence including promoter and terminator sequences at 5, 10 and 15 passages of plaque purified virus;
Prepare sufficient virus stock at P10-12 to conduct at least two animal studies; and
Conduct POC animal studies in dogs.
If both F +H genes cannot be incorporated into a single vaccine vector, PIV5-F and PIV5-H vectored vaccines will be synthesized separately.

PIV5-FeLV Vaccine Development Plans. To develop PIV5-gp70 vectored vaccines for FeLV, the following will be done:
Determine DNA sequence for FeLv gp70;
Select expression control elements;
Synthesize and clone gp70 gene in the desired insertion site of RG plasmid system;
Confirm sequence of gp70 gene and expression control elements;
Transfect and rescue recombinant virus in appropriate cell lines;
Confirm expression of gp70 protein from recombinant virus;
Prepare and store recombinant virus stocks;
Plaque purify recombinant viruses;
Confirm in vitro stability of gp70 protein expression and DNA sequences including promoter and terminator sequences at 5, 10 and 15 passages of plaque purified virus;
Prepare sufficient virus stock at P10-12 to conduct at least two animal studies; and
Conduct POC animal studies in cats.

PIV5-Feline Calicivirus Vaccine Development Plans. To develop PIV5-Calicivirus capsid vectored vaccines for feline calicivirus, the following will be done:
Determine DNA sequence for capsid gene of feline calicivirus;
Select expression control elements;
Synthesize and clone capsid gene in the desired insertion site of RG plasmid system;
Confirm Sequence of capsid gene and expression control elements;
Transfect and rescue recombinant virus in appropriate cell line;
Confirm expression of capsid protein from recombinant virus;
Prepare and store recombinant virus stocks;
Plaque purify recombinant viruses;
Confirm in vitro stability of capsid protein expression and DNA sequences including promoter and terminator sequences at 5, 10, and 15 passages of plaque purified virus;
Prepare sufficient virus stock at P10-12 to conduct at least two animal studies; and
Conduct POC animal studies in cats.

Example 7

Recombinant Piv5 Vaccine Encoding the Influenza Hemagglutinin Protects Against H5N1 Highly Pathogenic Avian Influenza Virus Infection when Delivered Intranasally or Intramuscularly New approaches for vaccination to prevent influenza virus infection are needed. Emerging viruses, such as H5N1 highly pathogenic avian influenza (HPAI) virus, pose not only pandemic threats, but also challenges in vaccine development and production. Parainfluenza virus 5 (PIV5) is an appealing vector for vaccine development. This example tested the efficacy PIV5-H5, which encodes the HA from H5N1 HPAI virus, in different vaccine schemes. A single intramuscular or intranasal immunization with live PIV5-H5 rapidly induced robust neutralizing serum antibody responses and protected against HPAI challenge, although mucosal IgA responses primed by intranasal immunization more effectively controlled virus replication in the lung. The PIV5-H5 vaccine incorporated the H5 HA into the virion and the efficacy of an inactivated format of the vaccine was tested. Inactivated PIV5-H5 primed neutralizing serum antibody responses and controlled H5N1 virus replication, although similar to other H5 antigen vaccines, it required a booster immunization to prime protective immune responses. Taken together, these results suggest that PIV5-HA vaccines and H5-specific vaccines in particular, may be utilized in multiple formats and by multiple routes of administration. This could avoid potential contraindications based upon intranasal administration alone and provide opportunities for broader applications, while using a single vaccine vector.

As shown in Example 3, a PIV5 vaccine expressing the HA of an H5N1 influenza virus is effective at protecting against HPAI H5N1 (A/VN/1203/04) challenge when delivered as a live intranasal vaccine in mice. While intranasal (IN) immunization is appealing, there are drawbacks. There are potential contraindications regarding the use of live, intranasal virus as a vaccine in immune-compromised populations. An injectable vaccine may avoid this issue and provide opportunity for mass vaccination in agricultural applications. This example compares the efficacy of rPIV5-H5 vaccines delivered by alternate routes and shows that rPIV5-H5 is protective against HPAI H5N1 challenge when administered not only intranasally, but intramuscularly as well. Moreover, inactivated PIV5-H5 vaccine was effective at protecting against H5N1 infection, although it requires a booster immunization.

Materials and Methods

Influenza viruses. Influenza A viruses used include VNH5N1-PR8/CDC-RG (H5N1; rgVN-PR8; provided by Dr. Ruben Donis, CDC, Atlanta, Ga.) and A/Vietnam/1203/04 (H5N1; provided by Richard Webby, St. Jude Children's Research Hospital, Memphis, Tenn.)). A/VN-PR8 was propagated in the allantoic cavity of embryonated hen eggs at 37° C. for 48-72 hours. β-propiolactone (BPL)-inactivated A/Vietnam/1203/04 was provided by Richard Webby from St. Jude Children's Research Hospital (Memphis, Tenn.). A/Vietnam/1203/04 was propagated in the allantoic cavity of embryonated hen eggs at 37° C. for 24 hours. All viruses were aliquoted and stored at −80° C. All experiments using live, highly pathogenic avian influenza viruses were reviewed and approved by the institutional biosafety program at the University of Georgia and were conducted in biosafety level 3, enhanced containment following guidelines for use of Select Agents approved by the CDC.

Mice. Female 6 to 8 week old BALB/c mice (Charles River Labs, Frederick, Md.) were used for all studies. Mouse immunizations and studies with BSL2 viruses were performed in enhanced BSL2 facilities in HEPA filtered isolators. Mouse HPAI infections were performed in enhanced BSL3 facilities in HEPA filtered isolators following guidelines approved by the institutional biosafety program at the University of Georgia and for use of Select Agents approved by the CDC. All animal studies were conducted under guidelines approved by the Animal Care and Use Committee of the University of Georgia.

Cells. Madin-Darby canine kidney (MDCK) cells were cultured in DMEM with 5% FBS, 5% L-glutamine, and an antibiotic/antimycotic solution (10,000 IU/ml penicillin, 10,000 ug/ml streptomycin, and 25 ug/ml amphotericin B) (Cellgro Mediatech, Inc). Vero cells were cultured in Minimum Essential Medium (MEM) (Thermo/Hyclone) with 10% FBS and antibiotic/antimycotic. Madin-Darby bovine kidney (MDBK) cultured in DMEM with 5% FBS, 5% L-glutamine, and an antibiotic/antimycotic solution (10,000 IU/ml penicillin, 10,000 ug/ml streptomycin, and 25 ug/ml amphotericin B) (Cellgro Mediatech, Inc). All cells were incubated at 37° C., 5% $CO_2$.

Construction of recombinant viruses. rPIV5-H5 (ZL46) was generated as described in the previous examples. Briefly, a recombinant PIV5 plasmids containing the HA gene was ZL46 (rPIV5-H5-SH/HN) generated. To generate ZL46 plasmid, the plasmid BH276 containing full length genome of PIV5 was used as the vector. The gene end (GE), intergenic region and gene start (GS) sequence between SH and HN gene was added into the primer to stop HA gene transcription and start HN gene transcription. The HA gene was them amplified. Viruses were then rescued and sequenced as described previously.

PIV5 and rPIV5 virus stocks were grown in MDBK cells (<p20) for 5-7 days in DMEM containing 2% FBS until their hema-adsorption titers plateaued. Media was collected and clarified by centrifuging at 3000 rpm for 10 minutes in an Eppendorf tabletop centrifuge (5810 R). Bovine serum albumin (BSA) was added to the clarified supernatant to bring the total solution to 1% BSA. The virus stocks were then aliquoted and frozen quickly in dry ice and stored at −80° C. Virus titers were then determined by plaque assay on VERO cells.

Virus Quantitation. PIV5 titers were determined by plaque assay on VERO cells. VERO cells were incubated with serial dilutions of virus samples made in DMEM with 1% BSA and antibiotic/antimycotic. Virus sample was then removed and overlayed with 1:1 low-melt agarose and DMEM with 2% FBS and antibiotic/antimycotic and incubated at 37° C. for 5-6 days. To detect plaques, the monolayers were then fixed with 10% buffered formalin and immunostained. Cells were permeabilized with 1× PBS with 2% FBS, 0.1% sodium azide, and 0.5% saponin (permeabilization buffer). PIV5 was detected using a 1:1000 dilution of antibodies specific to the shared region of the V and P proteins of PIV5 (V/P) for 1 hr. Horseradish peroxidase (HRP)-tagged goat-anti-mouse IgG (H&L) secondary antibody (Invitrogen) was then added and incubated for 30 min. To visualize plaques, TMB peroxidase substrate (prepared according to manufacturer's instructions) was added (Vector Labs, Inc). The plates were then washed and dried and the plaques were counted. Influenza titers were determined either by $TCID_{50}$ assay as previous described (Soboleski et al., 2011, *Plos One;* 6:e21937) or by plaque assay on MDCK cells. MDCK cells were incubated for 2 hours at 37° C. with serial dilutions of virus samples made in MEM with 1 mg/ml TPCK-treated trypsin (Worthington Biochemical). Diluted virus samples were then removed and monolayers were overlayed with 1.2% microcrystalline cellulose Avicel with 1 mg/ml TPCK-treated trypsin. Plates were incubated for 72 hours, the overlay gently washed off with PBS, fixed with cold methanol/acetone (40:60%), air-dried, counter-stained with crystal violet, and plaques visualized.

Purification and Coomassie staining of PIV5 virions. MDBK cells in T-150 flasks were infected with PIV5, ZL48, or ZL46 at an MOI of 0.1. The media were collected on 3 dpi and centrifuged at 3000 rpm for 10 min to remove cell debris. The clarified media were overlayed on 20% sucrose in NTE buffer (0.1 M NaCl, 0.01 M Tris-HCl, 0.001 M EDTA. pH 7.4). Samples were centrifuged at 40,000 rpm for 1.5 h at 4° C. Pellets were resuspended in 0.5 ml of PBS and mixed with 1.3 ml of 80% sucrose in NTE buffer. 1.8 ml 50% sucrose in NTE buffer were added, then 0.6 ml 10% sucrose in NTE buffer were added to get gradient sucrose solution. The gradient sucrose solution was then centrifuged at 45,000 rpm for 3 h at 4° C. The white bands formed by virions at the interface between 50% and 10% sucrose were collected and pelleted by centrifugation at 40,000 rpm for 1.5 h at 4° C. The pellets were resuspended in 0.5 ml PBS. The virions of PIV5, ZL48, ZL46 or ZL47 were analyzed by 10% SDS-PAGE gel and stained with Coomassie blue.

Western Blot. Vero cells were infected with an MOI of 5 PFU/cell of PIV5 or ZL46, or mock-infected. Cells were lysed using PBS with 2 mM ethylenediaminetetraacetic acid (EDTA), Roche Complete Mini protease inhibitor (Roche Applied Science), and 1% Triton-X-100 (octyl phenoxy polyethoxyethanol) (Sigma) 24 hours post-infection. Separation and western blotting was performed as described (Gabbard et al., 2009, *Prot Eng Des Sel;* 22:189-198). Hyper-immune serum from rg A/VN-PR8-infected mice was used as a primary antibody to detect HA and V/P-specific monoclonal antibodies were used to detect V/P. Precision Plus Protein WesternC (BioRad) was used as a standard.

Immunofluorescence. Vero cells were grown in 24-well plates and infected with PIV5 or ZL46 at a multiplicity of infection (MOI) of 5 PFU/cell, or mock-infected. At 24 hours post-infection, cells were fixed with 5% buffered formalin for 10 min at room temperature. Cells were then permeabilized with permeabilization buffer and then incubated for 1 hr with a 1:1000 dilution (1 μg/ml) of anti-HA (H5) A/VN/1203/04 monoclonal antibody (BEI Resources). A 1:250 dilution of PE goat anti-mouse Ig (BD Pharmingen) was applied for 45 min to detect HA. To detect PIV5, V/P-specific antibodies (diluted 1:1000) were then added and incubated for 1 hr. To visualize PIV5, an Alexa Fluor-488-labeled secondary antibody (Invitrogen), diluted 1:500, was added and incubated for 30 min and then washed. 0.5 mL PBS was added to each well and fluorescence was examined using an AMS EVOS fl fluorescent microscope. Cells were washed extensively between each step with PBS.

Dynamic light scattering (DLS). DLS was performed as described (Driskell et al., Tripp, 2011, *Analyst;* 136:3083-3090). Anti-HA (H5) A/VN/1203/04 mAb (BEI resources) was used. IgG was purified from serum using a NAb Protein G Spin Kit (Thermo) according to manufacturer instructions. Purified IgG was then desalted using zeba spin desalting columns (Thermo) according to manufacturer instructions. Desalted IgG was then concentrated using Amicon Ultra-4 Centrifugal Filter Units (Millipore) according to manufacturer instructions to a final volume of approximately 2 mLs. Protein was quantified using a Pierce BCA (bicinchoninic acid) Protein Assay kit (Thermo) according to manufacturer instructions. PIV5, ZL46, ZL48, rg A/VN-PR8, virus culture supernatant, allantoic fluid, and PBS were assayed.

Immunization. For vaccination with PIV5 and rPIV5-H5, 106 PFU PIV5 or rPIV5-ZL46 in 50 μl PBS was administered intranasally to mice anesthetized with 2,2,2-tribromoethanol in tert-amyl alcohol (Avertin; Aldrich Chemical Co). For sub-lethal rg A/VN-PR8 infection, 2,000 PFU virus in 50 μl PBS was administered as described for PIV5 vaccination. For rgA/VN-PR8 intramuscular vaccination, 2,000 PFU rgA/VN-PR8 was administered in 50 μl PBS in the caudal thigh muscle. For inactivated A/VN/1203/04 immunization, BPL-inactivated virus was resuspended at 256 hemagglutination units (HAU)/ml in 50 μl PBS, which was injected into each of the caudal thigh muscles (100 μl 25 HAU total). Blood was collected on day 21 post-immunization. Nasal washes and bronchial alveolar lavages (BAL) were performed on days 14 or 21 post-vaccination using 0.5 or 1 ml PBS respectively.

ELISA. HA (H5)-specific serum antibody titers were measured using an IgG ELISA. Immulon 2 HB 96-well microtiter plates (ThermoLabSystems) were coated with 2 μg/ml recombinant H5 protein and incubated at 4° C. overnight. Plates were then washed with KPL wash solution (KPL, Inc) and the wells blocked with 200 µl KPL Wash Solution with 5% non-fat dry milk and 0.5% BSA (blocking buffer) for 1 hr at room temperature. Serial dilutions of serum samples were made (in blocking buffer) and transferred to the coated plate and incubated for 1 hr. To detect bound serum antibodies, 100 µl of a 1:1000 dilution alkaline phosphatase-labeled goat anti-mouse IgG (KPL, Inc) in blocking buffer was added per well and incubated for 1 hr at room temperature. Plates were developed by adding 100 µl pNPP phosphatase substrate (KPL, Inc) per and the reaction allowed to develop at room temperature. Optical density (OD) was measured at 405 nm on a Bio-Tek Powerwave XS plate reader. The IgG titer was determined to be the lowest serum dilution with an OD greater than the mean OD of naive serum plus 2 standard deviations.

Microncutralization Assay. Influenza neutralizing antibody titers were measured in serum by a micro-neutralization assay with an ELISA endpoint. Heat inactivated serum was serially diluted in DMEM with 1% BSA, antibiotic/antimycotic, and 1 µg/ml TPCK trypsin. Diluted serum was then incubated 1000 $TCID_{50}$ rg A/VN-PR8 for two hours at 37° C. MDCK cells were then added and incubated at 37° C. for 18-24 hours. At the end of the incubation, wells were fixed with ice cold methanol and acetone (80:20 respectively) and an ELISA was performed as described above. The neutralization titer was determined to be the lowest serum dilution capable of neutralizing 1,000 TCID50 rg A/VN-PR8, as determined by an OD readout two times above the background OD.

Lymphocyte Harvest and Elispot. Twelve days post-vaccination with PIV5, ZL46, or rg A/VN-PR8, mediastinal lymph nodes (MLN) from mice were harvested, pooled, and homogenized. Lymphocytes were depleted of erythrocytes using Gey's Balanced Salt solution (Sigma-Aldrich) for 5 min at room temperature and debris removed. Cells were then counted using a Z2 Coulter Particle Count and Size Analyzer (Beckman Coulter). ELISpot to detect T-cell responses in lymphocytes to inactivated A/VN/1203/04 were performed as described (Tompkins et al., 2007, *Emerg Infect Dis;* 13:426-435). Cells were re-stimulated with inactivated A/VN/1203/04 (the equivalent of 10 HAU per well), Ebola GP P2 EYLFEVDNL as an irrelevant peptide (1 µg/ml), and Concanavalin A (2 µg/ml) in 50 µl Complete Tumour Medium (CTM). Spots were counted using AID ViruSpot Reader (Cell Technology, Inc).

Virus challenge experiments. BALB/c mice were first vaccinated as described and then bled as indicated. At least 3 days after the last bleed, mice were anesthetized and inoculated intranasally with 10 $LD_{50}$ A/Vietnam/1203/04 or 20,000 PFU of rg A/VN-PR8 diluted in 50 µl PBS. Mice were then monitored daily for morbidity and mortality with body weights measured every other day. On day 3 post-challenge, groups of mice were euthanized and their lungs collected into 1.0 ml PBS and homogenized. Homogenate was then cleared by centrifugation. A $TCID_{50}$ assay was then used to determine virus titers in cleared homogenate as described (Soboleski et al., 2011, *Plos One;* 6:e21937).

Statistical Analysis. Statistical differences in survival were determined by log-rank analysis. Differences in lung virus titers were determined by ANOVA, followed by a Dunnett's Multiple Comparison Test. $P \leq 0.05$ was considered significant. Statistical Analyses were performed using GraphPad Prism.

Results

Figures 34A, 34B, 34C:
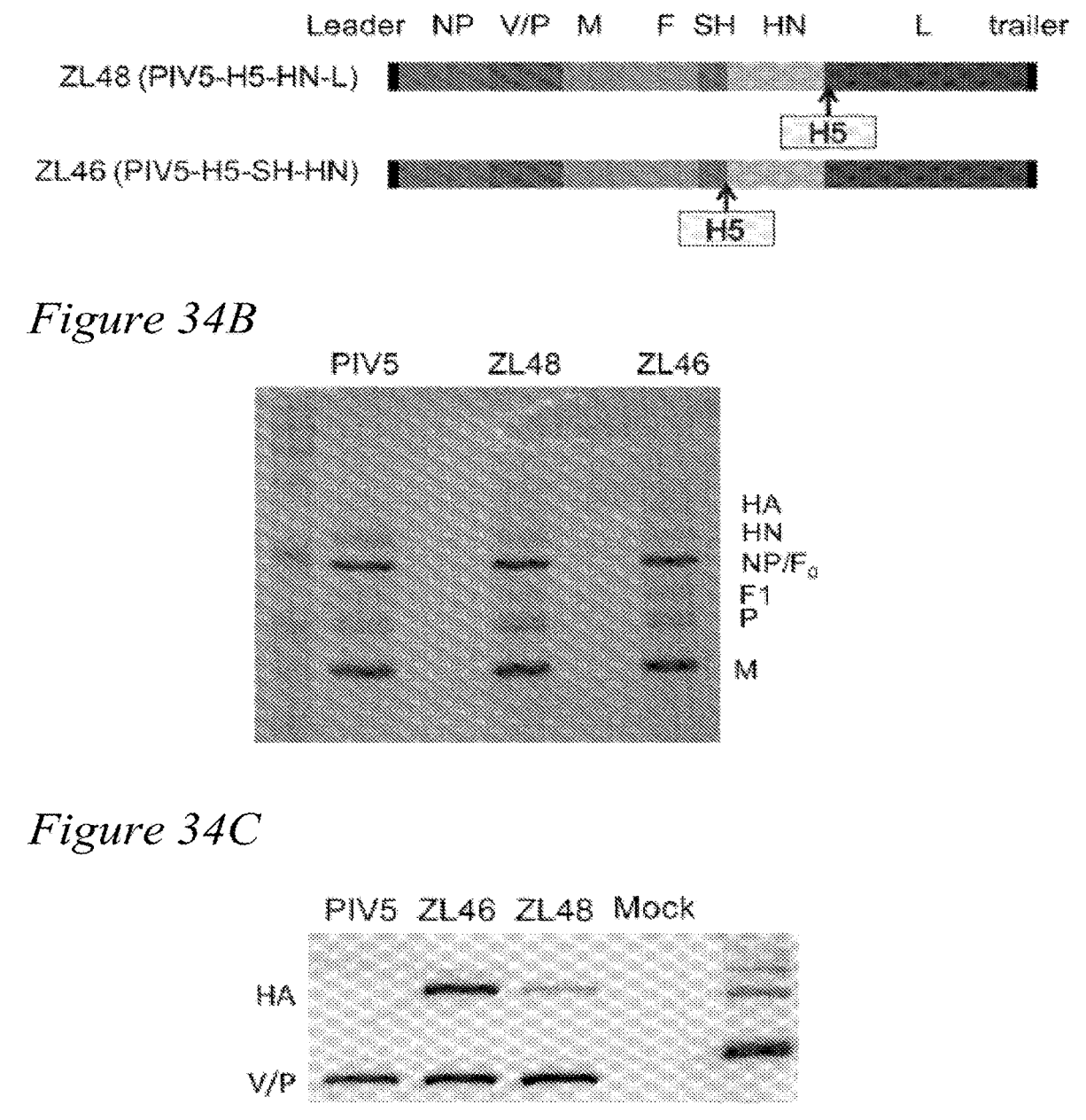

Expression and incorporation of HA in the rPIV5-H5 virion. To test for normal expression and packaging of recombinant PIV5 viruses, MDBK cells were infected with PIV5, ZL48, ZL46, or mock-infected. ZL48 has the H5 gene inserted between HN and L (Example 3) and was included as a comparable control to the previously published virus. Supernatants were collected, purified over sucrose, separated by SDS-PAGE, and Coomassie stained to visualize protein bands. Protein bands at sizes appropriate for PIV5 HN, NP, F, M and M proteins were readily visible in all samples, while a band at a size appropriate for influenza HA was visible in ZL48 and ZL46 samples, but not PIV5 (FIG. 34B). Identities of these bands have been confirmed by western blot.

To confirm that H5 HA was incorporated into the virion, dynamic light scattering (DLS) and gold nanoparticle (AuNP) labels were utilized to detect HA on the surface rPIV5 versus ZL46 virions. Cleared virus culture supernatants of PIV5, ZL46, and rgA/VN-PR8 were incubated with AuNP-labeled anti-HA (H5) antibodies and then measured for aggregation of the AuNP probes as previously described (Driskell et al., Tripp, 2011, *Analyst;* 136:3083-3090). The degree of AuNP aggregation correlates with the presence of virus containing specific HA, with increases in virus increasing aggregation and Z-shift. An increase in the mean hydrodynamic diameter (z-average) of 8 nm was observed for ZL46, compared to PIV5 (90.41±1.316 versus 82.08±0.605 nm, respectively), indicating that there was antigen-specific aggregation of the AuNP probes upon introduction of the viruses, suggesting that HA is present on the surface of the virion. The mean diameter observed for PIV5 was approximately the same size as culture supernatant or allantoic fluid alone (77.06±0.609 and 81.25±1.287 nm, respectively). The positive control, rgA/VN-PR8 virus, had a mean diameter of 113.67±1.475 nm.

Figure 34D:
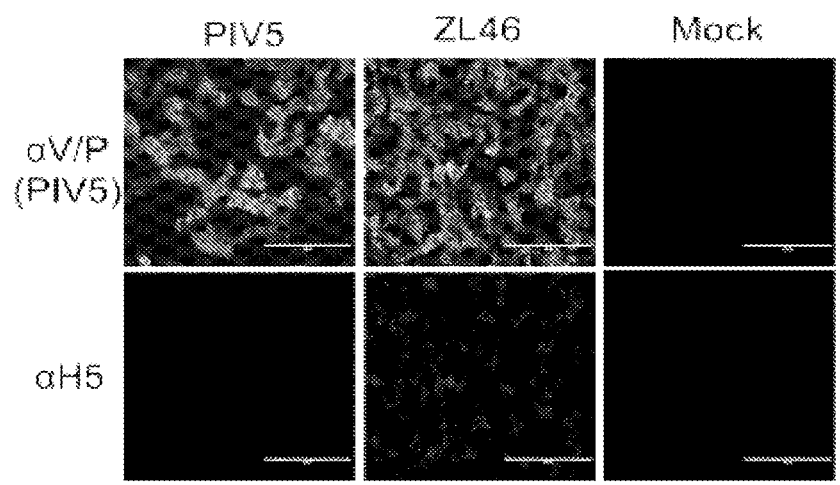

To confirm native HA was being expressed during PIV5-H5 infection, Vero cells were infected with PIV5, ZL46 (MOI=5) or mock infected and 24 hours later lysed and analyzed by western blot. Detection with polyclonal antiserum raised against the rgA/VN-PR8 (H5N1) virus visualized a 75 kD protein, the size of the influenza HAO monomer in the ZL46 cell lysate, but not the PIV5 or mock lysates (FIG. 34C). A 46 kDa band detected with the PIV5 V/P-specific mAb is present in all infected lysates. To confirm that the H5 HA is expressed on the surface of infected cells, immunofluorescence staining was performed. Vero cells infected with PIV5, ZL46 (MOI=5) or mock infected were stained with an anti-HA (H5) mAb or a monoclonal antibody specific for the V/P proteins of PIV5 (anti-V/P). Robust, equivalent expression of V/P was detected in both ZL46 and PIV5-infected cells, while H5 was detected only in ZL46-infected cells confirming that HA is being expressed in cells infected with rPIV5-H5 (FIG. 34D).

Intramuscular or intranasal immunization with PIV5-H5 induces HA-specific immune responses. Intranasal immunization with recombinant PIV5 constructs expressing the HA of an H3 virus or an H5 from HPAI H5N1 were shown to be protective against influenza virus challenge in mice (Example 3 and Tompkins et al., 2007, *Virology;* 362:139-150). However, intramuscular immunization, a route of immunization widely used for vaccination has not been tested. Moreover, since the H5 HA was detected in the rPIV5-H5 virion, it was possible that inactivated vaccine might induce protective immune responses, similar to the current inactivated influenza vaccines. To determine if rPIV5-H5 is immunogenic when administered intramuscularly (IM), mice were vaccinated with rPIV5-H5 IN with live virus (ZL46), and IM with live or inactivated (iZL46) virus. A last group of mice was given inactivated A/VN/1203/04 (iA/VN/1203/04) as a positive control and all groups were compared to mice given PIV5 intranasally (IN). Mice were bled on days 7, 14, and 21, and their sera assessed for HA-specific IgG and H5N1 influenza neutralizing antibodies. Mice vaccinated intransally or intramuscularly with rPIV5-H5 (ZL46) produced high levels of IgG as early as 7 or 14 days post-immunization, respectively (FIG. 35A), with titers comparable to mice immunized with inactivated whole influenza virus (iA/VN/1203/04). Similarly, ZL46 immunization IM or IN primed robust neutralizing serum antibodies (FIG. 35B), although inactivated influenza virus titer were higher by day 21 post-immunization. In contrast, mice vaccinated with inactivated ZL46 (iZL46) IM produced limited IgG and neutralizing antibody, suggesting that the amounts of HA antigen are insufficient to prime potent humoral responses or that PIV5 replication may be required to induce immunity. As expected, PIV5-vaccinated mice produced no detectable HA-specific IgG antibodies or rgA/VN-PR8-neutralizing antibodies (FIGS. 35A and 35B).

Figure 35C:
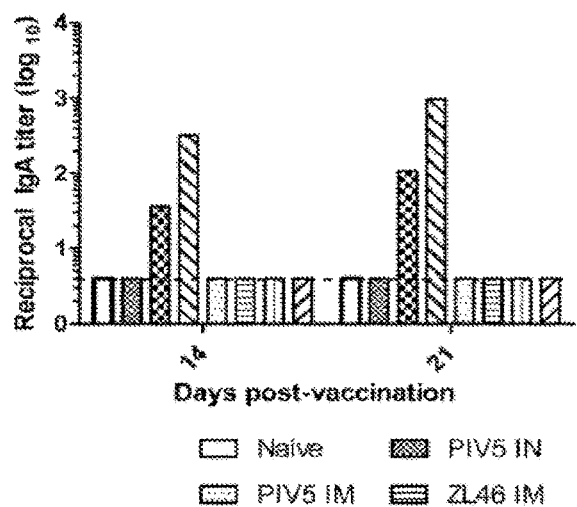
Figure 35D:
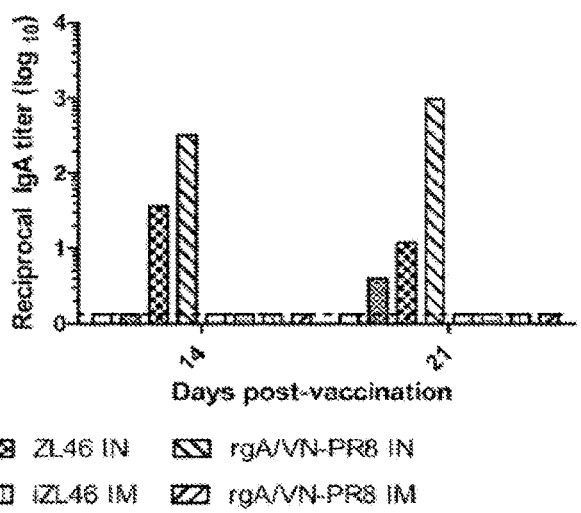

One advantage of intranasal immunization is the potential to induce a mucosal immune response. To assess differences in the IgA responses in mice vaccinated with rPIV5-H5 IM versus IN, mice were vaccinated with PIV5, rPIV5-H5 (ZL46) IM or IN, or inoculated with a sub-lethal dose of rgA/VN-PR8 and nasal washes and bronchial alveolar lavages (BAL) performed on days 14 or 21 post-immunization. No IgA was detectable in the nasal lavage or BAL fluid in mice vaccinated IM with rPIV5-H5. In contrast, intranasal administration of rPIV5-H5 induced robust IgA responses in both the nasal passages and lungs of immunized mice (FIGS. 35C and 35D, respectively). IgA levels were comparable to rgA/VN-PR8-infected mice on day 14, however the mucosal IgA response in influenza-inoculated mice continued to rise after day 14, likely due to the longer time of virus replication before clearance as compared to the rPIV5.

Figure 35E:
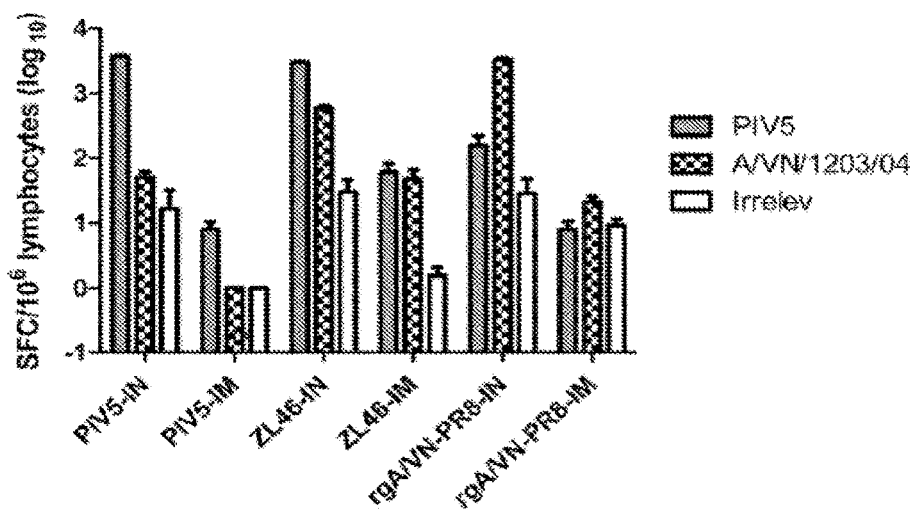

To assess differences in T cell priming with route of administration, groups of mice vaccinated IM or IN with rPIV5-H5 or rgA/VN-PR8 were euthanized on day 12 post-infection and lymph node lymphocytes assayed for influenza-specific, IFN-γ producing T cells. Intranasal vaccination with rPIV5-H5 or influenza virus primed robust influenza-specific T cell responses in draining lymph nodes, but also had increased non-specific responses as compared to IM-immunized mice (FIG. 35E). IM vaccination with rPIV5-H5 (ZL46) primed an A/VN/1203/04-specific T cell response more effectively that IM administration of rgA/VN-PR8, possibly due to improved replication of PIV5 in muscle tissue as compared to influenza virus. This would be an advantage for IM vaccination with PIV5, as T cells can play a role in protection against influenza virus infection.

Figure 36A:
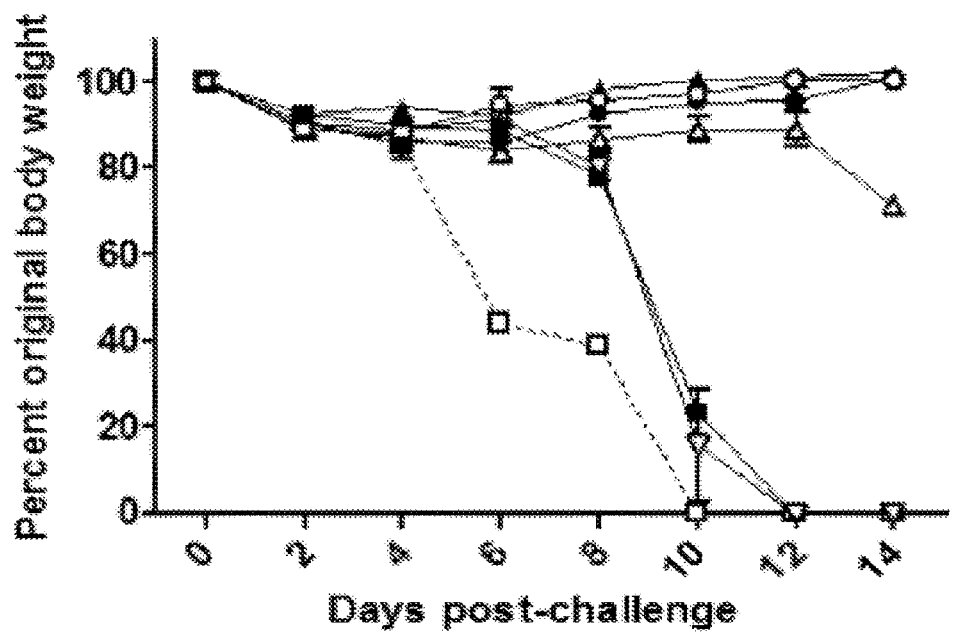
Figure 36B:
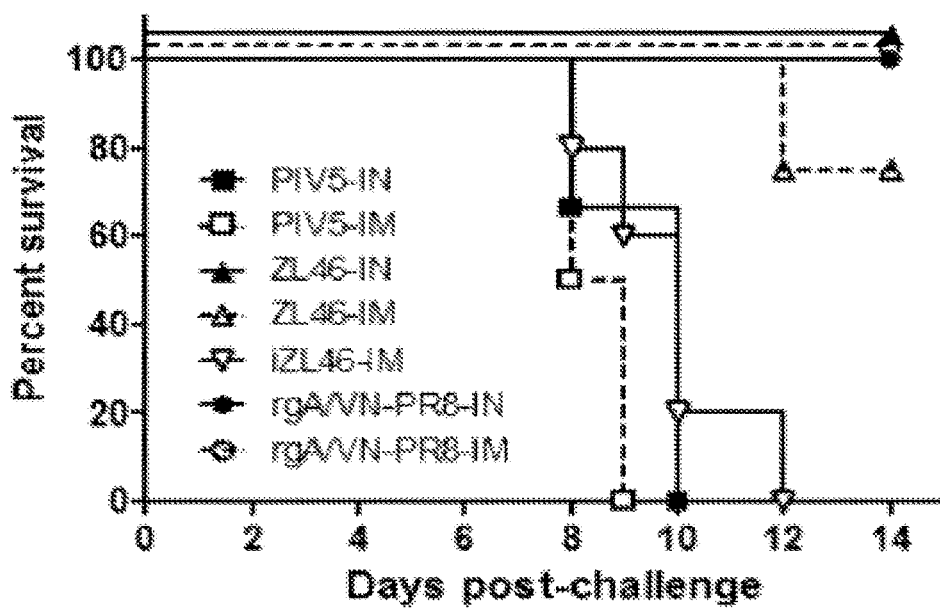
Figures 36C, 37A:
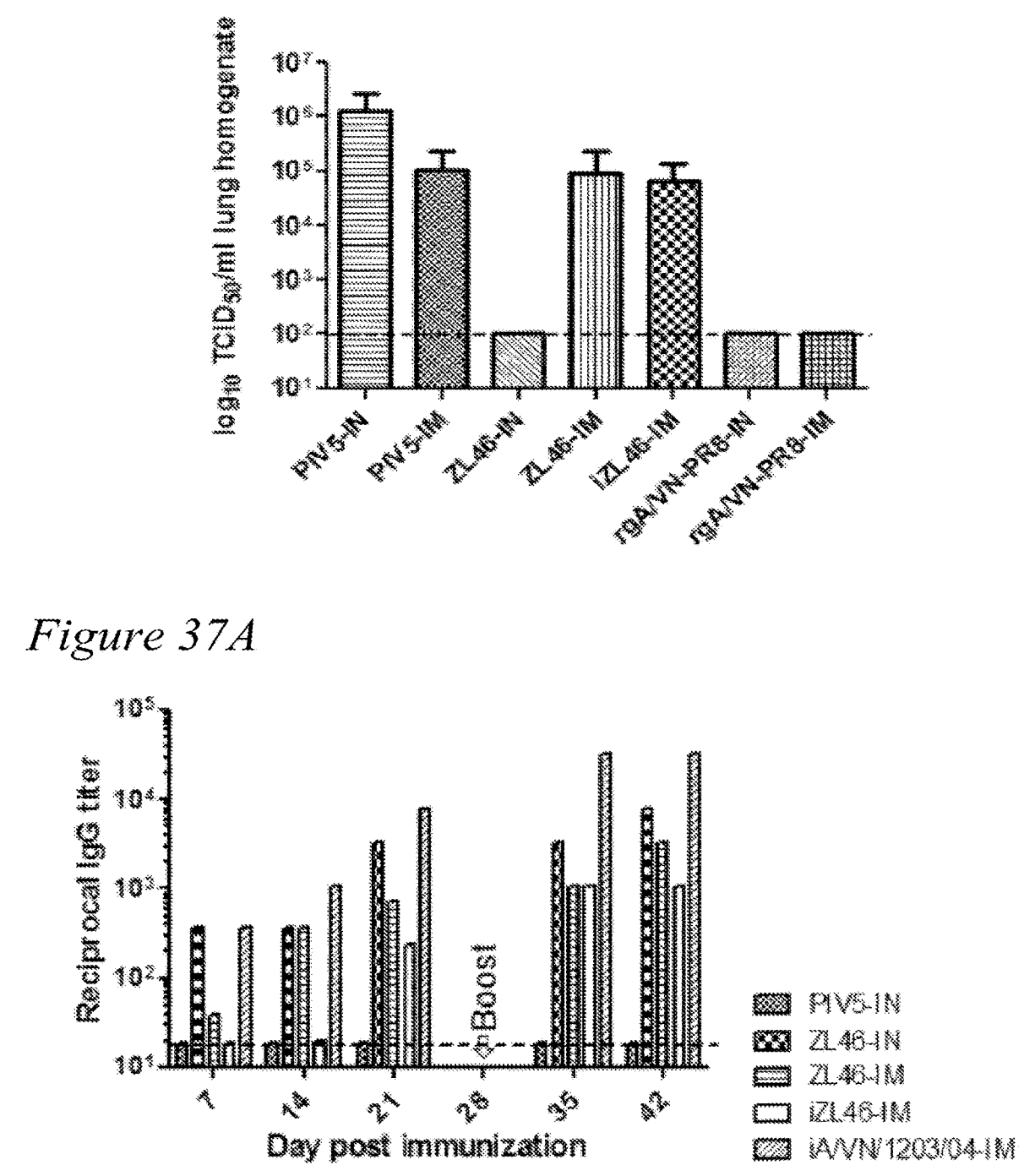

To determine if this mucosal response is necessary for protection against influenza virus infection, i.e. if IM immunization with rPIV5-H5 could protect against challenge, mice were vaccinated with PIV5, rPIV5-H5, or rgA/VN-PR8, delivered IN or IM. A group of mice were also vaccinated with inactivated PIV5-H5 IM (iZL46) to determine if the weak IgG responses detected (FIG. 35A) were protective. On day 28 post-immunization, mice were challenged with 10 LD50 HPAI H5N1 A/VN/1203/04. Consistent with previous results and observed antibody titers, mice vaccinated with rPIV5-H5 IN were protected from weight loss and mortality associated with HPAI H5N1 challenge (FIGS. 36A and 36B). Mice vaccinated with ZL46 IM were also protected from H5N1 challenge, however there was limited mortality and weight loss late in infection, suggesting the mucosal antibody responses are important for complete protection. Virus titers were assessed in a subset of mice three days post-challenge. H5N1 virus was undetectable in mice immunized with ZL46 or rgA/VN-PR8 IN. In contrast, mice immunized with ZL46 IM had no reduction in virus titer compared to PIV5 IM immunized mice, whereas rgA/VN-PR8 IM immunized mice also had no detectable virus (FIG. 36C). This suggests again that mucosal IgA primed by rPIV5-H5 IN immunization is important for complete protection. Alternatively, priming of immune responses to multiple influenza antigens, as from rgA/VN-PR8 immunization, may overcome the need to IgA responses. Protection was not observed in mice vaccinated with inactivated rPIV5-H5 (iZL46), confirming that live virus, and presumably replication, is required for induction of protective immunity. So, while both routes of administration are protective (as measured by weight loss and survival), induction of mucosal IgA response and/or the increased IFN-γ T cell numbers associated with IN immunization are limiting infection and virus replication in the lung.

Boosting enhances HA-specific immune responses associated with PIV5-H5 immunization. A single IM immunization with inactivated PIV5-HA induced limited HA-specific serum IgG (FIG. 34A), but no neutralizing antibodies (FIG. 34B) and provided no protection from infection (FIG. 36). Similar results have been seen with other H5 vaccine antigens (Lu et al., 1999, *J Virol;* 73:5903-5911), so to test whether a boost could increase the immune response to protective levels, ZL46-primed mice were bled weekly, boosted on day 28 post-priming and serum collected 7 and 14 days later. Mice immunized with live ZL46 IN or IM were compared to mice immunized IM with inactivated ZL46 (iZL46) or inactivated A/VN/1203/04 (iA/VN/1203/04).

Figure 37B:
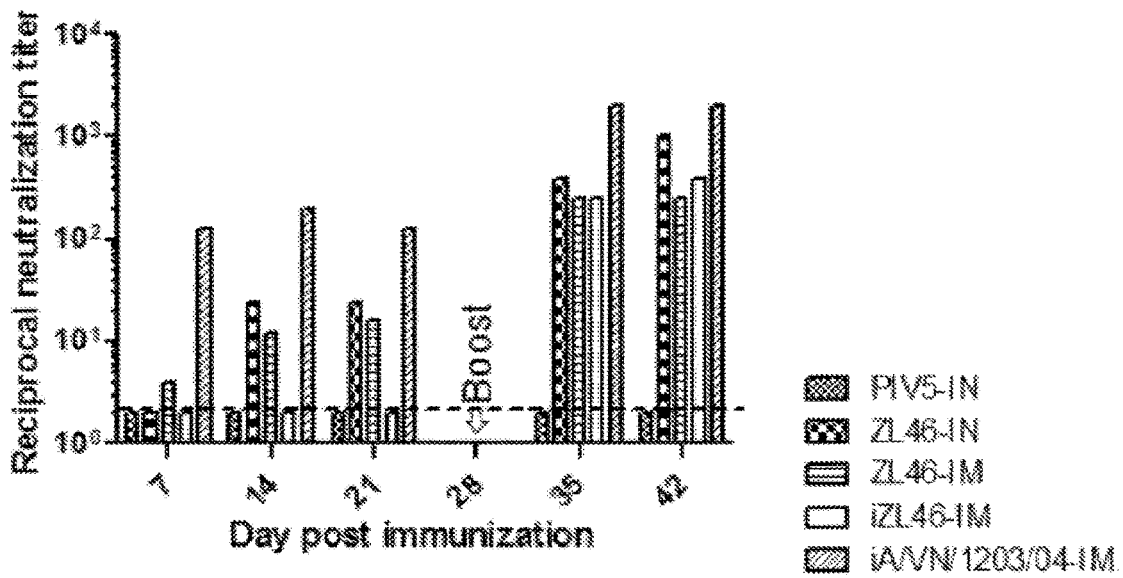
Figure 37C:
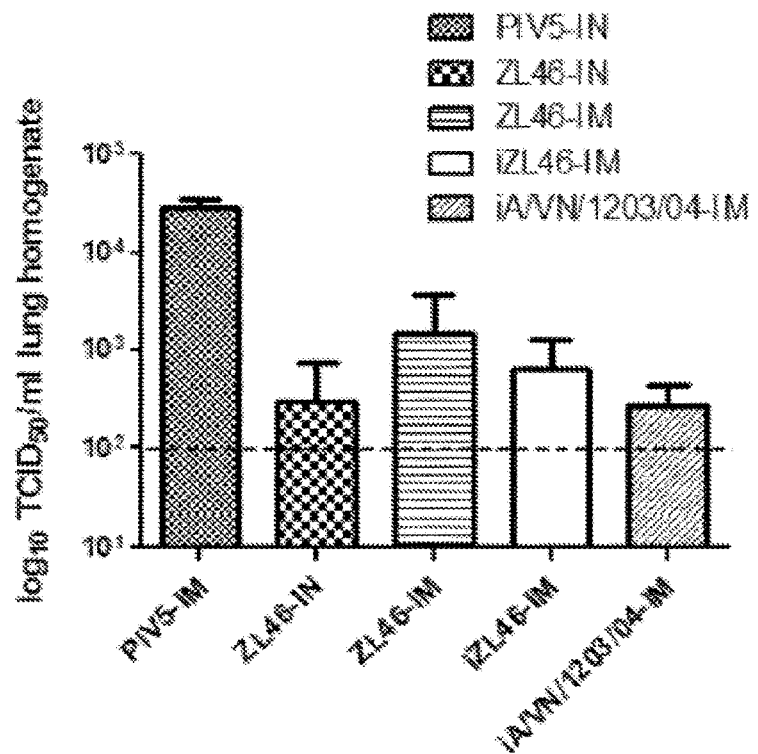

Once again, live ZL46 induced robust IgG and neutralizing antibody responses by 21 days post-priming with more modest IgG and no neutralizing antibody responses from iZL46. However, one week after boosting, all three ZL46 immunization methods (live IN, live IM, and inactivated IM) had robust HA-specific IgG and H5 neutralizing serum antibody responses (FIGS. 37A and 37B). Six weeks after boosting, mice were challenged with the rgA/VN-PR8 virus and three days later, euthanized to assess lung virus titers. Strikingly, all vaccinated mice (ZL46 IN or IM, iZL46 IM, iA/VN/1203/04 IM) had significantly reduced lung virus titers as compared to the PIV5-immunized control mice (FIG. 37C; P<0.05, ANOVA, followed by a Dunnett's Multiple Comparison Test), while none of the HA-vaccinated groups were significantly different from each other. While IN immunization with ZL46 continued to provide the best protection (⅗ mice had undetectable virus titers while all of the other ZL46-immunized mice all had detectable virus on day 3 post-challenge), IM immunization with live or inactivated PIV5-HA was effective at inducing protective neutralizing serum antibody responses, comparable to whole, inactivated wild type influenza virus.

Figure 34D:
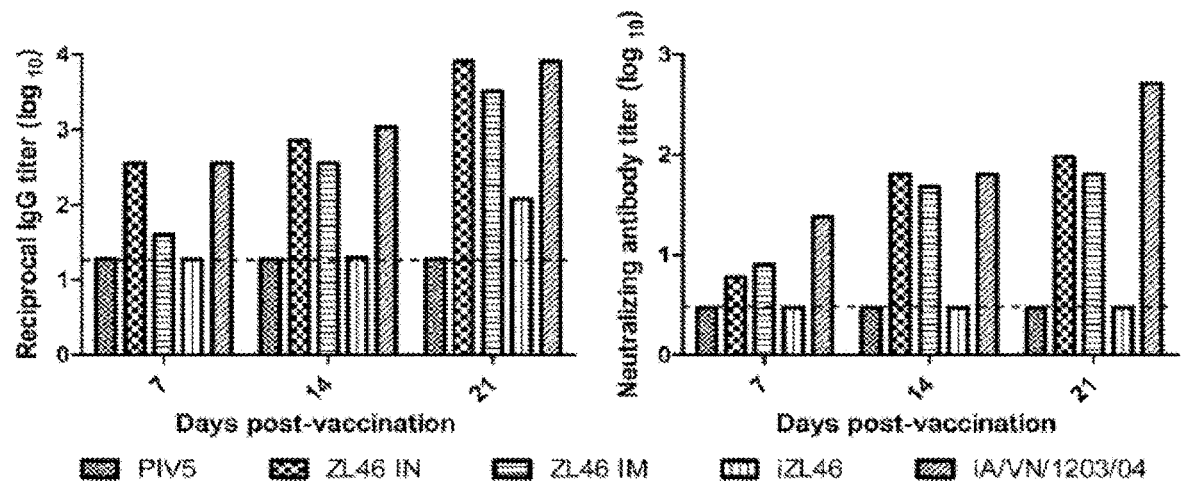

Inactivated vaccines against HPAI H5N1 viruses are generally poorly immunogenic in mammals, requiring high antigen doses, multiple immunizations, and adjuvants in some cases (Lipatov et al., 2006, *J Infect Dis;* 194:1040-1043; Lu et al., 1999, *J Virol;* 73:5903-5911; Treanor et al., 2001, *Vaccine;* 19:1732-1737; and Tumpey et al., 2001, *J Virol;* 75:5141-5150). Both live and inactivated HPAI vaccines have issues with production, including reduced yields of vaccine during production, difficulty generating seed strains, and safety concerns (Steel, 2011, *BioDrugs;* 25:285-298). With the present invention, a novel recombinant paramyxovirus vaccine vector, PIV5 that expresses the HA from H5N1 influenza virus has been developed that induces protective immunity against HPAI virus infection (see FIGS. 34-36 and Example 3). Here, the efficacy of this vaccine is assessed utilizing different immunization methods and comparing live and inactivated vaccine.

Intranasal immunization with live PIV5-H5 induces robust serum and mucosal antibody responses specific for the HA transgene. The HA-specific response induced by a single immunization with the avirulent PIV5-H5 vaccine is comparable to responses induced by sub-lethal infection with rgA/VN-PR8 influenza virus where the influenza immunized mice had clinical signs of illness and lost up to 15% of their (FIG. 35). Thus, PIV5 provides an appealing method for intranasal immunization without the concerns for reassortment posed by live-attenuated influenza vaccines.

Unlike influenza virus, which generally replicates in airway or gut epithelial cells due to receptor and protease requirements (Rott et al., 1995, *Am J Respir Crit Care Med;* 152:S16-19), PIV5 has the potential for broader cellular tropism. This feature makes it an appealing candidate for use as a live intramuscular vaccine. While, this also presents the possibility that a PIV5 vaccine could disseminate to other tissues, previous studies found no evidence of pathology in other tissues after intranasal PIV5 infection (Tompkins et al., 2007, *Emerg Infect Dis;* 13:426-435), suggesting intramuscular immunization with a rPIV5 vector would be safe, as well.

Intramuscular immunization with PIV5-H5 induces robust HA-specific and neutralizing serum antibody responses, comparable to intranasal immunization with PIV5-H5 or intramuscular immunization with whole inactivated H5N1 virus (FIG. 35). The intramuscular immunization with the live PIV5-H5 has the added advantage of priming robust HA-specific T cell responses as well. While the absence of mucosal antibody responses made the PIV5-H5 intramuscular immunization imperfect, it does provide a route of immunization potentially more appropriate for individuals with asthma or other contraindications for intranasal immunization. Moreover, it provides an opportunity for combining this vaccine with other injectable vaccines, as well as an injectable vaccine formulation, which may be appealing for agricultural applications.

Mucosal antibodies have been associated with protection from both homologous and heterosubtypic immunity. This example found that intramuscular administration of a live rPIV5-H5 vaccine failed to induce mucosal IgA responses, but protected against lethal H5N1 challenge (FIGS. 35 and 36). Mucosal (intranasal) immunization with the same vaccine primed comparable virus neutralizing serum antibody titers, but also induced virus-specific lung and nasal IgA (FIG. 35). These mice were also protected from mortality associated with a lethal H5N1 infection, but also had no detectable virus in the lung on day 3 post-infection. In contrast mice without detectable IgA (intramuscular immunized groups) had virus titers similar to control animals. Thus, while intramuscular immunization may have some advantages over intranasal immunization, particularly for individuals with chronic respiratory disease, intranasal immunization is likely to be the most effective route of administration.

Inactivated rPIV5-H5 was not efficacious when delivered one time intramuscularly. It is possible that the amount of HA incorporated into the virion is insufficient to effectively prime a protective antibody response against influenza infection; however whole-virus, inactivated influenza vaccines have failed to induce virus neutralizing serum antibody responses after a single immunization (Lipatov et al., 2006, *J Infect Dis;* 194:1040-1043; and Lu et al., 1999, *J Virol;* 73:5903-5911). Here, the inactivated homologous whole virus did induce neutralizing antibodies, possibly due to the high antigen dose (25 HAU); moreover the whole virus has the advantage of priming responses to multiple influenza antigens, which can contribute to protection from challenge. Alternatively, the influenza virus may contain other antigens or PAMPs that more effectively prime the response (i.e. act as an adjuvant) and the PIV5 virus lacks these stimulatory molecules. This is reflected in the reactogenicity seen with whole virion vaccines (Bernstein et al., 1982, *Pediatrics;* 69:404-408). In either case, replication competent rPIV5-H5 overcame this deficiency, priming both T cell and neutralizing antibody responses that protected against homologous HPAI challenge. Moreover, boosting with the inactivated PIV5-H5 vaccine (iZL46) was successful at priming influenza neutralizing antibody responses that reduced H5N1 virus titers after challenge comparably to live PIV5-H5 and inactivated H5N1 vaccine (FIG. 37). As PIV5 vaccines can be readily grown in vaccine-approved cell lines (e.g. Vero cells), PIV5-HA may provide an avenue for rapid, safe production of a traditional HA-specific inactivated pandemic influenza vaccine without the challenges associated with identification and development of influenza vaccine seed strains. Formulation of inactivated PIV5-HA vaccines with an adjuvant may enable priming of neutralizing antibody titers with a single immunization, similar to other H5 HA-based vaccines (Steel, 2011, *BioDrugs;* 25:285-298).

Although intranasal administration of rPIV5-HA has been shown to be safe in mice, respiratory delivery of live replicating virus-vectored vaccines can be of concern for asthmatic or immune-compromised patients. The option of intramuscular administration of live vaccine or the inactivated vaccine would be provide appealing alternatives to intranasal immunization, without a modification of the vaccine platform. This is in contrast to the current alternatives, where either a live-attenuated influenza virus vaccine or a split, inactivated wild type virus vaccine is delivered intranasal or intramuscular, respectively. Moreover, intramuscular immunization with a live or inactivated PIV5-HA vaccine could enable co-formulation with existing live or antigen-based (inactivated) vaccines, improving potential utility in mass-vaccination campaigns, in particular. Finally, the availability of multiple administration and formulation options would be useful for agricultural vaccination programs, where a universal production platform for diverse applications could provide a safer and more cost-effective option and improve vaccination. Thus, the PIV5-HA vaccine is a versatile vaccine platform for production of vaccines to protect against emerging or pandemic influenza viruses and H5N1 HPAI virus in particular.

Example 8

Single Dose Vaccination of Recombinant Parainfluenza Virus 5 Expressing NP From H5N1 Provides Broad Immunity Against Influenza A Viruses Influenza viruses often evade host immunity via antigenic drift and shift despite previous influenza virus infection and/or vaccination. Vaccines that match circulating virus strains are needed for optimal protection. Development of a universal influenza vaccine providing broadly cross-protective immunity will be of great advantage. The nucleoprotein (NP) of influenza A virus is highly conserved among all strains of influenza A viruses and has been explored as an antigen for developing a universal influenza virus vaccine. In this example, a recombinant parainfluenza virus 5 (PIV5) was generated that contained NP from H5N1 (A/Vietnam/1203/2004), a highly pathogenic avian influenza (HPAI) virus, between HN and L (PIV5-NP-HN/L) and its efficacy tested. PIV5-NP-HN/L induced humoral and T cell responses in mice. A single inoculation of PIV5-NP-HN/L provided complete protection against lethal heterosubtypic H1N1 challenge, and 50% protection against lethal H5N1 HPAI challenge. To improve efficacy, NP was inserted in different locations within the PIV5 genome. Recombinant PIV5 containing NP between F and SH (PIV5-NP-F/SH) or between SH and HN (PIV5-NP-SH/HN) provided better protection against H5N1 HPAI challenge than PIV5-NP-HN/L. These results indicate that PIV5 expressing the NP from H5N1 has the potential to be utilized as a universal influenza virus vaccine.

Influenza virus is a negative strand RNA virus with a segmented genome. Influenza A virus is associated with pandemics and is classified by its two major surface glycoproteins, hemagglutinin (HA) and neuraminidase (NA). There are 17 HA and 9 NA subtypes, differing by about 30% in protein homology, which are used to categorize influenza A virus into subtypes (e.g. H1N1, H3N2, H5N1, etc.). Point mutations in the antibody-binding sites of surface glycoproteins allow viruses to evade antibody-mediated immunity and re-infect humans and animals (antigenic drift). When different influenza A virus subtypes infect the same host, exchange of gene segments can occur, resulting in a new virus with a unique combination of viral genome (antigenic shift), which may give rise to pandemics. Influenza A virus causes significant morbidity and mortality each year. Strains currently circulating in humans (i.e. H1N1, H1N2, and H3N2) infect up to 15% of the world population and cause an average of 36,000 deaths and 226,000 hospitalizations in the United States (Harper et al., 2005, *MMWR Recomm Rep;* 54:1-40), as well as millions deaths worldwide (Influenza fact sheet, 2003, *Wkly Epidemiol Rec;* 78:77-80). Sporadic outbreaks of pandemic influenza have caused significant mortality over the past century, most notably the Spanish flu of 1918, and have caused over 50 million deaths worldwide (reviewed in Lipatov et al., Webster, 2004, *J Virol;* 78:8951-8959). On the horizon is another potentially pandemic strain of influenza, H5N1. This avian influenza virus has most notably emerged in Southeast Asia and led to the destruction of millions of birds, resulted in 608 reported human cases of which 359 were fatal since 2003.

A vaccine that can provide broad protection against different subtypes of influenza A viruses would be ideal. Vaccine candidates targeting conserved influenza virus proteins have been explored as potential universal influenza virus vaccines. The nucleoprotein (NP) of influenza A virus, which encapsidates the viral genome is well-conserved among all influenza viruses with over 90 percent homology of amino acid residues and has been identified as a component for developing a universal influenza virus vaccine. An adenovirus containing NP had been shown to provide protection against a homologous as well as a heterosubtypic influenza virus challenge (Price et al., 2010, *PLoS One;* 5:e13162). Moreover, a recombinant Modified Vaccinia Ankara (MVA) virus containing NP and M1 of influenza virus induced CD8+ T cells response and reduced symptom severity and virus shedding in humans in phase 1 and 2a trials, suggesting that NP can be utilized for developing a potential broadly protective influenza virus vaccine. Recombinant DNA vaccines expressing influenza antigen NP have been tested in animal models and shown to induce protective antibody and T cell responses; however, the need for repeated administration of DNA can be a hurdle for using a DNA-based vaccine against a rapidly spreading influenza virus pandemic.

As shown in the examples included herewith, PIV5-vectored vaccines are efficacious in animals. As shown in Example 3, a single dose intranasal (IN) inoculation of as little as $10^3$ pfu of PIV5 expressing HA of influenza A virus H5N1 protected against lethal H5N1 challenge in mice (see also Li et al., 2013, *J Virol;* 87:354-362). And, as shown in Example 2, a PIV5-based vaccine has been shown to induce protective immunity in dogs that were exposed to PIV5. Levels of immunity were comparable in dogs with and without prior PIV5 exposure, indicating that pre-existing anti-PIV5 immunity does not negatively affect the immunogenicity of a PIV5-based vaccine (see also Chen et al., 2012, *PLoS One;* 7:e50144).

In this example, a recombinant PIV5 was generated that contained the NP gene from a H5N1 HPAI (A/Vietnam/1203/2004) and its efficacy to protect against a lethal homologous as well as a heterosubtypic influenza virus challenge in mice was tested.

Materials and Methods

Cells. Monolayer cultures of MDBK, MDCK and Vero cells were maintained in DMEM containing 10% fetal bovine serum (FBS), 100 IU/ml penicillin, and 100 µg/ml streptomycin. BHK and BSR-T7 cells were maintained in DMEM containing 10% FBS, 10% tryptose phosphate broth (TPB). G418 was added to BSR-T7 cells. All cells were incubated at 37° C., 5% CO2. Virus-infected cells were cultured in media containing reduced FBS (2%). Plaque assays of PIV5 viruses were performed using BHK cells as described previously (He et al., 1997, *Virology;* 237:249-260). $TCID_{50}$ assays of influenza virus were performed using MDCK cells as described previously (Soboleski et al., 2011, *PLoS One;* 6:e21937).

Influenza viruses. A/Puerto Rico/8/34 (H1N1; PR8), X-31 (H3N2; A/Aichi/2/68 X PR8 reassortant) (Baez et al., 1980, *J Infect Dis;* 141:362-365), and rgA/VN-PR8 (H5N1; provided by Dr. Ruben Donis, CDC, Atlanta, Ga.) were propagated in the allantoic cavity of embryonated hen eggs at 37° C. for 48-72 hours. Highly-pathogenic A/Vietnam/1203/2004 (H5N1; provided by Richard Webby, St. Jude Children's Research Hospital, Memphis, Tenn.) was propagated in the allantoic cavity of embryonated hen eggs at 37° C. for 24 hours. All viruses were aliquoted and stored at −80° C. All experiments using live, highly pathogenic A/Vietnam/1203/2004 were reviewed and approved by the institutional biosafety program at the University of Georgia and were conducted in enhanced biosafety level 3 (BSL3+) containment following guidelines for use of Select Agents approved by the CDC.

Mice. 6 to 8 week old female BALB/c mice (Charles River Labs, Frederick, Md.) were used for all studies. Mice were anesthetized via intraperitoneal administration of Avertin (2,2,2-tribromoethanol) prior to all intranasal vaccinations and influenza virus challenges. Mouse immunizations and studies with BSL2 viruses were performed in enhanced BSL2 facilities in HEPA filtered isolators. Mouse HPAI infections were performed in enhanced BSL3 facilities in HEPA filtered isolators following guidelines approved by the institutional biosafety program at the University of Georgia and for use of Select Agents approved by the CDC. All animal studies were conducted under guidelines approved by the Institutional Animal Care and Use Committee of the University of Georgia.

Construction of recombinant plasmid. To generate a plasmid containing NP insertion between the HN and L genes in the PIV5 genome (PIV5-NP-HN/L), the plasmid BH311 containing the full length genome of PIV5 and an extra GFP gene between HN and L gene was used (He et al., 1997, *Virology*; 237:249-260). The ORF of NP from the high pathogenic H5N1 influenza virus (H5N1 HPAI, A/Vietnam/1203/2004). To generate plasmids containing NP insertion between M and F (PIV5-NP-M/F), F and SH (PIV5-NP-F/SH), or SH and HN (PIV5-NP-SH/HN), the plasmid BH276 containing the full length genome of PIV5 was used (He et al., 1997, *Virology*; 237:249-260). To obtain the NP gene, HPAI H5N1 RNA was extracted, and cDNA was generated. The cDNA was amplified to generate the NP gene using NP specific primers. The expression plasmid pET-15b-NP encoding a His tagged-H5N1-NP protein was constructed using the pET-15b vector.

Virus rescue and sequencing. The plasmids PIV5-NP-M/F, PIV5-NP-F/SH, PIV5-NP-SH/HN, or PIV5-NP-HN/L encoding the full length genome of PIV5 with NP gene insertion at the indicated gene junction, and three helper plasmids pPIV5-NP, pPIV5-P, and pPIV5-L encoding NP, P, and L proteins, were co-transfected into BSR-T7 cells at 95% confluency in 6-cm plates with Jetprime (Polyplus-transfection, Inc., New York). The amounts of plasmids used were as follows: 5 µg full length PIV5-NP plasmids, 1 µg pPIV5-NP, 0.3 µg pPIV5-P, and 1.5 g pPIV5-L. After 72 h incubation at 37° C., the media were harvested, and cell debris pelleted by low speed centrifugation (3,000 rpm, 10 min). Plaque assays were used to obtain single clones of recombinant viruses.

The full length genome of plaque-purified PIV5-NP viruses was sequenced. Total RNA from the media of PIV5-NP virus-infected Vero cells were purified using viral RNA extraction kit (Qiagen Inc, Valencia, Calif.). cDNAs were prepared using random hexamers and aliquots of the cDNA were then amplified in PCR reactions using appropriate oligonucleotide primer pairs as described previously (Example 3 and Li et al., 2013, *J Virol*; 87:354-362). PCR products were sequenced.

Detection of viral protein expression. Immunofluorescence (IF) and immunoprecipitation (TP) assays were used to detect expression of viral proteins. For IF assay, MDBK cells in 24-well plates were mock infected or infected with PIV5 or PIV5-NP-HN/L at a MOI of 0.1. At 2 dpi, the cells were washed with PBS and then fixed in 0.5% formaldehyde. The cells were permeabilized in 0.1% PBS-Saponin solution then incubated for 30 min with monoclonal anti-PIV5-V/P or anti-H5N1-NP antibodies. The cells were washed with PBS/1% BSA and incubated with FITC-labeled goat anti-mouse antibody. The cells were incubated for 30 min, washed, and examined and photographed using a fluorescence microscope (Advanced Microscopy Group).

For IP, MDBK cells in 6-well plates were mock infected or infected with PIV5 or PIV5-NP-HN/L at a MOI of 5. At 22 hpi, the cells were labeled with 35S-Met/Cys Promix (100 µCi/ml) for 2 hr. The cells were lysed in RIPA buffer and aliquots were immunoprecipitated using monoclonal anti-PIV5-V/P or anti-H5N1-NP antibodies. The precipitated proteins were resolved by 15% SDS-PAGE and examined by autoradiography using a Storm Phosphorimager (Molecular Dynamics Inc., Sunnyvale, Calif.).

Expression levels of H5-NP in virus-infected cells were compared using MDBK cells in 6-well plates that were mock infected or infected with PIV5, PIV5-NP-M/F, PIV5-NP-F/SH, PIV5-NP-SH/HN, or PIV5-NP-HN/L at a MOI of 5. The cells were collected at 2 dpi and fixed with 0.5% formaldehyde for 1 hr. The fixed cells were resuspended in FBS-DMEM (50:50) then permeabilized in 70% ethanol overnight. The cells were washed once with PBS and then incubated with mouse anti-H5N1 NP antibody or anti-PIV5-V/P antibody in PBS/1% BSA (1:200) for 1 hr at 4° C. The cells were stained with anti-mouse antibody labeled with phycoerythrin for 1 hr at 4° C. in the dark and then washed once with PBS /1% BSA. The fluorescence intensity was measured using a flow cytometer (BD LSR II).

Growth of viruses in vitro and in vivo. MDBK cells in 6-well plates were infected with PIV5, PIV5-NP-M/F, PIV5-NP-F/SH, PIV5-NP-SH/HN, or PIV5-NP-HN/L at a MOI of 0.1. The cells were then washed with PBS and maintained in DMEM-2% FBS. Media was collected at 0, 24, 48, 72, 96 and 120 hpi. The titers of viruses were determined by plaque assay on BHK cells.

To compare the growth of viruses in mice, 6-week old wild type BALB/cJ mice were vaccinated with $10^5$ pfu of PIV5, PIV5-NP-M/F, PIV5-NP-F/SH, PIV5-NP-SH/HN, or PIV5-NP-HN/L in 50 µl volume intranasally. Mice were euthanized and lungs harvested to determine virus titers at 3 days post infection.

ELISA. To generate purified influenza NP protein, the pET 15b-NP plasmid was transformed into BL21(DE3) pLysS E. coli competent cells. The recombinant 6X His-NP protein was purified using Ni-charged resin (Novagen) and examined by SDS-PAGE and Coomassie blue staining. For the generation of immune serum, mice were vaccinated with $10^6$ pfu of PIV5, PIV5-NP-HN/L or $10^5$ pfu of X31 intranasally and blood samples collected on day 21 post vaccination. Purified NP protein at 2 µg/ml was coated in 96-well plates at 4° C. overnight. ELISA was performed following manufacturer's instruction (KPL, Inc). Serial dilution of sera samples from PIV5, PIV5-NP-HN/L and X31 inoculated mice were added into coated plates. Goat anti-mouse IgG conjugated to AP (KPL, Inc) was added and plates were developed. Optical density (OD) was measured at 405 nm on a Bio-Tek Powerwave XS plate reader.

Interferon-γ (IFN-γ) ELISpot assay. To detect CTL response in spleens of vaccinated mice, IFN-γ ELISpot assay was performed. Mice were vaccinated using PBS, $10^7$ pfu of PIV5, PIV5-NP-F/SH, PIV5-NP-SH/HN, PIV5-NP-HN/L or 0.1 $LD_{50}$ of PR8 intranasally. At day 21 post vaccination, mice were sacrificed and spleens collected. Spleens were homogenized and washed with HBSS media. Gey's solution was added to remove the red blood cells. Splenocytes in Complete Tumor Medium (CTM) were added into 96-well plate (Millipor MAIPSWU10) pretreated with 70% ethanol and coated with anti-mouse IFN-γ mAb AN18 (Mabtech, Inc). Cells were mock re-stimulated or re-stimulated with Flu-NP 147-155 peptide (TYQRTRALV) (SEQ ID NO:9), Ebola GP P2 (EYLFEVDNL) (SEQ ID NO:10) as an irrelevant peptide, or PMA/ionomycin. Cultures were incubated at 37° C., 5% $CO_2$ for 48 hours. Splenocytes were removed and plates washed and incubated with biotinylated anti-mouse IFN-γ mAb R4-6A2 (Mabtech, Inc) at room temperature for 1 hr. After washing, plates were incubated with Streptavidin-alkaline phosphatase (KPL, Inc) and incubated at room temperature for 1 hr. Plates were developed using BCIP/NBT (KPL, Inc) solution. Spots were counted using an AID ViruSpot Reader (Cell Technology, Inc). Results are presented as the mean number of cytokine secreting cells subtracted by the mean number of mock stimulation per $10^6$ splenocytes.

Infection of mice with influenza A viruses. H1N1-Mice were immunized with a single dose of PBS, $10^6$ pfu of PIV5, PIV5-NP-HN/L or $10^5$ pfu of X31 intranasally. At day 21 post vaccination, mice were challenged with 10 LD50 A/PR/8/34 (H1N1). On day 3 post challenge, groups of mice were euthanized and the lungs were collected and homogenized. $TCID_{50}$ assay was used to determine virus titers in cleared homogenate.

H5N1-Mice were immunized with a single intranasal administration of PBS, $10^7$ pfu of PIV5, PIV5-NP-HN/L, PIV5-NP-F/SH, PIV5-NP-SH/HN, or 2000 pfu of rgA/VN-PR8. At day 21 post vaccination, mice were challenged with 10 or 20 LD50 H5N1 HPAI as indicated. Following challenge, mice were monitored daily for weight loss and survival. Mice were scored based upon clinical signs of infection (ruffled fur, hunched posture, dyspnea: 1 point each, <25% weight loss: 1 point, 25-35% weight loss: 2 points, >35% weight loss: 3 points, neurological symptoms: 3 points). Animals were humanely euthanized upon reaching 3 points. Challenges involving A/Vietnam/1203/2004 were conducted in ABSL3+ containment. All animal studies were conducted under guidelines approved by the Institutional Animal Care and Use Committee of the University of Georgia.

Results

Figures 38, 39A:
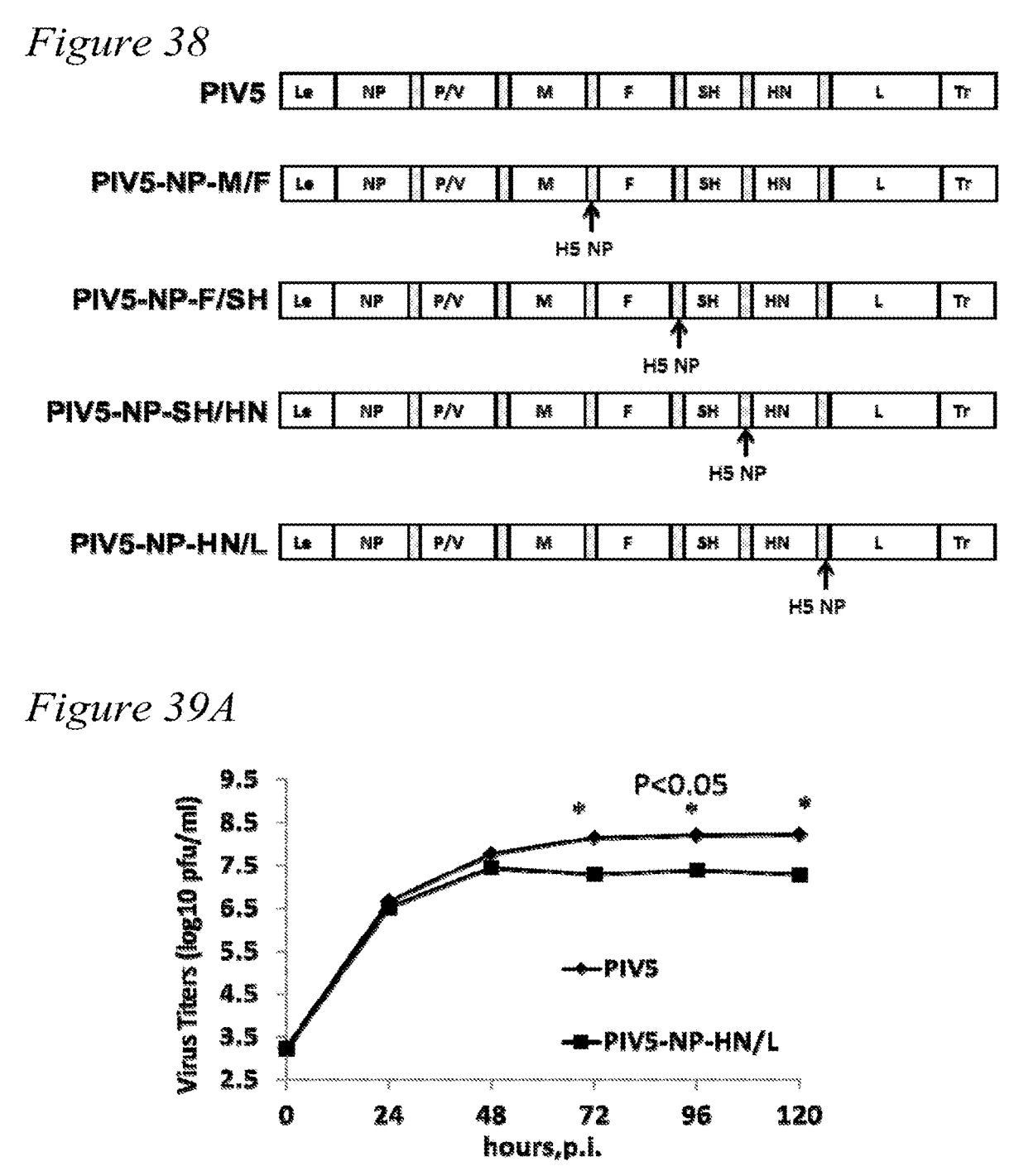

Generation and analysis of PIV5-NP-HN/L. To test whether recombinant PIV5 expressing NP from H5N1 HPAI can provide protection against different subtypes of influenza virus challenges in mice, the H5N1 HPAI NP gene was inserted into the cDNA of PIV5 between the HN and L genes (FIG. 38). The plasmid containing the PIV5 genome with NP gene inserted between HN and L gene was transfected along with three helper plasmids encoding PIV5 NP, P and L genes into BSR-T7 cells to recover infectious virus as describe previously (Sun et al., 2011, *J Virol;* 85:8376-8385). The infectious PIV5-NP-HN/L virus was plaque-purified and the full-length genome sequence of PIV5-NP-HN/L was determined using RT-PCR sequencing as described in Example 3 (see also Li et al., 2013, *J Virol;* 87:354-362 21). One plaque-purified clone matching the exact cDNA of the genome sequence was used for all further experiments.

Expression of NP from PIV5-NP-HN/L-infected cells was confirmed using immunofluorescence and immunoprecipitation assay. H5N1-NP protein was detected in PIV5-NP-HN/L-infected cells but not in mock or PIV5-infected cells. To test whether NP expression affected PIV5 viral protein expression levels, PIV5 viral proteins were immunoprecipitated using a PIV5-V/P antibody. No difference in PIV5 viral protein expression levels was observed between PIV5 and PIV5-NP-HN/L viruses.

Figure 39B:
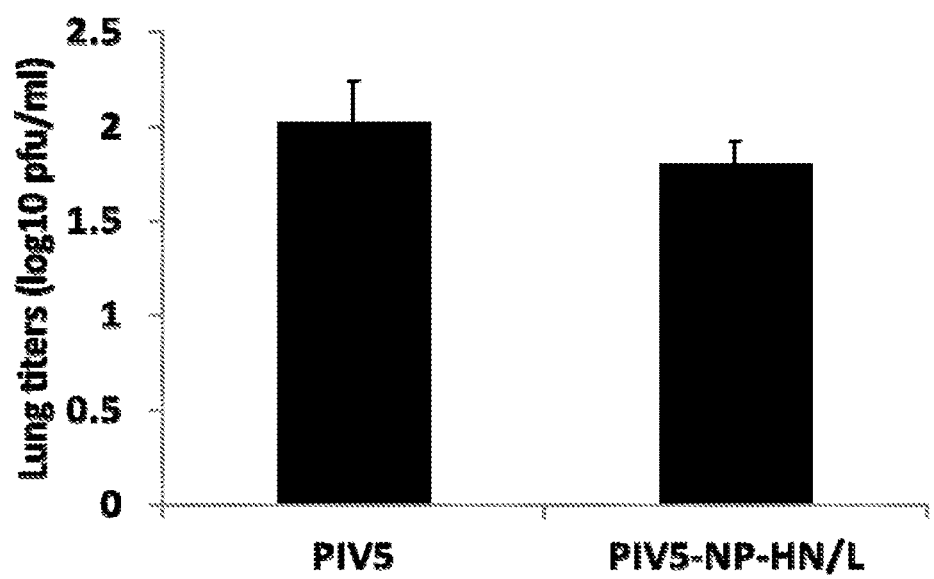

To compare growth of PIV5 and PIV5-NP-HN/L in tissue cultured cells, multiple-step growth curves were performed using MDBK cells. PIV5-NP-HN/L grew slightly slower than PIV5 (FIG. 39A). To examine growth of PIV5 and PIV5-NP-HN/L in vivo, BALB/c mice were vaccinated with $10^5$ pfu of PIV5 or PIV5-NP-HN/L intranasally. Titers of virus in the lungs of vaccinated mice were determined at 3 days post infection. The titers in the lungs of PIV5-NP-HN/L vaccinated mice were lower than that of PIV5 vaccinated mice; however, there was no significant difference between the two groups (FIG. 39B).

Figure 40:
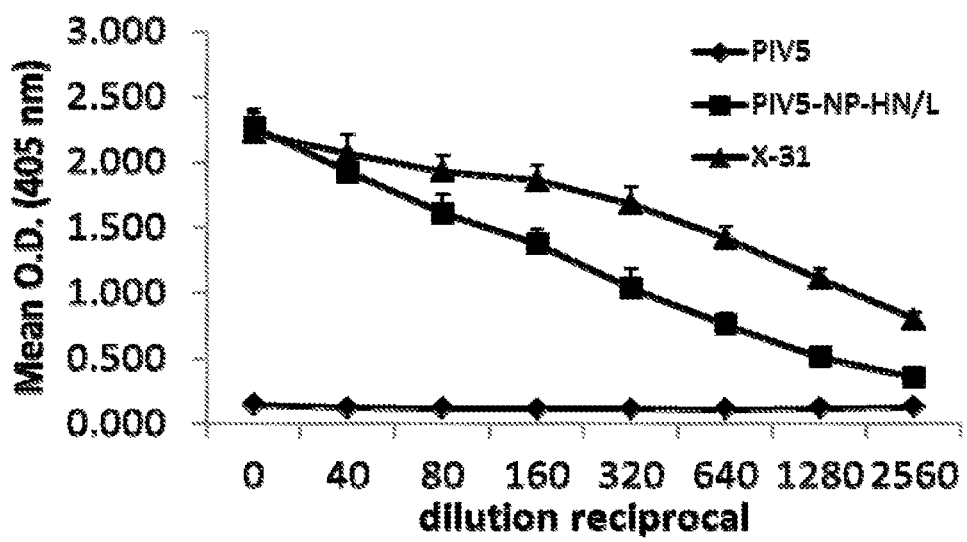
FIG. 40 shows NP-antibody levels in mice induced by PIV5-NP-HN/L. Mice were vaccinated with $10^6$ pfu of PIV5, PIV5-NP-HN/L or $10^5$ pfu of X31 intranasally. At day 21 post vaccination, blood samples were collected and sera prepared. ELISA was performed according to manufacturer's instruction (KPL, Inc) using purified H5N1-NP.

Immune responses to PIV5-NP-HN/L inoculation in mice. To investigate whether PIV5-NP-HN/L could generate NP-specific antibodies in vivo, mice were vaccinated with PIV5, PIV5-NP-HN/L or X31 intranasally. At day 21 post vaccination, blood samples were collected and sera prepared. Purified His-tagged NP protein from bacteria was used to coat 96-well plates. Serial-diluted sera samples were added to the plates. PIV5-NP-HN/L vaccination induced robust anti-NP serum IgG titers comparable to those induced by a live influenza virus infection (FIG. 40).

Figure 41:
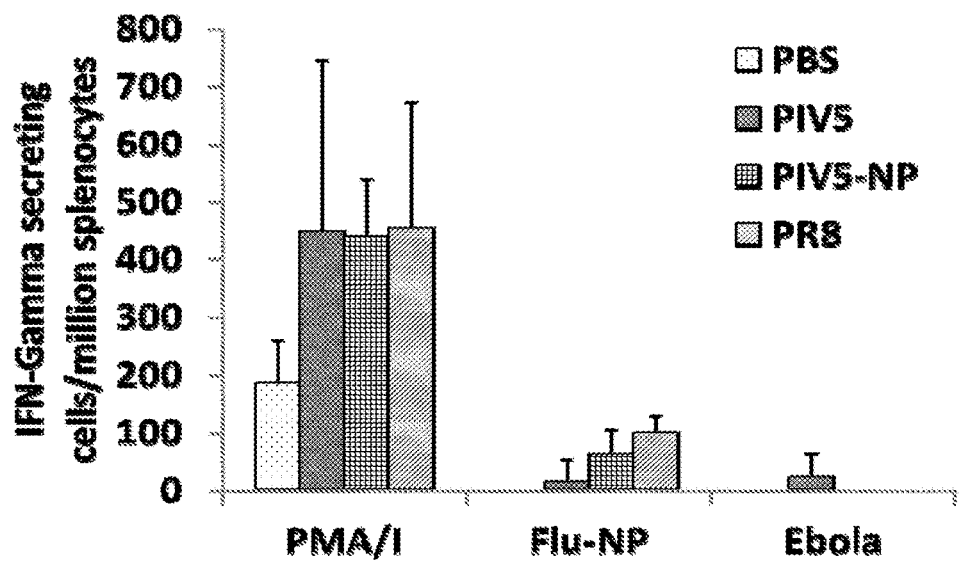
FIG. 41 shows T cell response in mice induced by PIV5-NP-HN/L. Mice were vaccinated with PBS, $10^7$ pfu of PIV5, PIV5-NP-HN/L or 0.1 $LD_{50}$ of PR8 intranasally (n=5 per group). At day 21 post vaccination, mice were sacrificed and spleens collected. Splenocytes were re-stimulated with Flu-NP, Ebola GP P2 as a negative control, or PMA/ionomycin as a positive control. Results are presented as the mean number of cytokine secreting cells per $10^6$ splenocytes.

To examine whether PIV5-NP can induce cellular immune response, mice were vaccinated with PBS, PIV5, PIV5-NP-HN/L or PR8 intranasally. At day 21 post vaccination, mice were euthanized and IFN-γELISpot assay was performed. PIV5-NP-HN/L-vaccinated mice induced a similar level of NP-specific CD8+ T cell response as compared to PR8-vaccinated mice (FIG. 41).

Figure 42A:
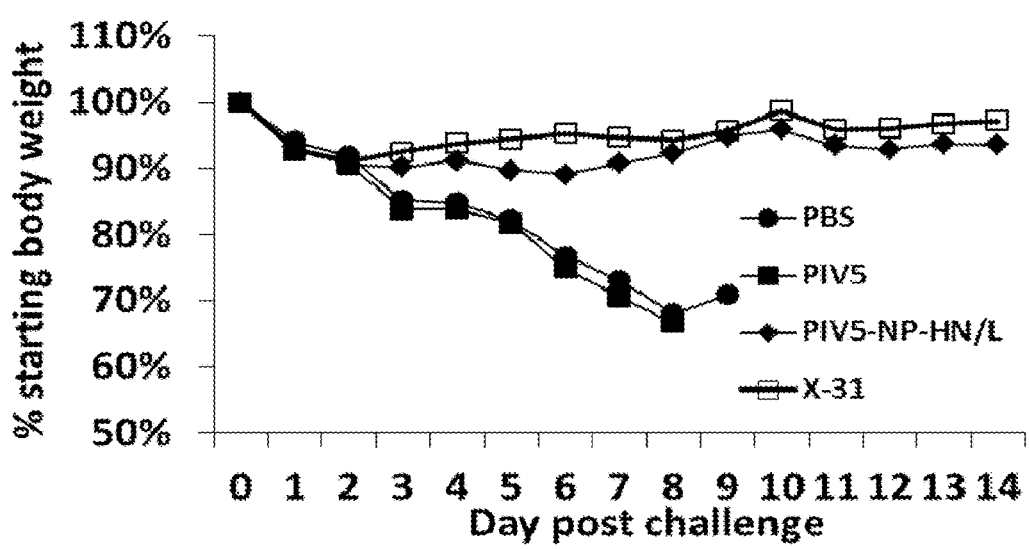
FIGS. 42A-42C show protection of PIV5-NP-HN/L against H1N1 challenge. Mice were vaccinated with PBS, $10^6$ pfu of PIV5, PIV5-NP-HN/L or $10^5$ pfu of X31 intranasally (n=10 per group). At day 21 post vaccination, mice were challenged with 10 $LD_{50}$ A/PR/8/34 (H1N1). Weight loss (FIG. 42A) and survival (FIG. 42B) were monitored daily for 14 days following challenge. Weight loss is presented as the average percentage of original weight (the day of challenge).
Figure 42B:
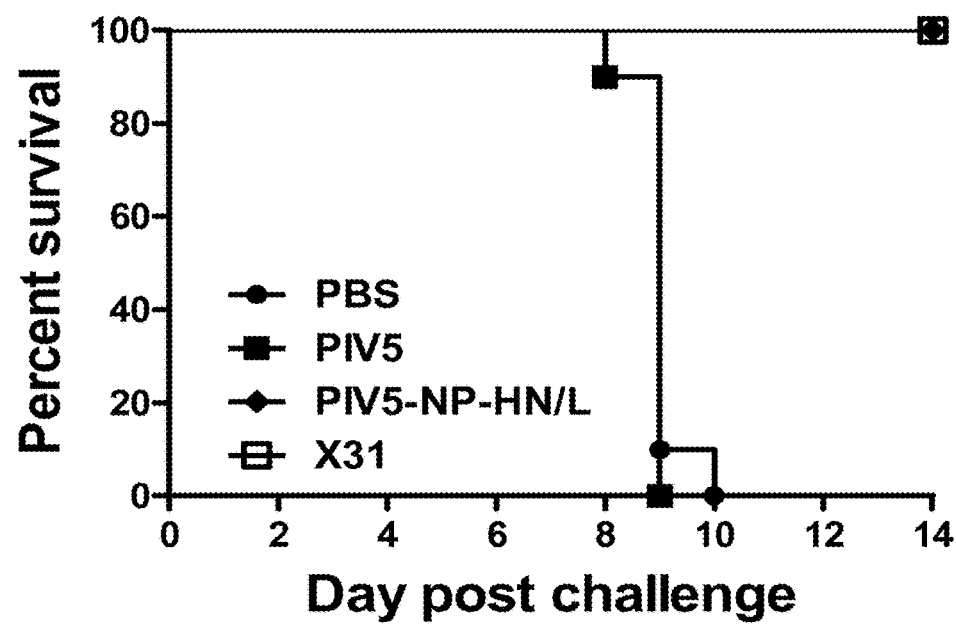
Figure 42C:
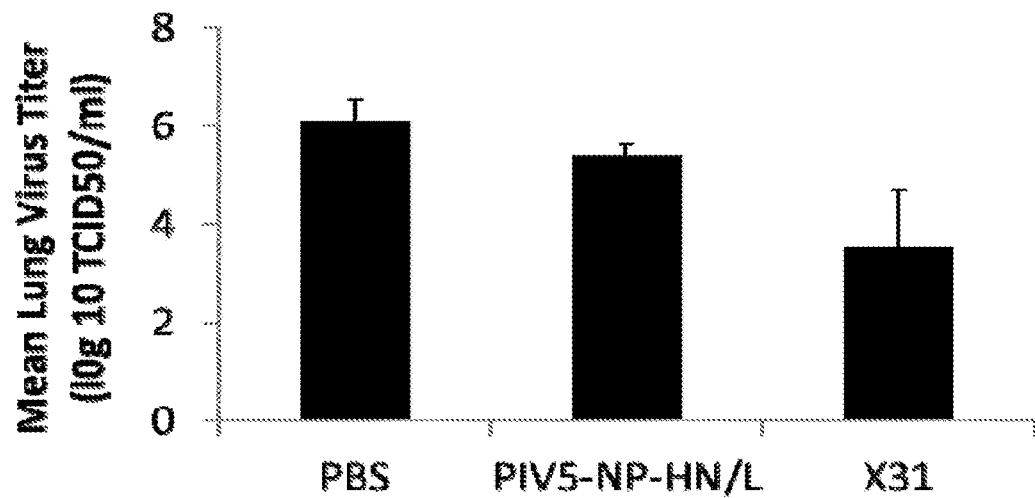

Determining efficacy of PIV5-NP-HN/L against heterosubtypic H1N1 challenge in mice. To examine if PIV5-NP-HN/L could provide cross-protection against a heterosubtypic H1N1 challenge, mice were immunized with a single dose of PIV5-NP-HN/L intranasally. At day 21 post vaccination, mice were challenged with 10 $LD_{50}$ A/PR/8/34 (H1N1). PBS and PIV5-immunized mice lost body weight and all mice died by day 10 after challenge. In contrast, all mice immunized with PIV5-NP-HN/L showed no significant weight loss during the time of experiment and all mice survived challenge (FIGS. 42A and 42B). This was comparable to the X31-primed positive control group. Influenza virus was detected in the lungs of PIV5-NP-HN/L-immunzed mice at 3 days post challenge (FIG. 42C) and although the virus titers in PIV5-NP-HN/L group were lower than those in the PBS group, there was no statistically significant difference between the two groups.

Figures 43A, 43B:
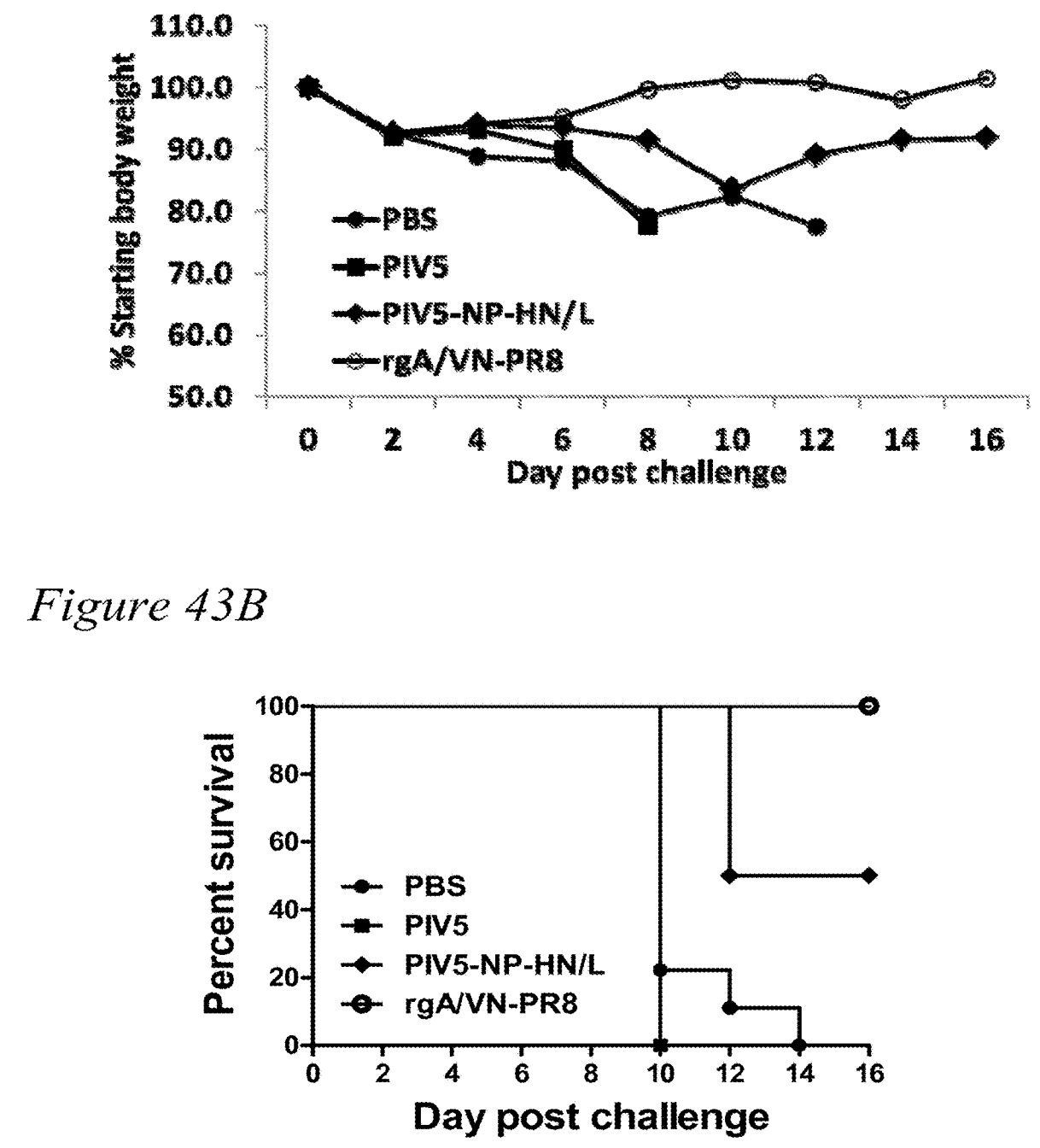

Determining efficacy of PIV5-NP-HN/L against H5N1 HPAI challenge in mice. To examine if PIV5-NP-HN/L could provide protection against a homologous H5N1 HPAI challenge, mice were immunized with a single dose of PIV5-NP-HN/L intranasally. At day 21 post vaccination, mice were challenged with 10 $LD_{50}$ H5N1 HPAT. All PBS and PIV5-immunized mice lost body weight and succumbed to the infection. Mice vaccinated with PIV5-NP-HN/L exhibited 50% survival following challenge with surviving mice losing less than 20% of their original body weight (FIGS. 43A and 43B).

Figures 44A, 44B:
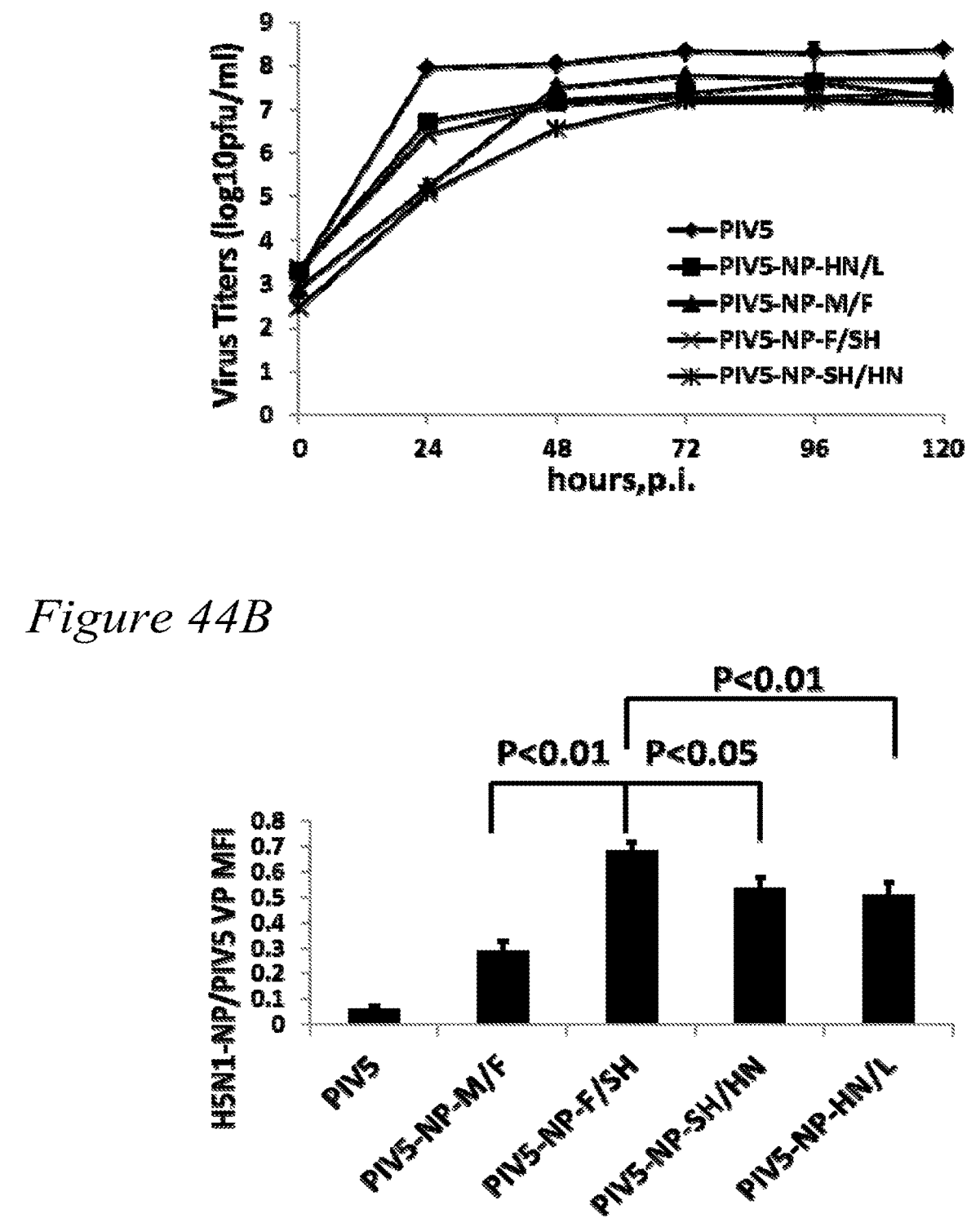
Figure 44C:
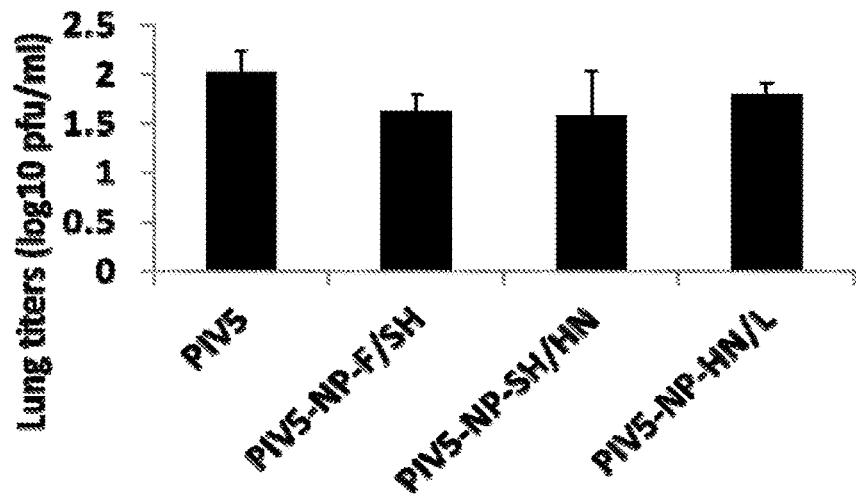

Generation and analysis of PIV5 expressing H5N1 NP at different locations within PIV5 genome. As shown in Example 3, insertion site within the PIV5 genome affected the immunogenicity of inserted antigens (see also Li et al., 2013, *J Virol;* 87:354-362 21). To investigate whether insertion of NP at different locations within PIV5 genome will result in improvement in efficacy of vaccine, NP was inserted between different gene junctions within PIV5 genome. NP insertion between the leader sequence and the NP gene did not result in a viable infectious virus. Because the insertion of a foreign gene upstream of the M gene within PIV5 genome affected virus growth in vitro and in vivo (Example 3 and Li et al., 2013, *J Virol;* 87:354-362), NP was inserted at the junction regions downstream of the M gene within PIV5 genome. PIV5-NP-M/F, PIV5-NP-F/SH, PIV5-NP-SH/HN, and PIV5-NP-HN/L grew similarly to each other and with a reduction in titer compared to PIV5 (FIG. 44A). The ratio of mean fluorescence intensity (MFI) of NP to PIV5 V/P was examined by flow cytometry to determine H5N1-NP protein expression levels. PIV5-NP-F/SH produced the highest ratio while PIV5-NP-SH/HN and PIV5-NP-HN/L produced similar ratios. PIV5-NP-M/F yielded the lowest ratio. These results suggest that PIV5-NP-F/SH induces the highest expression levels of NP (FIG. 44B). The capability of these viruses to replicate in mice was also compared. Although lung virus titers in mice vaccinated with PIV5-NP-F/SH, PIV5-NP-SH/HN, and PIV5-NP-HN/L were slightly lower than those of PIV5 only vaccinated mice, there were no significant differences at day 3 after vaccination (FIG. 44C).

Figure 45:
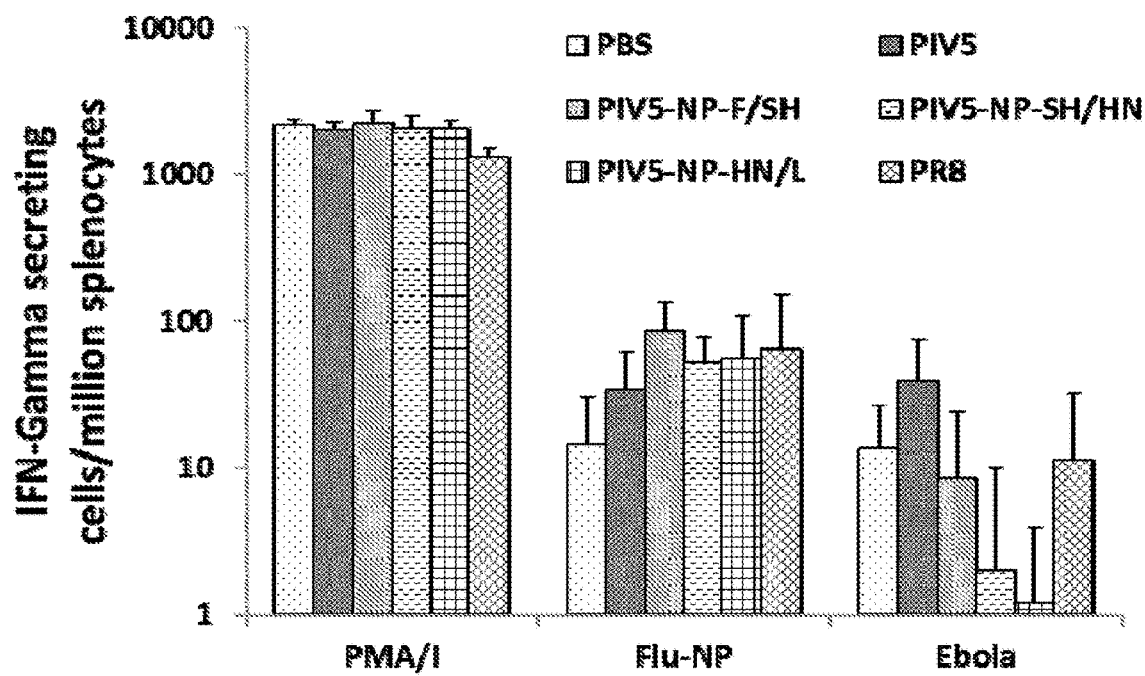
FIG. 45 shows PIV5-NP virus primes T cell responses. Mice were vaccinated with PBS, $10^7$ pfu of PIV5 or PIV5-NP viruses, or 0.1 $LD_{50}$ of PR8 intranasally (n=5 per group). At day 21 post vaccination, mice were sacrificed and spleens collected. Splenocytes were re-stimulated with Flu-NP, Ebola GP P2, or PMA/ionomycin. Results are presented as the mean number of cytokine secreting cells per $10^6$ splenocytes.

Cellular response to PIV5-NP virus infection. To determine whether expression levels of NP affected the immune responses as expected, mice were vaccinated with PBS, PIV5, PIV5-NP-FISH, PIV5-NP-SH/HN, PIV5-NP-HN/L or PR8 intranasally. At day 21 post vaccination, mice were euthanized and IFN-anELISpot assays performed. PIV5-NP vaccinated mice induced higher level of NP-specific CD8+ T cell response than PIV5 vaccinated mice. PIV5-NP-F/SH vaccinated mice produced the highest level of NP-specific CD8+ T cell response compared to other PIV5-NP viruses and PR8 vaccinated mice (FIG. 45), although the difference between PIV5 and PIV5-NP viruses, or between PIV5-NP viruses and PR8 was not statistically significant.

Figure 46A:
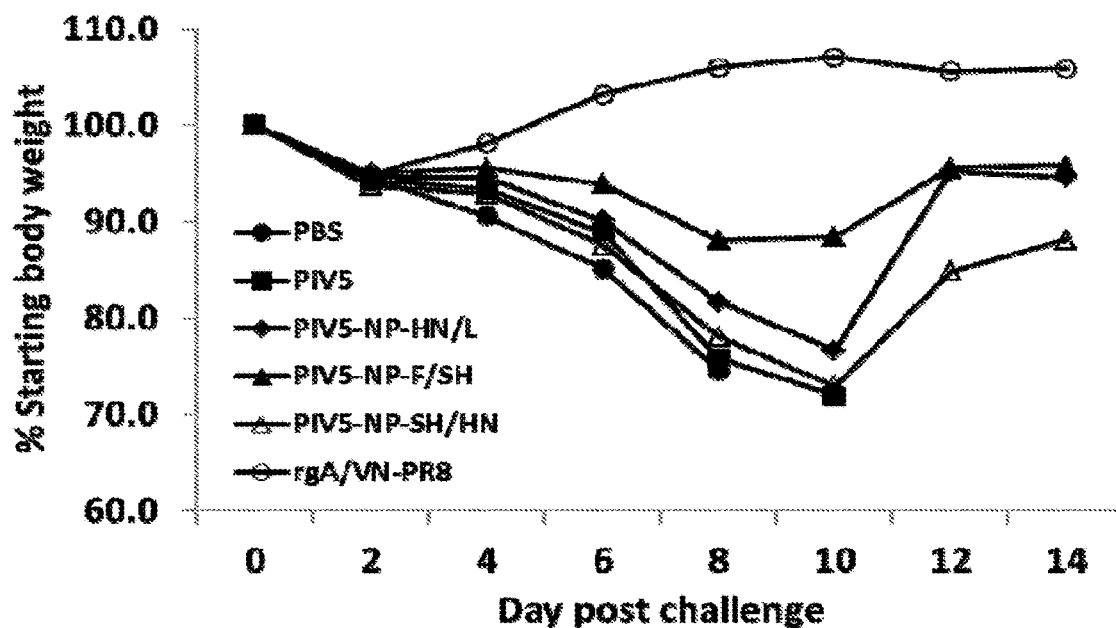
FIGS. 46A and 46B show protection of PIV5-NP viruses against H5N1 HPAI challenge. Mice were vaccinated with PBS, $10^7$ pfu of PIV5 or PIV5-NP viruses, or 2000 pfu of rgA/VN-PR8 intranasally (n=10 per group). At day 21 post vaccination, mice were challenged with 20 $LD_{50}$ H5N1 HPAI. Weight loss (FIG. 46A) and survival (FIG. 46B) were monitored for 14 days following influenza virus challenge. Weight loss is graphed as average percentage of original weight (the day of challenge).
Figure 46B:
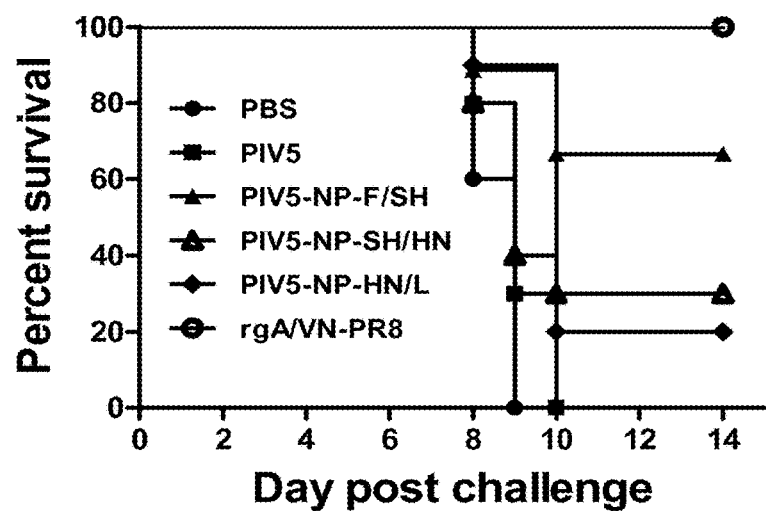

Determining efficacy of PIV5-NP virus against H5N1 HPAI challenge in mice. To investigate whether PIV5-NP-F/SH and PIV5-NP-SH/HN immunization could provide better protection against H5N1 HPAI challenge, mice were immunized with a single dose of PIV5-NP viruses intranasally. At day 21 post vaccination, mice were challenged with 20 $LD_{50}$ H5N1 HPAI. This higher challenge dose was used to maximize any possible differences among the different vaccine candidates. All PBS and PIV5-immunized mice lost body weight and succumbed to infection by 10 day post challenge. In contrast, 20% mice vaccinated with PIV5-NP-HN/L, 30% mice vaccinated with PIV5-NP-SH/HN, and 67% mice vaccinated with PIV5-NP-FISH survived challenge, indicating that insertion of NP between F and SH within PIV5 provided the best protection (FIGS. 46A and 46B).

Discussion

This example is the first report of a live viral vector based vaccine expressing a single NP gene that was completely protective against lethal H1N1 challenge and provided substantial protection (67%) against a highly lethal H5N1 challenge in a robust challenge model (20 $LD_{50}$ challenge) in mice, indicating that PIV5 is a more efficacious viral vector than AdV and VV for a NP-based vaccine.

Protective immunity against influenza A virus generated by NP is generally thought to be cell-mediated with antibodies against NP non-essential for NP-mediated protection. Recently though, reports indicate that anti-NP antibody may play a role in protective immunity. Consistent with anti-NP antibodies being non critical, a correlation between anti-NP serum titers and weight loss was not observed. This lack of correlation, however, does not exclude contribution of antibody in the protective immune responses. In this example, PIV5-NP-HN/L generated a robust NP-specific CD8+ T cell response as demonstrated in an IFN-γ ELISpot assay. PIV5-NP-HN/L immunized-mice induced a similar level of NP-specific CD8+ T cell responses as sub-lethal H1N1 infection (FIG. 40B). Consistent with the observation that cell-mediated immunity does not clear influenza virus infection, titers of challenge influenza viruses in the lungs of PBS and immunized mice were similar (FIG. 41C). PIV5-NP-F/SH immunized mice, which had the most NP-specific CD8+ T cell, had the highest survival rate (67%) after H5N1 HPAI challenge among the groups of mice immunized with different recombinant PIV5 expressing NP.

Transcriptional polarity is found in the Mononegavirale order which contains a single de facto promoter in the 3' end of genome, i.e., the leader sequence. Viral genes closer to the 3' end of the genome are transcribed in greater abundance than those towards the 5' end. In Example 3, insertion of HA from H5N1 HPAI between SH and HN in PIV5 (ZL46, PIV5-H5-SH/HN) resulted in better protection against H5N1 HPAI challenge than insertions at the junctions of NP and V/P, V/P and M, or HN and L of PIV5 (ZL48, PIV5-H5-HN/L), presumably because PIV5-H5-SH/HN produced the highest levels of HA expression without negatively affecting virus growth (see also Li et al., 2013, *J Virol;* 87:354-362 21). To improve efficacy of this PIV5-based NP vaccine, the NP gene was inserted upstream of the NP gene of PIV5, between the M and F genes, F and SH genes, and SH and HN genes. As reported in Example 3, insertion upstream of the NP gene of PIV5 did not lead to a viable recombinant PIV5, suggesting that insertion of foreign gene upstream of the NP gene of PIV5 is lethal. Interestingly, PIV5-NP-F/SH virus infected cells produced the highest levels of NP expression. PIV5-NP-M/F, which contained NP inserted closest to the 3' end leader sequence and should have the highest expression levels of NP, had the lowest expression level of NP (FIG. 43B).

The junction between M and F is the longest among all the junctions within PIV5 genome and the readthrough transcript from M to F is the highest among the junction regions of PIV5 (Parks et al., 2001, *J Virol;* 75:2213-2223). Likely, disrupting the M-F junction negatively affected the expression of the inserted gene. PIV5-NP-SH/HN and PIV5-NP-HN/L vaccinated mice induced similar levels of NP-specific CD8+ T cell response as PR8 (H1N1), PIV5-NP-F/SH vaccinated mice induced slightly higher level of T cell response although the difference was not statistically significant (FIG. 44). Intriguingly, the NP expression levels produced in PIV5-NP viruses infected cells correlated with the levels of NP-specific CD8+ T cell response, suggesting that increasing the expression level of foreign gene may lead to a higher level of cellular immune responses generated by the foreign gene.

Efficacy of these vaccine candidates will be improved by increasing inoculation dose and/or by using prime-boost regimen. PIV5-NP will be combined with other influenza virus antigens, such as M2, to further enhance its efficacy, leading to an influenza virus vaccine that is more efficacious than PIV5-NP alone.

Example 9

A Parainfluenza Virus 5 (PIV5)-based H5N1 Vaccine

This example will continue to develop a vaccine for H5N1 using PIV5 as a vector and explore the use of PIV5 as a vector for universal influenza virus vaccine. This example will include testing efficacies of recombinant PIV5 expressing H5N1 antigens against HPAI H5N1 challenge in ferrets. Recombinant PIV5 expressing H5N1 antigen HA, NA, NP, M1 and M2 (collectively referred to as PIV5-H5N1) have been generated. A single dose inoculation of some PIV5-H5N1 provided complete protection (no mortality, no morbidity and no challenge virus detected in lungs, which we define as sterilizing immunity) against lethal HPAI H5N1 challenge in mice. The efficacy of theses vaccine candidates will be tested in additional animal models, including, but not limited to, a ferret animal model. Ferret is the best small animal model for influenza virus infection. There is a remarkable similarity in the lung physiology and morphology between ferrets and humans. Ferrets are highly susceptible to infection with influenza viruses. Vaccine candidates will be tested in ferrets against H5N1 challenge. This example will further study the mechanisms of immunity generated by PIV5-based vaccine candidates in mice as well as in ferrets. This example will include improving efficacies of recombinant PIV5 expressing H5N1 antigens against H5N1 and developing a universal influenza virus vaccine. The vector will be further modified to achieve better efficacy and to reduce potential safety risk. rPIV5-NP provides protection not only against H5N1 challenge, but also against H1N1 challenge. Interestingly, recombinant PIV5 expressing NA of H1N1 not only completely protected lethal H1N1 challenge, but also partially protected against lethal H5N1 and H3N2 challenge. Vaccine candidates will be further modified not only to increase efficacy against H5N1 but also to provide better protection against heterosubtypic influenza virus challenge, leading towards a universal vaccine.

PIV5 is a novel vaccine vector for human, a novel viral vector for H5N1 and has the potential to be a vector for universal influenza virus vaccine. A NA-based vaccine based on PIV5 for influenza virus will be novel. Developing novel strategies to enhance immune responses by manipulating vector's ability to induce apoptosis. Developing novel strategies to enhance immune responses by regulating IFN signaling pathway.

There are three aims in this example. Aim one will be the testing recombinant PIV5 expressing HA of H5N1 (PIV5-H5) as a vaccine for H5N1. To test whether recombinant PIV5 expressing HA of H5N1 can protect mice against lethal challenge HPAI H5N1, the most lethal influenza virus in mice, a PIV5-H5 containing a H5 of H5N1 without cleavage site, which inactivated function of the HA protein, at the junction between the HN and L gene of PIV5 (ZL48 virus) has been generated. The virus grew as well as the wild type virus. All mice immunized with a single dose of $10^6$ pfu of ZL48 survived challenge and had no weight loss. H5N1 was not detected in the lungs of immunized mice. Antibody transfer experiment confirmed that anti-H5 antibody mediated the protection. While a single dose of PIV5-H5 inoculation protected mice against lethal H5N1 challenge completely, a second dose further boosted neutralizing antibody titers. That pre-existing vector immunity did not prevent boosting with a live virus is consistent with the report that anti-PIV5 antibodies do not prevent PIV5 infection (Young et al., 1990, *J Virol;* 64(11):5403-11). See Example 3 and Li et al., 2013, *J Virol;* 87(1):354-62 (59).

Increasing the expression level of H5 will likely improve the efficacy of the recombinant virus as a vaccine candidate. The distance to the leader sequence, the only de facto promoter for PIV5, reversely affects gene expression levels. The gene junction between the HN and L genes is the most distant to the leader sequence in PIV5. Moving the gene of interest from the HN-L gene junction closer to the leader sequence will increase level of the gene expression. The HA gene of H5N1 has been inserted in different locations within the PIV5 genome (FIG. 47; Example 3; and Li et al., 2013, *J Virol;* 87(1):354-62). As all constructs provided complete protection against H5N1 challenge in mice after a single high dose inoculation ($10^6$ pfu,)), a dose-response study was conducted ($10^3$, $10^4$, and $10^5$ pfu). All mice inoculated with $10^4$ pfu and above of ZL46, ZL47 or ZL48 survived lethal H5N1 challenge (Example 3; and Li et al., 2013, *J Virol;* 87(1):354-62). $10^3$ pfu of ZL46 protected 100% mice against H5N1 lethal challenge.

While ZL48 protected 70%, ZL47 only protected 30% of mice at a dose of $10^3$ pfu. Since routine human influenza virus immunization is mostly done through IM and live attenuated influenza virus vaccine is inoculated through IN, efficacies of IM and IN immunization were compared. While both IM and IN worked, IN provided better protection than IM. Interestingly, inactivated PIV5-H5 did not protect via IM or IN, suggesting that replication of PIV5 is essential for its efficacy, even in the IM inoculation. PIV5 is a respiratory infectious agent. Anti-HA IgA was detected in bronchial alveolar lavage and nasal wash of mice immunized with PIV5-H5 via IN route, suggesting that PIV5-based vaccine can generate robust mucosal immunity in respiratory tracts. See Example 7 and Mooney et al.

Testing the potential of other H5N1 proteins expressed using PIV5 as antigens for vaccine. Recombinant PIV5 expressing H5N1 proteins NA, M1, M2 and NP have been generated (FIG. 47A) and their efficacies as vaccine candidates tested against H5N1. PIV5 expressing H1 or N1 of H1N1 was also generated and tested. For all these constructs, the genes were inserted at the HN and L junction as a starting point to avoid potential detrimental effects on PIV5 genome replication. Except rPIV5-M2, all viruses grew well in tissue culture cells.

Inoculation of mice with ZL116 (FIG. 47A), which contains the NA gene of H5N1, completely protected mice against lethal H5N1 challenge. Furthermore, H5N1 was not detected in the lungs of rPIV5-N1 (H5N1)-immunized mice. This exciting result is the first time that a sterilizing immunity (no mortality, no morbidity and no challenge virus was detected in lung) against H5N1 has been observed using a viral vector-based NA vaccine. To investigate whether N1 of H5N1-mediated protection is specific and only limited to NA of H5N1, ZL108 (PIV5 expressing N1 from H1N1) was tested. Confirming the immunity generated by NA can be protective, rPIV5-N1 (H1N1) completely protected mice against lethal H1N1 challenge. Interestingly, rPIV5-N1 (H5N1) provided complete protection against lethal H1N1 challenge; rPIV5-N1 (H1N1) also provided partial protection (60%) against lethal H5N1 challenge. To further examine whether NA-based protection can be broad, rPIV5-N1 (H5N1) and rPIV5-N1 (H1N1) were tested against lethal H3N2 challenge. Surprisingly, rPIV5-N1 (H1N1) partially (40%) protected against H3N2 challenge while rPIV5-N1 (H5N1) did not protect at all.

NP of influenza A virus is well-conserved. Immunity generated by NP is thought to be cell-mediated. Recently, NP has been used as a component for developing a universal influenza virus vaccine (Soboleski et al., 2011, *PLoS One;* 6(7):e21937). A PIV5 expressing NP of H5N1 was generated and its efficacy tested against a lethal challenge with H1N1 virus (PR8 strain), a different subtype from H5N1. A single dose inoculation of mice with PIV5-NP provided 100 percent protection against lethal PR8 strain challenge. However, there were some weight losses (5 to 10%). Consistent with anti-NP being not critical, correlation was not observed between anti-NP titers and weight loss. Also, PR8 virus was not detected in the lungs of the immunized mice, consistent with the previous reports that NP-mediated immunity does not prevent influenza virus infection. In contrast, a VV expressing NP did not provide any protection against the challenge of the same virus and an adenovirus containing NP provides 80% protection against the lethal H1N1 challenge but the mice lost about 30% weight. That these PIV5 constructs worked better than AdV- and VV-based NP vaccine demonstrate that PIV5 is a better vaccine vector for influenza virus than AdV or VV (MVA).

PIV5-NP was then tested against lethal H5N1 challenge and saw partial protection from mortality and some weight loss (10 to 20%). While the protection against H5N1 was only 50%, it is the best that has been reported for a single dose vaccination with a viral vectored-NP vaccine candidate. This will be improved by increasing the immunization dose, changing the site of NP insertion within the PIV5 genome, modifying the PIV5 vector and combining this with other influenza virus antigens described herein.

Figure 47A:
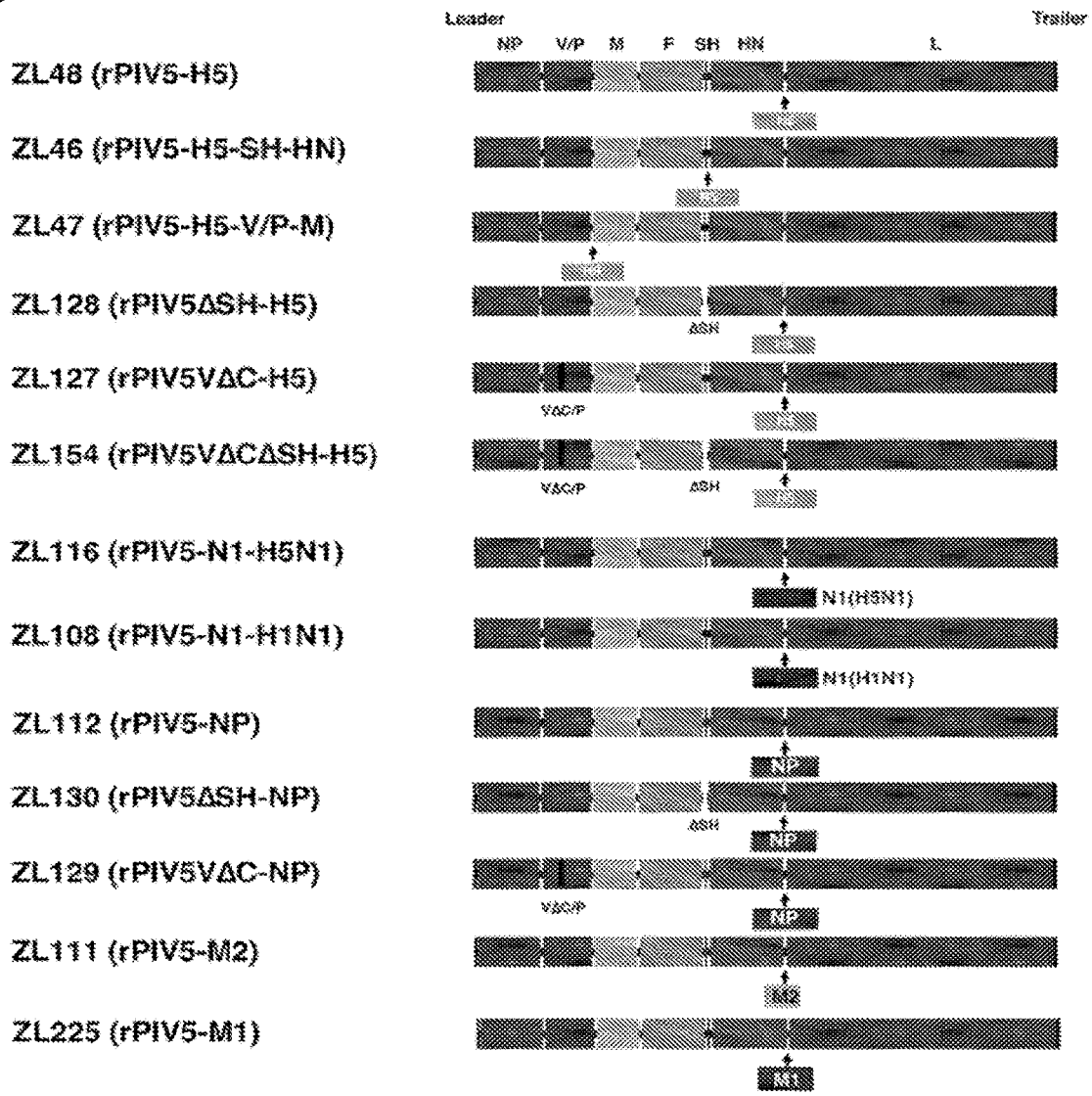

The M1 protein of influenza A virus is conserved. The efficacy of a recombinant PIV5 expressing M1 of H5N1 between HN and L (rPIV5-M1) was determined (FIG. 47A). Interestingly, rPIV5-M1 provided partial protection (70%) against lethal PR8 in mice. The less than ideal protection is most likely due to an unexpected mutation in the gene start sequence of the M1 gene. Recombinant PIV5 expressing M1 with better efficacy will be generated.

PIV5 mutants expressing H5 were generated (FIG. 47A). As a part of routine analysis of the recombinant viruses, the entire genome of the virus is plaque-purified and sequenced. While PIV5ΔSH-H5 (ZL128) has the exact input sequences, there are mutations in the genome of PIV5VΔC-H5 viruses. Previously, after rPIV5VΔC was passed in Vero cells, an interferon defective cell line, viruses with mutations that regained expression of the V protein as well as mutations at other sites emerged. This is likely due to the way that the deletion of the C-terminus was made and the importance of the V protein in virus replication. Because the V and P mRNAs are both transcribed from the same V/P gene, the entire coding sequence could not be deleted for V from the PIV5 genome without also deleting the N-terminal of the P protein, an essential part of viral RNA polymerase complex. Instead, multiple point mutations were introduced within the region of the V/P gene that is critical for transcribing both mRNAs to force the V/P gene only make the P mRNA, not the V mRNA. Many rPIV5VΔC-H5 clones were sequenced and they all contain mutations at different locations. Two clones of recovered viruses with different mutations besides intended mutations that abrogate expression of the C-terminus of the V protein were picked and tested. The rationale is that if all mutants have the same effects and the common feature is the lack of conserved C-terminus of V, it is likely that the lack of C-terminus of V is a determining factor in the phenotype. Immunity generated by the viruses was generated and efficacies of the recombinant viruses in mice against lethal H5N1 challenge tested. PIV5ΔSH-H5 had generated better antibody responses and cell-mediated responses than PIV5-H5. One of the two clones of PIV5VΔΔC-H5 examined, one had generated better antibody and the other generated better cell-mediated responses to H5. All mutant PIV5 provided better protection against H5N1 challenge than wild type PIV5. rPIV5VΔCΔSH-H5, rPIV5VΔC-NP and rPIV5ΔSH-NP mutants have been generated (FIG. 47A) and are being testing.

Immunization of dogs with prior exposure to PIV5 with rPIV5-H3. To examine whether pre-existing immunity to PIV5 negatively affects the use of PIV5 as a vaccine vector, PIV5-naive dogs and dogs that were vaccinated against PIV5 multiple times were then studied. The lack of neutralizing anti-PIV5 in PIV5-naive dogs was confirmed and neutralizing antibody (nAb) titers against PIV5 in PIV5-vaccinated dogs were as high as 300 (see Example 2 and Chen et al., 2012, *PLoS One;* 7(11):e50144). The dogs were vaccinated with PBS, PIV5 or rPTV5-H3 via IN route. The PIV5-naive dogs vaccinated with rPIV5-H3 had HAI titers ranging between 20 to 80 (average 42). The PIV5-positive dogs vaccinated with rPIV5-H3 had HAI titers ranging between 40 to 80 (average 77) (the difference of HAIs between two groups is not statistically significant), indicating that rPIV5-H3 vaccination generated immunity against influenza virus (a 4-fold increase of HAI titer or a HAI titer of 40 is considered protective against influenza virus infection) and suggesting that pre-existing anti-PIV5 nAb titers did not affect PIV5-based vaccine efficacy in dogs. The results were consistent with a previous report that nAb against PIV5 do not prevent PIV5 infection in mice (Young et al., 1990, *J Virol;* 64(11):5403-11). The dog's ability to clear a PIV5 infection remains undetermined. Since PIV5 has self-limiting replication in dogs, it is likely that cell-mediated immunity plays a critical role in clearing infection as well. Because it takes time for cell-mediated immunity to respond and be effective, this time lag provides a window of opportunity for PIV5-based live vaccine to replicate in cell and to generate a robust immune response.

Aim one will test efficacies of recombinant PIV5 expressing H5N1 antigens against H5N1 challenge in ferrets. PIV5-based H5N1 vaccine candidates that are effective against HPAI H5N1 challenge in mice have been obtained. Efficacy will be tested in additional animal models, including a ferret, as ferret is the best small animal model for influenza virus infection. Many vaccine candidates have been tested in mice, including the 13 listed in FIG. 47. These will be tested in ferrets. Since the primary goal is to develop H5N1 vaccine, PIV5-H5 will be tested first, since antibody against H5 is well-accepted parameter for evaluating efficacy of vaccine candidates. For PIV5-H5, ZL46 will be tested first because it is the most efficacious among all wild type PIV5-H5. Second, PIV5ΔSH-H5 (ZL128) will be tested, which is the best among the mutant PIV5-H5 and is stable as well. Determining whether activation of TNF-α by rPIV5ΔSH-H5 affects adaptive immune responses will be informative for designing new vaccines. Third, PIV5-N1 (H5N1) (ZL116) will be tested because no one has reported success of a viral vectored-NA vaccine in ferrets. The work will be essential to determine whether NA can be an effective antigen and whether PIV5 expressing NA can be effective in ferrets for influenza virus. Fourth, PIV5-NP (ZL112) will be tested in ferrets because immunity for NP-based vaccine is thought to be mediated through cellular immune responses. Not only will it be tested whether PIV5 expressing NP can be effective in ferrets, but also will a determination of whether PIV5-based vaccine can generate a robust cellular immune response in ferrets.

Examination of safety, stability and immunogenicity of PIV5-H5N1. Four sets of vaccine candidates will be tested: PIV5-H5, PIV5ΔSH-H5, PIV5-N1 and PIV5-NP. PBS and PIV5 will be included as negative control for each set. Inactivated H5N1 will be used as positive control. For the PIV5ΔSH-H5 (ZL128) vaccine, PIV5-H5 (ZL48) will also be included for comparison because they both contain H5 insertion at the same location within the PIV5 genome. Ferrets in a group of 6 will be inoculated with $10^6$ PFU of recombinant PIV5 parental virus (PIV5) or PIV5-H5N1, or PBS in 0.5 ml volume under anesthesia. As positive control for immunogenicity, 3 ferrets will be immunized intramuscularly (IM) with 15 ug of inactivated H5N1, which has been shown to induce HA-specific antibody responses and protect against lethal challenge in a ferret model of infection. Animals will be monitored for clinical symptoms (fever, lethargy, and weight loss) for 14 days. On days 2, 4, 6, 8, 10, 14 and 21 after inoculation, nasal washes will be collected and titers of virus in them will be determined using plaque assay. Nasal washes will also be assayed for mucosal antibody responses using a HA-specific IgA ELISA. Serum and whole blood will also be collected on days 0, 8, 14, and 21 to measure CBC, clinical chemistry, serum antibody responses and/or cell-mediated immune responses. On day four (peak of PIV5 shedding) after inoculation, three ferrets will be humanely euthanized and necropsied for gross pathology and microscopic pathologic changes. Also, lungs and nasal turbinates will be collected and titers of virus will be determined. Additional tissues will be collected for lymphocyte (immune response) analysis. Pathological changes will be examined using H&E staining. Remaining ferrets will be challenged with H5N1 on day 21 post-immunization.

For stability studies, nasal wash will be used to obtain viral RNA for direct RT-PCR sequencing, and/or cultured in Vero cells, and then used for RT-PCR sequencing in case there is insufficient virus in nasal washes for direct RT-PCR sequencing. For pathology studies, after gross pathology, tissues will be removed from the euthanized animal, placed on a grid, and 1 cm pieces selected (representing the entire organ) and fixed in 10% buffered formalin. Additional pieces will be collected for analysis of virus titer by plaque assay. Fixed tissues will be embedded in paraffin, sectioned at 3 microns, stained with hematoxylin and eosin (H&E), and examined by light microscopy, and scored blindly by a pathologist. If H&E results suggest it, tissues will be immunostained with virus-specific or lymphocyte-specific (e.g. CD4, CD8, B cell) mAbs and scored for level of virus antigen expression and/or lymphocyte infiltration.

Local immunity. Sites of induction of immune responses can alter the nature of the immune response and dramatically impact protective efficacy. Mucosal immunization has been shown to induce an influenza-specific mucosal IgA and IgG response that protects against both matched and heterosubtypic challenge. Intranasal PIV5 immunization has the potential to induce local influenza-specific T cell and immunoglobulin responses that mediate protection against influenza challenge. Local (i.e. lung) PIV5-specific and influenza specific immune responses will be assessed by analysis of nasal washes and lung (on days of euthanasia). Infiltrating lymphocyte populations will be collected by centrifugation and the BAL wash will be analyzed for mucosal Ig.

Cell mediated immunity (T cell) analysis T cell responses induced by vaccination and changes in T cell responses after challenge will be measured by antigen-specific IFN production. Specifically, lymphocytes from peripheral blood, BAL, spleen and/or draining lymph node will be assayed for influenza-specific T cell responses by re-stimulation with inactivated H5N1, reverse genetics 6:2 PR8:A/VN/1203/04, recombinant HA (NA or NP), or H5N1 HA (or NA, NP) peptide pools. IFN-γ responses will be determined by intracellular cytokine staining, ELISA, and/or ELISPOT assays. A variety of HA-specific peptide epitopes have been identified after influenza virus infection. While specific epitopes in the A/Vietnam/1203/04 HA for ferrets have not been identified, HA peptide libraries are available for H5N1 influenza viruses and immune cell populations can be screened for reactivity to identify peptide epitopes as needed.

Humoral immunity (antibody) analysis HA (NA or NP)-specific humoral immune responses in the serum, nasal wash, and BAL wash will be measured by standard ELISA assay using homologous (A/Vietnam/1203/04) or heterologous (A/Udorn) viruses or recombinant HA (NA or NP) as plate-bound antigens. Both IgA and IgG will be assessed using ferret class specific antibodies. HA-specific antibody titers will also be measured by virus mirconeutralization assay or HAI. Samples demonstrating reactivity against homologous A/VN/1203/04 (clade 1) HA will be assessed for cross-clade reactivity to A/Anhui/1/2005 (clade 2.3.4). All serum and BAL wash samples will be compared to corresponding pre-immune or control immunized samples.

Examination of efficacy of PIV5-H5N1 against H5N1 challenge. Challenge experiments will be performed in BSL3AG+ containment. Ferret immunized as above, will be inoculated IN with ten LD50 of H5N1. Ferrets will be monitored for clinical symptoms including activity, weight loss, and body temperature, and survival for 14 days. Nasal washes will be collected on day 2, 4, 6, and 8 post-infection and assayed for virus titer by TCID50 assay. On day 14, surviving animals will be bled to assay influenza-specific serum antibody.

Figure 47B:
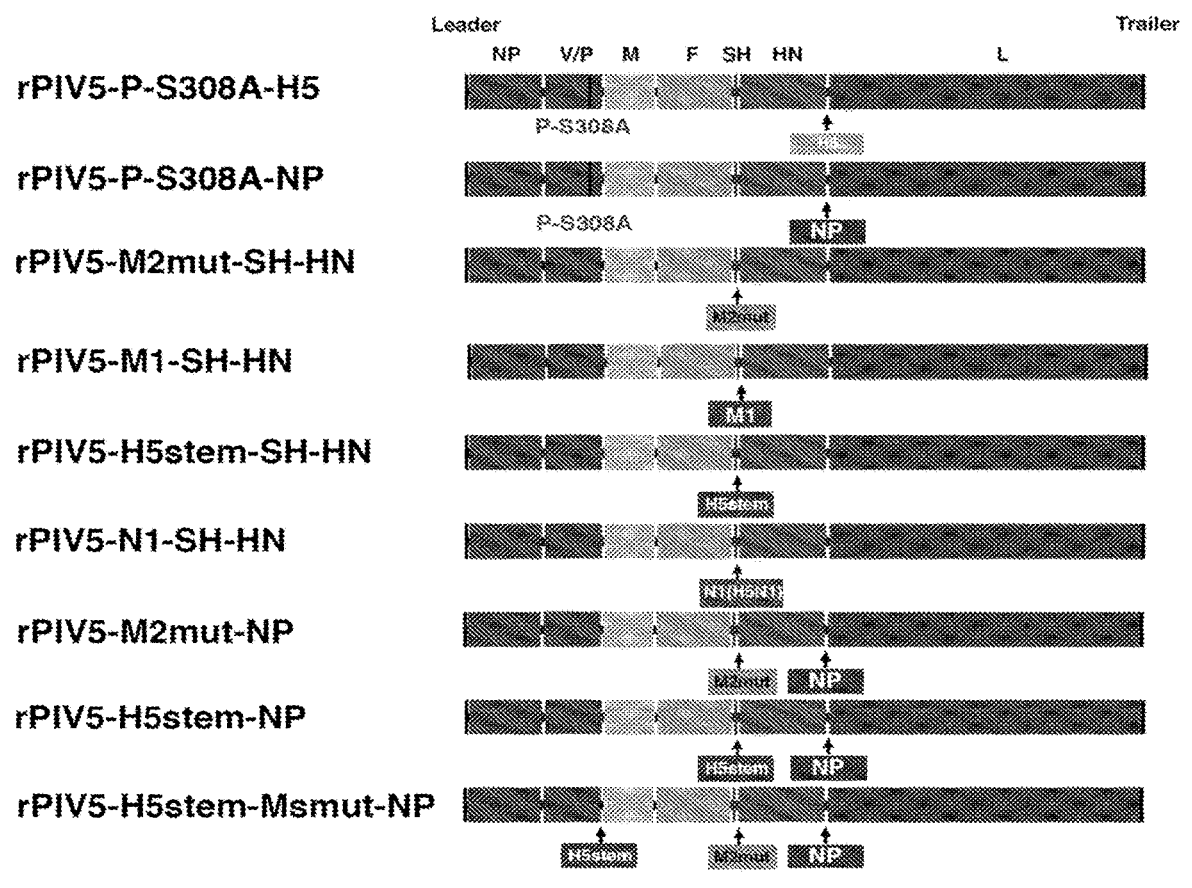

Ferrets were infected with wild type PIV5 or rPIV5-H5 (ZL46) and antibody titers against H5 measured using ELISA and viral neutralization assay. This vaccine candidate was effective in generating anti-H5 antibody titer that is considered protective (FIG. 47B). Because of results with PIV5-H5, PIV5-N1 and PIV5-NP in mice, and this experiment of PIV5-H5 in ferrets, it is expected that PIV5-H5 and PIV5-N1 will be immunogenic and effective in protecting ferrets against lethal H5N1 challenge. Robust cross-reactivity of sera from mice immunized with PIV5-H5 (H5N1, VN) to H5N1 Anhui (a clade 2 virus) has been observed, suggesting that PIV5-H5 (VN, Clade 1) will be protective against challenge from a Clade 2 virus.

Initial inoculation will start with $10^6$ PFU (FIG. 47B) of a vaccine candidate. If this is not sufficient for complete protection (no symptoms, no mortality and no detectable virus), the dose will be increased up to $10^8$ PFU per ferret. If a single dose is not sufficient for complete protection, a prime-boost regimen will be used to enhance immunity. All influenza virus-related reagents are readily available and purified NP and M1 have been produced for T cell analysis.

For this study in ferrets the reagents needed for effective immunological assays, such as anti-ferret antibodies, will be obtained from BEI and other commercial sources and cross-reactive antibodies can be used. Further, monoclonal antibodies against ferret proteins will be generated. Towards this end, two hybridomas of anti-CD4 of ferrets and three hybridomas of anti-IFN-β of ferrets have been developed.

Aim two includes improving efficacies of recombinant PIV5 expressing H5N1 antigens against H5N1 as well as heterosubtypic influenza virus challenge, to further improve PIV5-based H5N1 vaccine as well as to general potential universal influenza virus vaccine.

Incorporating mutations that induce IFN expression and blocks IFN signaling. It has been known that activation of innate immune responses such as IFN expression enhances adaptive immune responses. For viral vector, this is a double-edged sword. If a viral vector induces robust expression of IFN, this induction of IFN will in turn inhibit replication of the vector, reducing efficacy of the vector. A viral vector that allows induction of IFN production and still maintains its ability to block IFN signaling to enable its efficient replication will be ideal. Residues within PIV5 proteins that are capable of inducing expression of cytokines such as type I interferon have been identified (Sun D et al., 2009, *PLoS Pathog;* 5(7):e1000525). Residue of S157 of the P protein of PIV5 is a binding site for host kinase PLK1 and the residue of S308 of the P protein of PIV5 is a phosphorylation site of PLK1. Mutating S157 or S308 to amino acid residue A results in a virus that increases interferon-β expression. Most importantly, the virus still expresses a V protein that blocks IFN signaling. Thus, this is a viral vector that can induce IFN expression without negatively affecting its own replication. Recombinant PIV5 expressing H5 or NP will be generated (FIG. 47B) and immunogenicity and efficacy against H5N1 challenge in mice and in ferrets determined. HA will be used to test P-S308A's effect on antibody response and use NP to test P-S308A's effect on cell-mediated response.

Testing efficacy of mixed immunization with PIV5-NP with PIV5-NA, M1, M2 and/or HAstem as a universal vaccine. Since rPIV5-NP protected H1N1 as well as H5N1, and PIV5-N1 (H1N1) protected not only H1N1 challenge, but also H3N2, it is expected that a PIV5 expressing NP as well as other influenza virus antigens will be a good candidate for a universal influenza virus vaccine. First, whether a combination of two vaccines will provide synergy in protection will be tested. If they do, then they will be combined into a single viral vector. Since NP is known to provide broad protection, NP will be used as the base to mix with others. PIV5-NP will be tested with PIV5-NA, PIV5-M2 and/or PIV5-M1 as well as PIV5-HAstem (the Stem region of HA) in mice, and then in ferrets.

M2 is relatively conserved among influenza virus proteins. It has been shown that M2 can generate broad anti-influenza virus immunity. However, the present studies did not detect any protection when full-length functional M2 was expressed from PIV5. It is likely that this failure to elicit a M2 immune response is toxicity of M2 in PIV5-M2-infected cells. M2 is an ion channel and residues critical for this function have been identified. It is known that H37 and W41 are critical for ion channel activity. Mutating these residues abolish ion channel activity without affecting structure of M2 (M2 is a homotetramer with a single transmembrane domain). By disabling M2's ion channel activity, a PIV5 expressing high levels of M2 will be generated without killing-infected cells too quickly. Also, since epitopes for M2 arc known and they arc in the ectodomain of M2, a hybrid protein between SH of PIV5 and M2 will be generated. SH of PIV5 is a 44-amino acid residue long transmembrane protein with a 7-amino acid residue ectodomain. An ectodomain of M2 will be added to the ectodomain of SH (SH-M2). Recently, it has been reported that an antibody that recognizes the conserved region of HA which is the Stem region of HA is effective in preventing infection of all subtype of influenza viruses. The Stem region of HA from PIV5 will be expressed (FIG. 47B) and its immunogenicity examined in mice. The PIV5-M1 construct already provided 70% protection against lethal PR8 challenge. This virus will be further improved by using correct gene start sequence and by inserting M1 between SH and HN.

Generate PIV5 expressing more than one influenza virus antigens. For the sake of simplicity and avoiding unnecessary regulatory burdens, expressing multiple antigens from a single virus may be desirable compared to using a mixture of PIV5 expressing different antigens. The expression of NP will be combined with the expression of NA, HAstem, M1 and/or M2 from the same PIV5 (FIG. 47B).

Testing efficacy of PIV5 expressing multiple influenza virus antigens as a universal vaccine. Once a PIV5 expressing NA, NP, M2 mut and/or M1 are generated, their efficacies will be tested first in mice first against challenges from H1N1, H3N2 and H5N1. If they are efficacious in mice, they will be tested in ferrets.

Aim three includes studies to increase understanding immunity based on the PIV5 vector. The mechanisms of immunity generated by PIV5-based vaccine candidates will be further tested in mice as well as in ferrets. With traditional influenza virus vaccines, neutralizing antibodies to HA are generally considered the hallmark of protective immunity. However, immunization with a live vaccine increases the likelihood of generation of both humoral and cellular immune responses. These examples have shown that PIV5 expressing NA and NP provided protection at a level that has not been observed before. Altered antigen presentation by recombinant PIV5 viruses would have likely modified the immune response. It is thought that apoptotic pathways affect antigen presentation. Since the pathways leading to apoptosis induced by PIV5ΔSH and PIV5VΔC have been identified and are different, these viruses provide a unique opportunity to examine antigen presentation with viruses expressing the same antigen but activating different apoptosis pathways. It is possible that one apoptotic pathway may preferentially enhance antibody responses while the other may affect T cell responses. Understanding how apoptosis affects the immune response to virus infection will not only help us with designing a better H5N1 vaccine, but also provide general knowledge on vaccine design and immune responses. The PIV5-P-S308A-based vaccine will allow the study of effects of induction of IFN on adaptive immune responses without the concern over the effects of IFN on replication on viral vector. The immune mechanism of protection provided by rPIV5-H5, rPIV5-NA and rPIV5-NP will be addressed in this aim.

The mechanism of PIV5-induced protection will be examined by three methods. To determine if antibody is sufficient to protection, serum from naive, PIV5, PIV5-H5N1 (referring to all PIV5, mutation containing or not, expressing H5N1 antigens), or H5N1 immune mice will be passively transferred to naive mice. Transfer recipients will be challenged with H5N1 influenza. Some animals will be sacrificed for virus titer analysis at various days after challenge and other mice will be monitored for morbidity and mortality. To determine whether antibody is essential for protection, MT mice that are defective in antibody production will be used for immunization. If the immunized mice survive lethal challenge, it will indicate that antibody is not required and cell-mediated immune responses will be sufficient for protection. To assess the role of cellular immune responses, mice will be immunized as above and acutely deplete immune animals of distinct T cell subsets (CD4, CD8 or both) by mAb depletion. After depletion, the mice will be challenged with H5N1 influenza and protection will be assessed as above. Acute depletion studies can occasionally generate inconclusive date; e.g. depletion of CD4 and CD8 T cells does not abrogate protection, but the addition of a CD90 depletion results in complete loss of protection. There are a number of potential explanations for this unusual result, including incomplete depletion with the CD4 and CD8 specific mAbs or a role for a CD4/CD8 double negative cell in protection. Additionally, acute depletion not only removes primed T cells, but also naive T cells, eliminating any contribution of a primary response to challenge contributing to protection. Similar to passive serum transfer, adoptive transfer of primed T cells to a naive animal can directly describe a role for individual cell populations in a protective immune response. As an alternative to acute depletion, class I deficient mice will be used to assess the contribution of CD8+ (CTL) activity, immunizing wild type and β2m deficient mice and assessing protective efficacy. Class II (CD4+ T cell) deficient mice are another alternative approach, but have additional issues with induction of effective CTL and scrum antibody responses.

Example 10

Improved Rabies Vaccines

Rabies remains a major public health threat around the world and causes more than 70,000 human fatalities each year. Prevention of human rabies includes immunization of pet animals and wildlife carriers, pre-exposure immunization of people at risk, and post-exposure treatment of people bitten by rabid animals. Although inactivated rabies virus (RV) vaccines prepared from cell culture are safe and efficacious, they have disadvantages. First, these vaccines are expensive and thus beyond the reach of most people who need the vaccines in the developing countries. Furthermore, repeated immunizations with inactivated vaccines are required to produce a protective immune response. In addition, these inactivated vaccines always include adjuvants which may cause side effects. Thus, safer, cheaper, and more efficacious RV vaccines are needed.

This example has three aims. One, testing efficacies of rPIV5-G in dogs. Efficacies of rPIV5-G will be examined in dogs using different vaccination routes (intranasal, oral and intramuscular) and to determine dose response of rPIV5-G. Two, improving efficacies of recombinant PIV5 expressing G. Site of insertion of antigen within the PIV5 genome affected immunogenicity of vaccine candidate in animal. In earlier studies, the G gene of rabies virus has been inserted between the HN and L gene. G will be inserted at other locations within the PIV5 genome and test their efficacies in mice and dogs. Modifications to PIV5 can enhance immune responses to antigens. For instance, deletion of the SH gene resulted in increased immunity to a foreign gene compared to wild type PIV5. The genome of PIV5 will be modified to obtain maximal immunity to the G protein. And, three, testing immunity of other rabies viral proteins. While G is sufficient to generate protective immunity against rabies challenge, rabies viral protein N is also known to generate protective immunity. A recombinant PIV5 expressing N will be constructed and tested. In addition, we will incorporate M, a critical component of viral particle to generate a PIV5-based virus-like particle (VLP) and test their efficacies as a rabies vaccine.

This example will not only lead to a novel safe and efficacious rabies vaccine that can be delivered via multiple routes, but also provide a new strategy to develop vaccines for dogs and possibly wild animals. The knowledge gained from the work will guide design of PIV5-based vaccines for other diseases such as HIV and *Mycobacterium tuberculosis*.

Testing efficacies of rPIV5-G in dogs. Efficacies of rPIV5-G in dogs will be examined using different vaccination routes (intranasal, oral and intramuscular) and to determine dose response of rPIV5-G. Examination of safety, stability and immunogenicity of rPIV5-G in dogs The safety of PIV5 has essentially been tested in dogs as it is contained in the kennel cough vaccines. The safety and immunogenicity will be further tested in the highest possible dose by various routes of immunization. Dogs in a group of 8 will be inoculated with $10^8$ pfu of recombinant PIV5 parental virus (PIV5) or PIV5-G by IM, Oral or the IN route. As a control, rLBSNE (essentially SAG-2, a commercial rabies vaccine) will be included via IM. Animals will be monitored for clinical symptoms (fever, lethargy, and weight loss) for 14 days. On days 2, 4, 6, 8, 10, 14 and 21 after inoculation, nasal washes will be collected and titers of virus in them will be determined using plaque assay. Serum and whole blood will also be collected on days 0, 7, 14, and 21 to measure CBC, and clinical chemistry. On day 4 (peak of PIV5 shedding) after inoculation, dogs (4 from each group) will be humanely euthanized and necropsied for gross pathology and microscopic pathologic changes. Also, lungs and nasal turbinates will be collected and titers of virus will be determined. For pathology studies, after gross pathology, tissues will be removed from the euthanized animal, placed on a grid, and 1 cm pieces selected (representing the entire organ) and fixed in 10% buffered formalin. Additional pieces will be collected for analysis of virus titer by plaque assay. Fixed tissues will be embedded in paraffin, sectioned at 3 microns, stained with hematoxylin and eosin (H&E), and examined by light microscopy, and scored blindly. If H&E results suggest it, tissues will be immunostained with virus-specific or lymphocyte-specific (e.g. CD4, CD8, B cell) mAbs and scored for level of virus antigen expression and/or lymphocyte infiltration.

Nasal washes will also be assayed for mucosal antibody responses using a G-specific IgA ELISA. Serum and whole blood will also be collected on days 0, 7, 14, and 21 to measure antibody responses and/or cell-mediated immune responses. Remaining dogs (4 from each group) will be challenged with rabies on day 21 post-immunization.

Local immunity. Sites of induction of immune responses can alter the nature of the immune response and dramatically impact protective efficacy. Mucosal immunization has been shown to induce an influenza-specific mucosal IgA and IgG response that protects against both matched and heterosubtypic challenge. Intranasal PIV5 immunization has the potential to induce local rabies-specific T cell and immunoglobulin responses that mediate protection against rabies challenge. Local (i.e. lung) PIV5-specific and rabies specific immune responses will be assessed by analysis of nasal washes and lung (on days of euthanasia). Infiltrating lymphocyte populations will be collected by centrifugation and the BAL wash will be analyzed for mucosal Ig.

Cell mediated immunity (T cell) analysis T cell responses induced by vaccination and changes in T cell responses after challenge will be measured by antigen-specific IFN production. Specifically, lymphocytes from peripheral blood, BAL, spleen and/or draining lymph node will be assayed for rabies-specific T cell responses by re-stimulation with inactivated rabies virus. IFN-γ responses will be determined by intracellular cytokine staining, ELISA, and/or ELISPOT assays.

Humoral immunity (antibody) analysis Rabies-specific humoral immune responses in the serum, nasal wash, and BAL wash will be measured by standard ELISA assay using purified rabies virus as plate-bound antigens. Beoth IgA and IgG will be assessed using dog isotype specific antibodies. G-specific antibody titers will also be measured by virus mirconeutralization assay. All serum and BAL wash samples will be compared to corresponding pre-immune or sham-immunized samples.

The stability of the recombinant PIV5-G will be tested both in cell cultures and in dogs. In cell culture, the virus will be serially passaged in Vero cells for at least twenty passages. Virus will be harvested at each passage and stored at $-80°$ C. In dogs, the virus will be serially passaged for ten passages by the oral route. Viruses will be isolated from the oral cavity every other day for 6 days. The harvested or isolated viruses will be used for RT-PCR of the inserted G gene to make sure that the transgene is still in the genome of the recombinant virus. Nasal wash will be used to obtain viral RNA for direct RT-PCR sequencing in case there is insufficient virus in nasal washes for isolating live virus.

Examination of efficacy of PIV5-G against rabies challenge. Challenge experiments will be performed in BSL3AG+containment. Dogs immunized as above, will be inoculated IC with 500 mouse intracerebral $LD_{50}$ (MI-$CLD_{50}$) of a street rabies virus isolated from a Mexican dog. Dogs will be monitored for clinical symptoms including activity, weight loss, and body temperature (using microchip implants), and survival for 45 days. On day 14, surviving animals will be bled to assay rabies-specific serum antibody. At day 45 post-challenge, we will sacrifice the dogs and collect tissues from the dogs. Besides routine pathological studies, we will determine whether any rabies virus exists in brains of the dogs.

A single injection of rabies virus in dogs resulted in death within 14 days. Thus, the dogs will be observed for 45 days after challenge for cost saving. Since this vaccine candidate outperformed SAG-2, a commercial rabies vaccine (live attenuated), in mice, it is expected that this vaccine will also to do better than the SAG-2 in dogs. Since IN and IM inoculation provided 100 percent protection against a very robust rabies challenge in mice, it is expected that IN and IM inoculation of dogs will lead to excellent protection. However, for oral inoculation, it is possible that protection may be less ideal (less than 50%) even it is better than SAG-2. If this is the case newer candidates from specific aims two and three will be tested.

Improving efficacies of recombinant PIV5 expressing G. Site of insertion of antigen within the PIV5 genome affected immunogenicity of vaccine candidate in animal. That the base model, which contains wild type PIV5 genome with insertion of foreign genes at the junction of HN and L, worked well is encouraging. The G gene of rabies virus has been inserted between the HN and L gene. While rPIV5-G protected 100 percent with a single dose of $10^6$ pfu inoculation, 100 percent protection via IM required $10^8$ pfu and $10^8$ pfu oral inoculation only protected 50% mice (see Example 4). Increasing efficacies for IN and IM delivery will reduce the amount of viruses needed for an effective vaccination, thus, reducing the cost of IN and IM vaccination. Increasing efficacy of oral inoculation will enhance the applicability of the vaccine candidates in wild animals. G will be inserted at other locations within the PIV5 genome and test their efficacies in mice and dogs. Modifications to PIV5 can enhance immune responses to antigens and the genome of PIV5 will be modified to obtain maximal immunity to the G protein.

Expressing G between SH and HN. It has been known that insertion of HA between SH and HN gave the best immunity against H5N1. A recombinant PIV5 expressing G at the same location will be generated (FIG. 48) (rPIV5-G-SH/HN) and test its efficacy in mice and dogs. Expressing G in PIV5 lacking SH It has been known that deletion of SH resulted in increased immunity against the foreign gene. SH will be replaced with G, which results in deletion of SH as well as placing the G gene upstream of HN (FIG. 48) and the virus analyzed in tissue culture cells, examine its immunogenicity in mice and test its efficacy in mice and dogs.

Incorporating mutations that induce IFN expression and blocks IFN signaling. It has been known that activation of innate immune responses such as IFN expression enhances adaptive immune responses. For live attenuated virus, this is a double-edged sword. While many live viruses can induce robust expression of IFN, this induction of IFN will in turn inhibit replication of the live virus. In case of PIV5VΔC, the virus induces higher levels of IFN and IL-6 expression due to the lack of the V that inhibits IFN production as well as IFN signaling. A virus that allows induction of IFN production and still maintains its ability to block IFN signaling to enable its efficient replication will be ideal. Residues within PIV5 proteins that are capable of enhancing viral gene expression and inducing expression of cytokines such as type I interferon have been identified (Sun et al., 2009, *PLos Pathog;* 5(7):e1000525). Residue of S157 of the P protein of PIV5 are a binding site for host kinase PLK1 and the residue of S308 of the P protein of PIV5 is a phosphorylation site of PLK1. Mutating S157 or S308 to amino acid residue A, results in a virus that increases viral gene expression as well as induction of interferon expression. Most importantly, the virus still expresses a V protein that blocks IFN signaling. Recombinant PIV5 expressing G or N will be generated (FIG. 48) and their immunogenicity and efficacy examined against rabies challenge in mice and in dogs. G will be used to test P-S308A's effect on antibody response and use N to test P-S308A's effect on cell-mediated response. The mutations of P-S308A and ΔSH will be combined if the P-S308A is effective in elicit stronger immune responses to rabies virus antigens. These recombinant viruses will be tested in mice and in dogs as described above for safety and immunogenicity.

Efficacies of these vaccine candidates will be tested in mice first. Those that provide better protection than rPIV5-G will then be tested in dogs. To be considered better than rPIV5-G in mice, the candidate will have 100 percent protection rate via IN and IM with a lower dose than rPIV5-G, and/or better than 50 percent protection rate via oral inoculation.

Figure 48:
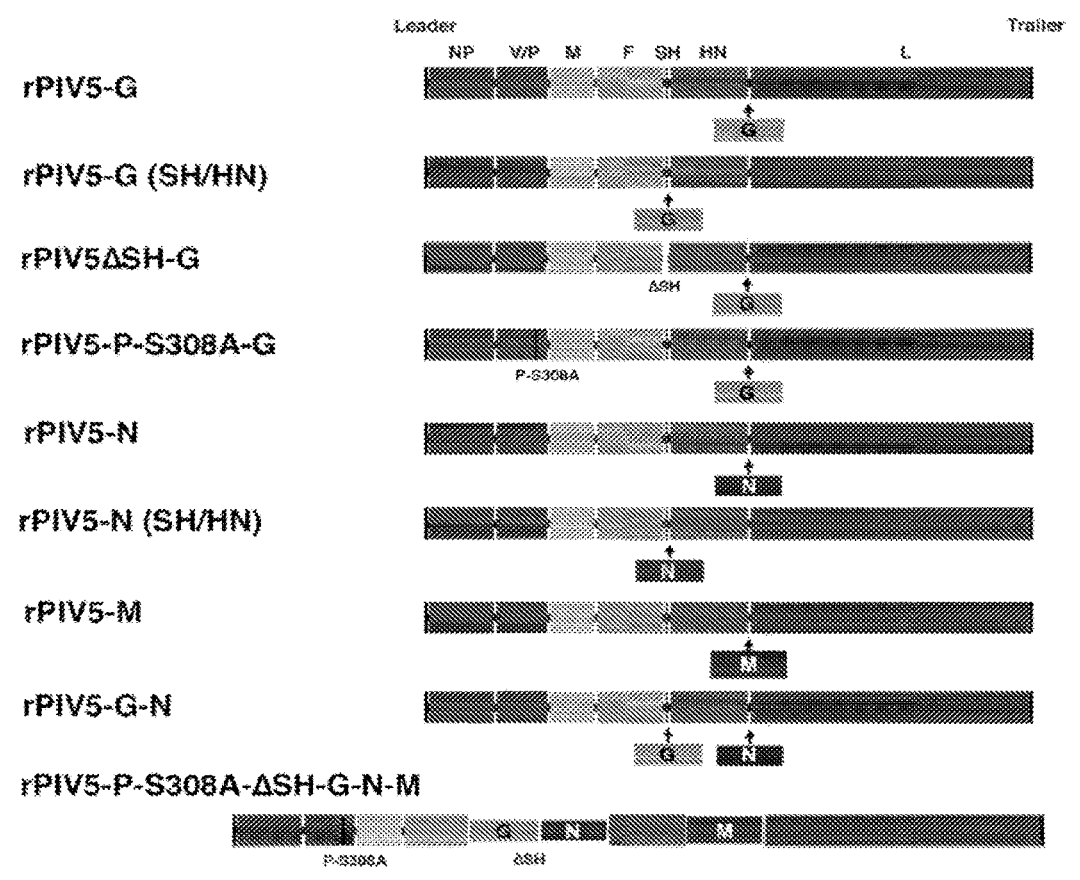

Testing immunity of other rabies viral proteins. While G is sufficient to generate protective immunity against rabies challenge, rabies viral N protein is also known to generate protective immunity. To further improve efficacy of PIV5-based rabies vaccine candidates, recombinant PIV5 expressing additional rabies viral proteins such as N and M will be constructed and tested (FIG. 48). M is known to be critical for virus assembly and budding. If G, N and M can all be expressed together, a virus-like particle (VLP) of rabies virus in rPIV5-G-N-M-infected cells will be generated.

Generate and test recombinant PIV5 expressing N. It has been known that N of rabies is immunogenic and the immunity can be protective. N will be inserted between HN and L of PIV5 first since the junction between HN and L is the most distant to the leader sequence and thus, the least likely to have any detrimental effect on PIV5 replication. Then N will be moved to the junction between SH and HN as in ZL46 (FIG. 48). Efficacies of these vaccine candidates will be tested in mice first by themselves as well as in combination with rPIV5-G. If the combination of rPIV5-N and rPIV5-G provides any protection than rPIV5-G alone, it will be tested in dogs.

Generate and test recombinant PIV5 expressing M. Viral vectors expressing NA and NP were not successful for influenza virus vaccine development, leading to the hypothesis that NA and NP were not ideal antigens for viral vector-based vaccine approach. However, NA and NP are capable antigens when expressed from PIV5. Thus, PIV5 can be used to generate immunity for antigens that were not known to be good antigens before. The effect of M on immunity against rabies has not been tested. The potential of M as an antigen will be tested in a PIV5-based vaccine. Like N, M will be inserted between HN and L, and then another another recombinant PIV5 expressing M between SH and HN (FIG. 48). Efficacies of these vaccine candidates will be tested in mice first by themselves as well as in combination with rPIV5-G. If the combination of rPIV5-M and rPIV5-G provides better protection than rPIV5-G alone, it will be tested in dogs. Efficacies of the combination of rPIV5-G, rPIV5-N and rPIV5-M will be tested in mice, then in dogs. Generate and test recombinant PIV5 expressing G and N, and/or M. Recombinant PIV5 expressing G and N will be generated (FIG. 48). M wil be inserted if sPIV5-M provides immunity against rabies challenge (FIG. 48).

Example 11

PIV5 as a Vaccine Against *Mycobacterium tuberculosis*

*Mycobacterium tuberculosis* (Mtb), the etiological agent of tuberculosis (TB), is an intracellular bacterial pathogen that kills approximately 1.4 million people each year and has infected a third of the world's population. Results from over a century of research and clinical use have shown that live vaccines offer the best protection against aerosol infections with Mtb. The most widely-administered vaccine in use today is BCG, which is a live, attenuated variant of Mycobacterium bovis, a closely-related species that causes tuberculosis in ruminants. The BCG vaccine is given subcutaneously at birth in most countries of the world, but protection is variable and wanes by adolescence. BCG administration to an immunosuppressed individual can disseminate and lead to a serious life-threatening infection. This inherent safety risk remains in second-generation BCG vaccines modified to express Mtb antigens and/or factors that imbue the bacteria with enhanced survival inside host cells. Additionally, immune responses to BCG vaccination cross react with the tuberculin skin test, the most widely used TB test in the world, making the results unreliable. For these reasons, the US and Canadian Public Health Services do not recommend using the BCG vaccine. Thus, there is a need for a safe and more-effective TB vaccine. This example will develop a novel TB vaccine based on parainfluenza virus 5 (PIV5).

PIV5 will be tested as a vaccine for Mtb. Since PIV5 is a respiratory virus, it may provide superior localized immunity against Mtb (a respiratory pathogen) than other viral vectors such as vaccinia virus, which is introduced via the parenteral route. This example will also be the first use of PIV5 to express bacterial antigens.

This example includes the following aims. One, generate and analyze recombinant PIV5 expressing Mtb antigens 85A (rPIV5PIV5-85A) and 85B (rPIV5PIV5-85B). PIV5 is a negative-stranded RNA virus. Manipulating its genome directly is impossible. Thus, a reverse-genetics system was developed in which cDNA of its entire RNA genome was cloned, making the RNA genome amendable to manipulation. This system, has been used to generate infectious PIV5 expressing a variety of foreign genes including the HA genes of influenza viruses. In this aim, recombinant viruses expressing Mtb antigens will be generated and confirmed and the safety profiles of these recombinant viruses examined in the mouse model. Two, evaluate immunogenicity and efficacy of recombinant viruses in vivo. Immunogenicity of the recombinant viruses will be examined in vaccinated mice. Protective efficacy of the viruses that generate robust immune responses in mice will evaluated by Mtb aerosol challenge. The murine aerosol infection model is accepted as a first line trial model for determining potency, safety, immune responsiveness and efficacy of new vaccine prior to subsequent trials in guinea pigs and/or non-human primates.

The BCG vaccine, which is an attenuated version of M. bovis developed nearly a century ago, is routinely used to vaccinate newborns against tuberculosis (TB). It is accepted by public health agencies worldwide as relatively safe and readily available in most countries. Immunization with BCG seems most helpful in infants and young children, reducing the incidence of severe, disseminated forms of TB. Controlled trials, however, have established that BCG offers variable levels of protection against the more prevalent pulmonary forms of the disease in adults. Furthermore, BCG vaccination seems to have the least effectiveness in the regions of the world that are most ravaged by TB, and has made no evident impact on the global TB epidemic. The estimated number of new cases of TB and the per capita incidence worldwide continues to rise each year. Although the incidence of TB in the United States is no longer rising, the disease remains a significant problem in immunosuppressed populations and in many cities, especially among immigrants. In the U.S., as elsewhere, the spread of multidrug-resistant strains of M. tuberculosis (Mtb) threatens the efficacy of current TB control efforts. The best hope for bringing the global epidemic of TB under control is the development of a new, effective TB vaccine. Because of this urgent need, a global research effort is underway, and a large number of candidate vaccines are being examined. Several candidate vaccines—including a recombinant BCG over-expressing antigen 85B (Ag85B), a modified vaccinia virus over-expressing Ag85A (MVA-85A), a fusion peptide encompassing two other antigens (termed 72f) combined with an adjuvant, another adjuvanted fusion protein containing Ag85B and ESAT-6, and a recombinant BCG expressing listeriolysin O from Listeria monocytogenes—are in phase I or phase II clinical trials. Of the three general types of vaccines: live attenuated, killed or "subunit," and DNA vaccines, live vaccines are thought to give the strongest, most durable protection against TB, as long as they arc reliably safe for all recipients—including the immunosuppressed.

The secreted protein components of the Antigen 85 complex (Ag85A and Ag85B) are some of the most commonly tested Mtb antigens for the various TB vaccine delivery systems. These proteins are expressed by infecting Mtb bacilli during the course of natural infection in humans and animals inducing both humoral and cell-mediated (CD4 and CD8) immune responses, and in animal models when administered as a pre-infection vaccine. The various vaccine constructs expressing these antigens have been shown to afford levels of protection in mice, guinea pigs, and monkeys when administered by parenteral and aerosol routes. One particular vaccine candidate, a live recombinant Modified Vaccinia virus Ankara (MVA) expressing Ag85A (MVA.85A) has shown significant protection when administered following BCG vaccination in small vertebrate models. It enhances vaccine and naturally-primed responses in humans and is currently undergoing Phase 2 clinical evaluation. In these studies, it was demonstrated that pulmonary immunization capitalizes on the location and capacity for targeting the antigen-presenting cells (mainly alveolar macrophages) in the lungs by engulfing the vaccine delivery vehicle. Likewise, vaccine constructs of this example will be examined for their ability to express Ag85A and Ag85B and will be administered to test animals via aerosol inoculation.

Experimental Design

Generating and analyzing PIV5 expressing Ag85A or Ag85B (PIV5-85A or 85B). Recombinant PIV5 expressing Mtb Ag85A or Ag85B (PIV5-85A and PIV5-85B) will be generated and virus growth characteristics and safety in vitro and in vivo analysed.

Generate recombinant PIV5 expressing Ag85A or Ag85B and analyze the viruses in vitro. The insertion of the H5 gene from influenza virus between the HN and L genes of PIV5 (PIV5-H5) provided sterilizing immunity against lethal H5N1 challenge in mice (Example 3). To generate recombinant PIV5 expressing Mtb Ag85A and Ag85B, the genes will be synthesized with optimized codon usage for human cells employing a commercial vendor (Genscript). The Mtb gene will then be combined with the gene end (GE), intergenic region (I) and gene start (GS), which are important for viral mRNA synthesis of PIV5. The sequences will be inserted between the HN and L genes. The PIV5-85A and PIV5-85B will be recovered, confirmed, and analyzed. The entire genome of the recombinant viruses will be sequenced to confirm that they match the input cDNA sequences.

Growth kinetics of the viruses, expression levels of viral proteins and expression levels of Ag85A and Ag85B in infected cells and secreted levels in the culture supernatants will be examined.

Examine the safety of PIV5-85A or 85B. High titer stocks of vaccine candidate viruses will be grown in Vero cells, aliquoted and stored at −80° C. for use in all in vivo studies. Virus titers after dilution will be confirmed by plaque assay prior to storage and at the time of immunization PIV5 infects many cell types because HN of PIV5 binds to sialic acid residues on cell surface. To investigate whether PIV5-85A or 85B has expanded tropism beyond PIV5, distribution of PIV5-85A or 85B in nude mice will be compared to PIV5. Nude mice will be injected with $10^7$ PFU of PIV5-85A, 85B, PIV5 control virus in 200 µl PBS or PBS alone via the tail vein. The weights of the mice will be monitored daily for the first seven days and then every three days for two weeks. Four mice from each group will be sacrificed at 0, 3, 7 and 14 days post inoculation. Half of the brain, lung, liver, spleen, heart and kidney will be collected, fixed and processed for H&E staining and pathological scoring as before. Half of the organs will be processed for immunohistochemistry staining with PIV5 antibodies.

In addition, wild type mice will be inoculated intranasally (i.n.) with $10^6$ PFU PIV5 parental virus (PIV5), PIV5-85A or 85B, or PBS. Immunized animals will be monitored for any signs of clinical symptoms (i.e. weight loss, ruffled fur, etc.). Additionally, lung virus titers and lung pathology will be examined to confirm that the various recombinant viruses maintain their ability to infect the host and not cause lung pathology. For pathology studies, lungs will be perfused with 10% buffered formalin via the trachea and placed in formalin for fixation. The lung lobes will be embedded in paraffin, sectioned at 5 microns, stained with hematoxylin and eosin (H&E), and examined by light microscopy. For each sample, four major pulmonary changes (peribronchiolar infiltrations; perivascular infiltrations; parenchymal infiltrations; subpleural infiltrations) will be subjectively scored without knowledge of treatment groups as follows: 0-3 with 0=no change and 3=greatest change and a total score determined. If H&E results show significant inflammation, tissues will be immunostained with virus-specific or lymphocyte-specific (e.g. CD4, CD8, B cell) mAbs and scored for level of virus antigen expression and/or lymphocyte infiltration.

Evaluate immunogenicity and efficacy of recombinant viruses in vivo. This challenge study is designed to compare log CFU of Mtb bacilli in the lungs and spleens of vaccinated groups to the non-vaccinated (control) group, determined by one-way analysis of variance. BCG will be used as positive control for comparison. Effective vaccine will reduce numbers of CFU of Mtb bacilli in the lungs and spleens at 4 and 8 weeks after challenge.

Examine the immunogenicity of PIV5-85A or PIV5-85B. PIV5- and Mtb Ag85A- or Ag85B-specific immune responses will be measured in PIV5-85A or PIV5-85B-immunized mice using a variety of endpoints. As controls, mice will be immunized intranasally with $10^6$ PFU of either PIV5 vaccine strain or subcutaneously with $10_5$ CFU of *M. bovis* BCG strain Danish (Statens Scrum Institut, Copenhagen; SSI). Frozen aliquots of *M. bovis*, BCG strain Danish will be acquired from SSI. BCG Danish in these aliquots has been grown to precise international specifications, aliquoted and viability determined prior to shipment. The required number of aliquots will be thawed immediately prior to vaccination. At various time points after immunization, we will measure local and systemic immunity to PIV5 and Ag85A or Ag85B. Mucosal immunization has been shown to induce an Mtb-specific mucosal IgA and IgG response. Thus, intranasal PIV5 immunization has the potential to induce local Mtb-specific T cell and immunoglobulin responses that mediate protection against Mtb challenge. Local (i.e. lung) PIV5-specific and Mtb-specific immune responses will be assessed by analysis of BAL samples collected at time points after immunization or challenge. Infiltrating lymphocyte populations will be collected by centrifugation and the BAL wash will be analyzed for mucosal immunoglobulins. Systemic responses will be assessed by analysis of serum antibody and splenic or mediastinal lymph node (MLN) lymphocyte populations.

Cell mediated immunity (T cell) analysis. T cell responses induced by vaccination and changes in T cell responses after challenge will be measured by antigen-specific IFN production. Specifically, lymphocytes from the BAL, spleen and/or draining lymph node will be assayed for PIV5- or Mtb-specific T cell responses by re-stimulation with PIV5, Mtb Ag85A or Ag85B proteins or PPD. IFN-γ responses will be determined by intracellular cytokine staining and/or ELISPOT assays. Other investigators demonstrated that IFNγ-producing ELISPOTS by mice immunized with the experimental MVA85A vaccine (now in Phase II clinical trials) can be used as a vaccine potency test (NIH/FDA TB Vaccine Workshop).

Humoral immunity (antibody) analysis. Although antibody is not known to play a critical role in Mtb immunity, humoral immunity after vaccination with PIV5-85A and PIV5-85B will be nonetheless examined. PIV5 is a novel vaccine vector for Mtb. It is possible a different and/or additional mechanism of protection may be used by PIV5-85A and PIV5-85B. For the humoral immunity studies, matched normal serum samples will be collected from mice 1 week prior to immunization by tail vein nick. Anti-PIV5 antibodies in the serum and BAL wash will be measured by PIV5-specific ELISA. Similarly, Mtb Ag85A- or Ag85B-specific humoral immune responses will be measured by standard ELISA assay using recombinant Ag85A or 85B as plate-bound antigens. In the ELISA assays, the isotypes (IgA, IgG1, IgG2a, IgG2b, and IgG3) of the antibodies will also be determined using appropriate secondary antibodies. All serum and BAL wash samples will be compared to the corresponding pre-immune sample.

Examine efficacy of PIV5-85A/PIV5-85B in a mouse challenge model. Intranasal PIV5-85A and PIV5-85B, subcutaneous BCG and non-vaccinated mice (groups of 20) will be challenged with 50-100 CFU of Mtb, and animals monitored up to 8 weeks. Virulent Mtb strain Erdman was banked by the FDA in 2005 and is available to investigators. The required number of aliquots will be thawed immediately prior to challenge. All mice will be exposed to Mtb Erdman using a Madison aerosol chamber. Prior to infection, unicellular cultures of Mtb will be placed in the aerosol chamber nebulizer jar with exposure cycle pre-set to deliver the appropriate infection dose. Following the timed exposure period, the infection chamber will be purged with clean, filtered air and the mouse groups will be returned to their cages. During each infection cycle the air stream carrying aerosolized Mtb bacilli will be sampled in an all glass impinger containing phosphate buffered saline (PBS) to calculate the actual infective dose (CFU) delivered to each group. 100 µl of PBS from each impinger (undiluted, 1 in 10, 1 in 100 and 1 in 1000 dilutions in PBS) will be inoculated in quadruplicate onto 7H11-OADC agar plates and incubated at 37° up to 6 weeks. In addition, every time a Madison aerosol chamber is utilized for challenge, 5 non-vaccinated mice will be sacrificed the day after the challenge to confirm actual exposure dose of Mtb to be 50 to 100 CFU in the lungs. Animal survival curves will be determined for each group up to 8 weeks, and tissue pathology/bacterial burden will be assessed at 4 and 8 weeks after challenge. All mice, regardless of vaccination route will be monitored daily during the first week for malaise; body temperature will also be measured during the first week of infection. All mice will be weighed weekly to detect anorexia or other adverse reactions that can affect weight. Subcutaneous BCG-injected mice will have their injection sites visually examined at first daily and then weekly. A scoring system for monitoring upper respiratory vaccine reactogenicity will be used to derive a quantitative score for each intranasally-vaccinated mouse. The elements of the scoring system will be: visible inflammation of the external nares (0-3), nasal discharge characterized as none, slight serous, marked serous, slight mucopurulent, or marked mucopurulent (0-4) and respiratory rate, which has been validated as an index that reflects nasal blockage of mice (0-3). 10 mice (half of the group) from each experimental group will be sacrificed at 4 weeks after challenge and the other half will be sacrificed at 8 weeks after challenge. After euthanasia, tissues including lungs, liver, spleens, and nasal tissues will be harvested and allocated to different experiments. Gross- and micro-histopathology studies will be conducted by a veterinary pathologist using a defined scoring system. The scoring system described previously for the clinical observations and the pathology studies also will be used to yield a quantitative measurement. Each of these measures will be compared by the Student t test for significant differences between groups.

Example 12

Additional PIV5 Antigen Constructs

Figures 49A, 49B:
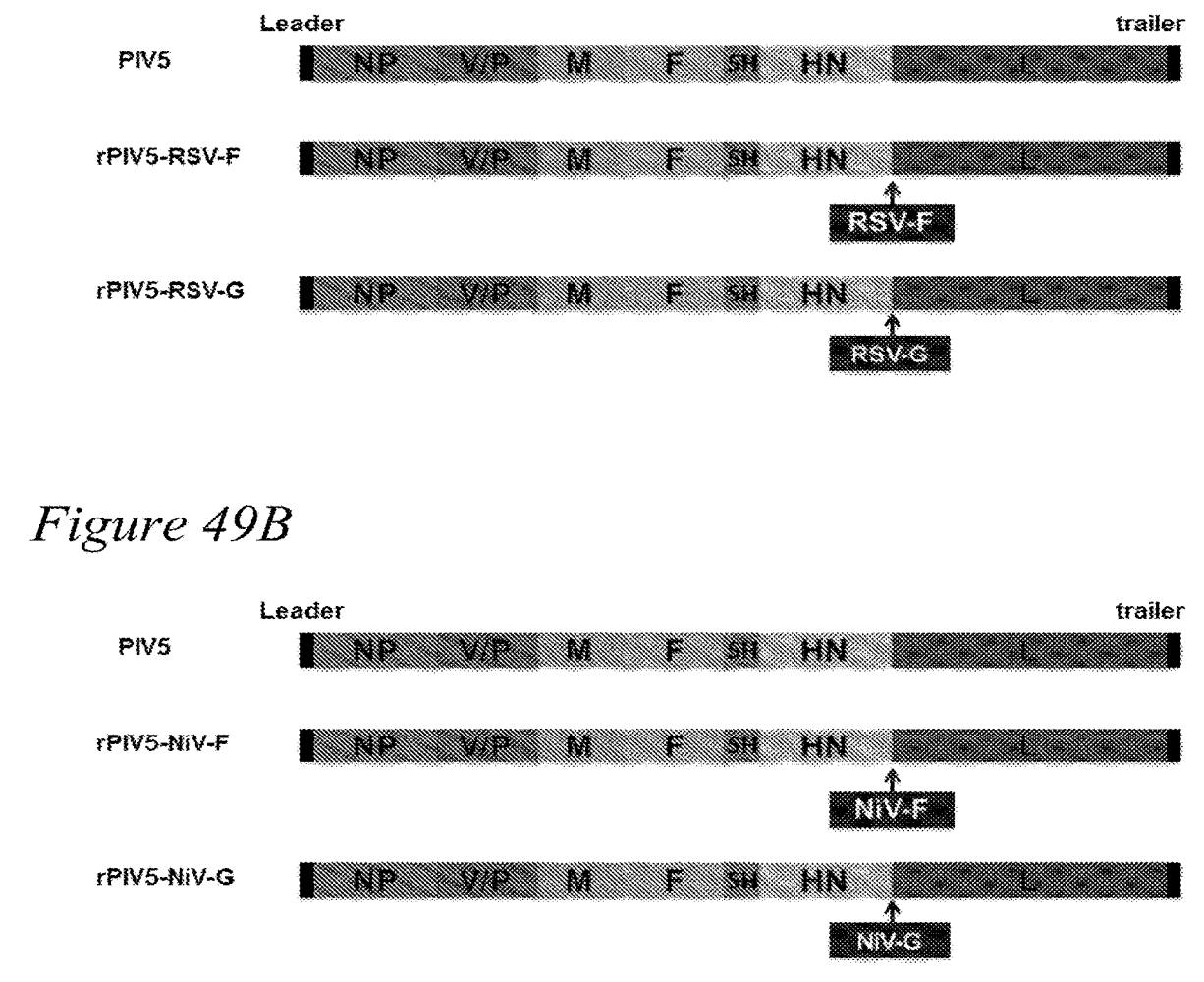
Figures 49C, 49D:
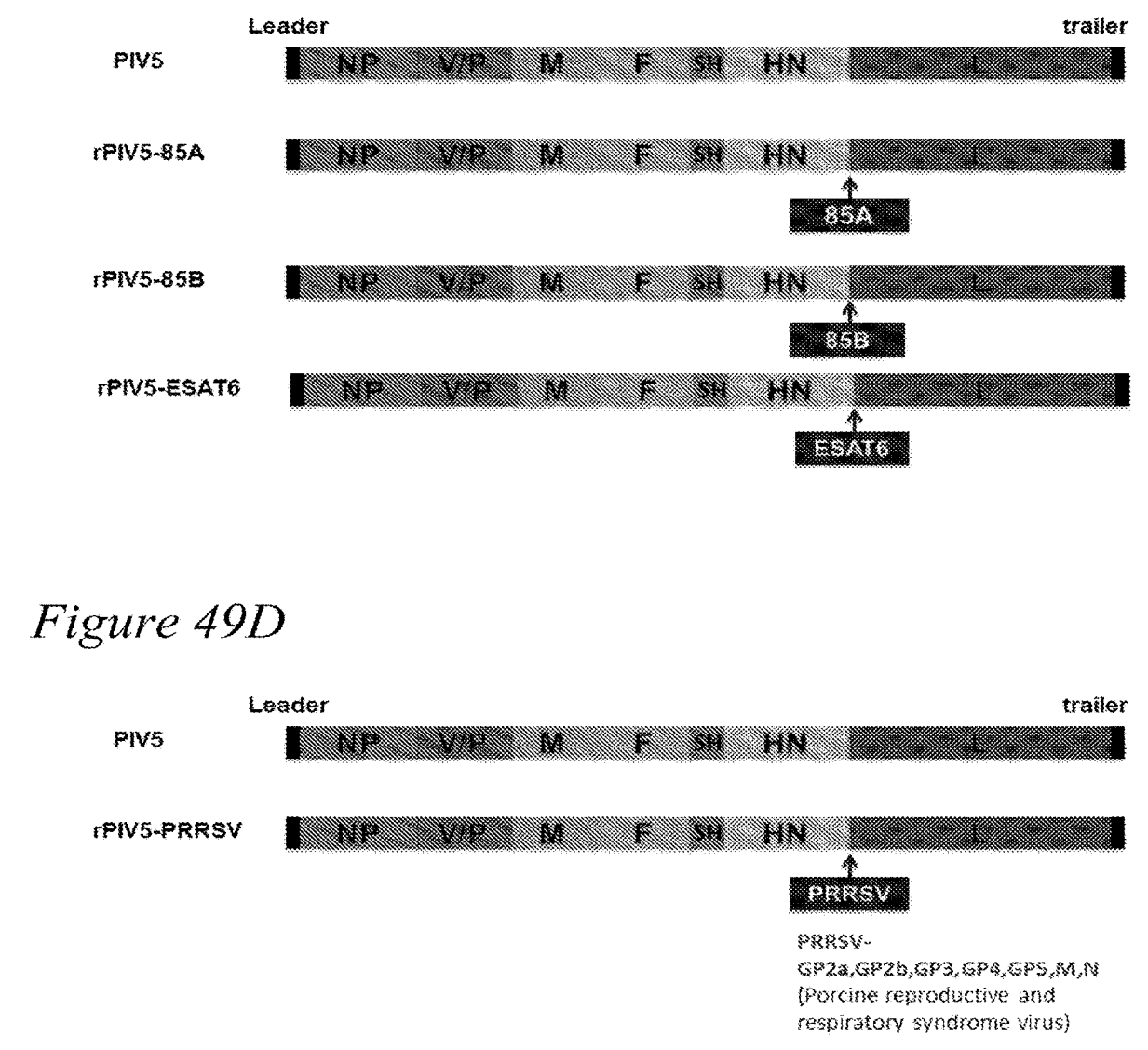
Figure 49E:
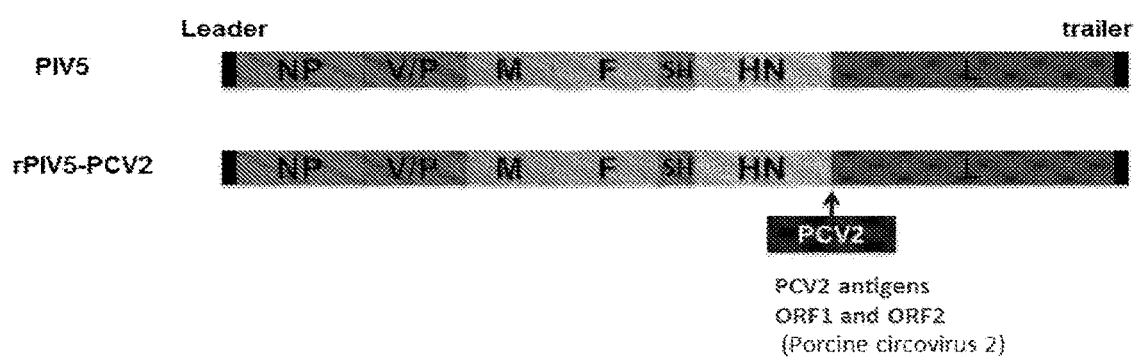
Figure 49F:
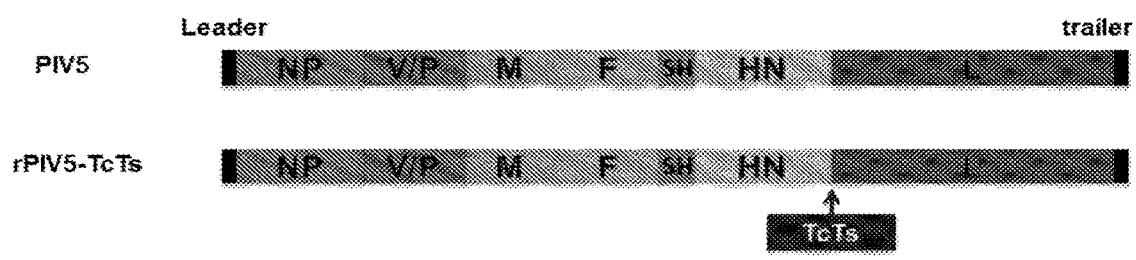
Figure 49G:
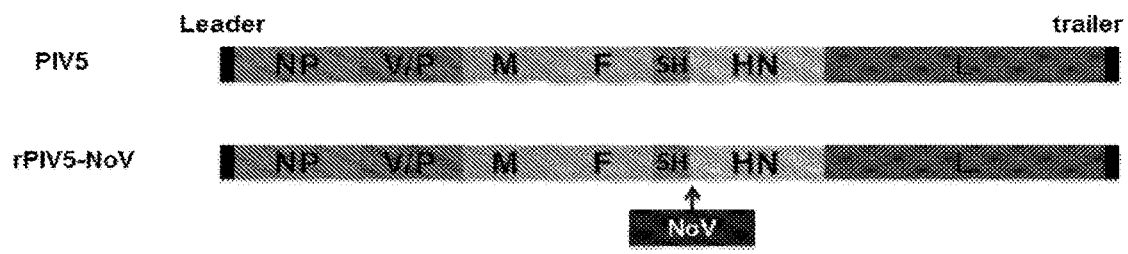
Figure 49H:
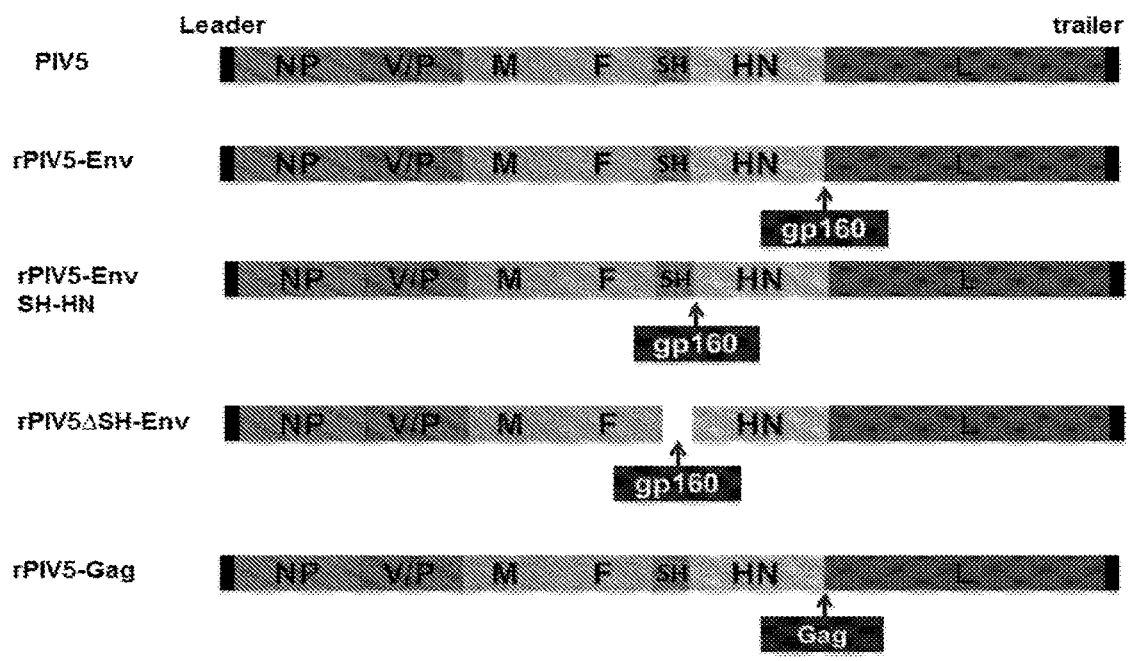

The following additional PIV5 antigen constructs shown in FIGS. 49A-49H have been made. This includes PIV5 constructs expressing RSV antigens F and G (FIG. 49A), PIV5 constructs expressing Nipah Virus antigens F and G (FIG. 49B), PIV5 constructs expressing *Mycobacteria tuberculosis* Antigens 85A, 85B and ESAT6 (FIG. 49C), PIV5 constructs expressing PRRSV antigens (FIG. 49D), PIV5 constructs expressing Porcine circovirus (PCV2) antigens (FIG. 49E), PIV5 constructs expressing *T. cruzi* antigen Ts (FIG. 49F), PIV5 constructs expressing Norovirus antigens (FIG. 49G), and PIV5 constructs expressing HIV antigens Env (gp160, gp140 or gp120 and Gag) (FIG. 49H).

Example 13

Additional PIV5 Vectors

With this example, all commercially available kennel cough vaccines were obtained and these PIV5 strains sequenced. The PIV5 strains isolated from the following commercial kennel cough vaccines were sequenced: BI, FD, Merck and Merial vaccines. Also sequenced were two PIV5 isolates deposited in ATCC; canine parainfluenza virus strain 78-238 (ATCC number VR-1573) (Evermann et al., 1980, *J Am Vet Med Assoc;* 177:1132-1134; and Evermann et al., 1981, *Arch Virol;* 68:165-172) and canine parainfluenza virus strain D008 (ATCC number VR-399) (Binn et al., 1967, *Proc Soc Exp Biol Med;* 126:140-145). The nucleotide sequences are compared in Table 2. This is the first comparison of sequences between the common lab strain (WR strain) and the kennel cough vaccine strains and wild type isolates (represented by the two strains obtained from ATCC).

TABLE 2

Sequence comparison of PIV5 (WR strain) and other strains. 78-238 and D008 are wild type strains from ATCC. BI (Boehringer Ingelheim), FD (Fort Dodge), Merck and Merial are vaccine strains isolated from commercial kennel cough vaccines.
Genome Sequence Identity (%)

| | PIV5 | 78-238 | D008 | BI | FD | Merck | Merial |
|---|---|---|---|---|---|---|---|
| PIV5 | | 98.0 | 99.0 | 99.2 | 98.9 | 98.9 | 99.0 |
| 78-238 | | | 98.5 | 98.4 | 98.3 | 98.3 | 98.5 |
| D008 | | | | 99.3 | 99.2 | 99.2 | 99.9 |
| BI | | | | | 99.3 | 99.3 | 99.3 |
| FD | | | | | | 99.9 | 99.2 |
| Merck | | | | | | | 99.2 |
| Merial | | | | | | | |

PIV5 constructs will be generated and tested based on PIV5 strains from current kennel cough vaccines and ATTC deposits. Interestingly, one of the vaccine strains (Merial) is almost identical to one of the wild type isolates (D008) (99.9% genome sequence identity), suggesting that people have been likely exposed to wild type PIV5 through vaccination of their dogs. Nonetheless, to mitigate potential concern of safety, recombinant PIV5 constructs based on kennel cough vaccine strains will be generated. The Merck vaccine strain will be used first as a base for vaccine constructs because it is the most different from our PIV5 strain (98.9% identity) and it has been widely used in dogs. A reverse genetics system will be generated for the Merck strain and H5 or NP inserted into the genome. Immunogenicity of PIV5-H5 vs. Merck-H5 and PIV5-NP vs. Merck-NP will be compared in mice and in ferrets. Further studies will utilize any of the strains listed in Table 2 and any of the vaccine antigen constructs described herein.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

SEQUENCE FREE LISTING

SEQ ID NO:1, 2, 9, and 10 Synthetic peptides
SEQ ID NO:3-8 Synthetic oligonucleotide primers

What is claimed is:

1. A viral expression vector comprising a parainfluenza virus 5 (PIV5) genome, the PIV5 genome comprising:
   a deletion of the gene encoding the small hydrophobic (SH) protein; and
   a heterologous nucleotide sequence expressing a heterologous polypeptide inserted within the PIV5 genome; and
   wherein the PIV5 genome lacks an SH protein.

2. The viral expression vector of claim 1, wherein the heterologous polypeptide is derived from human immunodeficiency virus (HIV), parainfluenza virus 1, parainfluenza virus 2, parainfluenza virus 3, parainfluenza virus 4, human respiratory syncytial virus, bovine respiratory syncytial virus, human metapneumovirus, avian influenza, canine influenza, avian metapneumovirus, Nipah virus, Hendra virus, rabies virus, Ebola virus, porcine circovirus, porcine reproductive and respiratory syncytial virus (RSV), swine influenza virus, New Castle disease virus, mumps virus, measles virus, canine distemper virus, feline leukemia virus, human calicivirus, veterinary calicivirus, human norovirus, veterinary norovirus, rinderpest virus, and/or *Mycobacterium tuberculosis*.

3. The viral expression vector of claim 1, wherein the heterologous polypeptide is derived from a bacteria or a parasite.

4. The viral expression vector of claim 1, wherein the heterologous polypeptide comprises hemagglutinin (HA), neuraminidase (NA), nucleocapsid protein (NP), M1, M2, PA, PB1, PB2, PB1-F2, NS1 or NS2 of influenza virus.

5. The viral expression vector of claim 4, wherein the influenza virus comprises influenza A, influenza B, or influenza C.

6. The viral expression vector of claim 4, wherein the heterologous polypeptide comprises a hemagglutinin (HA) from influenza A virus strain subtype H1 to H18.

7. The viral expression vector of claim 4, wherein the heterologous polypeptide comprises a hemagglutinin (HA) from influenza A virus strain H5N1, H3N2, or H1N1.

8. The viral expression vector of claim 4, wherein the heterologous polypeptide comprises an influenza neuraminidase (NA) from influenza type A subtype N1 to N10.

9. The viral expression vector of claim 4, wherein the heterologous polypeptide comprises an influenza NP, M1, M2, PA, PB1, PB2, PB1-F2, NS1 or NS2 from influenza A virus strain H1 to H17.

10. The viral expression vector of claim 1, wherein the heterologous polypeptide comprises the F protein or G protein of the rabies virus.

11. The viral expression vector of claim 1, wherein the heterologous polypeptide comprises the gp160 envelope protein of human immunodeficiency virus (HIV).

12. The viral expression vector of claim 1, wherein the heterologous nucleotide sequence is inserted within the PIV5 genome:
- between the hemagglutinin-neuraminidase(HN) gene and the large RNA polymerase protein (L) gene;
- closer to the leader than between the hemagglutinin-neuraminidase(HN) gene and the large RNA polymerase protein (L);
- upstream of the nucleocapsid protein (NP) gene of the PIV5 genome;
- immediately downstream of the leader sequence of the PIV5 genome;
- between the F gene and the SH gene of the PIV5 genome;
- between the VP gene and the matrix protein (M) gene of the PIV5 genome;
- between the M gene and the F gene of the PIV5 genome;
- between the nucleocapsid protein (NP) gene and the V/P gene of the PIV5 genome;
- between the leader sequence and the nucleocapsid protein (NP) gene of the PIV5 genome;
- replaces a portion of the F or HN gene;
- within the NP gene nucleotide sequence;
- within the V/P gene nucleotide sequence;
- within the M gene nucleotide sequence;
- within the F gene nucleotide sequence;
- within the HN gene nucleotide sequence; or
- within the L gene nucleotide sequence.

13. The viral expression vector of claim 1, wherein the PIV5 genome comprises one or more further mutations.

14. The viral expression vector of claim 13, wherein the further mutation comprises a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation of the fusion (F) protein, a mutation of the phosphoprotein (P), a mutation of the large RNA polymerase (L) protein, a mutation inducing apoptosis, or a combination thereof.

15. The viral expression vector of claim 13, wherein the mutation comprises PIV5 VAC.

16. A viral particle comprising a viral expression vector of claim 1.

17. A composition of the viral expression vector of claim 1.

18. A method of expressing a heterologous polypeptide in a cell, the method comprising contacting the cell with a viral expression vector of claim 1.

19. A method of inducing an immune response in a subject to a heterologous polypeptide, the method comprising administering a viral expression vector of claim 1 to the subject.

20. A method of expressing a heterologous polypeptide in a subject, the method comprising administering a viral expression vector of claim 1 to the subject.

* * * * *